United States Patent
da Costa e Silva et al.

(10) Patent No.: US 7,858,847 B2
(45) Date of Patent: Dec. 28, 2010

(54) PROTEIN KINASE STRESS-RELATED PROTEINS AND METHODS OF USE IN PLANTS

(75) Inventors: Oswaldo da Costa e Silva, Neustadt (DE); Nocha Van Thielen, Durham, NC (US); Ruoying Chen, Duluth, GA (US); Hans J. Bohnert, Champaign, IL (US); Rodrigo Sarria-Millan, Durham, NC (US)

(73) Assignee: BASF Plant Science GmbH (DE)

( * ) Notice: Subject to any disclaimer, the term of this patent is extended or adjusted under 35 U.S.C. 154(b) by 4 days.

(21) Appl. No.: 12/545,903

(22) Filed: Aug. 24, 2009

(65) Prior Publication Data

US 2009/0320158 A1    Dec. 24, 2009

Related U.S. Application Data

(60) Continuation of application No. 12/401,635, filed on Mar. 11, 2009, and a continuation of application No. 11/961,634, filed on Dec. 20, 2007, now Pat. No. 7,521,598, and a continuation of application No. 11/564,902, filed on Nov. 30, 2006, now Pat. No. 7,504,559, and a continuation of application No. 10/768,863, filed on Jan. 30, 2004, now Pat. No. 7,179, 962, and a division of application No. 09/828,313, filed on Apr. 6, 2001, now Pat. No. 6,867,351.

(60) Provisional application No. 60/196,001, filed on Apr. 7, 2000.

(51) Int. Cl.
*C12N 15/82* (2006.01)
*C12N 15/29* (2006.01)
*A01H 5/00* (2006.01)
*A01H 5/10* (2006.01)

(52) U.S. Cl. ............ 800/289; 435/419; 536/23.6; 800/298; 800/320; 800/320.1; 800/320.2; 800/320.3; 800/312; 800/314; 800/306; 800/322; 800/313; 800/317; 800/317.1; 800/317.2; 800/317.3; 800/317.4

(58) Field of Classification Search ............ None
See application file for complete search history.

(56) References Cited

U.S. PATENT DOCUMENTS 7,084,323 B1 * 8/2006 Sheen ............ 800/289

\* cited by examiner

*Primary Examiner*—Cynthia Collins
(74) *Attorney, Agent, or Firm*—Patricia A. McDaniels

(57) ABSTRACT

A transgenic plant transformed by a Protein Kinase Stress-Related Protein (PKSRP) coding nucleic acid, wherein expression of the nucleic acid sequence in the plant results in increased tolerance to environmental stress as compared to a wild type variety of the plant. Also provided are agricultural products, including seeds, produced by the transgenic plants. Also provided are isolated PKSRPs, and isolated nucleic acid coding PKSRPs, and vectors and host cells containing the latter.

22 Claims, 18 Drawing Sheets

Figure 2
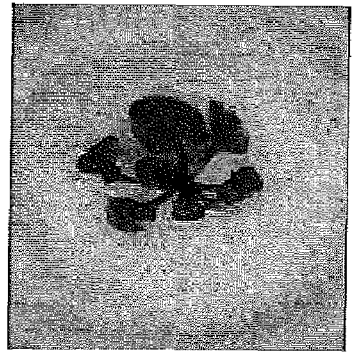
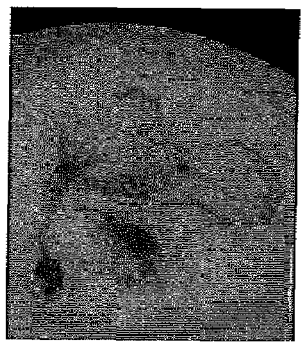
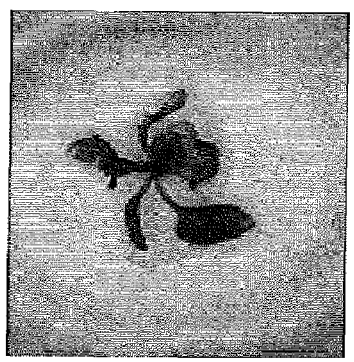
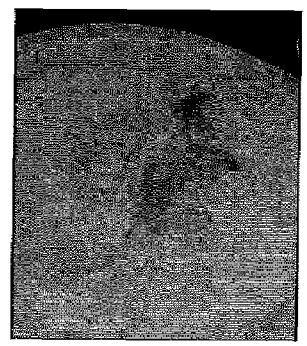
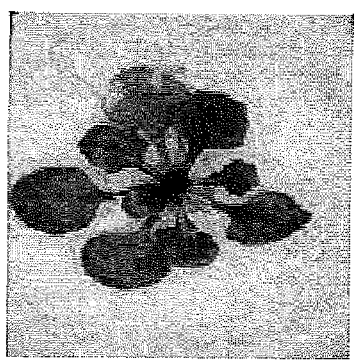
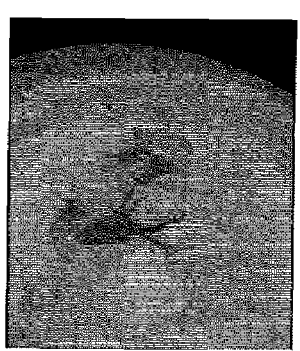
PpPK-6 Drought
Control Drought

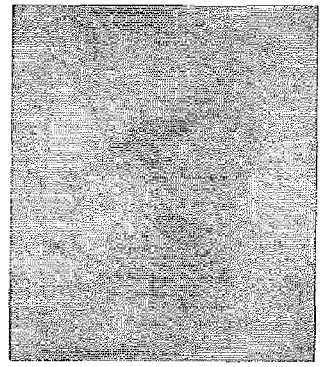
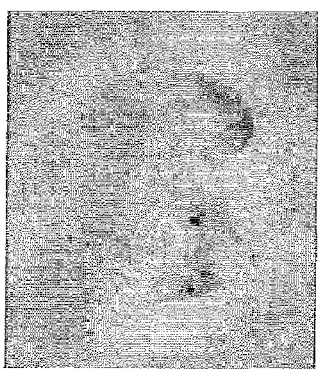
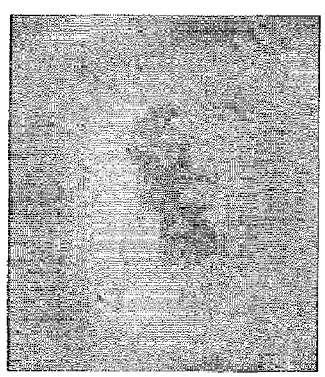
Figure 4

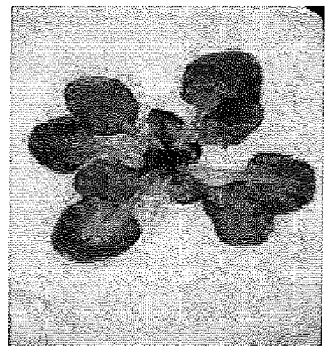
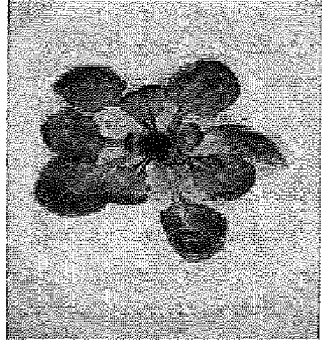
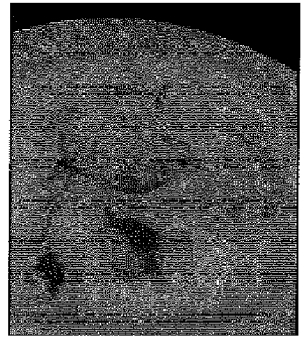
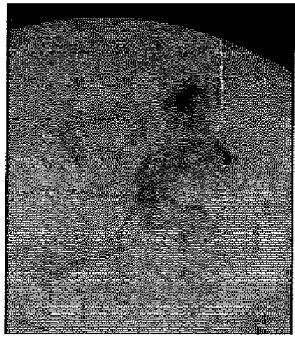
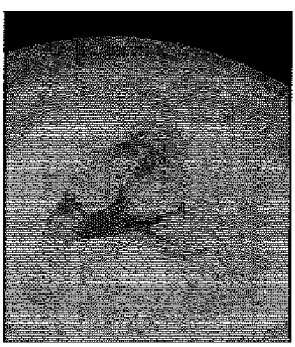
Figure 5

Figure 7
PpCK-1 Drought
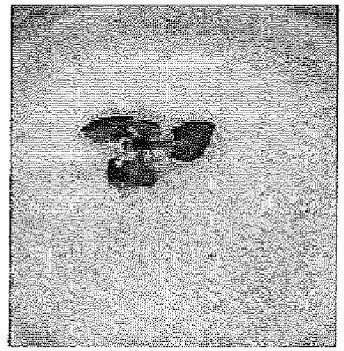
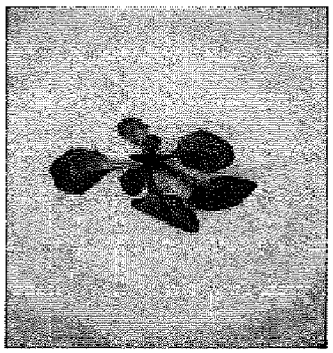
Control Drought
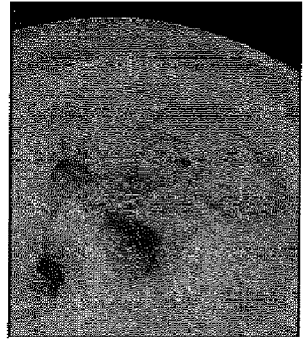
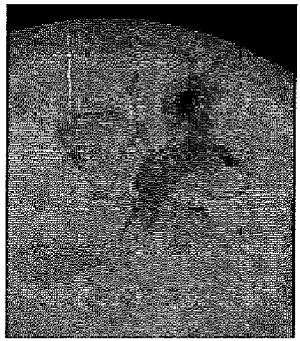
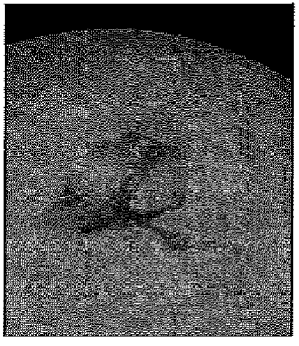

Figure 9
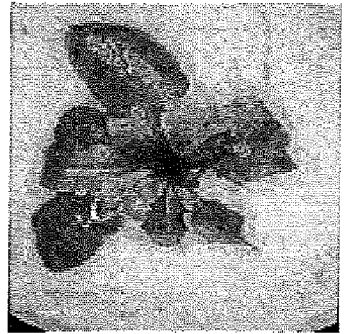
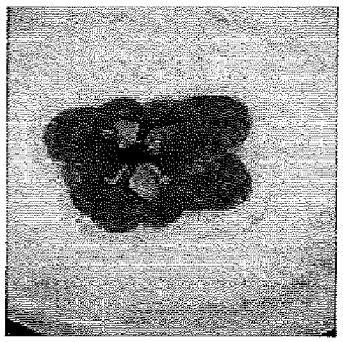
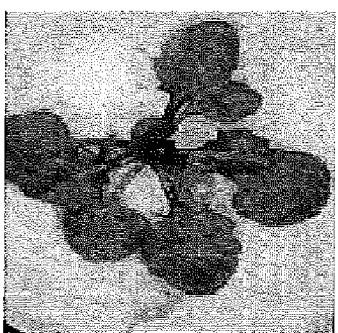
PpCK-2 Drought
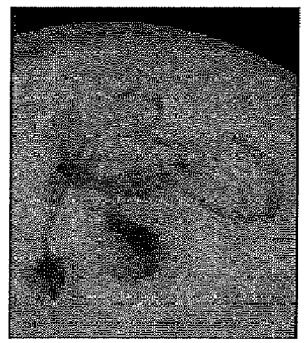
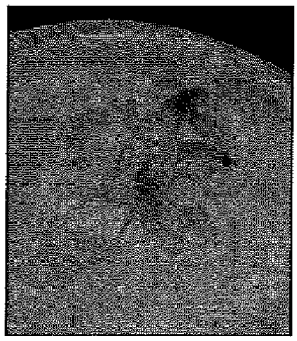
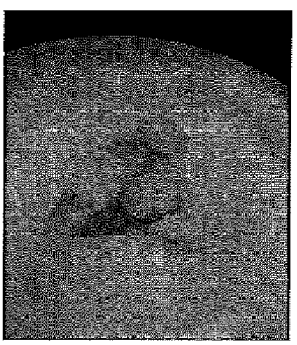
Control Drought

Figure 10
PpCK-3 Drought
Control Drought
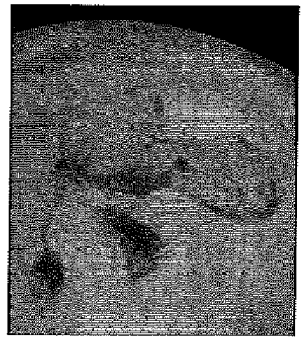
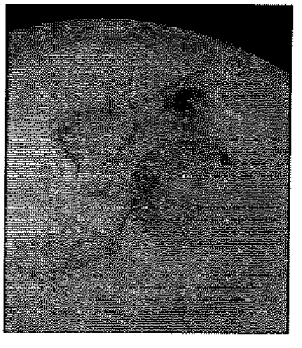
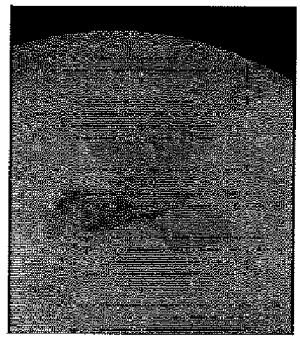

Figure 11
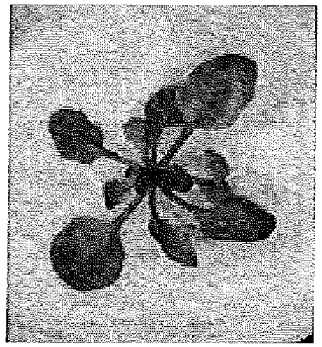
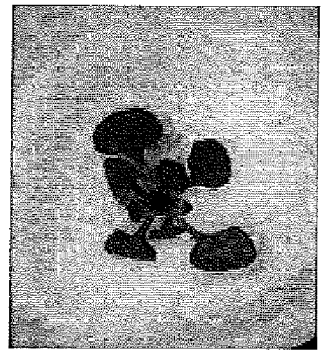
PpMPK-2 Drought
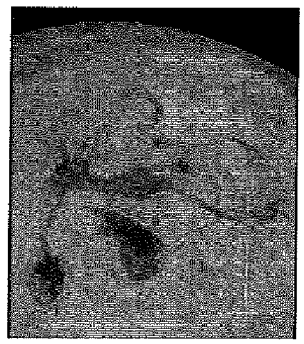
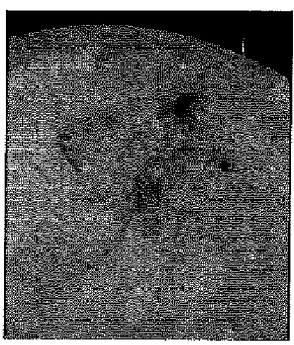
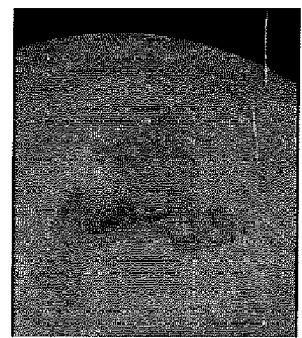
Control Drought Figure 13
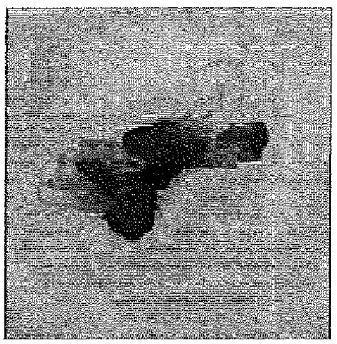
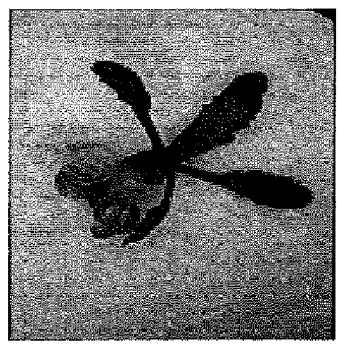
PpMPK-3 Drought
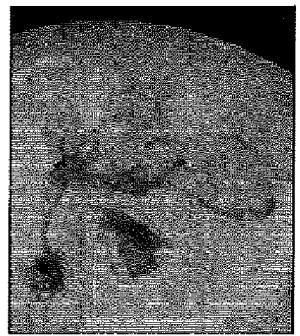
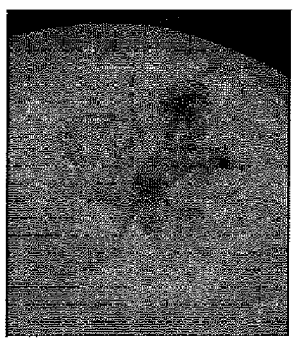
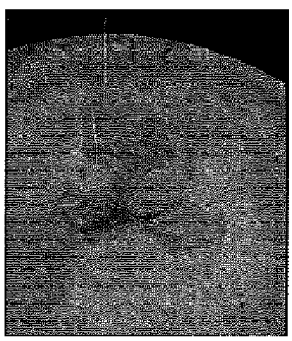
Control Drought Figure 14
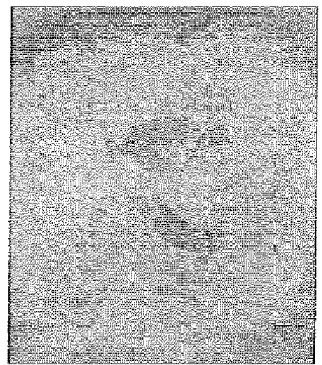
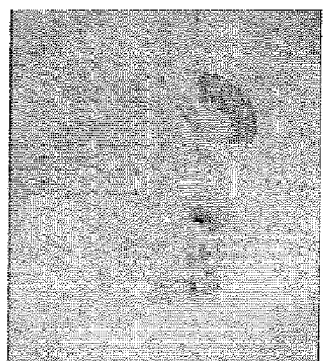
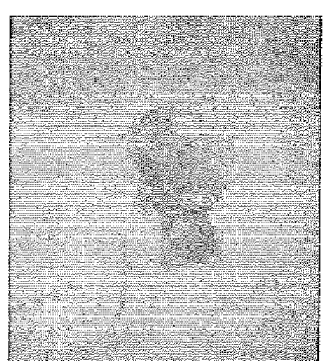

Figure 16
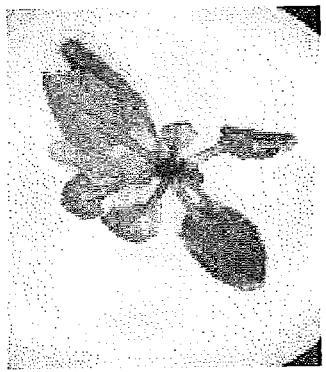 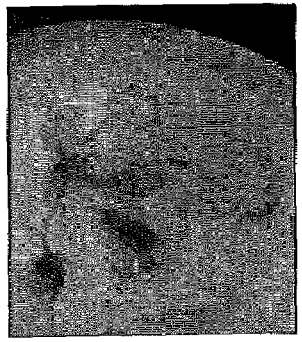
PpMPK-5 Drought | Control Drought
 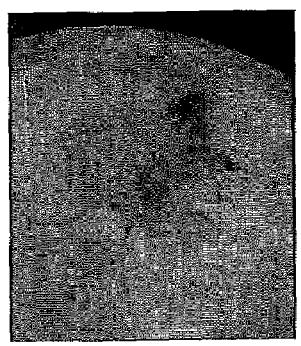
 

Figure 18
PpCPK-2 Drought
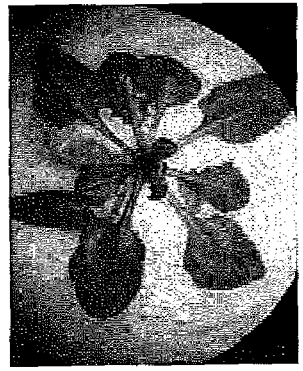
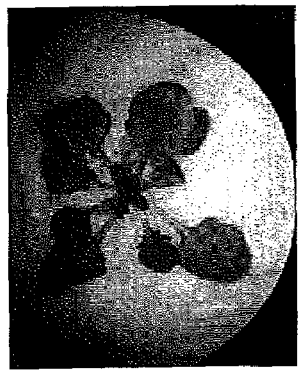
Control Drought
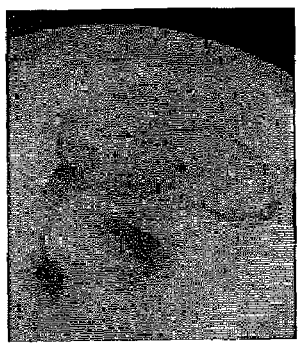
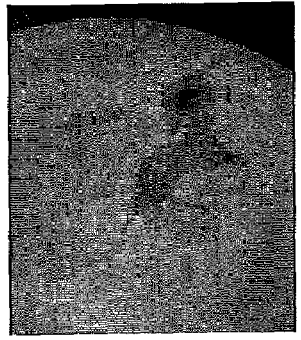
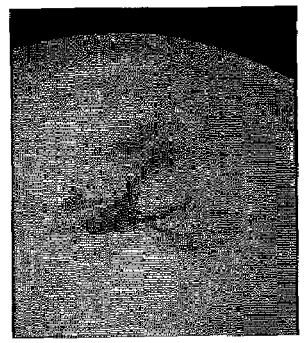

PROTEIN KINASE STRESS-RELATED PROTEINS AND METHODS OF USE IN PLANTS

CROSS REFERENCE TO RELATED APPLICATIONS

This application is a divisional of U.S. patent application Ser. No. 09/828,313, filed Apr. 6, 2001 and now U.S. Pat. No. 6,867,351, and is copending with U.S. patent application Ser. No. 12/401,635, filed Mar. 11, 2009, which is with U.S. patent application Ser. No. 11/961,634, filed Dec. 20, 2007, and now U.S. Pat. No. 7,521,598, which is a continuation of U.S. patent application Ser. No. 11/564,902, filed Nov. 30, 2006, and now U.S. Pat. No. 7,504,559, which is a continuation of U.S. patent application Ser. No. 10/768,863, filed Jan. 30, 2004 and now U.S. Pat. No. 7,179,962, which is a divisional of U.S. patent application Ser. No. 09/828,313, which claims the priority benefit of U.S. Provisional Application Ser. No. 60/196,001 filed Apr. 7, 2000. The contents of each of the above-identified applications are hereby incorporated by reference.

BACKGROUND OF THE INVENTION

1. Field of the Invention

This invention relates generally to nucleic acid sequences encoding proteins that are associated with abiotic stress responses and abiotic stress tolerance in plants. In particular, this invention relates to nucleic acid sequences encoding proteins that confer drought, cold, and/or salt tolerance to plants.

2. Background Art

Abiotic environmental stresses, such as drought stress, salinity stress, heat stress, and cold stress, are major limiting factors of plant growth and productivity. Crop losses and crop yield losses of major crops such as rice, maize (corn) and wheat caused by these stresses represent a significant economic and political factor and contribute to food shortages in many underdeveloped countries.

Plants are typically exposed during their life cycle to conditions of reduced environmental water content. Most plants have evolved strategies to protect themselves against these conditions of desiccation. However, if the severity and duration of the drought conditions are too great, the effects on plant development, growth and yield of most crop plants are profound. Furthermore, most of the crop plants are very susceptible to higher salt concentrations in the soil. Continuous exposure to drought and high salt causes major alterations in the plant metabolism. These great changes in metabolism ultimately lead to cell death and consequently yield Josses.

Developing stress-tolerant plants is a strategy that has the potential to solve or mediate at least some of these problems. However, traditional plant breeding strategies to develop new lines of plants that exhibit resistance (tolerance) to these types of stresses are relatively slow and require specific resistant lines for crossing with the desired line. Limited germplasm resources for stress tolerance and incompatibility in crosses between distantly related plant species represent significant problems encountered in conventional breeding. Additionally, the cellular processes leading to drought, cold and salt tolerance in model, drought- and/or salt-tolerant plants are complex in nature and involve multiple mechanisms of cellular adaptation and numerous metabolic pathways, This multi-component nature of stress tolerance has not only made breeding for tolerance largely unsuccessful, but has also limited the ability to genetically engineer stress tolerance plants using biotechnological methods.

Drought, cold as well as salt stresses have a common theme important for plant growth and that is water availability. Plants are exposed during their entire life cycle to conditions of reduced environmental water content. Most plants have evolved strategies to protect themselves against these conditions of desiccation. However, if the severity and duration of the drought conditions are too great, the effects on plant development, growth and yield of most crop plants are profound. Since high salt content in some soils result in less available water for cell intake, its effect is similar to those observed under drought conditions. Additionally, under freezing temperatures, plant cells loose water as a result of ice formation that starts in the apoplast and withdraws water from the symplast. Commonly, a plant's molecular response mechanisms to each of these stress conditions are common and protein kinases play an essential role in these molecular mechanisms.

Protein kinases represent a super family and the members of this family catalyze the reversible transfer of a phosphate group of ATP to serine, threonine and tyrosine amino acid side chains on target proteins. Protein kinases are primary elements in signaling processes in plants and have been reported to play crucial roles in perception and transduction of signals that allow a cell (and the plant) to respond to environmental stimuli. In particular, receptor protein kinases (RPKs) represent one group of protein kinases that activate a complex array of intracellular signaling pathways in response to the extracellular environment (Van der Gear et al., 1994 Annu. Rev. Cell Biol. 10:251-337). RPKs are single-pass transmembrane proteins that contain an amino-terminal signal sequence, extracellular domains unique to each receptor, and a cytoplasmic kinase domain, Ligand binding induces homo- or hetero-dimerization of RPKs, and the resultant close proximity of the cytoplasmic domains results in kinase activation by transphosphorylation. Although plants have many proteins similar to RPKs, no ligand has been identified for these receptor-like kinases (RLKs). The majority of plant RLKs that have been identified belong to the family of Serine/Threonine (Ser/Thr) kinases, and most have extracellular Leucine-rich repeats (Becraft, P W. 1998 Trends Plant Sci. 3:384-388).

Another type of protein kinase is the Ca+-dependent protein kinase (CDPK). This type of kinase has a calmodulin-like domain at the COOH terminus which allows response to Ca+ signals directly without calmodulin being present. Currently, CDPKs are the most prevalent Ser/Thr protein kinases found in higher plants. Although their physiological roles remain unclear, they are induced by cold, drought and abscisic acid (ABA) (Knight et al., 1991 Nature 352:524; Schroeder, J I and Thuleau, P., 1991 Plant Cell 3:555; Bush, D. S., 1995 Annu. Rev. Plant Phys. Plant Mol. Biol. 46:95; Urao, T. et al., 1994 Mol, Gen. Genet. 244:331).

Another type of signaling mechanism involves members of the conserved SNF1 Serine/Threonine protein kinase family. These kinases play essential roles in eukaryotic glucose and stress signaling. Plant SNF1-like kinases participate in the control of key metabolic enzymes, including HMGR, nitrate reductase, sucrose synthase, and sucrose phosphate synthase (SPS), Genetic and biochemical data indicate that sugar-dependent regulation of SNF1 kinases involves several other sensory and signaling components in yeast, plants and animals.

Additionally, members of the Mitogen-Activated Protein Kinase (MAPK) family have been implicated in the actions of numerous environmental stresses in animals, yeasts and plants. It has been demonstrated that both MAPK-like kinase activity and mRNA levels of the components of MAPK cascades increase in response to environmental stress and plant hormone signal transduction. MAP kinases are components of sequential kinase cascades, which are activated by phosphorylation of threonine and tyrosine residues by intermediate upstream MAP kinase kinases (MAPKKs). The MAPKKs are themselves activated by phosphorylation of serine and threonine residues by upstream kinases (MAPKKKs). A number of MAP Kinase genes have been reported in higher plants.

SUMMARY OF THE INVENTION

This invention fulfills in part the need to identify new, unique protein kinases capable of conferring stress tolerance to plants upon over-expression. The present invention provides a transgenic plant cell transformed by a Protein Kinase Stress-Related Protein (PKSRP) coding nucleic acid, wherein expression of the nucleic acid sequence in the plant cell results in increased tolerance to environmental stress as compared to a wild type variety of the plant cell. Namely, described herein are the protein kinases: 1) Ser/Thr Kinase and other type of kinases (PK-6, PK-7, PK-8 and PK-9); 2) Calcium dependent protein kinases (CDPK-1 and CDPK-2), 3) Casein Kinase homologs (CK-1, CK-2 and CK-3), and 4) MAP-Kinases (MPK-2, MPK-3, MPK-4 and MPK-5), all from *Physcomitrella patens*.

The invention provides in some embodiments that the PKSRP and coding nucleic acid are that found in members of the genus *Physcomitrella*. In another preferred embodiment, the nucleic acid and protein are from a *Physcomitrella patens*. The invention provides that the environmental stress can be salinity, drought, temperature, metal, chemical, pathogenic and oxidative stresses, or combinations thereof. In preferred embodiments, the environmental stress can be drought or cold temperature.

The invention further provides a seed produced by a transgenic plant transformed by a PKSRP coding nucleic acid, wherein the plant is true breeding for increased tolerance to environmental stress as compared to a wild type variety of the plant. The invention further provides a seed produced by a transgenic plant expressing a PKSRP, wherein the plant is true breeding for increased tolerance to environmental stress as compared to a wild type variety of the plant.

The invention further provides an agricultural product produced by any of the below-described transgenic plants, plant parts or seeds. The invention further provides an isolated PKSRP as described below. The invention further provides an isolated PKSRP coding nucleic acid, wherein the PKSRP coding nucleic acid codes for a PKSRP as described below.

The invention further provides an isolated recombinant expression vector comprising a PKSRP coding nucleic acid as described below, wherein expression of the vector in a host cell results in increased tolerance to environmental stress as compared to a wild type variety of the host cell. The invention further provides a host cell containing the vector and a plant containing the host cell.

The invention further provides a method of producing a transgenic plant with a PKSRP coding nucleic acid, wherein expression of the nucleic acid in the plant results in increased tolerance to environmental stress as compared to a wild type variety of the plant comprising: (a) transforming a plant cell with an expression vector comprising a PKSRP coding nucleic acid, and (b) generating from the plant cell a transgenic plant with an increased tolerance to environmental stress as compared to a wild type variety of the plant. In preferred embodiments, the PKSRP and PKSRP coding nucleic acid are as described below.

The present invention further provides a method of identifying a novel PKSRP, comprising (a) raising a specific antibody response to a PKSRP, or fragment thereof, as described below; (b) screening putative PKSRP material with the antibody, wherein specific binding of the antibody to the material indicates the presence of a potentially novel PKSRP; and (c) identifying from the bound material a novel PKSRP in comparison to known PKSRP, Alternatively, hybridization with nucleic acid probes as described below can be used to identify novel PKSRP nucleic acids.

The present invention also provides methods of modifying stress tolerance of a plant comprising, modifying the expression of a PKSRP nucleic acid in the plant, wherein the PKSRP is as described below. The invention provides that this method can be performed such that the stress tolerance is either increased or decreased. Preferably, stress tolerance is increased in a plant via increasing expression of a PKSRP nucleic acid.

BRIEF DESCRIPTION OF THE DRAWINGS

FIG. 2 shows the results of a drought stress test with over-expressing PpPK-6 transgenic plants and wild-type *Arabidopsis* lines. The transgenic lines display a tolerant phenotype. Individual transformant lines are shown.

FIG. 4 shows the results of a freezing stress test with over-expressing PpPK-7 transgenic plants and wild-type *Arabidopsis* lines. The transgenic lines display a tolerant phenotype. Individual transformant lines are shown.

FIG. 5 shows the results of a drought stress test with over-expressing PpPK-9 transgenic plants and wild-type *Arabidopsis* lines. The transgenic lines display a tolerant phenotype. Individual transformant lines are shown.

FIG. 7 shows the results of a drought stress test with over-expressing PpCK-1 transgenic plants and wild-type *Arabidopsis* lines. The transgenic lines display a tolerant phenotype. Individual transformant lines are shown.

FIG. 9 shows the results of a drought stress test with over-expressing PpCK-2 transgenic plants and wild-type *Arabidopsis* lines. The transgenic lines display a tolerant phenotype. Individual transformant lines are shown.

FIG. 10 shows the results of a drought stress test with over-expressing PpCK-3 transgenic plants and wild-type *Arabidopsis* lines. The transgenic lines display a tolerant phenotype. Individual transformant lines are shown.

FIG. 11 shows the results of a drought stress test with over-expressing PpMPK-2 transgenic plants and wild-type *Arabidopsis* lines. The transgenic lines display a tolerant phenotype. Individual transformant lines are shown.

FIG. 13 shows the results of a drought stress test with over-expressing PpMPK-3 transgenic plants and wild-type *Arabidopsis* lines. The transgenic lines display a tolerant phenotype. Individual transformant lines are shown.

FIG. 14 shows the results of a freezing stress test with over-expressing PpMPK-3 transgenic plants and wild-type *Arabidopsis* lines. The transgenic lines display a tolerant phenotype. Individual transformant lines are shown.

FIG. 16 shows the results of a drought stress test with over-expressing PpMPK-5 transgenic plants and wild-type *Arabidopsis* lines. The transgenic lines display a tolerant phenotype. Individual transformant lines are shown.

FIG. 18 shows the results of a drought stress test with over-expressing PpCPK-2 transgenic plants and wild-type *Arabidopsis* lines. The transgenic lines display a tolerant phenotype. Individual transformant lines are shown.

DETAILED DESCRIPTION OF THE INVENTION

Figure 1:
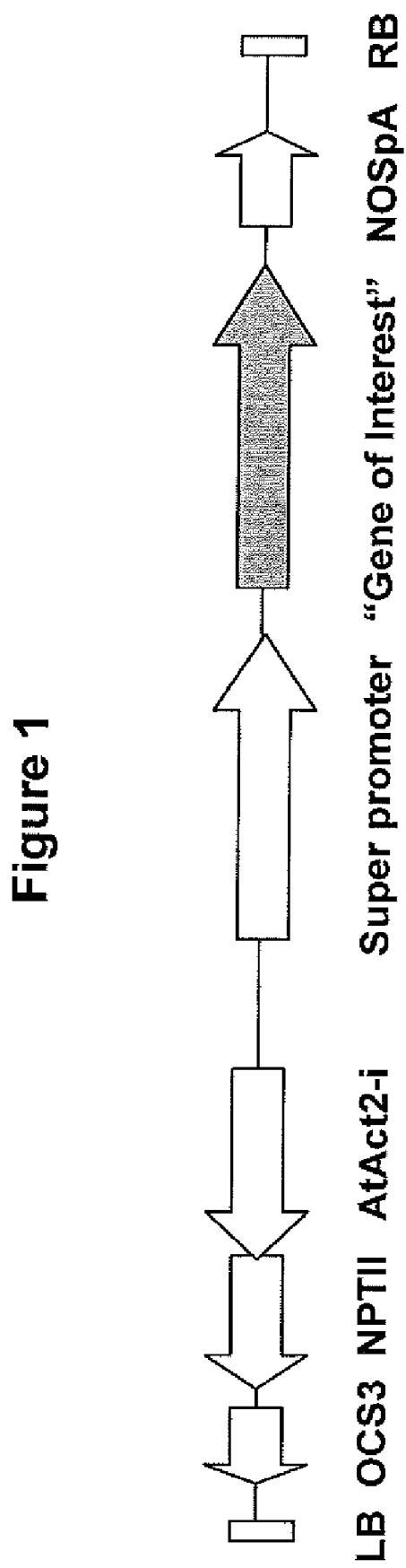
FIG. 1 shows a diagram of the plant expression vector pBPSSC022 containing the super promoter driving the expression of SEQ ID NOs: 14, 15, 16, 17, 18, 19, 20, 21, 22, 23, 24, 25 and 26 ("Desired Gene"). The components are: NPTII kanamycin resistance gene (Bevan M, Nucleic Acids Res. 26:8711-21, 1984), AtAct2-i promoter (An Y Q et al., Plant J 10:107-121 1996), OCS3 terminator (During K, Transgenic Res. 3:138-140, 1994), NOSpA terminator (Jefferson et al., EMBO J. 6:3901-7 1987).
Figure 3:
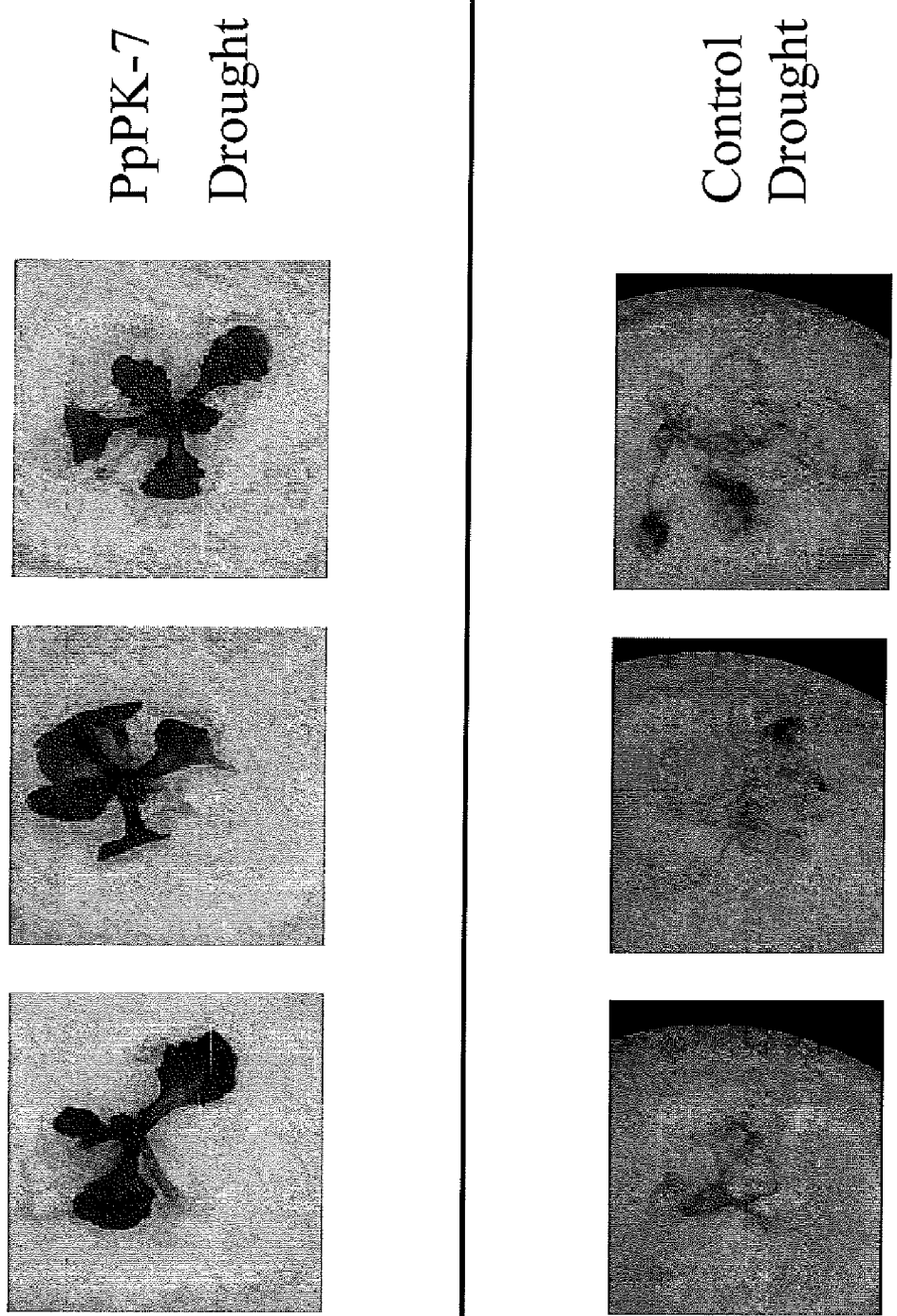
FIG. 3 shows the results of a drought stress test with over-expressing PpPK-7 transgenic plants and wild-type *Arabidopsis* lines. The transgenic lines display a tolerant phenotype. Individual transformant lines are shown.
Figure 6:
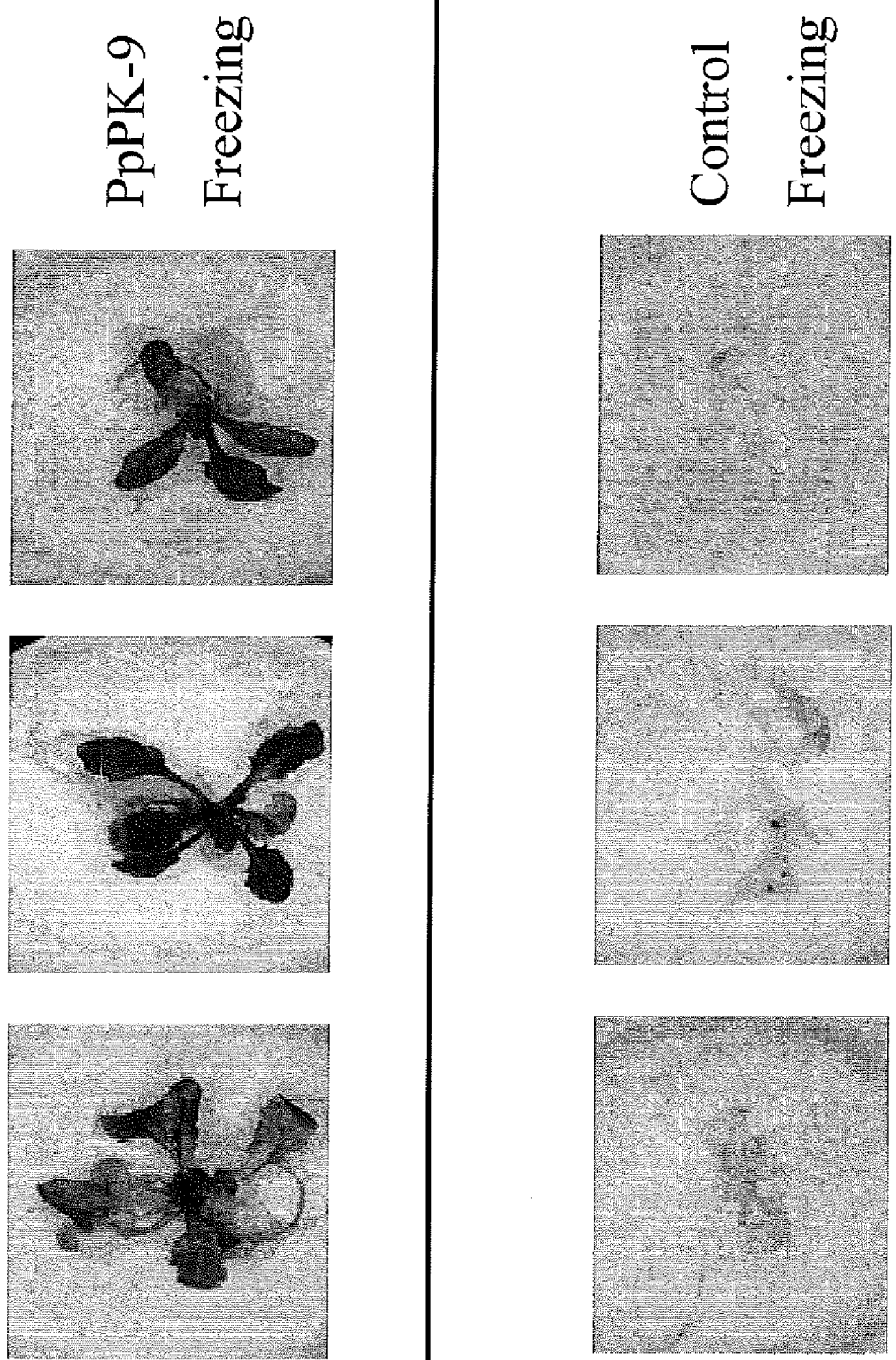
FIG. 6 shows the results of a freezing stress test with over-expressing PpPK-9 transgenic plants and wild-type *Arabidopsis* lines. The transgenic lines display a tolerant phenotype. Individual transformant lines are shown.
Figure 8:
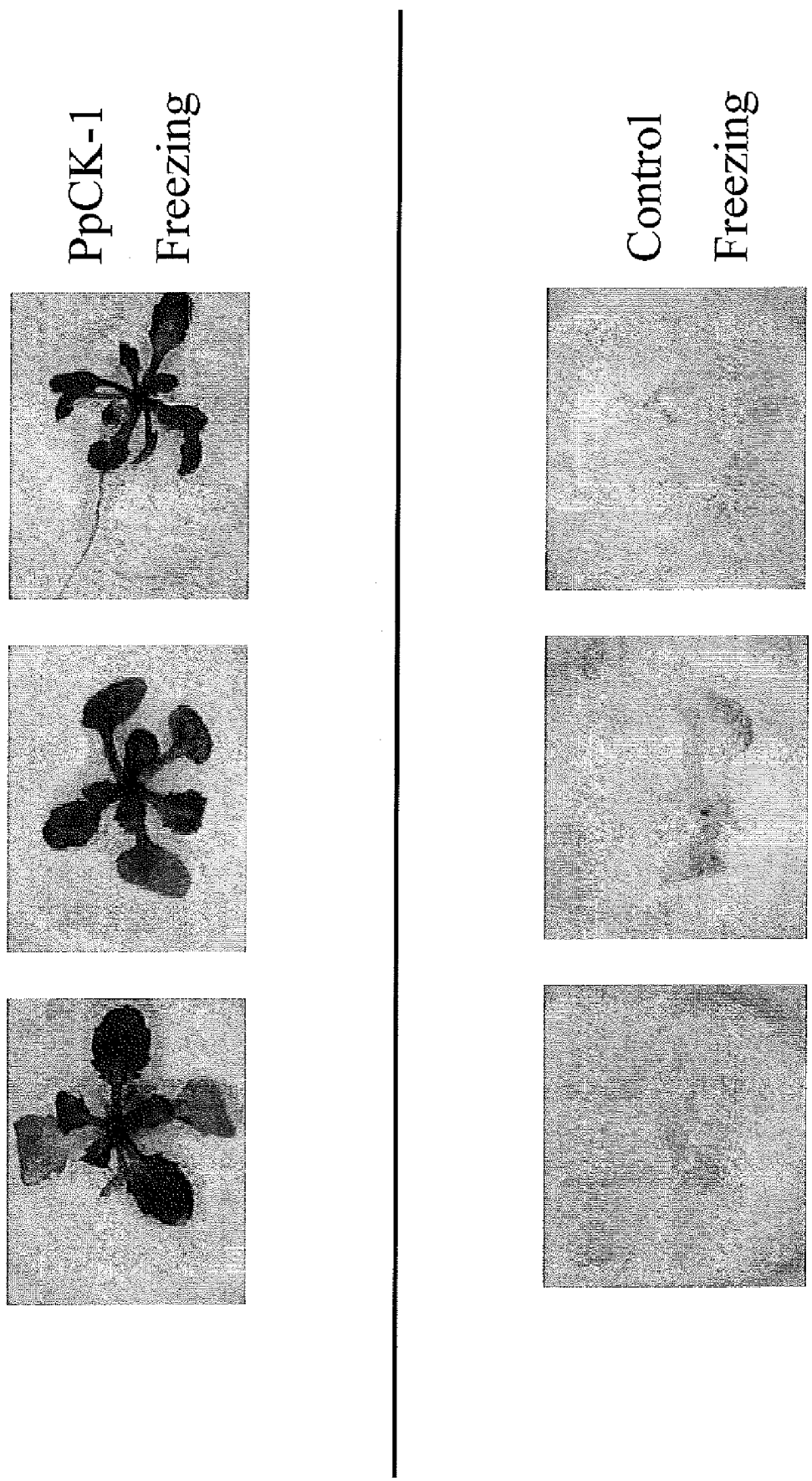
FIG. 8 shows the results of a freezing stress test with over-expressing PpCK-1 transgenic plants and wild-type *Arabidopsis* lines. The transgenic lines display a tolerant phenotype. Individual transformant lines are shown.
Figure 12:
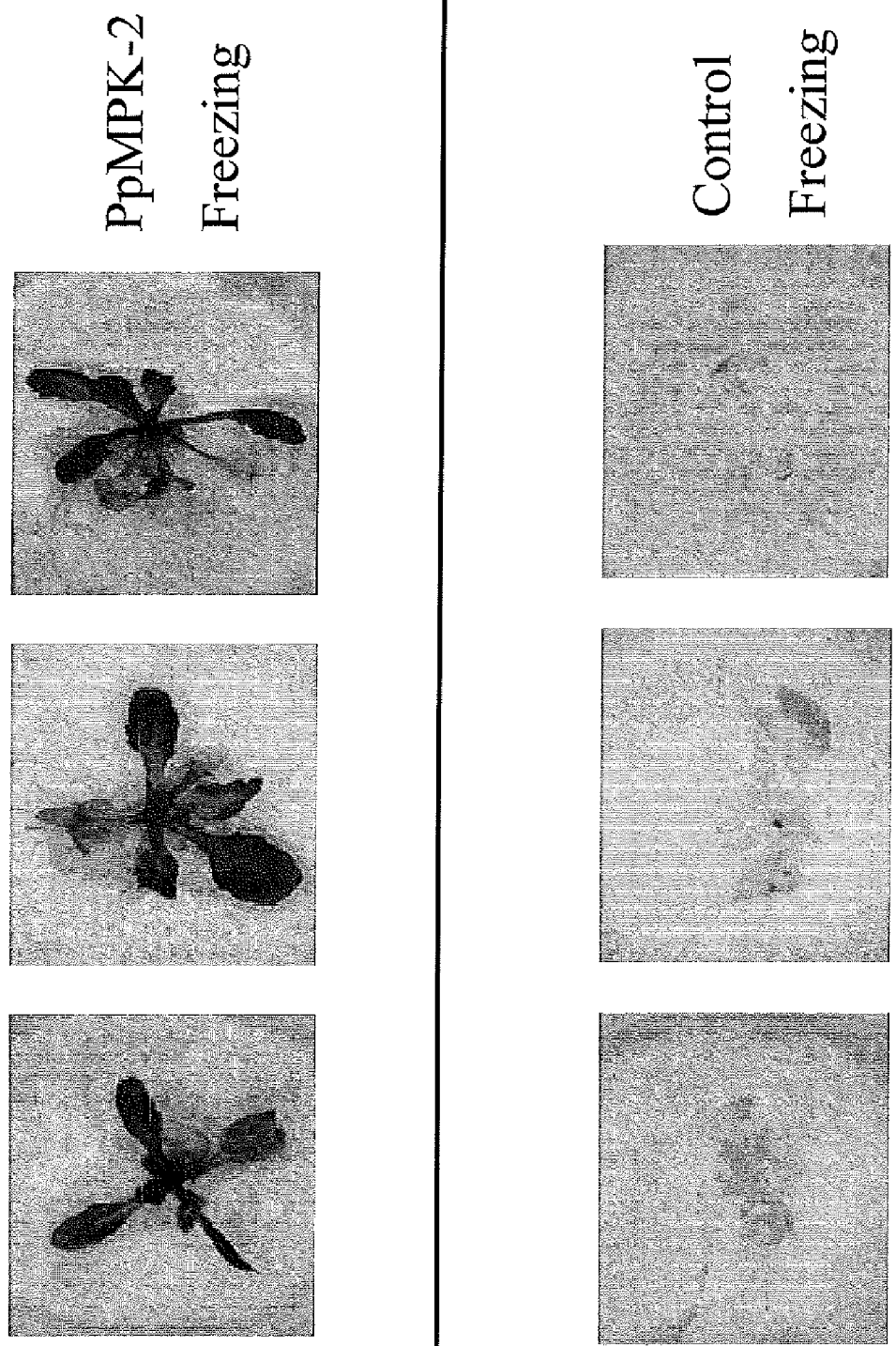
FIG. 12 shows the results of a freezing stress test with over-expressing PpMPK-2 transgenic plants and wild-type *Arabidopsis* lines. The transgenic lines display a tolerant phenotype. Individual transformant lines are shown.
Figure 15:
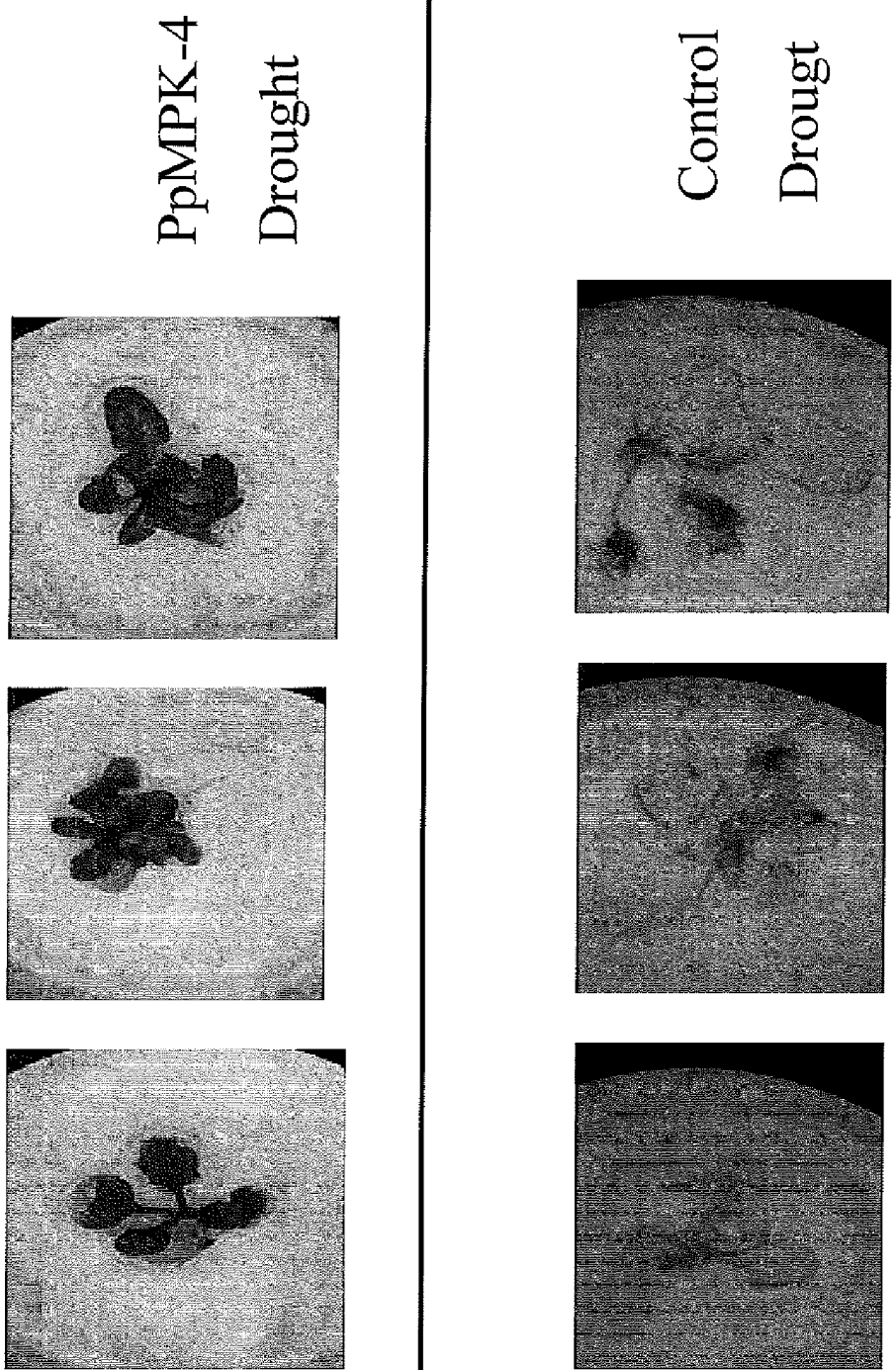
FIG. 15 shows the results of a drought stress test with over-expressing PpMPK-4 transgenic plants and wild-type *Arabidopsis* lines. The transgenic lines display a tolerant phenotype. Individual transformant lines are shown.
Figure 17:
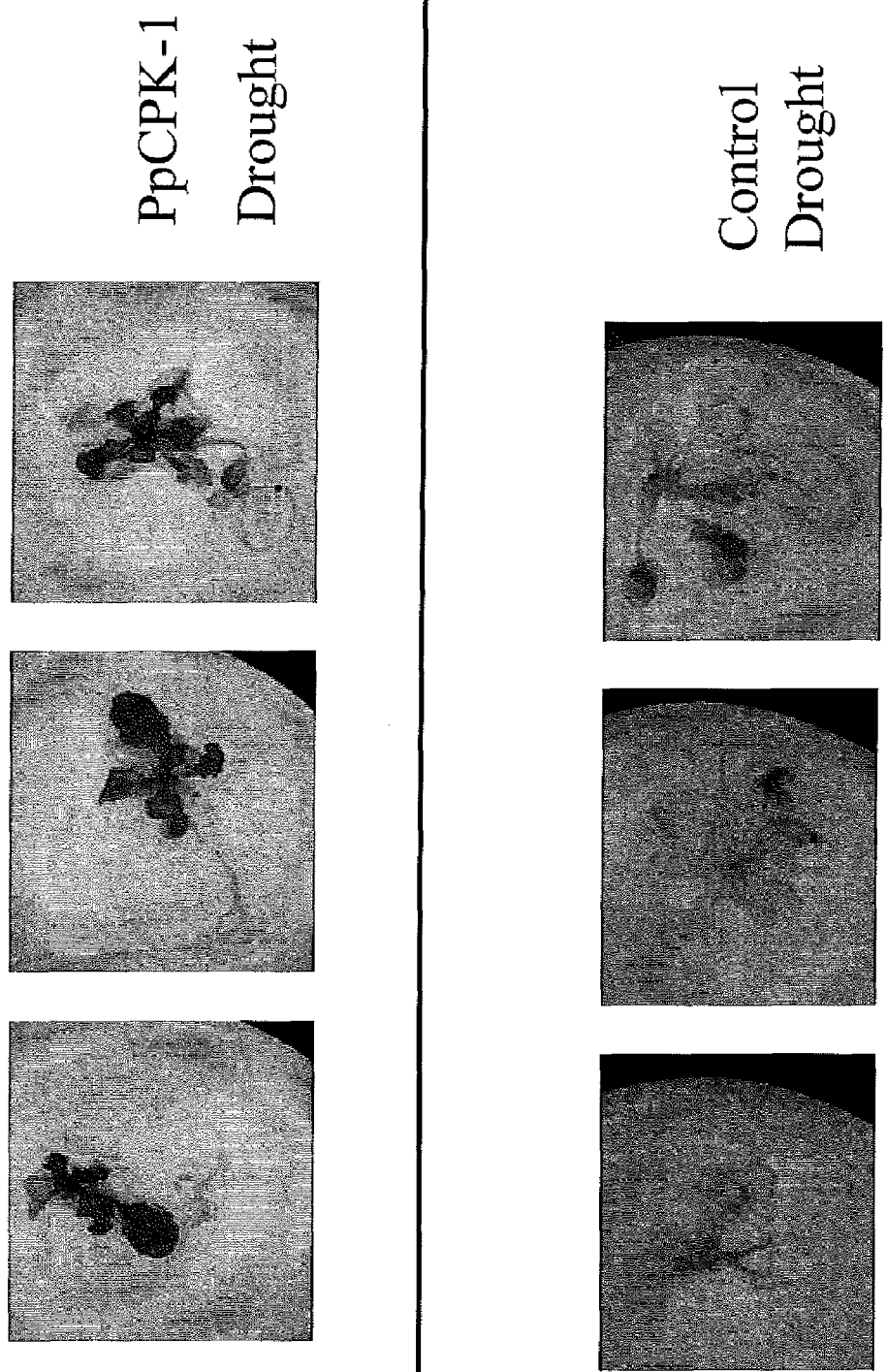
FIG. 17 shows the results of a drought stress test with over-expressing PpCPK-1 transgenic plants and wild-type *Arabidopsis* lines. The transgenic lines display a tolerant phenotype. Individual transformant lines are shown.

The present invention may be understood more readily by reference to the following detailed description of the preferred embodiments of the invention and the Examples included herein. However, before the present compounds, compositions, and methods are disclosed and described, it is to be understood that this invention is not limited to specific nucleic acids, specific polypeptides, specific cell types, specific host cells, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting. In particular, the designation of the amino acid sequences as protein "Protein Kinase Stress-Related Proteins" (PKSRPs), in no way limits the functionality of those sequences.

The present invention provides a transgenic plant cell transformed by a PKSRP coding nucleic acid, wherein expression of the nucleic acid sequence in the plant cell results in increased tolerance to environmental stress as compared to a wild type variety of the plant cell. The invention further provides transgenic plant parts and transgenic plants containing the plant cells described herein. Also provided is a plant seed produced by a transgenic plant transformed by a PKSRP coding nucleic acid, wherein the seed contains the PKSRP coding nucleic acid, and wherein the plant is true breeding for increased tolerance to environmental stress as compared to a wild type variety of the plant. The invention further provides a seed produced by a transgenic plant expressing a PKSRP, wherein the seed contains the PKSRP, and wherein the plant is true breeding for increased tolerance to environmental stress as compared to a wild type variety of the plant. The invention also provides an agricultural product produced by any of the below-described transgenic plants, plant parts and plant seeds.

As used herein, the term "variety" refers to a group of plants within a species that share constant characters that separate them from the typical form and from other possible varieties within that species. While possessing at least one distinctive trait, a variety is also characterized by some variation between individuals within the variety, based primarily on the Mendelian segregation of traits among the progeny of succeeding generations. A variety is considered "true breeding" for a particular trait if it is genetically homozygous for that trait to the extent that, when the true-breeding variety is self-pollinated, a significant amount of independent segregation of the trait among the progeny is not observed. In the present invention, the trait arises from the transgenic expression of one or more DNA sequences introduced into a plant variety.

The present invention describes for the first time that the *Physcomitrella patens* PKSRPs, PK-6, PK-7, PK-8, PK-9, CK-1, CK-2, CK-3, MPK-2, MPK-3, MPK-4, MPK-5, CPK-1 and CPK-2, are useful for increasing a plant's tolerance to environmental stress. Accordingly, the present invention provides isolated PKSRPs selected from the group consisting of PK-6, PK-7, PK-8, PK-9, CK-1, CK-2, CK-3, MPK-2, MPK-3, MPK-4, MPK-5, CPK-1 and CPK-2, and homologs thereof. In preferred embodiments, the PKSRP is selected from 1) Protein Kinase-6 (PK-6) protein as defined in SEQ ID NO:27; 2) Protein Kinase-7 (PK-7) protein as defined in SEQ ID NO:28; 3) Protein Kinase-8 (PK-8) protein as defined in SEQ ID NO:29; 4) Protein Kinase-9 (PK-9) protein as defined in SEQ ID NO:30; 5) Casein Kinase homologue (CK-1) protein as defined in SEQ ID NO:31; 6) Casein Kinase homologue-2 (CK-2) protein as defined in SEQ ID NO:32; 7) Casein Kinase homologue-3 (CK-3) protein as defined in SEQ ID NO:33; 8) MAP Kinase-2 (MPK-2) protein as defined in SEQ ID NO:34; 9) MAP Kinase-3 (MPK-3) protein as defined in SEQ ID NO:35; 10) MAP Kinase-4 (MPK-4) protein as defined in SEQ ID NO:36; 11) MAP Kinase-5 (MPK-5) protein as defined in SEQ ID NO:37, 12) Calcium dependent protein kinase-1 (CPK-1) protein as defined in SEQ ID NO:38; 13) Calcium dependent protein kinase-2 (CPK-2) protein as defined in SEQ ID NO:39; and homologs and orthologs thereof, Homologs and orthologs of the amino acid sequences are defined below.

The PKSRPs of the present invention are preferably produced by recombinant DNA techniques. For example, a nucleic acid molecule encoding the protein is cloned into an expression vector (as described below), the expression vector is introduced into a host cell (as described below) and the PKSRP is expressed in the host cell. The PKSRP can then be isolated from the cells by an appropriate purification scheme using standard protein purification techniques. Alternative to recombinant expression, a PKSRP polypeptide, or peptide can be synthesized chemically using standard peptide synthesis techniques. Moreover, native PKSRP can be isolated from cells (e.g., *Physcomitrella patens*), for example using an anti-PKSRP antibody, which can be produced by standard techniques utilizing a PKSRP or fragment thereof.

The invention further provides an isolated PKSRP coding nucleic acid. The present invention includes PKSRP coding nucleic acids that encode PKSRPs as described herein. In preferred embodiments, the PKSRP coding nucleic acid is selected from 1) Protein Kinase-6 (PK-6) nucleic acid as defined in SEQ ID NO:14; 2) Protein Kinase-7 (PK-7) nucleic acid as defined in SEQ ID NO:15; 3) Protein Kinase-8 (PK-8) nucleic acid as defined in SEQ ID NO:16; 4) Protein Kinase-9 (PK-9) nucleic acid as defined in SEQ ID NO:17; 5) Casein Kinase homolog (CK-1) nucleic acid as defined in SEQ ID NO:18; 6) Casein Kinase homolog-2 (CK-2) nucleic acid as defined in SEQ ID NO:19; 7) Casein Kinase homolog-3 (CK-3) nucleic acid as defined in SEQ ID NO:20; 8) MAP Kinase-2 (MPK-2) nucleic acid as defined in SEQ ID NO:21; 9) MAP Kinase-3 (MPK-3) nucleic acid as defined in SEQ ID NO:22; 10) MAP Kinase-4 (MPK-4) nucleic acid as defined in SEQ ID NO:23; 11) MAP Kinase-5 (MPK-5) nucleic acid as defined in SEQ ID NO:24; 12) Calcium dependent protein kinase-1 (CPK-1) nucleic acid as defined in SEQ ID NO:25; 13) Calcium dependent protein kinase-2 (CPK-2) nucleic acid as defined in SEQ ID NO:26 and homologs and orthologs thereof. Homologs and orthologs of the nucleotide sequences are defined below. In one preferred embodiment, the nucleic acid and protein are isolated from the plant genus *Physcomitrella*. In another preferred embodiment, the nucleic acid and protein are from a *Physcomitrella patens* (*P. patens*) plant.

As used herein, the term "environmental stress" refers to any sub-optimal growing condition and includes, but is not limited to, sub-optimal conditions associated with salinity, drought, temperature, metal, chemical, pathogenic and oxidative stresses, or combinations thereof. In preferred embodiments, the environmental stress can be salinity, drought, or temperature, or combinations thereof, and in particular, can be high salinity, low water content or low temperature. It is also to be understood that as used in the specification and in the claims, "a" or "an" can mean one or more, depending upon the context in which it is used. Thus, for example, reference to "a cell" can mean that at least one cell can be utilized.

As also used herein, the terms "nucleic acid" and "nucleic acid molecule" are intended to include DNA molecules (e.g., cDNA or genomic DNA) and RNA molecules (e.g., mRNA) and analogs of the DNA or RNA generated using nucleotide analogs. This term also encompasses untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. The nucleic acid molecule can be single-stranded or double-stranded, but preferably is double-stranded DNA.

An "isolated" nucleic acid molecule is one that is substantially separated from other nucleic acid molecules which are present in the natural source of the nucleic acid. Preferably, an "isolated" nucleic acid is free of some of the sequences which naturally flank the nucleic acid (i.e., sequences located at the 5' and 3' ends of the nucleic acid) in the genomic DNA of the organism from which the nucleic acid is derived. For example, in various embodiments, the isolated PKSRP nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., a *Physcomitrella patens* cell). Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized.

A nucleic acid molecule of the present invention, e.g., a nucleic acid molecule having a nucleotide sequence of SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25 or SEQ ID NO:26, or a portion thereof, can be isolated using standard molecular biology techniques and the sequence information provided herein. For example, a *P. patens* PKSRP cDNA can be isolated from a *P. patens* library using all or portion of one of the sequences of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 and SEQ ID NO:13. Moreover, a nucleic acid molecule encompassing all or a portion of one of the sequences of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 and SEQ ID NO:13 can be isolated by the polymerase chain reaction using oligonucleotide primers designed based upon this sequence. For example, mRNA can be isolated from plant cells (e.g., by the guanidinium-thiocyanate extraction procedure of Chirgwin et al., 1979 Biochemistry 18:5294-5299) and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon one of the nucleotide sequences shown in SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12 and SEQ ID NO:13. A nucleic acid molecule of the invention can be amplified using cDNA or, alternatively, genomic DNA, as a template and appropriate oligonucleotide primers according to standard PCR amplification techniques, The nucleic acid molecule so amplified can be cloned into an appropriate vector and characterized by DNA sequence analysis. Furthermore, oligonucleotides corresponding to a PKSRP nucleotide sequence can be prepared by standard synthetic techniques, e.g., using an automated DNA synthesizer.

In a preferred embodiment, an isolated nucleic acid molecule of the invention comprises one of the nucleotide sequences shown in SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25 and SEQ ID NO:26. These cDNAs comprise sequences encoding the PKSRPs (i.e., the "coding region", indicated in Table 1), as well as 5' untranslated sequences and 3' untranslated sequences. It is to be understood that SEQ ID NO:14, SEQ ID NO:15, SEQ ID NO:16, SEQ ID NO:17, SEQ ID NO:8, SEQ ID NO:9, SEQ ID NO:20, SEQ ID NO:21, SEQ ID NO:22, SEQ ID NO:23, SEQ ID NO:24, SEQ ID NO:25 and SEQ ID NO:26 comprise both coding regions and 5' and 3' untranslated regions. Alternatively, the nucleic acid molecules of the present invention can comprise only the coding region of any of the sequences in SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25 or SEQ ID NO:26 or can contain whole genomic fragments isolated from genomic DNA. A coding region of these sequences is indicated as "ORF position". The present invention also includes PKSRP coding nucleic acids that encode PKSRPs as described herein. Preferred is a PKSRP coding nucleic acid that encodes a PKSRP selected from the group consisting of, PK-6 (SEQ ID NO:27), PK-7 (SEQ ID NO:28), PK-8 (SEQ ID NO:29), PK-9 (SEQ ID NO:30), CK-1 (SEQ ID NO:31), CK-2 (SEQ ID NO:32), CK-3 (SEQ ID NO:33), MPK-2 (SEQ ID NO:34), MPK-3

(SEQ ID NO:35), MPK-4 (SEQ YD NO:36), MPK-5 (SEQ ID NO:37), CPK-1 (SEQ ID NO:38) and CPK-2 (SEQ ID NO:39).

Moreover, the nucleic acid molecule of the invention can comprise only a portion of the coding region of one of the sequences in SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25 and SEQ ID NO:26, for example, a fragment which can be used as a probe or primer or a fragment encoding a biologically active portion of a PKSRP. The nucleotide sequences determined from the cloning of the PKSRP genes from P. patens allow for the generation of probes and primers designed for use in identifying and/or cloning PKSRP homologs in other cell types and organisms, as well as PKSRP homologs from other mosses and related species.

Portions of proteins encoded by the PKSRP nucleic acid molecules of the invention are preferably biologically active portions of one of the PKSRPs described herein. As used herein, the term "biologically active portion of" a PKSRP is intended to include a portion, e.g., a domain/motif, of a PKSRP that participates in a stress tolerance response in a plant, has an activity as set forth in Table 1, or participates in the transcription of a protein involved in a stress tolerance response in a plant. To determine whether a PKSRP, or a biologically active portion thereof, can participate in transcription of a protein involved in a stress tolerance response in a plant, or whether repression of a PKSRP results in increased stress tolerance in a plant, a stress analysis of a plant comprising the PKSRP may be performed. Such analysis methods are well known to those skilled in the art, as detailed in Example 7. More specifically, nucleic acid fragments encoding biologically active portions of a PKSRP can be prepared by isolating a portion of one of the sequences in SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38 and SEQ ID NO:39, expressing the encoded portion of the PKSRP or peptide (e.g., by recombinant expression in vitro) and assessing the activity of the encoded portion of the PKSRP or peptide.

Biologically active portions of a PKSRP are encompassed by the present invention and include peptides comprising amino acid sequences derived from the amino acid sequence of a PKSRP, e.g., an amino acid sequence of SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38 or SEQ ID NO:39, or the amino acid sequence of a protein homologous to a PKSRP, which include fewer amino acids than a full length PKSRP or the full length protein which is homologous to a PKSRP, and exhibit at least one activity of a PKSRP. Typically, biologically active portions (e.g., peptides which are, for example, 5, 10, 15, 20, 30, 35, 36, 37, 38, 39, 40, 50, 100 or more amino acids in length) comprise a domain or motif with at least one activity of a PKSRP. Moreover, other biologically active portions in which other regions of the protein are deleted, can be prepared by recombinant techniques and evaluated for one or more of the activities described herein. Preferably, the biologically active portions of a PKSRP include one or more selected domains/motifs or portions thereof having biological activity.

The invention also provides PKSRP chimeric or fusion proteins. As used herein, a PKSRP "chimeric protein" or "fusion protein" comprises a PKSRP polypeptide operatively linked to a non-PKSRP polypeptide. A PKSRP polypeptide refers to a polypeptide having an amino acid sequence corresponding to a PKSRP, whereas a non-PKSRP polypeptide refers to a polypeptide having an amino acid sequence corresponding to a protein which is not substantially homologous to the PKSRP, e.g., a protein that is different from the PKSRP and is derived from the same or a different organism. Within the fusion protein, the term "operatively linked" is intended to indicate that the PKSRP polypeptide and the non-PKSRP polypeptide are fused to each other so that both sequences fulfill the proposed function attributed to the sequence used. The non-PKSRP polypeptide can be fused to the N-terminus or C-terminus of the PKSRP polypeptide. For example, in one embodiment, the fusion protein is a GST-PKSRP fusion protein in which the PKSRP sequences are fused to the C-terminus of the GST sequences. Such fusion proteins can facilitate the purification of recombinant PKSRPs. In another embodiment, the fusion protein is a PKSRP containing a heterologous signal sequence at its N-terminus. In certain host cells (e.g., mammalian host cells), expression and/or secretion of a PKSRP can be increased through use of a heterologous signal sequence.

Preferably, a PKSRP chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, for example, Current Protocols in Molecular Biology, Eds. Ausubel et al. John Wiley & Sons: 1992). Moreover, many expression vectors are commercially available that already encode a fusion moiety (e.g., a GST polypeptide). A PKSRP encoding nucleic acid can be cloned into such an expression vector such that the fusion moiety is linked in-frame to the PKSRP.

In addition to fragments and fusion proteins of the PKSRPs described herein, the present invention includes homologs and analogs of naturally occurring PKSRPs and PKSRP encoding nucleic acids in a plant. "Homologs" are defined herein as two nucleic acids or proteins that have similar, or "homologous", nucleotide or amino acid sequences, respectively. Homologs include allelic variants, orthologs, paralogs, agonists and antagonists of PKSRPs as defined hereafter. The term "homolog" further encompasses nucleic acid molecules that differ from one of the nucleotide sequences shown in SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25 and SEQ ID NO:26 (and portions thereof) due to degeneracy of the genetic code and thus encode the same PKSRP as that encoded by the nucleotide sequences shown in SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25 or SEQ ID NO:26. As used herein a "naturally occurring" PKSRP refers to a PKSRP amino acid sequence that occurs in nature. Preferably, a naturally occurring PKSRP comprises an amino acid sequence selected from the group consisting of SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38 and SEQ ID NO:39.

An agonist of the PKSRP can retain substantially the same, or a subset, of the biological activities of the PKSRP. An antagonist of the PKSRP can inhibit one or more of the activities of the naturally occurring form of the PKSRP. For example, the PKSRP antagonist can competitively bind to a downstream or upstream member of the cell membrane component metabolic cascade that includes the PKSRP, or bind to a PKSRP that mediates transport of compounds across such membranes, thereby preventing translocation from taking place.

Nucleic acid molecules corresponding to natural allelic variants and analogs, orthologs and paralogs of a PKSRP cDNA can be isolated based on their identity to the *Physcomitrella patens* PKSRP nucleic acids described herein using PKSRP cDNAs, or a portion thereof, as a hybridization probe according to standard hybridization techniques under stringent hybridization conditions. In an alternative embodiment, homologs of the PKSRP can be identified by screening combinatorial libraries of mutants, e.g., truncation mutants, of the PKSRP for PKSRP agonist or antagonist activity. In one embodiment, a variegated library of PKSRP variants is generated by combinatorial mutagenesis at the nucleic acid level and is encoded by a variegated gene library. A variegated library of PKSRP variants can be produced by, for example, enzymatically ligating a mixture of synthetic oligonucleotides into gene sequences such that a degenerate set of potential PKSRP sequences is expressible as individual polypeptides, or alternatively, as a set of larger fusion proteins (e.g., for phage display) containing the set of PKSRP sequences therein. There are a variety of methods that can be used to produce libraries of potential PKSRP homologs from a degenerate oligonucleotide sequence. Chemical synthesis of a degenerate gene sequence can be performed in an automatic DNA synthesizer, and the synthetic gene is then ligated into an appropriate expression vector. Use of a degenerate set of genes allows for the provision, in one mixture, of all of the sequences encoding the desired set of potential PKSRP sequences. Methods for synthesizing degenerate oligonucleotides are known in the art (see, e.g., Narang, S. A., 1983 Tetrahedron 39:3; Itakura et al., 1984 Annu. Rev. Biochem. 53:323; Itakura et al., 1984 Science 198:1056; Ike et al., 1983 Nucleic Acid Res. 11:477).

In addition, libraries of fragments of the PKSRP coding regions can be used to generate a variegated population of PKSRP fragments for screening and subsequent selection of homologs of a PKSRP. In one embodiment, a library of coding sequence fragments can be generated by treating a double stranded PCR fragment of a PKSRP coding sequence with a nuclease under conditions wherein nicking occurs only about once per molecule, denaturing the double stranded DNA, renaturing the DNA to form double stranded DNA, which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the PKSRP.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of PKSRP homologs. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique that enhances the frequency of functional mutants in the libraries, can be used in combination with the screening assays to identify PKSRP homologs (Arkin and Yourvan, 1992 PNAS 89:7811-7815; Delgrave et al., 1993 Protein Engineering 6(3):327-331). In another embodiment, cell based assays can be exploited to analyze a variegated PKSRP library, using methods well known in the art. The present invention further provides a method of identifying a novel PKSRP, comprising (a) raising a specific antibody response to a PKSRP, or a fragment thereof, as described herein; (b) screening putative PKSRP material with the antibody, wherein specific binding of the antibody to the material indicates the presence of a potentially novel PKSRP; and (c) analyzing the bound material in comparison to known PKSRP, to determine its novelty.

To determine the percent homology of two amino acid sequences (e.g., one of the sequences of SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38 and SEQ ID NO:39 and a mutant form thereof), the sequences are aligned for optimal comparison purposes (e.g., gaps can be introduced in the sequence of one protein or nucleic acid for optimal alignment with the other protein or nucleic acid). The amino acid residues at corresponding amino acid positions or nucleotide positions are then compared. When a position in one sequence (e.g., one of the sequences of SEQ ID NO:27, SEQ ID NO:28, SEQ ID NO:29, SEQ ID NO:30, SEQ ID NO:31, SEQ ID NO:32, SEQ ED NO:33, SEQ ID NO:34, SEQ ID NO:35, SEQ ID NO:36, SEQ ID NO:37, SEQ ID NO:38 and SEQ ID NO:39) is occupied by the same amino acid residue as the corresponding position in the other sequence (e.g., a mutant form of the sequence selected from the polypeptide of SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38 and SEQ ID NO:39), then the molecules are homologous at that position (i.e., as used herein amino acid or nucleic acid "homology" is equivalent to amino acid or nucleic acid "identity"). The same type of comparison can be made between two nucleic acid sequences.

The percent homology between the two sequences is a function of the number of identical positions shared by the sequences (i.e., % homology=numbers of identical positions/total numbers of positions×100). Preferably, the amino acid sequences included in the present invention are at least about 50-60%, preferably at least about 60-70%, and more preferably at least about 70-80%, 80-90%, 90-95%, and most preferably at least about 96%, 97%, 98%, 99% or more homologous to an entire amino acid sequence shown in SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38 or SEQ ID NO:39. In yet another embodiment, at least about 50-60%, preferably at least about 60-70%, and more preferably at least about 70-80%, 80-90%, 90-95%, and most preferably at least about 96%, 97%, 98%, 99% or more homologous to an entire amino acid sequence encoded by a nucleic acid sequence shown in SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25 or SEQ ID NO:26. In other embodiments, the preferable length of sequence comparison for proteins is at least 15 amino acid residues, more preferably at least 25 amino acid residues, and most preferably at least 35-amino acid residues.

In another preferred embodiment, an isolated nucleic acid molecule of the invention comprises a nucleotide sequence which is at least about 50-60%, preferably at least about 60-70%, more preferably at least about 70-80%, 80-90%, or 90-95%, and even more preferably at least about 95%, 96%, 97%, 98%, 99% or more homologous to a nucleotide sequence shown in SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25 or SEQ ID NO:26, or a portion thereof. The preferable length of sequence comparison for nucleic acids is at least 75 nucleotides, more preferably at least 100 nucleotides and most preferably the entire length of the coding region.

It is also preferable that the homologous nucleic acid molecule of the invention encodes a protein or portion thereof which includes an amino acid sequence which is sufficiently homologous to an amino acid sequence of SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38 or SEQ ID NO:39 such that the protein or portion thereof maintains the same or a similar function as the amino acid sequence to which it is compared. Functions of the PKSRP amino acid sequences of the present invention include the ability to participate in a stress tolerance response in a plant, or more particularly, to participate in the transcription of a protein involved in a stress tolerance response in a *Physcomitrella patens* plant. Examples of such activities are described in Table 1.

In addition to the above described methods, a determination of the percent homology between two sequences can be accomplished using a mathematical algorithm. A preferred, non-limiting example of a mathematical algorithm utilized for the comparison of two sequences is the algorithm of Karlin and Altschul (1990 Proc. Natl. Acad. Sci. USA 90:5873-5877). Such an algorithm is incorporated into the NBLAST and XBLAST programs of Altschul, et al. (1990 J. Mol. Biol. 215:403-410).

BLAST nucleic acid searches can be performed with the NBLAST program, score=100, wordlength=12 to obtain nucleic acid sequences homologous to the PKSRP nucleic acid molecules of the invention. Additionally, BLAST protein searches can be performed with the XBLAST program, score=50, wordlength=3 to obtain amino acid sequences homologous to PKSRPs of the present invention. To obtain gapped alignments for comparison purposes, Gapped BLAST can be utilized as described in Altschul et al. (1997 Nucleic Acids Res. 25:3389-3402). When utilizing BLAST and Gapped BLAST programs, the default parameters of the respective programs (e.g., XBLAST and NBLAST) can be used. Another preferred non-limiting example of a mathematical algorithm utilized for the comparison of sequences is the algorithm of Myers and Miller (CABIOS 1989). Such an algorithm is incorporated into the ALIGN program (version 2.0) that is part of the GCG sequence alignment software package. When utilizing the ALIGN program for comparing amino acid sequences, a PAM120 weight residue table, a gap length penalty of 12 and a gap penalty of 4 can be used to obtain amino acid sequences homologous to the PKSRPs of the present invention.

To obtain gapped alignments for comparison purposes, Gapped BLAST can be utilized as described in Altschul et al. (1997 Nucleic Acids Res. 25:3389-3402). When utilizing BLAST and Gapped BLAST programs, the default parameters of the respective programs (e.g., XBLAST and NBLAST) can be used. Another preferred non-limiting example of a mathematical algorithm utilized for the comparison of sequences is the algorithm of Myers and Miller (CABIOS 1989). Such an algorithm is incorporated into the ALIGN program (version 2.0) that is part of the GCG sequence alignment software package. When utilizing the ALIGN program for comparing amino acid sequences, a PAM120 weight residue table, a gap length penalty of 12 and a gap penalty of 4 can be used.

Finally, homology between nucleic acid sequences can also be determined using hybridization techniques known to those of skill in the art. Accordingly, an isolated nucleic acid molecule of the invention comprises a nucleotide sequence which hybridizes, e.g., hybridizes under stringent conditions, to one of the nucleotide sequences shown in SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25 and SEQ ID NO:26, or a portion thereof. More particularly, an isolated nucleic acid molecule of the invention is at least 15 nucleotides in length and hybridizes under stringent conditions to the nucleic acid molecule comprising a nucleotide sequence of SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25 or SEQ ID NO:26. In other embodiments, the nucleic acid is at least 30, 50, 100, 250 or more nucleotides in length.

As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75% or more homologous to each other typically remain hybridized to each other. Such stringent conditions are known to those skilled in the art and can be found in *Current Protocols in Molecular Biology*, 6.3.1-6.3.6, John Wiley & Sons, N.Y. (1989). A preferred, non-limiting example of stringent hybridization conditions are hybridization in 6× sodium chloride/sodium citrate (SSC) at about 45° C., followed by one or more washes in 0.2×SSC, 0.1% SDS at 50-65° C. Preferably, an isolated nucleic acid molecule of the invention that hybridizes under stringent conditions to a sequence of SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25 or SEQ ID NO:26 corresponds to a naturally occurring nucleic acid molecule. As used herein, a "naturally occurring" nucleic acid molecule refers to an RNA or DNA molecule having a nucleotide sequence that occurs in nature (e.g., encodes a natural protein). In one embodiment, the nucleic acid encodes a naturally occurring *Physcomitrella patens* PKSRP.

Using the above-described methods, and others known to those of skill in the art, one of ordinary skill in the art can isolate homologs of the PKSRPs comprising amino acid sequences shown in SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38 or SEQ ID NO:39. One subset of these homologs are allelic variants. As used herein, the term "allelic variant" refers to a nucleotide sequence containing polymorphisms that lead to changes in the amino acid sequences of a PKSRP and that exist within a natural population (e.g., a plant species or variety), Such natural allelic variations can typically result in 1-5% variance in a PKSRP nucleic acid. Allelic variants can be identified by sequencing the nucleic acid sequence of interest in a number of different plants, which can be readily carried out by using hybridization probes to identify the same PKSRP genetic locus in those plants. Any and all such nucleic acid variations and resulting amino acid polymorphisms or variations in a PKSRP that are the result of natural allelic variation and that do not alter the functional activity of a PKSRP, are intended to be within the scope of the invention.

Moreover, nucleic acid molecules encoding PKSRPs from the same or other species such as PKSRP analogs, orthologs and paralogs, are intended to be within the scope of the present invention. As used herein, the term "analogs" refers to two nucleic acids that have the same or similar function, but that have evolved separately in unrelated organisms; As used herein, the term "orthologs" refers to two nucleic acids from different species, but that have evolved from a common ancestral gene by speciation. Normally, orthologs encode proteins having the same or similar functions. As also used herein, the term "paralogs" refers to two nucleic acids that are related by duplication within a genome. Paralogs usually have different functions, but these functions may be related (Tatusov, R. L. et al. 1997 Science 278(5338):631-637). Analogs, orthologs and paralogs of a naturally occurring PKSRP can differ from the naturally occurring PKSRP by post-translational modifications, by amino acid sequence differences, or by both. Post-translational modifications include in vivo and in vitro chemical derivatization of polypeptides, e.g., acetylation, carboxylation, phosphorylation, or glycosylation, and such modifications may occur during polypeptide synthesis or processing or following treatment with isolated modifying enzymes. In particular, orthologs of the invention will generally exhibit at least 80-85%, more preferably 90%, and most preferably 95%, 96%, 97%, 98% or even 99% identity or homology with all or part of a naturally occurring PKSRP amino acid sequence and will exhibit a function similar to a PKSRP. Orthologs of the present invention are also preferably capable of participating in the stress response in plants. In one embodiment, the PKSRP orthologs maintain the ability to participate in the metabolism of compounds necessary for the construction of cellular membranes in *Physcomitrella patens*, or in the transport of molecules across these membranes.

In addition to naturally-occurring variants of a PKSRP sequence that may exist in the population, the skilled artisan will further appreciate that changes can be introduced by mutation into a nucleotide sequence of SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25 or SEQ ID NO:26, thereby leading to changes in the amino acid sequence of the encoded PKSRP, without altering the functional ability of the PKSRP, For example, nucleotide substitutions leading to amino acid substitutions at "non-essential" amino acid residues can be made in a sequence of SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25 or SEQ ID NO:26. A "non-essential" amino acid residue is a residue that can be altered from the wild-type sequence of one of the PKSRPs without altering the activity of said PKSRP, whereas an "essential" amino acid residue is required for PKSRP activity. Other amino acid residues, however, (e.g., those that are not conserved or only semi-conserved in the domain having PKSRP activity) may not be essential for activity and thus are likely to be amenable to alteration without altering PKSRP activity.

Accordingly, another aspect of the invention pertains to nucleic acid molecules encoding PKSRPs that contain changes in amino acid residues that are not essential for PKSRP activity. Such PKSRPs differ in amino acid sequence from a sequence contained in SEQ ID NO:27, SEQ ID NO:28, SEQ ID NO:29, SEQ ID NO:30, SEQ JD NO:31, SEQ ID NO:32, SEQ ID NO:33, SEQ ID NO:34, SEQ ID NO:35, SEQ ID NO:36, SEQ ID NO:37, SEQ ID NO:38 or SEQ ID NO:39, yet retain at least one of the PKSRP activities described herein. In one embodiment, the isolated nucleic acid molecule comprises a nucleotide sequence encoding a protein, wherein the protein comprises an amino acid sequence at least about 50% homologous to an amino acid sequence of SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38 and SEQ ID NO:39. Preferably, the protein encoded by the nucleic acid molecule is at least about 50-60% homologous to one of the sequences of SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38 and SEQ ID NO:39, more preferably at least about 60-70% homologous to one of the sequences of SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36; SEQ ID NO:37, SEQ ID NO:38 and SEQ ID NO:39, even more preferably at least about 70-80%, 80-90%, 90-95% homologous to one of the sequences of SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38 and SEQ ID NO:39, and most preferably at least about 96%, 97%, 98%, or 99% homologous to one of the sequences of SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38 and SEQ ID NO:39. The preferred PKSRP homologs of the present invention are preferably capable of participating in the a stress tolerance response in a plant, or more particularly, participating in the transcription of a protein involved in a stress tolerance response in a *Physcomitrella patens* plant, or have one or more activities set forth in Table 1.

An isolated nucleic acid molecule encoding a PKSRP homologous to a protein sequence of SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38 or SEQ ID NO:39 can be created by introducing one or more nucleotide substitutions, additions or deletions into a nucleotide sequence of SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25 or SEQ ID NO:26 such that one or more amino acid substitutions, additions or deletions are introduced into the encoded protein. Mutations can be introduced into one of the sequences of SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25 and SEQ ID NO:26 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain.

Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a PKSRP is preferably replaced with another amino acid residue from the same side chain family. Alternatively, in another embodiment, mutations can be introduced randomly along all or part of a PKSRP coding sequence, such as by saturation mutagenesis, and the resultant mutants can be screened for a PKSRP activity described herein to identify mutants that retain PKSRP activity. Following mutagenesis of one of the sequences of SEQ ID NO:14, SEQ ID NO:15, SEQ ID NO:16, SEQ ID NO; 17, SEQ ID NO:18, SEQ ID NO:19, SEQ ID NO:20, SEQ ID NO:21, SEQ ID NO:22, SEQ ID NO:23, SEQ ID NO:24, SEQ ID NO:25 and SEQ ID NO:26, the encoded protein can be expressed recombinantly and the activity of the protein can be determined by analyzing the stress tolerance of a plant expressing the protein as described in Example 7.

In addition to the nucleic acid molecules encoding the PKSRPs described above, another aspect of the invention pertains to isolated nucleic acid molecules that are antisense thereto. An "antisense" nucleic acid comprises a nucleotide sequence that is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire PKSRP coding strand, or to only a portion thereof. In one embodiment, an antisense nucleic acid molecule is antisense to a "coding region" of the coding strand of a nucleotide sequence encoding a PKSRP. The term "coding region" refers to the region of the nucleotide sequence comprising codons that are translated into amino acid residues (e.g., the entire coding region of, comprises nucleotides 1 to . . . ). In another embodiment, the antisense nucleic acid molecule is antisense to a "noncoding region" of the coding strand of a nucleotide sequence encoding a PKSRP. The term "noncoding region" refers to 5' and 3' sequences that flank the coding region that are not translated into amino acids (i.e., also referred to as 5' and 3' untranslated regions).

In a preferred embodiment, an isolated nucleic acid molecule of the invention comprises a nucleic acid molecule which is a complement of one of the nucleotide sequences shown in SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25 and SEQ ID NO:26, or a portion thereof. A nucleic acid molecule that is complementary to one of the nucleotide sequences shown in SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25 and SEQ ID NO:26 is one which is sufficiently complementary to one of the nucleotide sequences shown in SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25 and SEQ ID NO:26 such that it can hybridize to one of the nucleotide sequences shown in SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25 and SEQ ID NO:26, thereby forming a stable duplex.

Given the coding strand sequences encoding the PKSRPs disclosed herein (e.g., the sequences set forth in SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25 and SEQ ID NO:26), antisense nucleic acids of the invention can be designed according to the rules of Watson and Crick base pairing. The antisense nucleic acid molecule can be complementary to the entire coding region of PKSRP mRNA, but more preferably is an oligonucleotide which is antisense to only a portion of the coding or noncoding region of PKSRP mRNA. For example, the antisense oligonucleotide can be complementary to the region surrounding the translation start site of PKSRP mRNA. An antisense oligonucleotide can be, for example, about 5, 10, 15, 20, 25, 30, 35, 40, 45 or 50 nucleotides in length.

An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methyl inosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a cell or generated in situ such that they hybridize with or bind to cellular mRNA and/or genomic DNA encoding a PKSRP to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. The antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic (including plant) promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al., 1987 Nucleic Acids. Res. 15:6625-6641). The antisense nucleic acid molecule can also comprise a 2'-o-methylribonucleotide (Inoue et al., 1987 Nucleic Acids Res. 15:6131-6148) or a chimeric RNA-DNA analogue (Inoue et al., 1987 FEBS Lett. 215:327-330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes described in Haselhoff and Gerlach, 1988 Nature 334:585-591) can be used to catalytically cleave PKSRP mRNA transcripts to thereby inhibit translation of PKSRP mRNA. A ribozyme having specificity for a PKSRP-encoding nucleic acid can be designed based upon the nucleotide sequence of a PKSRP cDNA, as disclosed herein (i.e., SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25 or SEQ ID NO:26) or on the basis of a heterologous sequence to be isolated according to methods taught in this invention. For example, a derivative of a *Tetrahymena* L-19 IVS RNA can be constructed in which the nucleotide sequence of the active site is complementary to the nucleotide sequence to be cleaved in a PKSRP-encoding mRNA. See, e.g., Cech et al. U.S. Pat. No. 4,987,071 and Cech et al. U.S. Pat. No. 5,116,742. Alternatively, PKSRP mRNA can be used to select a catalytic RNA having a specific ribonuclease activity from a pool of RNA molecules. See, e.g., Bartel, D. and Szostak, J. W., 1993 Science 261:1411-1418.

Alternatively, PKSRP gene expression can be inhibited by targeting nucleotide sequences complementary to the regulatory region of a PKSRP nucleotide sequence (e.g., a PKSRP promoter and/or enhancer) to form triple helical structures that prevent transcription of a PKSRP gene in target cells. See generally, Helene, C., 1991 Anticancer Drug Des. 6(6):569-84; Helene, C. et al., 1992 Ann. N.Y. Acad. Sci. 660:27-36; and Maher, L. J., 1992 Bioassays 14(12):807-15.

In addition to the PKSRP nucleic acids and proteins described above, the present invention encompasses these nucleic acids and proteins attached to a moiety. These moieties include, but are not limited to, detection moieties, hybridization moieties, purification moieties, delivery moieties, reaction moieties, binding moieties, and the like. A typical group of nucleic acids having moieties attached are probes and primers. The probes and primers typically comprise a substantially isolated oligonucleotide. The oligonucleotide typically comprises a region of nucleotide sequence that hybridizes under stringent conditions to at least about 12, preferably about 25, more preferably about 40, 50 or 75 consecutive nucleotides of a sense strand of one of the sequences set forth in SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25 and SEQ ID NO:26, an anti-sense sequence of one of the sequences set forth in SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25 and SEQ ID NO:26, or naturally occurring mutants thereof. Primers based on a nucleotide sequence of SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25 or SEQ ID NO:26 can be used in PCR reactions to clone PKSRP homologs. Probes based on the PKSRP nucleotide sequences can be used to detect transcripts or genomic sequences encoding the same or homologous proteins, In preferred embodiments, the probe further comprises a label group attached thereto, e.g. the label group can be a radioisotope, a fluorescent compound, an enzyme, or an enzyme co-factor. Such probes can be used as a part of a genomic marker test kit for identifying cells which express a PKSRP, such as by measuring a level of a PKSRP-encoding nucleic acid, in a sample of cells, e.g., detecting PKSRP mRNA levels or determining whether a genomic PKSRP gene has been mutated or deleted.

In particular, a useful method to ascertain the level of transcription of the gene (an indicator of the amount of mRNA available for translation to the gene product) is to perform a Northern blot (for reference see, for example, Ausubel et al., 1988 Current Protocols in Molecular Biology, Wiley: New York). This information at least partially demonstrates the degree of transcription of the transformed gene. Total cellular RNA can be prepared from cells, tissues or organs by several methods, all well-known in the art, such as that described in Bormann, E. R. et al., 1992 Mol. Microbiol. 6:317-326. To assess the presence or relative quantity of protein translated from this mRNA, standard techniques, such as a Western blot, may be employed. These techniques are well known to one of ordinary skill in the art. (See, for example, Ausubel et al., 1988 Current Protocols in Molecular Biology, Wiley: New York).

The invention further provides an isolated recombinant expression vector comprising a PKSRP nucleic acid as described above, wherein expression of the vector in a host cell results in increased tolerance to environmental stress as compared to a wild type variety of the host cell. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, Gene Expression Technology: Methods in Enzymology 185, Academic Press, San Diego, Calif. (1990) or see: Gruber and Crosby, in: Methods in Plant Molecular Biology and Biotechnology, eds. Glick and Thompson, Chapter 7, 89-108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., PKSRPs, mutant forms of PKSRPs, fusion proteins, etc.).

The recombinant expression vectors of the invention can be designed for expression of PKSRPs in prokaryotic or eukaryotic cells. For example, PKSRP genes can be expressed in bacterial cells such as *C. glutamicum*, insect cells (using baculovirus expression vectors), yeast and other fungal cells (see Romanos, M. A. et al., 1992 Foreign gene expression in yeast: a review, Yeast 8:423-488; van den Hondel, C. A. M. J. J. et al., 1991 Heterologous gene expression in filamentous fungi, in: More Gene Manipulations in Fungi, J. W. Bennet & L. L. Lasure, eds., p. 396-428: Academic Press: San Diego; and van den Hondel, C. A. M. J. J., & Punt, P. J., 1991 Gene transfer systems and vector development for filamentous fungi, in: Applied Molecular Genetics of Fungi, Peberdy, J. F. et al., eds., p. 1-28, Cambridge University Press: Cambridge), algae (Falciatore et al., 1999 Marine Biotechnology 1(3):239-251), ciliates of the types: Holotrichia, Peritrichia, Spirotrichia, Suctoria, Tetrahymena, Paramecium, Colpidium, Glaucoma, Platyophrya, Potomacus, Pseudocohnilembus, Euplotes, Engelmanieila, and *Stylonychia*, especially of the genus *Stylonychia lemnae* with vectors following a transformation method as described in WO 98/01572 and multicellular plant cells (see Schmidt, R. and Willmitzer, L., 1988 High efficiency *Agrobacterium* tionefaciens-mediatsd transformation of *Arabidopsis thaliana* leaf and cotyledon explants, Plant Cell Rep. 583-586); Plant Molecular Biology and Biotechnology, C Press, Boca Raton, Fla., chapter 6/7, S.71-119 (1993); F. F. White, B. Jenes et al., Techniques for Gene Transfer, in: Transgenic Plants, Vol. 1, Engineering and Utilization, eds. Kung und R. Wu, 128-43, Academic Press: 1993; Potrykus, 1991 Annu. Rev. Plant Physiol. Plant Molec. Biol. 42:205-225 and references cited therein) or mammalian cells. Suitable host cells are discussed further in Goeddel, *Gene Expression Technology: Methods in Enzymology* 185, Academic Press: San Diego, Calif. (1990). Alternatively, the recombinant expression vector can be transcribed and translated in vitro, for example using T7 promoter regulatory sequences and T7 polymerase.

Expression of proteins in prokaryotes is most often carried out with vectors containing constitutive or inducible promoters directing the expression of either fusion or non-fusion proteins. Fusion vectors add a number of amino acids to a protein encoded therein, usually to the amino terminus of the recombinant protein but also to the C-terminus or fused within suitable regions in the proteins. Such fusion vectors typically serve three purposes: 1) to increase expression of a recombinant protein; 2) to increase the solubility of a recombinant protein; and 3) to aid in the purification of a recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase.

Typical fusion expression vectors include pGEX (Pharmacia Biotech Inc; Smith, D. B. and Johnson, K. S., 1988 Gene 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. In one embodiment, the coding sequence of the PKSRP is cloned into a pGEX expression vector to create a vector encoding a fusion protein comprising, from the N-terminus to the C-terminus, GST-thrombin cleavage site-X protein. The fusion protein can be purified by affinity chromatography using glutathione-agarose resin. Recombinant PKSRP unfused to GST can be recovered by cleavage of the fusion protein with thrombin.

Examples of suitable inducible non-fusion *E. coli* expression vectors include pTrc (Amann et al., 1988 Gene 69:301-315) and pET 11d (Studier et al., *Gene Expression Technology: Methods in Enzymology* 185, Academic Press, San Diego, Calif. (1990)60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a co-expressed viral RNA polymerase (T7 gn1). This viral polymerase is supplied by host strains BL21(DE3) or HMS174(DE3) from a resident λ prophage harboring a T7 gn1 gene under the transcriptional control of the lacUV 5 promoter.

One strategy to maximize recombinant protein expression is to express the protein in a host bacteria with an impaired capacity to proteolytically cleave the recombinant protein (Gottesman, S., *Gene Expression Technology: Methods in Enzymology* 185, Academic Press, San Diego, Calif. (1990)

119-128). Another strategy is to alter the sequence of the nucleic acid to be inserted into an expression vector so that the individual codons for each amino acid are those preferentially utilized in the bacterium chosen for expression, such as *C. glatamicum* (Wada et al., 1992 Nucleic Acids Res. 20:2111-2118). Such alteration of nucleic acid sequences of the invention can be carried out by standard DNA synthesis techniques.

In another embodiment, the PKSRP expression vector is a yeast expression vector. Examples of vectors for expression in yeast *S. cerevisiae* include pYepSec1 (Baldari, et al., 1987 Embo J. 6:229-234), pMFa (Kurjan and Herskowitz, 1982 Cell 30:933-943), pJRY88 (Schultz et al., 1987 Gene 54:113-123), and pYES2 (Invitrogen Corporation, San Diego, Calif.). Vectors and methods for the construction of vectors appropriate for use in other fungi, such as the filamentous fungi, include those detailed in: van den Hondel, C. A. M. J. J. & Punt, P. J. (1991) "Gene transfer systems and vector development for filamentous fungi, in: Applied Molecular Genetics of Fungi, J. F. Peberdy, et al., eds, p. 1-28, Cambridge University Press: Cambridge.

Alternatively, the PKSRPs of the invention can be expressed in insect cells using baculovirus expression vectors. Baculovirus vectors available for expression of proteins in cultured insect cells (e.g., Sf 9 cells) include the pAc series (Smith et al., 1983 Mol. Cell. Biol. 3:2156-2165) and the pVL series (Lucklow and Summers, 1989 Virology 170:31-39).

In yet another embodiment, a PKSRP nucleic acid of the invention is expressed in mammalian cells using a mammalian expression vector. Examples of mammalian expression vectors include pCDM8 (Seed, B., 1987 Nature 329:840) and pMT2PC (Kaufman et al., 1987 EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual*. 2$^{nd}$, ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987 Genes Dev. 1:268-277), lymphoid-specific promoters (Calame and Eaton, 1988 Adv. Immunol. 43:235-275), in particular promoters of T cell receptors (Winoto and Baltimore, 1989 EMBO J. 8:729-733) and immunoglobulins (Banerji et al., 1983 Cell 33:729-740; Queen and Baltimore, 1983 Cell 33:741-748), neuron-specific promoters (e.g., the neurofilament promoter; Byrne and Ruddle, 1989 PNAS 86:5473-5477), pancreas-specific promoters (Edlund et al., 1985 Science 230:912-916), and mammary gland-specific promoters (e.g., milk whey promoter; U.S. Pat. No. 4,873,316 and European Application Publication No. 264,166). Developmentally-regulated promoters are also encompassed, for example, the murine hox promoters (Kessel and Gruss, 1990 Science 249:374-379) and the fetoprotein promoter (Campes and Tilghman, 1989 Genes Dev. 3:537-546).

In another embodiment, the PKSRPs of the invention may be expressed in unicellular plant cells (such as algae) (see Falciatore et al., 1999 Marine Biotechnology 1(3):239-251 and references therein) and plant cells from higher plants (e.g., the spermatophytes, such as crop plants). Examples of plant expression vectors include those detailed in: Becker, D., Kemper, E., Schell, J. and Masterson, R., 1992 New plant binary vectors with selectable markers located proximal to the left border, Plant Mol. Biol. 20: 1195-1197; and Bevan, M. W., 1984 Binary *Agrobacterium* vectors for plant transformation, Nucl. Acid. Res. 12:8711-8721; Vectors for Gene Transfer in Higher Plants; in: Transgenic Plants, Vol. 1, Engineering and Utilization, eds.: Kung and R. Wu, Academic Press, 1993, S. 15-38.

A plant expression cassette preferably contains regulatory sequences capable of driving gene expression in plant cells and operably linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., 1984 EMBO J. 3:835) or functional equivalents thereof but also all other terminators functionally active in plants are suitable.

As plant gene expression is very often not limited on transcriptional levels, a plant expression cassette preferably contains other operably linked sequences like translational enhancers such as the overdrive-sequence containing the 5'-untranslated leader sequence from tobacco mosaic virus enhancing the protein per RNA ratio (Gallie et al., 1987 Nucl. Acids Research 15:8693-8711).

Plant gene expression has to be operably linked to an appropriate promoter conferring gene expression in a timely, cell or tissue specific manner. Preferred are promoters driving constitutive expression (Benfey et al., 1989 EMBO J. 8:2195-2202) like those derived from plant viruses like the 35S CAMV (Franck et al., 1980 Cell 21:285-294), the 19S CaMV (see also U.S. Pat. No. 5,352,605 and PCT Application No. WO 8402913) or plant promoters like those from Rubisco small subunit described in U.S. Pat. No. 4,962,028.

Other preferred sequences for use in plant gene expression cassettes are targeting-sequences necessary to direct the gene product in its appropriate cell compartment (for review see Kermode, 1996 Crit. Rev. Plant Sci. 15(4):285-423 and references cited therein) such as the vacuole, the nucleus, all types of plastids like amyloplasts, chloroplasts, chromoplasts, the extracellular space, mitochondria, the endoplasmic reticulum, oil bodies, peroxisomes and other compartments of plant cells.

Plant gene expression can also be facilitated via an inducible promoter (for review see Gatz, 1997 Annu. Rev. Plant Physiol. Plant Mol. Biol. 48:89-108). Chemically inducible promoters are especially suitable if gene expression is wanted to occur in a time specific manner. Examples of such promoters are a salicylic acid inducible promoter (PCT Application No. WO 95/19443), a tetracycline inducible promoter (Gatz et al., 1992 Plant J. 2:397-404) and an ethanol inducible promoter (PCT Application No. WO 93/21334).

Also, suitable promoters responding to biotic or abiotic stress conditions are those such as the pathogen inducible PRP1-gene promoter (Ward et al., 1993 Plant. Mol. Biol. 22:361-366), the heat inducible hsp80-promoter from tomato (U.S. Pat. No. 5,187,267), cold inducible alpha-amylase promoter from potato (PCT Application No. WO 96/12814) or the wound-inducible pinII-promoter (European Patent No. 375091). For other examples of drought, cold, and salt-inducible promoters, such as the RD29A promoter, see Yamaguchi-Shinozalei et al. (1993 Mol. Gen. Genet. 236:331-340).

Especially preferred are those promoters that confer gene expression in specific tissues and organs, such as guard cells and the root hair cells. Suitable promoters include the napin-gene promoter from rapeseed (U.S. Pat. No. 5,608,152), the USP-promoter from *Vicia faba* (Baeumlein et al., 1991 Mol Gen Genet. 225(3):459-67), the oleosin-promoter from *Arabidopsis* (PCT Application No. WO 98/45461), the phasedin-promoter from *Phaseolus vulgaris* (U.S. Pat. No. 5,504,200), the Bce-4-promoter from *Brassica* (PCT Application No. WO 91/13980) or the legumin B4 promoter (LeB4; Baeumlein et al., 1992 Plant Journal, 2(2):233-9) as well as promoters conferring seed specific expression in monocot plants like maize, barley, wheat, rye, rice, etc. Suitable promoters to note are the lpt2 or lpt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, maize zein gene, oat glutelin gene, *Sorghum* kasirin-gene and rye secalin gene).

Also especially suited are promoters that confer plastid-specific gene expression since plastids are the compartment where lipid biosynthesis occurs. Suitable promoters are the viral RNA-polymerase promoter described in PCT Application No. WO 95/16783 and PCT Application No. WO 97/06250 and the clpP-promoter from *Arabidopsis* described in PCT Application No. WO 99/46394.

The invention further provides a recombinant expression vector comprising a PKSRP DNA molecule of the invention cloned into the expression vector in an antisense orientation. That is, the DNA molecule is operatively linked to a regulatory sequence in a manner that allows for expression (by transcription of the DNA molecule) of an RNA molecule that is antisense to a PKSRP mRNA. Regulatory sequences operatively linked to a nucleic acid molecule cloned in the antisense orientation can be chosen which direct the continuous expression of the antisense RNA molecule in a variety of cell types. For instance, viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus wherein antisense nucleic acids are produced under the control of a high efficiency regulatory region. The activity of the regulatory region can be determined by the cell type into which the vector is introduced. For a discussion of the regulation of gene expression using antisense genes see Weintraub, H. et al., Antisense RNA as a molecular tool for genetic analysis, Reviews—Trends in Genetics, Vol. 1(1)1986 and Mol et al., 1990 FEBS Letters 268:427-430.

Another aspect of the invention pertains to host cells into which a recombinant expression vector of the invention has been introduced. The terms "host cell" and "recombinant host cell" are used interchangeably herein. It is understood that such terms refer not only to the particular subject cell but they also apply to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a PKSRP can be expressed in bacterial cells such as *C. glutamicum*, insect cells, fungal cells or mammalian cells (such as Chinese hamster ovary cells (CHO) or COS cells), algae, ciliates, plant cells, fungi or other microorganisms like *C. glutamicum*. Other suitable host cells are known to those skilled in the art.

Vector DNA can be introduced into prokaryotic or eukaryotic cells via conventional transformation or transfection techniques. As used herein, the terms "transformation", "transfection", "conjugation" and "transduction" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, natural competence, chemical-mediated transfer and electroporation. Suitable methods for transforming or transfecting host cells including plant cells can be found in Sambrook, et al. (Molecular Cloning: A Laboratory Manual. $2^{nd}$, ed. Cold Spring Harbor Laboratory, Cold Spring Harbor Laboratory Press, Cold Spring Harbor, N.Y., 1989) and other laboratory manuals such as Methods in Molecular Biology, 1995, Vol. 44, *Agrobacterium* protocols, ed: Gartland and Davey, Humana Press, Totowa, N.J. As biotic and abiotic stress tolerance is a general trait wished to be inherited into a wide variety of plants like maize, wheat, rye, oat, triticale, rice, barley, soybean, peanut, cotton, rapeseed and canola, *manihot*, pepper, sunflower and tagetes, solanaceous plants like potato, tobacco, eggplant, and tomato, *Vicia* species, pea, alfalfa, bushy plants (coffee, cacao, tea), *Salix* species, trees (oil palm, coconut), perennial grasses and forage crops, these crop plants are also preferred target plants for a genetic engineering as one further embodiment of the present invention.

In particular, the invention provides a method of producing a transgenic plant with a PKSRP coding nucleic acid, wherein expression of the nucleic acid(s) in the plant results in increased tolerance to environmental stress as compared to a wild type variety of the plant comprising: (a) transforming a plant cell with an expression vector comprising a PKSRP nucleic acid, and (b) generating from the plant cell a transgenic plant with a increased tolerance to environmental stress as compared to a wild type variety of the plant. The invention also provides a method of increasing expression of a gene of interest within a host cell as compared to a wild type variety of the host cell, wherein the gene of interest is transcribed in response to a PKSRP, comprising: (a) transforming the host cell with an expression vector comprising a PKSRP coding nucleic acid, and (b) expressing the PKSRP within the host cell, thereby increasing the expression of the gene transcribed in response to the PKSRP, as compared to a wild type variety of the host cell.

For such plant transformation, binary vectors such as pBinAR can be used (Hofgen and Willmitzer, 1990 Plant Science 66:221-230). Construction of the binary vectors can be performed by ligation of the cDNA in sense or antisense orientation into the T-DNA. 5-prime to the cDNA a plant promoter activates transcription of the cDNA. A polyadenylation sequence is located 3-prime to the cDNA. Tissue-specific expression can be achieved by using a tissue specific promoter. For example, seed-specific expression can be achieved by cloning the napin or LeB4 or USP promoter 5-prime to the cDNA. Also, any other seed specific promoter element can be used. For constitutive expression within the whole plant, the CaMV 35S promoter can be used. The expressed protein can be targeted to a cellular compartment using a signal peptide, for example for plastids, mitochondria or endoplasmic reticulum (Kermode, 1996 Crit. Rev. Plant Sci. 4(15):285-423). The signal peptide is cloned 5-prime in frame to the cDNA to archive subcellular localization of the fusion protein. Additionally, promoters that are responsive to abiotic stresses can be used with, such as the *Arabidopsis* promoter RD29A, the nucleic acid sequences disclosed herein. One skilled in the art will recognize that the promoter used should be operatively linked to the nucleic acid such that the promoter causes transcription of the nucleic acid which results in the synthesis of an mRNA which encodes a polypeptide. Alternatively, the RNA can be an antisense RNA for use in affecting subsequent expression of the same or another gene or genes.

Alternate methods of transfection include the direct transfer of DNA into developing flowers via electroporation or *Agrobacterium* mediated gene transfer. *Agrobacterium* mediated plant transformation can be performed using for example the GV3101(pMP90) (Koncz and Schell, 1986 Mol. Gen. Genet. 204:383-396) or LBA4404 (Clontech) *Agrobacterium tumefaciens* strain. Transformation can be performed by standard transformation and regeneration techniques (Deblaere et al., 1994 Nucl, Acids. Res. 13:4777-4788; Gelvin, Stanton B. and Schilperoort, Robert A, Plant Molecular Biology Manual, $2^{nd}$ Ed.-Dordrecht: Kluwer Academic Publ, 1995.—in Sect, Ringbuc Zentrale Signatur: BT11-P ISBN 0-7923-2731-4; Glick, Bernard R.; Thompson, John E, Methods in Plant Molecular Biology and Biotechnology, Boca Raton: CRC Press, 1993.-360 S, ISBN 0-8493-5164-2). For example, rapeseed can be transformed via cotyledon or hypocotyl transformation (Moloney et al., 1989 Plant cell Report 8:238-242; De Block et al., 1989 Plant Physiol. 91:694-701). Use of antibiotica for *Agrobacterium* and plant selection depends on the binary vector and the *Agrobacterium* strain used for transformation. Rapeseed selection is normally performed using kanamycin as selectable plant marker. *Agrobacterium* mediated gene transfer to flax can be performed using, for example, a technique described by Mlynarova et al., 1994 Plant Cell Report 13:282-285. Additionally, transformation of soybean can be performed using for example a technique described in European Patent No. 0424 047, U.S. Pat. No. 5,322,783, European Patent No. 0397 687, U.S. Pat. No. 5,376,543 or U.S. Pat. No. 5,169,770. Transformation of maize can be achieved by particle bombardment, polyethylene glycol mediated DNA uptake or via the silicon carbide fiber technique. (See, for example, Freeling and Walbot "The maize handbook" Springer Verlag: New York (1993) ISBN 3-540-97826-7). A specific example of maize transformation is found in U.S. Pat. No. 5,990,387 and a specific example of wheat transformation can be found in PCT Application No. WO 93/07256.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate or in plants that confer resistance towards a herbicide such as glyphosate or glufosinate. Nucleic acid molecules encoding a selectable marker can be introduced into a host cell on the same vector as that encoding a PKSRP or can be introduced on a separate vector. Cells stably transfected with the introduced nucleic acid molecule can be identified by, for example, drug selection (e.g., cells that have incorporated the selectable marker gene will survive, while the other cells die).

To create a homologous recombinant microorganism, a vector is prepared which contains at least a portion of a PKSRP gene into which a deletion, addition or substitution has been introduced to thereby alter, e.g., functionally disrupt, the PKSRP gene. Preferably, the PKSRP gene is a *Physcomitrella patens* PKSRP gene, but it can be a homolog from a related plant or even from a mammalian, yeast, or insect source. In a preferred embodiment, the vector is designed such that, upon homologous recombination, the endogenous PKSRP gene is functionally disrupted (i.e., no longer encodes a functional protein; also referred to as a knock-out vector).

Alternatively, the vector can be designed such that, upon homologous recombination, the endogenous PKSRP gene is mutated or otherwise altered but still encodes a functional protein (e.g., the upstream regulatory region can be altered to thereby alter the expression of the endogenous PKSRP). To create a point mutation via homologous recombination, DNA-RNA hybrids can be used in a technique known as chimeraplasty (Cole-Strauss et al., 1999 Nucleic Acids Research 27(5): 1323-1330 and Kmiec, 1999 Gene therapy American Scientist. 87(3):240-247). Homologous recombination procedures in *Physcomitrella patens* are also well known in the art and are contemplated for use herein.

Whereas in the homologous recombination vector, the altered portion of the PKSRP gene is flanked at its 5' and 3' ends by an additional nucleic acid molecule of the PKSRP gene to allow for homologous recombination to occur between the exogenous PKSRP gene carried by the vector and an endogenous PKSRP gene, in a microorganism or plant. The additional flanking PKSRP nucleic acid molecule is of sufficient length for successful homologous recombination with the endogenous gene. Typically, several hundreds of base pairs up to kilobases of flanking DNA (both at the 5' and 3' ends) are included in the vector (see e.g., Thomas, K. R., and Capecchi, M. R., 1987 Cell 51:503 for a description of homologous recombination vectors or Strepp et al., 1998 PNAS, 95 (8):4368-4373 for cDNA based recombination in *Physcomitrella patens*). The vector is introduced into a microorganism or plant cell (e.g., via polyethylene glycol mediated DNA), and cells in which the introduced PKSRP gene has homologously recombined with the endogenous PKSRP gene are selected using art-known techniques.

In another embodiment, recombinant microorganisms can be produced that contain selected systems which allow for regulated expression of the introduced gene. For example, inclusion of a PKSRP gene on a vector placing it under control of the lac operon permits expression of the PKSRP gene only in the presence of IPTG. Such regulatory systems are well known in the art.

A host cell of the invention, such as a prokaryotic or eukaryotic host cell in culture, can be used to produce (i.e., express) a PKSRP. Accordingly, the invention further provides methods for producing PKSRPs using the host cells of the invention. In one embodiment, the method comprises culturing the host cell of invention (into which a recombinant expression vector encoding a PKSRP has been introduced, or into which genome has been introduced a gene encoding a wild-type or altered PKSRP) in a suitable medium until PKSRP is produced. In another embodiment, the method further comprises isolating PKSRPs from the medium or the host cell.

Another aspect of the invention pertains to isolated PKSRPs, and biologically active portions thereof. An "isolated" or "purified" protein or biologically active portion thereof is free of some of the cellular material when produced by recombinant DNA techniques, or chemical precursors or other chemicals when chemically synthesized. The language "substantially free of cellular material" includes preparations of PKSRP in which the protein is separated from some of the cellular components of the cells in which it is naturally or recombinantly produced. In one embodiment, the language "substantially free of cellular material" includes preparations of a PKSRP having less than about 30% (by dry weight) of non-PKSRP material (also referred to herein as a "contaminating protein"), more preferably less than about 20% of non-PKSRP material, still more preferably less than about 10% of non-PKSRP material, and most preferably less than about 5% non-PKSRP material.

When the PKSRP or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of PKSRP in which the protein is separated from chemical precursors or other chemicals that are involved in the synthesis of the protein. In one embodiment, the language "substantially free of chemical precursors or other chemicals" includes preparations of a PKSRP having less than about 30% (by dry weight) of chemical precursors or non-PKSRP chemicals, more preferably less than about 20% chemical precursors or non-PKSRP chemicals, still more preferably less than about 10% chemical precursors or non-PKSRP chemicals, and most preferably less than about 5% chemical precursors or non-PKSRP chemicals. In preferred embodiments, isolated proteins, or biologically active portions thereof, lack contaminating proteins from the same organism from which the PKSRP is derived. Typically, such proteins are produced by recombinant expression of, for example, a *Physcomitrella patens* PKSRP in plants other than *Physcomitrella patens* or microorganisms such as *C. glutamicum*, ciliates, algae or fungi.

The nucleic acid molecules, proteins, protein homologs, fusion proteins, primers, vectors, and host cells described herein can be used in one or more of the following methods: identification of *Physcomitrella patens* and related organisms; mapping of genomes of organisms related to *Physcomitrella patens*; identification and localization of *Physcomitrella patens* sequences of interest; evolutionary studies; determination of PKSRP regions required for function; modulation of a PKSRP activity; modulation of the metabolism of one or more cell functions; modulation of the transmembrane transport of one or more compounds; and modulation of stress resistance.

The moss *Physcomitrella patens* represents one member of the mosses. It is related to other mosses such as *Ceratodon purpureus* which is capable of growth in the absence of light. Mosses like *Ceratodon* and *Physcomitrella* share a high degree of homology on the DNA sequence and: polypeptide level allowing the use of heterologous screening of DNA molecules with probes evolving from other mosses or organisms, thus enabling the derivation of a consensus sequence suitable for heterologous screening or functional annotation and prediction of gene functions in third species. The ability to identify such functions can therefore have significant relevance, e.g., prediction of substrate specificity of enzymes. Further, these nucleic acid molecules may serve as reference points for the mapping of moss genomes, or of genomes of related organisms.

The PKSRP nucleic acid molecules of the invention have a variety of uses. Most importantly, the nucleic acid and amino acid sequences of the present invention can be used to transform plants, thereby inducing tolerance to stresses such as drought, high salinity and cold. The present invention therefore provides a transgenic plant transformed by a PKSRP nucleic acid (coding or antisense), wherein expression of the nucleic acid sequence in the plant results in increased tolerance to environmental stress as compared to a wild type variety of the plant. The transgenic plant can be a monocot or a dicot. The invention further provides that the transgenic plant can be selected from maize, wheat, rye, oat, tritkale, rice, barley, soybean, peanut, cotton, rapeseed, canola, *manihot*, pepper, sunflower, tagetes, solanaceous plants, potato, tobacco, eggplant, tomato, *Vicia* species, pea, alfalfa, coffee, cacao, tea, *Salix* species, oil palm, coconut, perennial grass and forage crops, for example.

In particular, the present invention describes using the expression of PK-6, PK-7, PK-8, PK-9, CK-1, CK-2, CK-3, MPK-2, MPK-3, MPK-4, MPK-5, CPK-1 and CPK-2 of *Physcomitrella patens* to engineer drought-tolerant, salt-tolerant and/or cold-tolerant plants. This strategy has herein been demonstrated for *Arabidopsis thaliana*, Rapeseed/Canola, soybeans, corn and wheat but its application is not restricted to these plants. Accordingly, the invention provides a transgenic plant containing a PKSRP selected from PK-6 (SEQ ID NO:27), PK-7 (SEQ ID NO:28), PK-8 (SEQ ID NO:29), PK-9 (SEQ ID NO:30), CK-1 (SEQ ID NO:31), CK-2 (SEQ ID NO:32), CK-3 (SEQ ID NO:33), MPK-2 (SEQ ID NO:34), MPK-3 (SEQ ID NO:35), MPK-4 (SEQ ID NO:36), MPK-5 (SEQ ID NO:37), CPK-1 (SEQ ID NO:38) and CPK-2 (SEQ ID NO:39), wherein the environmental stress is drought, increased salt or decreased or increased temperature. In preferred embodiments, the environmental stress is drought or decreased temperature.

The present invention also provides methods of modifying stress tolerance of a plant comprising, modifying the expression of a PKSRP in the plant. The invention provides that this method can be performed such that the stress tolerance is either increased or decreased. In particular, the present invention provides methods of producing a transgenic plant having an increased tolerance to environmental stress as compared to a wild type variety of the plant comprising increasing expression of a PKSRP in a plant.

The methods of increasing expression of PKSRPs can be used wherein the plant is either transgenic or not transgenic. In cases when the plant is transgenic, the plant can be transformed with a vector containing any of the above described PKSRP coding nucleic acids, or the plant can be transformed with a promoter that directs expression of native PKSRP in the plant, for example. The invention provides that such a promoter can be tissue specific. Furthermore, such a promoter can be developmentally regulated. Alternatively, non-transgenic plants can have native PKSRP expression modified by inducing a native promoter.

The expression of PK-6 (SEQ ID NO:14), PK-7 (SEQ ID NO:15), PK-8 (SEQ ID NO:16), PK-9 (SEQ ID NO:17), CK-1 (SEQ ID NO:18), CK-2 (SEQ ID NO:19), CK-3 (SEQ ID NO:20), MPK-2 (SEQ ID NO:21), MPK-3 (SEQ ID NO:22), MPK-4 (SEQ ID NO:23), MPK-5 (SEQ ID NO:24), CPK-1 (SEQ ID NO:25) and CPK-2 (SEQ ID NO:26) in target plants can be accomplished by, but is not limited to, one of the following examples: (a) constitutive promoter, (b) stress-inducible promoter, (c) chemical-induced promoter, and (d) engineered promoter over-expression with for example zinc-finger derived transcription factors (Greisman and Pabo, 1997 Science 275:657). The later case involves identification of the PK-6 (SEQ ID NO:27), PK-7 (SEQ ID NO:28), PK-8 (SEQ ID NO:29), PK-9 (SEQ ID NO:30), CK-1 (SEQ ID NO:31), CK-2 (SEQ ID NO:32), CK-3 (SEQ ID NO:33), MPK-2 (SEQ ID NO:34), MPK-3 (SEQ ID NO:35), MPK-4 (SEQ ID NO:36), MPK-5 (SEQ ID NO:37), CPK-1 (SEQ ID NO:38) or CPK-2 (SEQ ID NO:39) homologs in the target plant as well as from its promoter. Zinc-finger-containing recombinant transcription factors are engineered to specifically interact with the PK-6 (SEQ ID NO:27), PK-7 (SEQ ID NO:28), PK-8 (SEQ ID NO:29), PK-9 (SEQ ID NO:30), CK-1 (SEQ ID NO:31), CK-2 (SEQ ID NO:32), CK-3 (SEQ ID NO:33), MPK-2 (SEQ ID NO:34), MPK-3 (SEQ ID NO:35), MPK-4 (SEQ ID NO:36), MPK-5 (SEQ ID NO:37), CPK-1 (SEQ ID NO:38) or CPK-2 (SEQ ID NO:39) homolog and transcription of the corresponding gene is activated.

In addition to introducing the PKSRP nucleic acid sequences into transgenic plants, these sequences can also be used to identify an organism as being *Physcomitrella patens* or a close relative thereof. Also, they may be used to identify the presence of *Physcomitrella patens* or a relative thereof in a mixed population of microorganisms. The invention provides the nucleic acid sequences of a number of *Physcomitrella patens* genes; by probing the extracted genomic DNA of a culture of a unique or mixed population of microorganisms under stringent conditions with a probe spanning a region of a *Physcomitrella patens* gene which is unique to this organism, one can ascertain whether this organism is present.

Further, the nucleic acid and protein molecules of the invention may serve as markers for specific regions of the genome. This has utility not only in the mapping of the genome, but also in functional studies of *Physcomitrella patens* proteins. For example, to identify the region of the genome to which a particular *Physcomitrella patens* DNA-binding protein binds, the *Physcomitrella patens* genome could be digested, and the fragments incubated with the DNA-binding protein. Those fragments that bind the protein may be additionally probed with the nucleic acid molecules of the invention, preferably with readily detectable labels. Binding of such a nucleic acid molecule to the genome fragment enables the localization of the fragment to the genome map of *Physcomitrella patens*, and, when performed multiple times with different enzymes, facilitates a rapid determination of the nucleic acid sequence to which the protein binds. Further, the nucleic acid molecules of the invention may be sufficiently homologous to the sequences of related species such that these nucleic acid molecules may serve as markers for the construction of a genomic map in related mosses.

The PKSRP nucleic acid molecules of the invention are also useful for evolutionary and protein structural studies. The metabolic and transport processes in which the molecules of the invention participate are utilized by a wide variety of prokaryotic and eukaryotic cells; by comparing the sequences of the nucleic acid molecules of the present invention to those encoding similar enzymes from other organisms, the evolutionary relatedness of the organisms can be assessed. Similarly, such a comparison permits an assessment of which regions of the sequence are conserved and which are not, which may aid in determining those regions of the protein that are essential for the functioning of the enzyme. This type of determination is of value for protein engineering studies and may give an indication of what the protein can tolerate in terms of mutagenesis without losing function.

Manipulation of the PKSRP nucleic acid molecules of the invention may result in the production of PKSRPs having functional differences from the wild-type PKSRPs. These proteins may be improved in efficiency or activity, may be present in greater numbers in the cell than is usual, or may be decreased in efficiency or activity.

There are a number of mechanisms by which the alteration of a PKSRP of the invention may directly affect stress response and/or stress tolerance. In the case of plants expressing PKSRPs, increased transport can lead to improved salt and/or solute partitioning within the plant tissue and organs. By either increasing the number or the activity of transporter molecules which exportionic molecules from the cell, it may be possible to affect the salt tolerance of the cell.

The effect of the genetic modification in plants, *C. glutamicum*, fungi, algae, or ciliates on stress tolerance can be assessed by growing the modified microorganism or plant under less than suitable conditions and then analyzing the growth characteristics and/or metabolism of the plant. Such analysis techniques are well known to one skilled in the art, and include dry weight, wet weight, protein synthesis, carbohydrate synthesis, lipid synthesis, evapotranspiration rates, general plant and/or crop yield, flowering, reproduction, seed setting, root growth, respiration rates, photosynthesis rates, etc. (Applications of HPLC in Biochemistry in: Laboratory Techniques in Biochemistry and Molecular Biology, vol. 17; Rehm et al., 1993 Biotechnology, vol. 3, Chapter ITT: Product recovery and purification, page 469-714, VCH: Weinheim; Belter, P. A. et al., 1988 Bioseparations: downstream processing for biotechnology, John Wiley and Sons; Kennedy, J. F. and Cabral, J. M. S., 1992 Recovery processes for biological materials, John Wiley and Sons; Shaeiwitz, J. A. and Henry, J. D., 1988 Biochemical separations, in: Ulmann's Encyclopedia of Industrial Chemistry, vol. B3, Chapter 11, page 1-27, VCH: Weinheim; and Dechow, F. J. (1989) Separation and purification techniques in biotechnology, Noyes Publications).

For example, yeast expression vectors comprising the nucleic acids disclosed herein, or fragments thereof, can be constructed and transformed into *Saccharomyces cerevisiae* using standard protocols. The resulting transgenic cells can then be assayed for fail or alteration of their tolerance to drought, salt, and temperature stress. Similarly, plant expression vectors comprising the nucleic acids disclosed herein, or fragments thereof, can be constructed and transformed into an appropriate plant cell such as *Arabidopsis*, soy, rape, maize, wheat, *Medicago truncatida*, etc., using standard protocols. The resulting transgenic cells and/or plants derived there from can then be assayed for fail or alteration of their tolerance to drought, salt, and temperature stress.

The engineering of one or more PKSRP genes of the invention may also result in PKSRPs having altered activities which indirectly impact the stress response and/or stress tolerance of algae, plants, ciliates or fungi or other microorganisms like *C. glutamicum*. For example, the normal biochemical processes of metabolism result in the production of a variety of products (e.g., hydrogen peroxide and other reactive oxygen species) which may actively interfere with these same metabolic processes (for example, peroxynitrite is known to nitrate tyrosine side chains, thereby inactivating some enzymes having tyrosine in the active site (Groves, J. T., 1999 Curr. Opin. Chem. Biol. 3(2):226-235). While these products are typically excreted, cells can be genetically altered to transport more products than is typical for a wild-type cell. By optimizing the activity of one or more PKSRPs of the invention which are involved in the export of specific molecules, such as salt molecules, it may be possible to improve the stress tolerance of the cell.

Additionally, the sequences disclosed herein, or fragments thereof, can be used to generate knockout mutations in the genomes of various organisms, such as bacteria, mammalian cells, yeast cells, and plant cells (Girke, T., 1998 The Plant Journal 15:39-48). The resultant knockout cells can then be evaluated for their ability or capacity to tolerate various stress conditions, their response to various stress conditions, and the effect on the phenotype and/or genotype of the mutation. For other methods of gene inactivation see U.S. Pat. No. 6,004,804 "Non-Chimeric Mutational Vectors" and Puttaraju et al., 1999 Spliceosome-mediated RNA trans-splicing as a tool for gene therapy Nature Biotechnology 17:246-252.

The aforementioned mutagenesis strategies for PKSRPs resulting in increased stress resistance are not meant to be limiting; variations on these strategies will be readily apparent to one skilled in the art. Using such strategies, and incorporating the mechanisms disclosed herein, the nucleic acid and protein molecules of the invention may be utilized to generate algae, ciliates, plants, fungi or other microorganisms like C. glutamicum expressing mutated PKSRP nucleic acid and protein molecules such that the stress tolerance is improved.

The present invention also provides antibodies that specifically bind to a PKSRP, or a portion thereof, as encoded by a nucleic acid described herein. Antibodies can be made by many well-known methods (See, e.g. Harlow and Lane, "Antibodies; A Laboratory Manual" Cold Spring Harbor Laboratory, Cold Spring Harbor, N.Y., (1988)). Briefly, purified antigen can be injected into an animal in an amount and in intervals sufficient to elicit an immune response. Antibodies can either be purified directly, or spleen cells can be obtained from the animal. The cells can then fused with an immortal cell line and screened for antibody secretion. The antibodies can be used to screen nucleic acid clone libraries for cells secreting the antigen. Those positive clones can then be sequenced. (See, for example, Kelly et al., 1992 Bio/Technology 10:163-167; Bebbington et al., 1992 Bio/Technology 10:169-175).

The phrases "selectively binds" and "specifically binds" with the polypeptide refer to a binding reaction that is determinative of the presence of the protein in a heterogeneous population of proteins and other biologies. Thus, under designated immunoassay conditions, the specified antibodies bound to a particular protein do not bind in a significant amount to other proteins present in the sample. Selective binding of an antibody under such conditions may require an antibody that is selected for its specificity for a particular protein. A variety of immunoassay formats may be used to select antibodies that selectively bind with a particular protein. For example, solid-phase ELISA immunoassays are routinely used to select antibodies selectively immunoreactive with a protein. See Harlow and Lane "Antibodies, A Laboratory Manual" Cold Spring Harbor Publications, New York, (1988), for a description of immunoassay formats and conditions that could be used to determine selective binding.

In some instances, it is desirable to prepare monoclonal antibodies from various hosts. A description of techniques for preparing such monoclonal antibodies may be found in Stites et al., editors, "Basic and Clinical Immunology," (Lange Medical Publications, Los Altos, Calif., Fourth Edition) and references cited therein, and in Harlow and Lane ("Antibodies, A Laboratory Manual" Cold Spring Harbor Publications, New York, 1988).

Throughout this application, various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1

Growth of Physcomitrella patens Cultures

For this study, plants of the species Physcomitrella patens (Hedw.) B. S. G. from the collection of the genetic studies section of the University of Hamburg were used. They originate from the strain 16/14 collected by H. L. K. Whitehouse in Gransden Wood, Huntingdonshire (England), which was subcultured from a spore by Engel (1968, Am. J. Bot. 55, 438-446). Proliferation of the plants was carried out by means of spores and by means of regeneration of the gametophytes. The protonema developed from the haploid spore as a chloroplast-rich chloronema and chloroplast-low caulonema, on which buds formed after approximately 12 days, These grew to give gametophores bearing antheridia and archegonia. After fertilization, the diploid sporophyte with a short seta and the spore capsule resulted, in which the meiospores matured.

Culturing was carried out in a climatic chamber at an air temperature of 25° C. and light intensity of 55 micromol s$^{-1}$ m$^{-2}$ (white light; Philips TL 65W/25 fluorescent tube) and a light/dark change of 16/8 hours. The moss was either modified in liquid culture using Knop medium according to Reski and Abel (1985, Planta 165:354-358) or cultured on Knop solid medium using 1% oxoid agar (Unipath, Basingstoke, England). The protonemas used for RNA and DNA isolation were cultured in aerated liquid cultures. The protonemas were comminuted every 9 days and transferred to fresh culture medium.

Example 2

Total DNA Isolation from Plants

The details for the isolation of total DNA relate to the working up of one gram fresh weight of plant material. The materials used include the following buffers: CTAB buffer: 2% (w/v) N-cethyl-N,N,N-trimethylammonium bromide (CTAB); 100 mM Tris HCl pH 8.0; 1.4 M NaCl; 20 mM EDTA; N-Laurylsarcosine buffer: 10% (w/v) N-laurylsarcosine; 100 mM Tris HCl pH 8.0; 20 mM EDTA.

The plant material was triturated under liquid nitrogen in a mortar to give a fine powder and transferred to 2 ml Eppendorf vessels. The frozen plant material was then covered with a layer of 1 ml of decomposition buffer (1 ml CTAB buffer, 100 µl of N-laurylsarcosine buffer, 20 µl of β-mercaptoethanol and 10 µl of proteinase K solution, 10 mg/ml) and incubated at 60° C. for one hour with continuous shaking. The homogenate obtained was distributed into two Eppendorf vessels (2 ml) and extracted twice by shaking with the same volume of chloroform/isoamyl alcohol (24:1). For phase separation, centrifugation was carried out at 8000×g and room temperature for 15 minutes in each case. The DNA was then precipitated at −70° C. for 30 minutes using ice-cold isopropanol. The precipitated DNA was sedimented at 4° C. and 10,000 g for 30 minutes and resuspended in 180 µl of TE buffer (Sambrook et al., 1989, Cold Spring Harbor Laboratory Press: ISBN 0-87969-309-6). For further purification, the DNA was treated with NaCl (1.2 M final concentration) and precipitated again at −70° C. for 30 minutes using twice the volume of absolute ethanol. After a washing step with 70% ethanol, the DNA was dried and subsequently taken up in 50 μl of H₂O+ RNAse (50 mg/ml final concentration). The DNA was dissolved overnight at 4° C. and the RNAse digestion was subsequently carried out at 37° C. for 1 hour. Storage of the DNA took place at 4° C.

Example 3

Isolation of Total RNA and Poly-(A)+ RNA and cDNA Library Construction from *Physcomitrella Patens*

For the investigation of transcripts, both total RNA and poly-(A)+ RNA were isolated. The total RNA was obtained from wild-type 9 day old protonemata following the GTC-method (Reski et al. 1994, Mol. Gen. Genet., 244:352-359). The Poly(A)+ RNA was isolated using Dyna Beads® (Dynal, Oslo, Norway) following the instructions of the manufacturers protocol. After determination of the concentration of the RNA or of the poly(A)+ RNA, the RNA was precipitated by addition of 1/10 volumes of 3 M sodium acetate pH 4.6 and 2 volumes of ethanol and stored at −70° C.

For cDNA library construction, first strand synthesis was achieved using Murine Leukemia Virus reverse transcriptase (Roche, Mannheim, Germany) and oligo-d(T)-primers, second strand synthesis by incubation with DNA polymerase I, Klenow enzyme and RNAseH digestion at 12° C. (2 hours), 16° C. (1 hour) and 22° C. (1 hour). The reaction was stopped by incubation at 65° C. (10 minutes) and subsequently transferred to ice. Double stranded DNA molecules were blunted by T4-DNA-polymerase (Roche, Mannheim) at 37° C. (30 minutes). Nucleotides were removed by phenol/chloroform extraction and Sephadex G50 spin columns. EcoRI adapters (Pharmacia, Freiburg, Germany) were ligated to the cDNA ends by T4-DNA-ligase (Roche, 12° C., overnight) and phosphorylated by incubation with polynucleotide kinase (Roche, 37° C., 30 minutes). This mixture was subjected to separation on a low melting agarose gel. DNA molecules larger than 300 base pairs were eluted from the gel, phenol extracted, concentrated on Elutip-D-columns (Schleicher and Schuell, Dassel, Germany) and were ligated to vector arms and packed into lambda ZAPII phages or lambda ZAP-Express phages using the Gigapack Gold Kit (Stratagene, Amsterdam, Netherlands) using material and following the instructions of the manufacturer.

Example 4

Sequencing and Function Annotation of *Physcomitrella patens* ESTs cDNA libraries as described in Example 3 were used for DNA sequencing according to standard methods, and in particular, by the chain termination method using the ABI PRISM Big Dye Terminator Cycle Sequencing Ready Reaction Kit (Perkin-Elmer, Weiterstadt, Germany). Random Sequencing was carried out subsequent to preparative plasmid recovery from cDNA libraries via in vivo mass excision, retransformation, and subsequent plating of DH10B on agar plates (material and protocol details from Stratagene, Amsterdam, Netherlands). Plasmid DNA was prepared from overnight grown *E. coli* cultures grown in Luria-Broth medium containing ampicillin (see Sambrook et al. 1989 Cold Spring Harbor Laboratory Press: ISBN 0-87969-309-6) on a Qiagene DNA preparation robot (Qiagen, Hilden) according to the manufacturer's protocols. Sequencing primers with the following nucleotide sequences were used:

| 5'-CAGGAAACAGCTATGACC-3' | SEQ ID NO: 40 |
| 5'-CTAAAGGGAACAAAAGCTG-3' | SEQ ID NO: 41 |
| 5'-TGTAAAACGACGGCCAGT-3' | SEQ ID NO: 42 |

Sequences were processed and annotated using the software package EST-MAX commercially provided by Bio-Max (Munich, Germany), The program incorporates practically all bioinformatics methods important for functional and structural characterization of protein sequences. For reference the website at pedant.mips.biochem.mpg.de. The most important algorithms incorporated in EST-MAX are: FASTA: Very sensitive sequence database searches with estimates of statistical significance; Pearson W. R. (1990) Rapid and sensitive sequence comparison with FASTP and FASTA. Methods Enzymol. 183:63-98; BLAST: Very sensitive sequence database searches with estimates of statistical significance. Altschul S. F., Gish W., Miller W., Myers E. W., and Lipman D. J. Basic local alignment search tool. Journal of Molecular Biology 215:403-10; PREDATOR: High-accuracy secondary structure prediction from single and multiple sequences. Frishman, D. and Argos, P. (1997)75% accuracy in protein secondary structure prediction. Proteins, 27:329-335; CLUSTALW: Multiple sequence alignment. Thompson, J. D., Higgins, D. G. and Gibson, T. J. (1994) CLUSTAL W: improving the sensitivity of progressive multiple sequence alignment through sequence weighting, positions-specific gap penalties and weight matrix choice. Nucleic Acids Research, 22:4673-4680; TMAP: Transmembrane region prediction from multiply aligned sequences. Persson, B. and Argos, P. (1994) Prediction of transmembrane segments in proteins utilizing multiple sequence alignments. J. Mol. Biol. 237:182-192; ALOM2: Transmembrane region prediction from single sequences. Klein, P., Kanehisa, M., and DeLisi, C. Prediction of protein function from sequence properties: A discriminate analysis of a database. Biochim. Biophys. Acta 787:221-226 (1984). Version 2 by Dr. K. Nakai; PROSEARCH: Detection of PROSTTE protein sequence patterns. Kolakowski L. F. Jr., Leunissen J. A. M., Smith J. E. (1992) ProSearch: fast searching of protein sequences with regular expression patterns related to protein structure and function. Biotechniques 13, 919-921; BLIMPS: Similarity searches against a database of ungapped blocks. J. C. Wallace and Henikoff S., (1992); PATMAT: A searching and extraction program for sequence, pattern and block queries and databases, CABIOS 8:249-254. Written by Bill Alford.

Example 5

Identification of *Physcomitrella Patens* ORFs Corresponding to PK-6, PK-7, PK-8, PK-9, CK-1, CK-2, CK-3, MPK-2, MPK-3, MPK-4, MPK-5, CPK-1 and CPK-2

The *Physcomitrella patens* partial cDNAs (ESTs) shown in Table 1 below were identified in the *Physcomitrella patens* EST sequencing program using the program EST-MAX through BLAST analysis. The Sequence Identification Numbers corresponding to these ESTs are as follows: PK-6 (SEQ ID NO:1), PK-7 (SEQ ID NO:2), PK-8 (SEQ ID NO:3), PK-9 (SEQ ID NO:4), CK-1 (SEQ ID NO:5), CK-2 (SEQ JD NO:6), CK-3 (SEQ ID NO:7), MPK-2 (SEQ ID NO:8), MPK-3 (SEQ ID NO:9), MPK-4 (SEQ ID NO:10), MPK-5 (SEQ ID NO:11), CPK-1 (SEQ ID NO:12) and CPK-2 (SEQ ID NO:13),

TABLE 1

| Name | Functional categories | Function | Sequence code | ORF position |
|---|---|---|---|---|
| PpPK-6 | Protein Kinase | serine/threonine protein kinase like protein | c_pp004044242r | 1-474 |
| PpPK-7 | Protein Kinase | cdc2-like protein kinase cdc2MsF | s_pp001031042f | 1-267 |
| PpPK-8 | Protein Kinase | protein kinase homolog F13C5.120 | c_pp004044100r | 1-581 |
| PpPK-9 | Protein Kinase | protein kinase; similar to human PKX1 | c_pp004071077r | 709-137 |
| PpCK-1 | Protein Kinase | receptor protein kinase | c_pp001062017r | 1160-1 |
| PpCK-2 | Protein Kinase | kasein kinase | c_pp004038371r | 1909-1421 |
| PpCK-3 | Protein Kinase | casein kinase II catalytic subunit | c_pp004076164r | 2-877 |
| PpMPK-2 | Protein Kinase | mitogen-activated protein kinase 6 | c_pp004041329r | 952-293 |
| PpMPK-3 | Protein Kinase | big MAP kinase 1c | c_pp004061263r | 221-550 |
| PpMPK-4 | Protein Kinase | protein kinase MEK1 (EC 2.7.1.—) | c_pp001064077r | 1153-596 |
| PpMPK-5 | Protein Kinase | protein kinase MEK1 | c_pp004064129r | 114-233 |
| PpCPK-1 | Protein Kinase | protein kinase | c_pp004014376r | 1084-173 |
| PpCPK-2 | Protein Kinase | calcium-dependent protein kinase | c_pp004038141r | 422-1213 |
| PpPK-6 | Protein Kinase | cdc2-like protein kinase cdc2MsF | s_pp001031042f | 1-267 |

TABLE 2

Degree of Amino Acid Identity and Similarity of PpPK-6 and Other Homologous Proteins GCG Gap program was used: gap penalty: 10; gap extension penalty: 0.1; score matrix: blosum62)

| | Swiss-Prot # | | | | |
|---|---|---|---|---|---|
| | O81106 | Q9LUL4 | Q9ZQZ2 | Q9MAS2 | Q9LK66 |
| Protein name | LEUCINE-RICH REPEAT TRANS-MEMBRANE PROTEIN KINASE 2 | SERINE/THREONINE PROTEIN KINASE-LIKE PROTEIN | PUTATIVE LRR RECEPTOR-LINKED PROTEIN KINASE | PUTATIVE LRR RECEPTOR PROTEIN KINASE | PROTEIN KINASE-LIKE PROTEIN |
| Species | Zea mays (Maize) | Arabidopsis thaliana (Mouse-ear cress) | A. thaliana | A. thaliana | A. thaliana |
| Identity % | 42% | 42% | 38% | 37% | 37% |
| Similarity % | 54% | 52% | 50% | 49% | 48% |

TABLE 3

Degree of Amino Acid Identity and Similarity of PpPK-7 and Other Homologous Proteins GCG Gap program was used: gap penalty: 10; gap extension penalty: 0.1; score matrix: blosum62)

| | Swiss-Prot # | | | | |
|---|---|---|---|---|---|
| | P25859 | O49120 | Q38774 | P93321 | Q9ZVI4 |
| Protein name | CELL DIVISION CONTROL PROTEIN 2 HOMOLOG B | CYCLIN-DEPENDENT KINASE 1 | CELL DIVISION CONTROL PROTEIN 2 HOMOLOG C | CDC2 KINASE HOMOLOG CDC2MSD | PUTATIVE SERINE/THREONINE PROTEIN KINASE |
| Species | A. thaliana | Dunaliella tertiolecta | Antirrhinum majus (Garden snapdragon) | Medicago sativa (Alfalfa) | A. thaliana |
| Identity % | 70% | 68% | 70% | 69% | 69% |
| Similarity % | 79% | 76% | 81% | 79% | 77% |

TABLE 4

Degree of Amino Acid Identity and Similarity of PpPK-8 and Other Homologous Proteins GCG Gap program was used: gap penalty: 10; gap extension penalty: 0.1; score matrix: blosum62)

| | Swiss-Prot # | | | | |
|---|---|---|---|---|---|
| | O82754 | Q9M085 | Q02779 | Q05609 | Q39886 |
| Protein name | PUTATIVE SERINE/THREONINE KINASE | PROTEIN KINASE-LIKE PROTEIN | MITOGEN-ACTIVATED PROTEIN KINASE KINASE KINASE 10 | SERINE/THREONINE-PROTEIN KINASE CTR1 | PROTEIN KINASE |
| Species | A. thaliana | A. thaliana | Homo sapiens (Human) | A. thaliana | Glycine max (Soybean) |
| Identity % | 25% | 26% | 27% | 27% | 26% |
| Similarity % | 42% | 40% | 38% | 40% | 40% |

TABLE 5

Degree of Amino Acid Identity and Similarity of PpPK-9 and Other Homologous Proteins GCG Gap program was used: gap penalty: 10; gap extension penalty: 0.1; score matrix: blosum62)

| | Swiss-Prot # | | | | |
|---|---|---|---|---|---|
| | Q9SL77 | P34099 | Q9TXB8 | P40376 | Q9SXP9 |
| Protein name | PUTATIVE CAMP-DEPENDENT PROTEIN KINASE | CAMP-DEPENDENT PROTEIN KINASE CATALYTIC SUBUNIT | SERINE/THREONINE PROTEIN KINASE | CAMP-DEPENDENT PROTEIN KINASE CATALYTIC SUBUNIT | CAMP-DEPENDENT PROTEIN KINASE CATALYTIC SUBUNIT |
| Species | A. thaliana | Dictyostelium discoideum (Slime mold) | Dictyostelium | Schizosaccharomyces pombe (Fission yeast) | Euglena gracilis |
| Identity % | 45% | 33% | 32% | 33% | 28% |
| Similarity % | 60% | 48% | 48% | 50% | 40% |

TABLE 6

Degree of Amino Acid Identity and Similarity of PpCK-1 and Other Homologous Proteins GCG Gap program was used: gap penalty: 10; gap extension penalty: 0.1; score matrix: blosum62)

| | Swiss-Prot # | | | | |
|---|---|---|---|---|---|
| | Q9SZI1 | Q9ZUP4 | P42158 | Q9LW62 | Q39050 |
| Protein name | COL-0 CASEIN KINASE I-LIKE PROTEIN | PUTATIVE CASEIN KINASE I | CASEIN KINASE I, DELTA ISOFORM LIKE | CASEIN KINASE | CASEIN KINASE I |
| Species | A. thaliana. | A. thaliana | A. thaliana | A. thaliana | A. thaliana |
| Identity % | 49% | 48% | 48% | 46% | 40% |
| Similarity % | 62% | 61% | 61% | 58% | 52% |

TABLE 7

Degree of Amino Acid Identity and Similarity of PpCK-2 and Other Homologous Proteins GCG Gap program was used: gap penalty: 10; gap extension penalty: 0.1; score matrix: blosum62)

| | Swiss-Prot # | | | | |
|---|---|---|---|---|---|
| | Q9SZI1 | P42158 | Q9ZWB3 | Q9ZUP4 | Q9LSX4 |
| Protein name | COL-0 CASEIN KINASE I-LIKE PROTEIN | CASEIN KINASE I | ADK1 | PUTATIVE CASEIN KINASE I | CASEIN KINASE I |
| Species | A. thaliana. | A. thaliana | A. thaliana | A. thaliana | A. thaliana |
| Identity % | 64% | 59% | 60% | 58% | 57% |
| Similarity % | 73% | 66% | 72% | 67% | 69% |

TABLE 8

Degree of Amino Acid Identity and Similarity of PpCK-3 and Other Homologous Proteins GCG Gap program was used: gap penalty: 10; gap extension penalty: 0.1; score matrix: blosum62)

| | Swiss-Prot # | | | | |
|---|---|---|---|---|---|
| | O64816 | Q9ZR52 | P28523 | Q9SN18 | Q08466 |
| Protein name | PUTATIVE CASEIN KINASE II CATALYTIC SUBUNIT | CASEIN KINASE II ALPHA SUBUNIT | CASEIN KINASE II, ALPHA CHAIN | CASEIN KINASE II, ALPHA CHAIN 2 (CK II) | CASEIN KINASE II, ALPHA CHAIN 2 |
| Species | A. thaliana | Zea mays (Maize) | Z. mays | A. thaliana | A. thaliana |
| Identity % | 87% | 89% | 89% | 88% | 88% |
| Similarity % | 93% | 94% | 93% | 93% | 93% |

TABLE 9

Degree of Amino Acid Identity and Similarity of PpMPK-2 and Other Homologous Proteins GCG Gap program was used: gap penalty: 10; gap extension penalty: 0.1; score matrix: blosum62)

| | Swiss-Prot # | | | | |
|---|---|---|---|---|---|
| | Q9M136 | Q40531 | Q39024 | Q40353 | Q07176 |
| Protein name | MAP KINASE 4 | MITOGEN-ACTIVATED PROTEIN KINASE HOMOLOG NTF6 | MITOGEN-ACTIVATED PROTEIN KINASE HOMOLOG 4 | MITOGEN-ACTIVATED PROTEIN KINASE HOMOLOG MMK2 | MITOGEN-ACTIVATED PROTEIN KINASE HOMOLOG MMK1 |
| Species | A. thaliana | Nicotiana tabacum (Common tobacco) | A. thaliana | M. sativa | M. sativa |
| Identity % | 70% | 69% | 69% | 68% | 66% |
| Similarity % | 80% | 78% | 80% | 79% | 76% |

TABLE 10

Degree of Amino Acid Identity and Similarity of PpMPK-3 and Other Homologous Proteins GCG Gap program was used: gap penalty: 10; gap extension penalty: 0.1; score matrix: blosum62)

| | Swiss-Prot # | | | | |
|---|---|---|---|---|---|
| | Q9SUX2 | P13983 | Q41192 | O70495 | Q9RLD9 |
| Protein name | EXTENSIN-LIKE PROTEIN | EXTENSIN | NAPRP3 | PLENTY-OF-PROLINES-101 | FERULOYL-COA SYNTHETASE |

TABLE 10-continued

Degree of Amino Acid Identity and Similarity of PpMPK-3 and Other Homologous Proteins GCG Gap program was used: gap penalty: 10; gap extension penalty: 0.1; score matrix: blosum62)

| | Swiss-Prot # | | | | |
|---|---|---|---|---|---|
| | Q9SUX2 | P13983 | Q41192 | O70495 | Q9RLD9 |
| Species | A. thaliana | N. tabacum | Nicotiana alata (Winged tobacco) (Persian tobacco) | Mus musculus (Mouse) | Pseudomonas sp. |
| Identity % | 12% | 15% | 22% | 18% | 11% |
| Similarity % | 21% | 22% | 30% | 26% | 20% |

TABLE 11

Degree of Amino Acid Identity and Similarity of PpMPK-4 and Other Homologous Proteins GCG Gap program was used: gap penalty: 10; gap extension penalty: 0.1; score matrix: blosum62)

| | Swiss-Prot # | | | | |
|---|---|---|---|---|---|
| | O49975 | O48616 | Q9M6Q9 | O80395 | Q9S7U9 |
| Protein name | PROTEIN KINASE ZMMEK1 | MAP KINASE KINASE | MAP KINASE KINASE | MAP KINASE KINASE 2 | MAP2K BETA PROTEIN |
| Species | Z. mays | Lycopersicon esculentum (Tomato) | N. tabacum | A. thaliana | A. thaliana |
| Identity % | 59% | 54% | 53% | 50% | 50% |

TABLE 12

Degree of Amino Acid Identity and Similarity of PpMPK-5 and Other Homologous Proteins GCG Gap program was used: gap penalty: 10; gap extension penalty: 0.1; score matrix: blosum62)

| | Swiss-Prot # | | | | |
|---|---|---|---|---|---|
| | O49975 | O48616 | Q9M6Q9 | O80395 | Q9S7U9 |
| Protein name | PROTEIN KINASE ZMMEK1 | MAP KINASE KINASE | MAP KINASE KINASE | MAP KINASE KINASE 2 | MAP2K BETA PROTEIN |
| Species | Z. mays | L. esculentum | N. tabacum | A. thaliana | A. thaliana |
| Identity % | 59% | 54% | 53% | 50% | 50% |
| Similarity % | 72% | 66% | 66% | 62% | 62% |

TABLE 13

Degree of Amino Acid Identity and Similarity of PpCPK-1 and Other Homologous Proteins GCG Gap program was used: gap penalty: 10; gap extension penalty: 0.1; score matrix: blosum62)

| | Swiss-Prot # | | | | |
|---|---|---|---|---|---|
| | Q9SCS2 | O04290 | P53681 | P93520 | Q41792 |
| Protein name | CDPK-RELATED PROTEIN KINASE | CDPK-RELATED PROTEIN KINASE | CDPK-RELATED PROTEIN KINASE | CALCIUM/CALMODULIN-DEPENDENT PROTEIN KINASE HOMOLOG | CDPK-RELATED PROTEIN KINASE |
| Species | A. thaliana | A. thaliana | Daucus carota (Carrot) | Z. mays | Z. mays |
| Identity % | 64% | 64% | 63% | 63% | 63% |
| Similarity % | 76% | 76% | 75% | 73% | 74% |

TABLE 14

Degree of Amino Acid Identity and Similarity of PpCPK-2 and Other Homologous Proteins GCG Gap program was used: gap penalty: 10; gap extension penalty: 0.1; score matrix: blosum62)

| | Swiss-Prot # | | | | |
|---|---|---|---|---|---|
| | Q9S7Z4 | Q42479 | Q41790 | O81390 | Q9ZPM0 |
| Protein name | CALCIUM-DEPENDENT PROTEIN KINASE | CALCIUM-DEPENDENT PROTEIN KINASE | CALCIUM-DEPENDENT PROTEIN KINASE | CALCIUM-DEPENDENT PROTEIN KINASE | CA2+-DEPENDENT PROTEIN KINASE |
| Species | Marchantia polymorpha (Liverwort) | A. thaliana | Z. mays | N. tabacum | Mesembryanthemum crystallinum (Common ice plant) |
| Identity % | 66% | 62% | 59% | 59% | 59% |
| Similarity % | 75% | 73% | 70% | 68% | 70% |

Example 6

Cloning of the Full-Length *Physcomitrella Patens* cDNA Encoding for PK-6, PK-7, PK-8, PK-9, CK-1, CK-2, CK-3, MPK-2, MPK-3, MPK-4, MPK-5, CPK-1 and CPK-2

To isolate the clones encoding PK-6 (SEQ ID NO:14), PK-7 (SEQ ID NO:15), PK-8 (SEQ ID NO:16), PK-9 (SEQ ID NO:17), CK-1 (SEQ ID NO:18), CK-2 (SEQ ID NO:19), CK-3 (SEQ ID NO:20), MPK-2 (SEQ ID NO:21), MPK-3 (SEQ ID NO:22), MPK-4 (SEQ ID NO:23), MPK-5 (SEQ ID NO:24), CPK-1 (SEQ ID NO:25) and CPK-2 (SEQ ID NO:26) from *Physcomitrella patens*, cDNA libraries were created with SMART RACE cDNA Amplification kit (Clontech Laboratories) following manufacturer's instructions. Total RNA isolated as described in Example 3 was used as the template. The cultures were treated prior to RNA isolation as follows; Salt Stress: 2, 6, 12, 24, 48 hours with 1-M NaCl-supplemented medium; Cold Stress: 4° C. for the same time points as for salt; Drought Stress: cultures were incubated on dry filter paper for the same time points as for salt.

5'RACE Protocol

The EST sequences PK-6 (SEQ ID NO:1), PK-7 (SEQ ID NO:2), PK-8 (SEQ ID NO:3), PK-9 (SEQ ID NO:4), CK-1 (SEQ ID NO:5), CK-2 (SEQ ID NO:6), CK-3 (SEQ ID NO:7), MPK-2 (SEQ ID NO:8), MPK-3 (SEQ ID NO:9), MPK-4 (SEQ ID NO:10), MPK-5 (SEQ ID NO:11), CPK-1 (SEQ ID NO:12) and CPK-2 (SEQ ID NO:13) identified from the database search as described in Example 4 were used to design oligos for RACE (see Table 15). The extended sequences for these genes were obtained by performing Rapid Amplification of cDNA Ends polymerase chain reaction (RACE PCR) using the Advantage 2 PCR kit (Clontech Laboratories) and the SMART RACE cDNA amplification kit (Clontech Laboratories) using a Biometra T3 Thermocycler following the manufacturer's instructions. The sequences obtained from the RACE reactions corresponded to full-length coding regions of CC-2 and CC-3 and were used to design oligos for full-length cloning of the respective genes (see below frill-length amplification).

Full-Length Amplification

Full-length clones corresponding PK-6 (SEQ ID NO:14), PK-7 (SEQ ID NO:15), PK-8 (SEQ ID NO:16), PK-9 (SEQ ID NO; 17), CK-1 (SEQ ID NO:18), CK-2 (SEQ ID NO:19), CK-3 (SEQ ID NO:20), MPK-2 (SEQ ID NO:21), MPK-3 (SEQ ID NO:22), MPK-4 (SEQ ID NO:23), MPK-5 (SEQ ID NO:24), CPK-1 (SEQ ID NO:25) and CPK-2 (SEQ ID NO:26) were obtained by performing polymerase chain reaction (PCR) with gene-specific primers (see Table 15) and the original EST as the template. The conditions for the reaction were standard conditions with PWO DNA polymerase (Roche). PCR was performed according to standard conditions and to manufacturer's protocols (Sambrook et al., 1989 Molecular Cloning, A Laboratory Manual. 2nd Edition. Cold Spring Harbor Laboratory Press. Cold Spring Harbor, N.Y., Biometra T3 Thermocycler). The parameters for the reaction were: five minutes at 94° C. followed by five cycles of one minute at 94° C., one minute at 50° C. and 1.5 minutes at 72° C. This was followed by twenty five cycles of one minute at 94° C., one minute at 65° C. and 1.5 minutes at 72° C.

The amplified fragments were extracted from agarose gel with a QIAquick Gel Extraction Kit (Qiagen) and ligated into the TOPO pCR 2.1 vector (Invitrogen) following manufacturer's instructions. Recombinant vectors were transformed into Top10 cells (Invitrogen) using standard conditions (Sambrook et al. 1989. Molecular Cloning, A Laboratory Manual. 2nd Edition. Cold Spring Harbor Laboratory Press. Cold Spring Harbor, N.Y.). Transformed cells were selected for on LB agar containing 100 µg/ml carbenicillin, 0.8 mg X-gal (5-bromo-4-chloro-3-indoryl-β-D-galactoside) and 0.8 mg IPTG (isopropylthio-β-D-galactoside) grown overnight at 37° C. White colonies were selected and used to inoculate 3 ml of liquid LB containing 100 µg/ml ampicillin and grown overnight at 37° C. Plasmid DNA was extracted using the QIAprep Spin Miniprep Kit (Qiagen) following manufacturer's instructions. Analyses of subsequent clones and restriction mapping was performed according to standard molecular biology techniques (Sambrook et al., 1989 Molecular Cloning, A Laboratory Manual. 2nd Edition. Cold Spring Harbor Laboratory Press. Cold Spring Harbor, N.Y.).

TABLE 15

Scheme and primers used for cloning of full-length clones

| Gene | Final product Sites | Isolation Method | Primers Race | Primers RT-PCR |
|---|---|---|---|---|
| PpPK-6 | XmaI/HpaI | 5' RACE and RT-PCR for Full-length clone | RC782: (SEQ ID NO: 43) CCACGGTCTTCGGC TGCTGGTCGTG RC783: (SEQ ID NO: 44) GCAGCACAGCACC ACCAGCGGCTAT ............ NVT: (SEQ ID NO: 45) GCGCCCAGTGAGTA GCTCCAGCATT | RC858: (SEQ ID NO: 46) ATCCCGGGTGAGTA TCACTTACGGTGGC GA RC859: (SEQ ID NO: 47) GCGTTAACTCGACC AAGGTCACTATTCC AAGCA |
| PpPK-7 | XmaI/HpaI | 5' RACE and RT-PCR for Full-length clone | RC250: (SEQ ID NO: 48) CGGTGCCCACCTCG TTCCTGTGGTT | RC590: (SEQ ID NO: 49) ATCCCGGGAGTGGG TGGTTGGACTGTAA GGA RC591: (SEQ ID NO: 50) GCGTTAACCTTCGTC TTGGACAGGTAGAG GTTAC |
| PpPK-8 | XmaI/HpaI | 5' RACE and RT-PCR for Full-length clone | (SEQ ID NO: 51) GACTCAGCCCCGTA ATCCTTCAACA | RC1016: (SEQ ID NO: 52) ATCCCGGGCAACGA GAAGCATTCGAGAT GGC RC1021: (SEQ ID NO: 53) GCGTTAACGAGCAT CACGATACTCGGTG ATTTC |
| PpPK-9 | XmaI/SacI | 5' RACE and RT-PCR for Full-length clone | RC263: (SEQ ID NO: 54) CGACGGCTAATACC ACGTTGGCGACCA | RC831: (SEQ ID NO: 55) ATCCCGGGCTGTGA TGTCGGTGTGGTGCT CTGC RC832: (SEQ ID NO: 56) GCGAGCTCGCACCA CTGAATGATGGAGA CTCAGG |
| PpCK-1 | XmaI/HpaI | 5' RACE and RT-PCR for Full-length clone | NVT: (SEQ ID NO: 57) CGACCGCAGCCCAT GAGGAAGTTAT | RC614: (SEQ ID NO: 58) ATCCCGGGCTCACG TAGTGCACTGAACT CTGTC RC615: (SEQ ID NO: 59) GCGTTAACATGCCC ATCTTCTCATACTCA GACC |
| PpCK-2 | XmaI/HpaI | 5' RACE and RT-PCR for Full-length clone | NVT: (SEQ ID NO: 60) CTCGCCTACCAAGC CCCATTAGAAA | RC1012: (SEQ ID NO: 61) ATCCCGGGTTGTCG AGGACGGAGAGAGA AGAG RC1015: (SEQ ID NO: 62) GCGTTAACCCTTAGG AATCGTATGGCAGA GAGCT |
| PpCK-3 | HpaI/SacI | 5' RACE and RT-PCR for Full-length clone | NVT: (SEQ ID NO: 63) GCTTCACAATGTTG GGCCCTCCACA | RC640: (SEQ ID NO: 64) GCGTTAACGGGAGG AAGGTCGGGGAAG |

TABLE 15-continued

Scheme and primers used for cloning of full-length clones

| Gene | Final product Sites | Isolation Method | Primers Race | Primers RT-PCR |
|---|---|---|---|---|
| | | | | AGACG<br>RC641:<br>(SEQ ID NO: 65)<br>GCGAGCTCAGCGCT<br>TCGCACAACTGAGA<br>AACCT |
| PpMPK-2 | XmaI/HpaI | 5' RACE and RT-PCR for Full-length clone | NVT:<br>(SEQ ID NO: 66)<br>ACGAGAAGGTTGGT<br>GGGCTTCAAGT | RC664:<br>(SEQ ID NO: 67)<br>ATCCCGGGCGAGCC<br>ATGGCGCCACTTGCTT<br>RC665:<br>(SEQ ID NO: 68)<br>GCGTTAACGCCGAG<br>CAACAATGTCTGCT<br>GGATG |
| PpMPK-3 | XmaI/HpaI | 5' RACE and RT-PCR for Full-length clone | RC268:<br>(SEQ ID NO: 69)<br>CCCGGTAAGCCATC<br>GGAGTGTGGAA | RC662:<br>(SEQ ID NO: 70)<br>ATCCCGGGCTTGTAT<br>TGGCTCGGATAATTT<br>RC663:<br>(SEQ ID NO: 71)<br>GCGTTAACGGCAAT<br>ATCTGCACAGCCGTT<br>CACT |
| PpMPK-4 | XmaI/SacI | 5' RACE and RT-PCR for Full-length clone | NVT:<br>(SEQ ID NO: 72)<br>GTGTCTCGCTGGGC<br>CAAGGAATGAA | RC1001:<br>(SEQ ID NO: 73)<br>ATCCCGGGCGGTCG<br>AGTCGTATTAGGTG<br>TTGTTTC<br>RC1005:<br>(SEQ ID NO: 74)<br>GAGCTCCGGTAGGT<br>CCGACCTCTTCAATTG |
| PpMPK-5 | XmaI/SacI | 5' RACE and RT-PCR for Full-length clone | RC266:<br>(SEQ ID NO: 75)<br>GACGACGCGAAGC<br>CCGGTGTGGTTGA | RC572:<br>(SEQ ID NO: 76)<br>ATCCCGGGAGAGGC<br>TGATCTGATGCTACA<br>GT<br>RC573:<br>(SEQ ID NO: 77)<br>ATGAGCTCTGGCGG<br>ATTGGCGAGGTAGT<br>TCGAC |
| PpCPK-1 | XmaI/HpaI | 5' RACE and RT-PCR for Full-length clone | RC526:<br>(SEQ ID NO: 78)<br>CGGCGCAACGTAGT<br>ATGCGCTTCCA<br>. . . . . . . . . . . . . . .<br>RC723N:<br>(SEQ ID NO: 79)<br>CGCGGTGAACAAC<br>ACCTTGCAGGTGAC<br>RC767:<br>(SEQ ID NO: 80)<br>GCTCGGGTCAGCCC<br>TCAACACCGCA<br>. . . . . . . . . . . . . . .<br>NVT:<br>(SEQ ID NO: 81)<br>GTTAAAGCTTGTGC<br>AGCAGTCATGC | RC817:<br>(SEQ ID NO: 82)<br>ATCCCGGGTGTAGG<br>CGGGCGAGGTTCGA<br>TGC<br>RC818:<br>(SEQ ID NO: 83)<br>GCGTTAACGACAAC<br>CGGAGTAGAACGGC<br>AGTCCA |
| PpCPK-2 | XmaI/HpaI | 5' RACE and RT-PCR for Full-length clone | NVT:<br>(SEQ ID NO: 84)<br>AGAAGCGAGGAAT<br>GGGCAGGGACGA | RC703:<br>(SEQ ID NO: 85)<br>ATCCCGGGCGAACT<br>GCGATCTGAGATTC<br>CAAC<br>RC704: |

TABLE 15-continued

Scheme and primers used for cloning of full-length clones

| Gene | Final product Sites | Isolation Method | Primers Race | Primers RT-PCR |
|---|---|---|---|---|
| | | | | (SEQ ID NO: 86)<br>GCGTTAACGAGATC<br>CAACCGAAGCCATC<br>CTACGA |

Example 7

Engineering Stress-Tolerant *Arabidopsis* Plants by Over-Expressing the Genes PK-6, PK-7, PK-8, PK-9, CK-1, CK-2, CK-3, MPK-2, MPK-3, MPK-4, MPK-5, CPK-1 and CPK-2

Binary Vector Construction: Kanamycin

The plasmid construct pACGH101 was digested with PstI (Roche) and FseI (NEB) according to manufacturers' instructions. The fragment was purified by agarose gel and extracted via the Qiaex II DNA Extraction kit (Qiagen). This resulted in a vector fragment with the *Arabidopsis* Actin2 promoter with internal intron and the OCS3 terminator. Primers for PCR amplification of the NPTII gene were designed as follows:

```
5'NPT-Pst:
                                        (SEQ ID NO: 87)
GCG-CTG-CAG-ATT-TCA-TTT-GGA-GAG-GAC-ACG

3'NPT-Fse:
                                        (SEQ ID NO: 88)
CGC-GGC-CGG-CCT-CAG-AAG-AAC-TCG-TCA-AGA-AGG-CG.
```

The 0.9 kilobase NPTII gene was amplified via PCR from pCambia 2301 plasmid DNA [94° C. 60 sec, {94° C. 60 sec, 61° C. (−0.1° C. per cycle) 60 sec, 72° C. 2 min}×25 cycles, 72° C. 10 min on Biometra T-Gradient machine], and purified via the Qiaquick PCR Extraction kit (Qiagen) as per manufacturer's instructions. The PCR DNA was then subcloned into the pCR-BluntII TOPO vector (Invitrogen) pursuant to the manufacturer's instructions (NPT-Topo construct). These ligations were transformed into Top 10 cells (Invitrogen) and grown on LB plates with 50 ug/ml kanamycin sulfate overnight at 37° C. Colonies were then used to inoculate 2 ml LB media with 50 ug/ml kanamycin sulfate and grown overnight at 37° C. Plasmid DNA was recovered using the Qiaprep Spin Miniprep kit (Qiagen) and sequenced in both the 5' and 3' directions using standard conditions. Subsequent analysis of the sequence data using VectorNTI software revealed no PCR errors present in the NPTII gene sequence.

The NPT-Topo construct was then digested with PstI (Roche) and FseI (NEB) according to manufacturers' instructions. The 0.9 kilobase fragment was purified on agarose gel and extracted by Qiaex II DNA Extraction kit (Qiagen). The Pst/Fse insert fragment from NPT-Topo and the Pst/Fse vector fragment from pACGH101 were then ligated together using T4 DNA Ligase (Roche) following manufacturer's instructions. The ligation was then transformed into Top 10 cells (Invitrogen) under standard conditions, creating pBPSsc019 construct, Colonies were selected on LB plates with 50 ug/ml kanamycin sulfate and grown overnight at 37° C. These colonies were then used to inoculate 2 ml LB media with 50 ug/ml kanamycin sulfate and grown overnight at 37° C. Plasmid DNA was recovered using the Qiaprep Spin Miniprep kit (Qiagen) following the manufacturer's instructions.

The pBPSSC019 construct was digested with KpnI and BsaI (Roche) according to manufacturer's instructions. The fragment was purified via agarose gel and then extracted via the Qiaex U DNA Extraction kit (Qiagen) as per its instructions, resulting in a 3 kilobase Act-NPT cassette, which included the *Arabidopsis* Actin2 promoter with internal intron, the NPTII gene and the OCS3 terminator.

The pBPSJH001 vector was digested with SpeI and ApaI (Roche) and blunt-end filled with Klenow enzyme and 0.1 mM dNTPs (Roche) according to manufacture's instructions. This produced a 10.1 kilobase vector fragment minus the Gentamycin cassette, which was recircularized by self-ligating with T4 DNA Ligase (Roche), and transformed into Top10 cells (Invitrogen) via standard conditions. Transformed cells were selected for on LB agar containing 50 μg/ml kanmycin sulfate and grown overnight at 37° C. Colonies were then used to inoculate 2 ml of liquid LB containing 50 μg/ml kanamycin sulfate and grown overnight at 37° C. Plasmid DNA was extracted using the QIAprep Spin Miniprep Kit (Qiagen) following manufacture's instructions. The recircularized plasmid was then digested with KpnI (Roche) and extracted from agarose gel via the Qiaex II DNA Extraction kit (Qiagen) as per manufacturer's instructions.

The Act-NPT Kpn-cut insert and the Kpn-cut pBPSJH001 recirculated vector were then ligated together using T4 DNA Ligase (Roche) and transformed into Top10 cells (Invitrogen) as per manufacturers' instructions. The resulting construct, pBPSsc022, now contained the Super Promoter, the GUS gene, the NOS terminator, and the Act-NPT cassette. Transformed cells were selected for on LB agar containing 50 μg/ml kanamycin sulfate and grown overnight at 37° C. Colonies were then used to inoculate 2 ml of liquid LB containing 50 μg/ml kanamycin sulfate and grown overnight at 37° C. Plasmid DNA was extracted using the QIAprep Spin Miniprep Kit (Qiagen) following manufacturer's instructions. After confirmation of ligation success via restriction digests, pBPSsc022 plasmid DNA was further propigated and recovered using the Plasmid Midiprep Kit (Qiagen) following the manufacturer's instructions.

Subcloning of PK-6, PK-7. PK-8. PK-9, CK-1. CK-2. CK-3. MPK-2. MPK-3. MPK-4. MPK-5, CPK-1 and CPK-2 into the Binary Vector The fragments containing the different *Physcomitrella patens* protein kinases were subcloned from the recombinant PCR2.1 TOPO vectors by double digestion with restriction enzymes (see Table 16) according to manufacturer's instructions. The subsequence fragment was excised from agarose gel with a QIAquick Gel Extraction Kit (QIAgen) according to manufacture's instructions and ligated into the binary vectors pGMSG, cleaved with XmaI and Ecl136II and dephosphorylated prior to ligation. The resulting recombinant pGMSG contained the corresponding transcription factor in the sense orientation under the constitutive super promoter.

TABLE 16

Listed are the names of the various constructs of the *Physcomitrella patens* transcription factors used for plant transformation

| Gene | Enzymes used to generate gene fragment | Enzymes used to restrict pBPSJH001 | Binary Vector Construct |
|---|---|---|---|
| PpPK-6 | XmaI/HpaI | XmaI/SacI | pBPSJyw022 |
| PpPK-7 | XmaI/HpaI | XmaI/Ecl136 | pBPSJyw012 |
| PpPK-8 | XmaI/HpaI | XmaI/Ecl136 | pBPSJYW030 |
| PpPK-9 | XmaI/SacI | XmaI/SacI | PBPSERG010 |
| PpCK-1 | XmaI/HpaI | XmaI/Ecl136 | pBPSSY012 |
| PpCK-2 | XmaI/HpaI | XmaI/Ecl136 | pBPSJyw034 |
| PpCK-3 | HpaI/SacI | SmaI/SacI | pBPSSY011 |
| PpMPK-2 | XmaI/HpaI | XmaI/Ecl136 | pBPSSY016 |
| PpMPK-3 | XmaI/HpaI | XmaI/Ecl136 | pBPSJyw014 |
| PpMPK-4 | XmaI/SacI | XmaI/SacI | pBPSJyw025 |
| PpMPK-5 | XmaI/SacI | XmaI/SacI | PBPSERG009 |
| PpCPK-1 | XmaI/HpaI | XmaI/Ecl136 | PBPSERG019 |
| PpCPK-2 | XmaI/HpaI | XmaI/Ecl136 | pBPSJyw008 |

*Agrobacterium* Transformation

The recombinant vectors were transformed into *Agrobacterium tumefaciens* C58C1 and PMP90 according to standard conditions (Hoefgen and Willmitzer, 1990).

Plant Transformation

*Arabidopsis thaliana* ecotype C24 were grown and transformed according to standard conditions (Bechtold 1993, Acad. Sci. Paris. 316:1194-1199; Bent et al. 1994, Science 265:1856-1860).

Screening of Transformed Plants

T1 seeds were sterilized according to standard protocols (Xiong et al. 1999, Plant Molecular Biology Reporter 17:159-170). Seeds were plated on ½ Murashige and Skoog media (MS) (Sigma-Aldrich) pH 5.7 with KOH, 0.6% agar and supplemented with 1% sucrose, 0.5 g/L 2-[N-Morpholino] ethansulfonic acid (MES) (Sigma-Aldrich), 50 µg/ml kanamycin (Sigma-Aldrich), 500 µg/ml carbenicillan (Sigma-Aldrich) and 2 µg/ml benomyl (Sigma-Aldrich). Seeds on plates were vernalized for four days at 4° C. The seeds were germinated in a climatic chamber at an air temperature of 22° C. and light intensity of 40 micromol $s^{-1}$ $m^{-2}$ (white light; Philips TL 65W/25 fluorescent tube) and 16 hours light and 8 hours dark day length cycle. Transformed seedlings were selected after 14 days and transferred to ½ MS media pH 5.7 with KOH 0.6% agar plates supplemented with 0.6% agar, 1% sucrose, 0.5 g/L MES (Sigma-Aldrich), and 2 µg/ml benomyl (Sigma-Aldrich) and allowed to recover for five-seven days.

Drought Tolerance Screening

T1 seedlings were transferred to dry, sterile filter paper in a petri dish and allowed to desiccate for two hours at 80% RH (relative humidity) in a Percieval Growth Cabinet MLR-350H, micromole $s^{-1}$ $m^{-2}$ (white light; Philips TL 65W/25 fluorescent tube). The RH was then decreased to 60% and the seedlings were desiccated further for eight hours. Seedlings were then removed and placed on 14 MS 0.6% agar plates supplemented with 2 µg/ml benomyl (Sigma-Aldrich) and 0.5 g/L MES (Sigma-Aldrich) and scored after five days.

Under drought stress conditions, PpPK-6 over-expressing *Arabidopsis thaliana* plants showed a 95% (20 survivors from 21 stressed plants) survival rate to the stress screening; PpPK-8, 40% (2 survivors from 5 stressed plants), PpPK-9, 78% (38 survivors from 49 stressed plants), PpCK-1, 50% (5 survivors from 10 stressed plants), PpCK-2, 52% (16 survivors from 31 stressed plants), PpCK-3, 60% (3 survivors from 5 stressed plants), PpMPK-2, 100% (52 survivors from 52 stressed plants), PpMPK-3, 98% (44 survivors from 45 stressed plants), PpMPK-4, 92% (11 survivors from 12 stressed plants), PpMPK-5, 100% (9 survivors from 9 stressed plants), PpCPK-1, 60% (12 survivors from 20 stressed plants), PpCPK-2, 89% (17 survivors from 19 stressed plants), whereas the untransformed control only showed an 11% survival rate (1 survivor from 9 stressed plants). It is noteworthy that the analyses of these transgenic lines were performed with T1 plants, and therefore, the results will be better when a homozygous, strong expresser is found.

TABLE 17

Summary of the drought stress tests

| | Drought Stress Test | | |
|---|---|---|---|
| Gene Name | Number of survivors | Total number of plants | Percentage of survivors |
| PpPK-6 | 20 | 21 | 95% |
| PpPK-8 | 2 | 5 | 40% |
| PpPK-9 | 38 | 49 | 78% |
| PpCK-1 | 5 | 10 | 50% |
| PpCK-2 | 16 | 31 | 52% |
| PpCK-3 | 3 | 5 | 60% |
| PpMPK-2 | 52 | 52 | 100% |
| PpMPK-3 | 44 | 45 | 98% |
| PpMPK-4 | 11 | 12 | 92% |
| PpMPK-5 | 9 | 9 | 100% |

Freezing Tolerance Screening

Seedlings were moved to petri dishes containing ½ MS 0.6% agar supplemented with 2% sucrose and 2 µg/ml benomyl. After four days, the seedlings were incubated at 4° C. for 1 hour and then covered with shaved ice. The seedlings were then placed in an Environmental Specialist ES2000 Environmental Chamber and incubated for 3.5 hours beginning at −1.0° C. decreasing 1° C./hour. The seedlings were then incubated at −5.0° C. for 24 hours and then allowed to thaw at 5° C. for 12 hours. The water was poured off and the seedlings were scored after 5 days.

Under freezing stress conditions, PpPK-7 over-expressing *Arabidopsis thaliana* plants showed a 73% (8 survivors from 11 stressed plants) survival rate to the stress screening; PpPK-9, 100% (45 survivors from 45 stressed plants), PpCK-1, 100% (14 survivors from 14 stressed plants), PpMPK-2, 68% (36 survivors from 53 stressed plants), PpMPK-3, 92% (24 survivors from 26 stressed plants), PpCPK-2, 64% (7 survivors from 11 stressed plants), whereas the untransformed control only showed a 2% survival rate (1 survivor from 48 stressed plants). It is noteworthy that the analyses of these transgenic lines were performed with T1 plants, and therefore, the results will be better when a homozygous, strong expresser is found.

Table 18

TABLE 18

Summary of the freezing stress tests

| | Freezing Stress Test | | |
|---|---|---|---|
| Gene Name | Number of survivors | Total number of plants | Percentage of survivors |
| PpPK-7 | 8 | 11 | 73% |
| PpPK-9 | 45 | 45 | 100% |
| PpCK-1 | 14 | 14 | 100% |
| PpMPK-2 | 36 | 53 | 68% |
| PpMPK-3 | 24 | 26 | 92% |
| PpCPK-2 | 7 | 11 | 64% |
| Control | 1 | 48 | 2% |

Salt Tolerance Screening

Seedlings were transferred to filter paper soaked in ½ MS and placed on ½ MS 0.6% agar supplemented with 2 µg/ml benomyl the night before the salt tolerance screening. For the salt tolerance screening, the filter paper with the seedlings was moved to stacks of sterile filter paper, soaked in 50 mM NaCl, in a petri dish. After two hours, the filter paper with the seedlings was moved to stacks of sterile filter paper, soaked with 200 mM NaCl, in a petri dish. After two hours, the filter paper with the seedlings was moved to stacks of sterile filter paper, soaked in 600 mM NaCl, in a petri dish. After 10 hours, the seedlings were moved to petri dishes containing 14 MS 0.6% agar supplemented with 2 µg/ml benomyl. The seedlings were scored after 5 days.

The transgenic plants are screened for their improved salt tolerance demonstrating that transgene expression confers salt tolerance.

Example 8

Detection of the PK-6, PK-7, PK-8, PK-9, CK-1, CK-2, CK-3, MPK-2, MPK-3, MPK-4, MPK-5, CPK-1 and CPK-2 Transgenes in the Transgenic *Arabidopsis* Lines One leaf from a wild type and a transgenic *Arabidopsis* plant was homogenized in 250 µl Hexadecyltrimethyl ammonium bromide (CTAB) buffer (2% CTAB, 1.4 M NaCl, 8 mM EDTA and 20 mM Tris pH 8.0) and 1 µl β-mercaptoethanol. The samples were incubated at 60-65° C. for 30 minutes and 250 µl of Chloroform was then added to each sample. The samples were vortexed for 3 minutes and centrifuged for 5 minutes at 18,000×g. The supernatant was taken from each sample and 150 µl isopropanol was added. The samples were incubated at room temperature for 15 minutes, and centrifuged for 10 minutes at 18,000×g. Each pellet was washed with 70% ethanol, dried, and resuspended in 20 µl TE. 4 µl of above suspension was used in a 20 µl PCR reaction using Tag DNA polymerase (Roche Molecular Biochemicals) according to the manufacturer's instructions.

Binary vector plasmid with each gene cloned in was used as positive control, and the wild-type C24 genomic DNA was used as negative control in the PCR reactions. 10 µl PCR reaction was analyzed on 0.8% agarose-ethidium bromide gel.

PpPk-6: The primers used in the reactions are:

```
GCTGACACGCCAAGCCTCGCTAGTC          (SEQ ID NO: 89)
GCGTTAACTCGACCAAGGTCACTATTCCAAGCA  (SEQ ID NO: 90)
```

The PCR program was as following: 30 cycles of 1 minute at 94° C., 1 minute at 62° C. and 4 minutes at 72° C., followed by 10 minutes at 72° C. A 2.8 kb fragment was produced from the positive control and the transgenic plants.

PpPk-7: The primers used in the reactions are:

```
GCTGACACGCCAAGCCTCGCTAGTC          (SEQ ID NO: 89)
GCGTTAACCTTCGTCTTGGACAGGTAGAGGTTAC (SEQ ID NO: 91)
```

The primers were used in the first round of reactions with the following program: 30 cycles of 1 minute at 94° C., 1 minute at 62° C. and 4 minutes at 72° C., followed by 10 minutes at 72° C. A 1.1 kb fragment was generated from the positive control and the T1 transgenic plants.

PpPK-8: The primers used in the reactions were:

```
GCTGACACGCCAAGCCTCGCTAGTC          (SEQ ID NO: 89)
GCGTTAACGAGCATCACGATACTCGGTGATTTC  (SEQ ID NO: 92)
```

The PCR program was as following: 30 cycles of 1 minute at 94° C., 1 minute at 62° C. and 4 minutes at 72° C., followed by 10 minutes at 72° C. A 1.6 kb fragment was produced from the positive control and the transgenic plants.

PpPK-9: The primers used in the reactions are:

```
GCTGACACGCCAAGCCTCGCTAGTC          (SEQ ID NO: 89)
GCGAGCTCGCACCACTGAATGATGGAGACTCAGG (SEQ ID NO: 93)
```

The PCR program was as following: 30 cycles of 1 minute at 94° C., 1 minute at 62° C. and 4 minutes at 72° C., followed by 10 minutes at 72° C. A 1.4 kb fragment was produced from the positive control and the transgenic plants.

PpCK-1: The primers used in the reactions are:

```
GCTGACACGCCAAGCCTCGCTAGTC          (SEQ ID NO: 89)
GCGTTAACATGCCCATCTTCTCATACTCAGACC  (SEQ ID NO: 94)
```

The PCR program was as following: 30 cycles of 1 minute at 94° C., 1 minute at 62° C. and 4 minutes at 72° C., followed by 10 minutes at 72° C. A 1.7 kb fragment was produced from the positive control and the transgenic plants.

PpCK-2: The primers used in the reactions are:

```
GCTGACACGCCAAGCCTCGCTAGTC          (SEQ ID NO: 89)
GCGTTAACCTTAGGAATCGTATGGCAGAGAGCT  (SEQ ID NO: 95)
```

The PCR program was as following: 30 cycles of 1 minute at 94° C., 1 minute at 62° C. and 4 minutes at 72° C., followed by 10 minutes at 72° C. A 1.9 kb fragment was produced from the positive control and the transgenic plants.

PpCK-3: The primers used in the reactions are:

```
GCTGACACGCCAAGCCTCGCTAGTC          (SEQ ID NO: 89)
GCGAGCTCAGCGCTTCGCACAACTGAGAAACCT  (SEQ ID NO: 96)
```

The PCR program was as following: 30 cycles of 1 minute at 94° C., 1 minute at 62° C. and 4 minutes at 72° C., followed by 10 minutes at 72° C. A 1.2 kb fragment was produced from the positive control and the transgenic plants.

PpMPK-2: The primers used in the reactions are:

```
GCTGACACGCCAAGCCTCGCTAGTC          (SEQ ID NO: 89)

GCGTTAACGGCAATATCTGCACAGCCGTTCACT  (SEQ ID NO: 97)
```

The PCR program was as following: 30 cycles of 1 minute at 94° C., 1 minute at 62° C. and 4 minutes at 72° C., followed by 10 minutes at 72° C. A 1.7 kb fragment was produced from the positive control and the transgenic plants.

PpMPK-3: The primers used in the reactions are:

```
GCTGACACGCCAAGCCTCGCTAGTC          (SEQ ID NO: 89)

GCGTTAACGGCAATATCTGCACAGCCGTTCACT  (SEQ ID NO: 98)
```

The PCR program was as following: 30 cycles of 1 minute at 94° C., 1 minute at 62° C. and 4 minutes at 72° C., followed by 10 minutes at 72° C. A 2.2 kb fragment was produced from the positive control and the transgenic plants.

PpMPK-4: The primers used in the reactions are:

```
GCTGACACGCCAAGCCTCGCTAGTC          (SEQ ID NO: 89)

GAGCTCCGGTAGGTCCGACCTCTTCAATTG     (SEQ ID NO: 99)
```

The PCR program was as following: 30 cycles of 1 minute at 94° C., 1 minute at 62° C. and 4 minutes at 72° C., followed by 10 minutes at 72° C. A 1.7 kb fragment was produced from the positive control and the transgenic plants.

PpMPK-5: The primers used in the reactions are:

```
GCTGACACGCCAAGCCTCGCTAGTC          (SEQ ID NO: 89)

ATGAGCTCTGGCGGATTGGCGAGGTAGTTCGAC  (SEQ ID NO: 100)
```

The PCR program was as following: 30 cycles of 1 minute at 94° C., 1 minute at 62° C. and 4 minutes at 72° C., followed by 10 minutes at 72° C. A 1.4 kb fragment was produced from the positive control and the transgenic plants.

PpCPK-1: The primers used in the reactions are:

```
GCTGACACGCCAAGCCTCGCTAGTC          (SEQ ID NO: 89)

GCGTTAACGACAACCGGAGTAGAACGGCAGTCCA (SEQ ID NO: 101)
```

The PCR program was as following: 30 cycles of 1 minute at 94° C., 1 minute at 62° C. and 4 minutes at 72° C., followed by 10 minutes at 72° C. A 2.3 kb fragment was produced from the positive control and the transgenic plants.

PpCPK-2: The primers used in the reactions are:

```
GCTGACACGCCAAGCCTCGCTAGTC          (SEQ ID NO: 89)

GCGTTAACGAGATCCAACCGAAGCCATCCTACGA (SEQ ID NO: 102)
```

The PCR program was as following: 30 cycles of 1 minute at 94° C., 1 minute at 62° C. and 4 minutes at 72° C., followed by 10 minutes at 72° C. A 2.2 kb fragment was produced from the positive control and the transgenic plants.

The transgenes were successfully amplified from the T1 transgenic lines, but not from the wild type C24. This result indicates that the T1 transgenic plants contain at least one copy of the transgenes. There was no indication of existence of either identical or very similar genes in the untransformed *Arabidopsis thaliana* control which could be amplified by this method.

Example 9

Detection of the PK-6, PK-7, PK-8, PK-9, CK-1, CK-2, CK-3, MPK-2, MPK-3, MPK-4, MPK-5, CPK-1 and CPK-2 Transgene mRNA in Transgenic *Arabidopsis* Lines Transgene expression was detected using RT-PCR. Total RNA was isolated from stress-treated plants using a procedure adapted from (Verwoerd et al., 1989 NAR 17:2362). Leaf samples (50-100 mg) were collected and ground to a fine powder in liquid nitrogen. Ground tissue was resuspended in 500 µl of a 80° C., 1:1 mixture, of phenol to extraction buffer (100 mM LiCl, 100 mM Tris pH8, 10 mM EDTA, 1% SDS), followed by brief vortexing to mix. After the addition of 250 µl of chloroform, each sample was vortexed briefly. Samples were then centrifuged for 5 minutes at 12,000×g. The upper aqueous phase was removed to a fresh eppendorf tube. RNA was precipitated by adding $^{1}/_{10}^{th}$ volume 3M sodium acetate and 2 volumes 95% ethanol. Samples were mixed by inversion and placed on ice for 30 minutes. RNA was pelleted by centrifugation at 12,000×g for 10 minutes. The supernatant was removed and pellets briefly air-dried. RNA sample pellets were resuspended in 10 µl DEPC treated water. To remove contaminating DNA from the samples, each was treated with RNase-free DNase (Roche) according to the manufacturer's recommendations. cDNA was synthesized from total RNA using the $1^{st}$ Strand cDNA synthesis kit (Boehringer Mannheim) following manufacturer's recommendations.

PCR amplification of a gene-specific fragment from the synthesized cDNA was performed using Taq DNA polymerase (Roche) and gene-specific primers (see Table 15 for primers) in the following reaction: 1×PCR buffer, 1.5 mM $MgCl_2$, 0.2 µM each primer, 0.2 µM dNTPs, 1 unit polymerase, 5 µl cDNA from synthesis reaction. Amplification was performed under the following conditions: Denaturation, 95° C., 1 minute; annealing, 62° C., 30 seconds; extension, 72° C., 1 minute, 35 cycles; extension, 72° C., 5 minutes; hold, 4° C., forever. PCR products were run on a 1% agarose gel, stained with ethidium bromide, and visualized under UV light using the Quantity-One gel documentation system (Bio-Rad).

Expression of the transgenes was detected in the T1 transgenic line. This result indicated that the transgenes are expressed in the transgenic lines and strongly suggested that their gene product improved plant stress tolerance in the transgenic line. On the other hand, no expression of identical or very similar endogenous genes could be detected by this method. These results are in agreement with the data from Example 7. This greatly supports our statement that the observed stress tolerance is due to the introduced transgene.

```
PpPK-6
                                    (SEQ ID NO: 103)
     CCCAGTAATAGCAGGGTTGGAGGAA (SEQ ID NO: 104)
     GGCTGCCTGAAGATCCGCTACAGAG

PpPK-7
                                    (SEQ ID NO: 105)
     CGTCAGGCTACTTTGCGTGGAGCAC (SEQ ID NO: 106)
```

```
                                    -continued
CGGTGCTGGCTAACACCAGGCCAGA

PpPK-8
                                                      (SEQ ID NO: 107)
ATCCCGGGCAACGAGAAGCATTCGAGATGGC (SEQ ID NO: 108)
GCGTTAACGAGCATCACGATACTCGGTGATTTC

PpPK-9
                                                      (SEQ ID NO: 109)
CGTGGCATCTCTCCCGATGTTCTTA (SEQ ID NO: 110)
GGCCAACTGAAGGCGTGTCATGATC

PpCK-1
                                                      (SEQ ID NO: 111)
CTCGAGGGCTCGTTCACCGTGACCT (SEQ ID NO: 112)
CGGAGGTAACAGTAGTCAGGCTGCTC

PpCK-2
                                                      (SEQ ID NO: 113)
CCGCGACCCTTCCACGCATCAGCAT (SEQ ID NO: 114)
CCTCCAGGAAGCCTGCGCCGAGAAG

PpCK-3
                                                      (SEQ ID NO: 115)
GGACATTGTCCGTGATCAGCAATCGA (SEQ ID NO: 116)
CAGCCTCTGGAACAACCAGACGCTG

PpMPK-2
                                                      (SEQ ID NO: 117)
GTCACCGCGAGGTACAAGCCACCAC (SEQ ID NO: 118)
GCAGCTCTGGAGCTCTGTACCACCT

PpMPK-3
                                                      (SEQ ID NO: 119)
ACGGCCACGTCGAGAATCTGAGCAA (SEQ ID NO: 120)
CGAAGTGCTCGCAAGCAATGCCGAA

PpMPK-4
                                                      (SEQ ID NO: 121)
ATCCCGGGCGGTCGAGTCGTATTAGGTGTTGTTTC (SEQ ID NO: 122)
GAGCTCCGGTAGGTCCGACCTCTTCAATTG

PpMPK-5
                                                      (SEQ ID NO: 123)
GGGCAACTGTCAATAGCAGACCTGGA (SEQ ID NO: 124)
GCAAGTCCCAACGAACGTGTCTCGCT

PpCPK-1
                                                      (SEQ ID NO: 125)
GCGAAGATGACGACTGCTATTGCGA (SEQ ID NO: 126)
CGTGATGACTCCAATGCTCCATACG

PpCPK-2
                                                      (SEQ ID NO: 127)
GCCAGCATCGAGGTCAGTATCCGGTGT (SEQ ID NO: 128)
GTCTGTGGCCTTCAGAGGCGCATCCTC
```

Amplification was performed under the following conditions; Denaturation, 95° C., 1 minute; annealing, 62° C., 30 seconds; extension, 72° C., 1 minute, 35 cycles; extension, 72° C., 5 minutes; hold, 4° C., forever. PCR products were run on a 1% agarose gel, stained with ethidium bromide, and visualized under UV light using the Quantity-One gel documentation system (Bio-Rad).

Expression of the transgenes was detected in the T1 transgenic line. These results indicated that the transgenes are expressed in the transgenic lines and strongly suggested that their gene product improved plant stress tolerance in the transgenic lines. In agreement with the previous statement, no expression of identical or very similar endogenous genes could be detected by this method. These results are in agreement with the data from Example 7.

Example 10

Engineering Stress-Tolerant Soybean Plants by Over-Expressing the PK-6, PK-7, PK-8, PK-9, CK-1, CK-2, CK-3, MPK-2, MPK-3, MPK-4, MPK-5, CPK-1 and CPK-2 gene The constructs pBPSJyw022, pBPSJyw012, pBPSJYW030, PBPSERG010, pBPSSY012, pBPSJyw034, pBPSSY011, pBPSSY016, pBPSJyw014, pBPSJyw025, PBPSERG009, PBPSERG019 and pBPSJyw008 are used to transform soybean as described below.

Seeds of soybean are surface sterilized with 70% ethanol for 4 minutes at room temperature with continuous shaking, followed by 20% (v/v) Clorox supplemented with 0.05% (v/v) Tween for 20 minutes with continuous shaking. Then, the seeds are rinsed 4 times with distilled water and placed on moistened sterile filter paper in a Petri dish at room temperature for 6 to 39 hours. The seed coats are peeled off, and cotyledons are detached from the embryo axis. The embryo axis is examined to make sure that the meristematic region is not damaged. The excised embryo axes are collected in a half-open sterile Petri dish and air-dried to a moisture content less than 20% (fresh weight) in a sealed Petri dish until further use.

*Agrobacterium tumefaciens* culture is prepared from a single colony in LB solid medium plus appropriate antibiotics (e.g. 100 mg/l streptomycin, 50 mg/l kanamycin) followed by growth of the single colony in liquid LB medium to an optical density at 600 nm of 0.8. Then, the bacteria culture is pelleted at 7000 rpm for 7 minutes at room temperature, and resuspended in MS (Murashige and Skoog, 1962) medium supplemented with 100 μM acetosyringone. Bacteria cultures are incubated in this pre-induction medium for 2 hours at room temperature before use. The axis of soybean zygotic seed embryos at approximately 15% moisture content are imbibed for 2 hours at room temperature with the pre-induced *Agrobacterium* suspension culture. The embryos are removed from the imbibition culture and are transferred to Petri dishes containing solid MS medium supplemented with 2% sucrose and incubated for 2 days, in the dark at room temperature. Alternatively, the embryos are placed on top of moistened (liquid MS medium) sterile filter paper in a Petri dish and incubated under the same conditions described above. After this period, the embryos are transferred to either solid or liquid MS medium supplemented with 500 mg/L carbenicillin or 300 mg/L cefotaxime to kill the *agrobacteria*. The liquid medium is used to moisten the sterile filter paper. The embryos are incubated during 4 weeks at 25° C., under 150 μmol m$^{-2}$ sec$^{-1}$ and 12 hours photoperiod. Once the seedlings produce roots, they are transferred to sterile metromix soil. The medium of the in vitro plants is washed off before transferring the plants to soil. The plants are kept under a plastic cover for 1 week to favor the acclimatization process. Then the plants are transferred to a growth room where they are incubated at 25° C., under 150 μmol m$^{-2}$ sec$^{-1}$ light intensity and 12 hours photoperiod for about 80 days.

The transgenic plants are then screened for their improved drought, salt and/or cold tolerance according to the screening method described in Example 7 to demonstrate that transgene expression confers stress tolerance.

Example 11

Engineering Stress-Tolerant Rapeseed/Canola Plants by Over-Expressing the PK-6, PK-7, PK-8, PK-9, CK-1, CK-2, CK-3, MPK-2, MPK-3, MPK-4, MPK-5, CPK-1 and CPK-2 Genes The constructs pBPSJyw022, pBPSJyw012, pBPSJYW030, PBPSERG010, pBPSSY012, pBPSJyw034, pBPSSY011, pBPSSY016, pBPSJyw014, pBPSJyw025, PBPSERG009, PBPSERG019 and pBPSJyw008 are used to transform rapeseed/canola as described below.

The method of plant transformation described herein is also applicable to *Brassica* and other crops. Seeds of canola are surface sterilized with 70% ethanol for 4 minutes at room temperature with continuous shaking, followed by 20% (v/v) Clorox supplemented with 0.05% (v/v) Tween for 20 minutes, at room temperature with continuous shaking. Then, the seeds are rinsed 4 times with distilled water and placed on moistened sterile filter paper in a Petri dish at room temperature for 18 hours. Then the seed coats are removed and the seeds are air dried overnight in a half-open sterile Petri dish. During this period, the seeds lose approx. 85% of its water content. The seeds are then stored at room temperature in a sealed Petri dish until further use. DNA constructs and embryo imbibition are as described in Example 10. Samples of the primary transgenic plants (TO) are analyzed by PCR to confirm the presence of T-DNA. These results are confirmed by Southern hybridization in which DNA is electrophoresed on a 1% agarose gel and transferred to a positively charged nylon membrane (Roche Diagnostics). The PCR DIG Probe Synthesis Kit (Roche Diagnostics) is used to prepare a digoxigenin-labelled probe by PCR, and used as recommended by the manufacturer.

The transgenic plants are then screened for their improved stress tolerance according to the screening method described in Example 7 to demonstrate that transgene expression confers drought tolerance.

Example 12

Engineering Stress-Tolerant Corn Plants by Over-Expressing the PK-6, PK-7, PK-8, PK-9, CK-1, CK-2, CK-3, MPK-2, MPK-3, MPK-4, MPK-5, CPK-1 and CPK-2Genes The constructs pBPSJyw022, PBPSJyw012, pBPSJYW030, PBPSERG010, pBPSSY012, pBPSJyw034, pBPSSY011, pBPSSY016, pBPSJyw014, pBPSJyw025, PBPSERG009, PBPSERG019 and pBPSJyw008 are used to transform corn as described below.

Transformation of maize (*Zea Mays* L.) is performed with the method described by Ishida et al. 1996. Nature Biotch 14745-50. Immature embryos are co-cultivated with *Agrobacterium tumefaciens* that carry "super binary" vectors, and transgenic plants are recovered through organogenesis. This procedure provides a transformation efficiency of between 2.5% and 20%. The transgenic plants are then screened for their improved drought, salt and/or cold tolerance according to the screening method described in Example 7 to demonstrate that transgene expression confers stress tolerance.

Example 13

Engineering Stress-Tolerant Wheat Plants by Over-Expressing the PK-6, PK-7, PK-8, PK-9, CK-1, CK-2, CK-3, MPK-2, MPK-3, MPK-4, MPK-5, CPK-1 and CPK-2

The constructs pBPSJyw022, PBPSJyw012, pBPSJYW030, PBPSERG010, pBPSSY012, pBPSJyw034, pBPSSY011, pBPSSY016, pBPSJyw014, PBPSJyw025, PBPSERG009, PBPSERG019 and pBPSJyw008 are used to transform wheat as described below.

Transformation of wheat is performed with the method described by Ishida et al. 1996 Nature Biotch. 14745-50. Immature embryos are co-cultivated with *Agrobacterium tumefaciens* that carry "super binary" vectors, and transgenic plants are recovered through organogenesis. This procedure provides a transformation efficiency between 2.5% and 20%. The transgenic plants are then screened for their improved stress tolerance according to the screening method described in Example 7 to demonstrate that transgene expression confers drought tolerance.

Example 14

Identification of Homologous and Heterologous Genes

Gene sequences can be used to identify homologous or heterologous genes from cDNA or genomic libraries. Homologous genes (e.g. full-length cDNA clones) can be isolated via nucleic acid hybridization using for example cDNA libraries. Depending on the abundance of the gene of interest, 100,000 up to 1,000,000 recombinant bacteriophages are plated and transferred to nylon membranes. After denaturation with alkali, DNA is immobilized on the membrane by e.g. UV cross linking. Hybridization is carried out at high stringency conditions. In aqueous solution hybridization and washing is performed at an ionic strength of 1 M NaCl and a temperature of 68° C. Hybridization probes are generated by e.g. radioactive ($^{32}$P) nick transcription labeling (High Prime, Roche, Mannheim, Germany). Signals are detected by autoradiography.

Partially homologous or heterologous genes that are related but not identical can be identified in a manner analogous to the above-described procedure using low stringency hybridization and washing conditions. For aqueous hybridization, the ionic strength is normally kept at 1 M NaCl while the temperature is progressively lowered from 68 to 42° C.

Isolation of gene sequences with homologies (or sequence identity/similarity) only in a distinct domain of (for example 10-20 amino acids) can be carried out by using synthetic radio labeled oligonucleotide probes. Radio labeled oligonucleotides are prepared by phosphorylation of the 5-prime end of two complementary oligonucleotides with T4 polynucleotide kinase. The complementary oligonucleotides are annealed and ligated to form concatemers. The double stranded concatemers are than radiolabeled by, for example, nick transcription. Hybridization is normally performed at low stringency conditions using high oligonucleotide concentrations.

Oligonucleotide hybridization solution:
6×SSC
0.01 M sodium phosphate
1 mM EDTA (pH 8)
0.5% SDS
100 μg/ml denatured salmon sperm DNA
0.1% nonfat dried milk During hybridization, temperature is lowered stepwise to 5-10° C. below the estimated oligonucleotide Tm or down to room temperature followed by washing steps and autoradiography. Washing is performed with low stringency such as 3 washing steps using 4×SSC. Further details are described by Sambrook, J. et al. (1989), "Molecular Cloning: A Laboratory Manual", Cold Spring Harbor Laboratory Press or Ausubel, F. M. et al. (1994) "Current Protocols in Molecular Biology", John Wiley & Sons.

Example 15

Identification of Homologous Genes by Screening Expression Libraries with Antibodies cDNA clones can be used to produce recombinant protein for example in *E. coli* (e.g. Qiagen QIAexpress pQE system). Recombinant proteins are then normally affinity purified via Ni-NTA affinity chromatography (Qiagen). Recombinant proteins are then used to produce specific antibodies for example by using standard techniques for rabbit immunization. Antibodies are affinity purified using a Ni-NTA column saturated with the recombinant antigen as described by Gu et al., 1994 BioTechniques 17:257-262. The antibody can than be used to screen expression cDNA libraries to identify homologous or heterologous genes via an immunological screening (Sambrook, J. et al. (1989), "Molecular Cloning: A Laboratory Manual", Cold Spring Harbor Laboratory Press or Ausubel, F. M. et al. (1994) "Current Protocols in Molecular Biology", John Wiley & Sons).

Example 16

In Vivo Mutagenesis

In vivo mutagenesis of microorganisms can be performed by passage of plasmid (or other vector) DNA through *E. coli* or other microorganisms (e.g. *Bacillus* spp. or yeasts such as *Saccharomyces cerevisiae*) which are impaired in their capabilities to maintain the integrity of their genetic information. Typical mutator strains have mutations in the genes for the DNA repair system (e.g., mutHLS, mutD, mutT, etc.; for reference, see Rupp, W. D. (1996) DNA repair mechanisms, in: *Escherichia coli* and *Salmonella*, p. 2277-2294, ASM: Washington.) Such strains are well known to those skilled in the art. The use of such strains is illustrated, for example, in Greener, A. and Callahan, M. (1994) *Strategies* 7:32-34. Transfer of mutated DNA molecules into plants is preferably done after selection and testing in microorganisms. Transgenic plants are generated according to various examples within the exemplification of this document.

Example 17

In vitro Analysis of the Function of *Physcomitrella* Genes in Transgenic Organisms The determination of activities and kinetic parameters of enzymes is well established in the art. Experiments to determine the activity of any given altered enzyme must be tailored to the specific activity of the wild-type enzyme, which is well within the ability of one skilled in the art. Overviews about enzymes in general, as well as specific details concerning structure, kinetics, principles, methods, applications and examples for the determination of many enzyme activities may be found, for example, in the following references: Dixon, M., and Webb, E. C., (1979) Enzymes. Longmans: London; Fersht, (1985) Enzyme Structure and Mechanism. Freeman: New York; Walsh, (1979) Enzymatic Reaction Mechanisms. Freeman: San Francisco; Price, N. C., Stevens, L. (1982) Fundamentals of Enzymology. Oxford Univ. Press: Oxford; Boyer, P. D., ed. (1983) The Enzymes, $3^{rd}$ ed. Academic Press: New York; Bisswanger, H., (1994) Enzymkinetik, $2^{nd}$ ed. VCH: Weinheim (ISBN 3527300325); Bergmeyer, H. U., Bergmeyer, J., Graβ1, M., eds. (1983-1986) Methods of Enzymatic Analysis, $3^{rd}$ ed., vol. I-XII, Verlag Chemie: Weinheim; and Ullmann's Encyclopedia of Industrial Chemistry (1987) vol. A9, Enzymes. VCH: Weinheim, p. 352-363.

The activity of proteins which bind to DNA can be measured by several well-established methods, such as DNA band-shift assays (also called gel retardation assays). The effect of such proteins on the expression of other molecules can be measured using reporter gene assays (such as that described in Kolmar, H. et al. (1995) *EMBO J.* 14:3895-3904 and references cited therein). Reporter gene test systems are well known and established for applications in both pro- and eukaryotic cells, using enzymes such as β-galactosidase, green fluorescent protein, and several others.

The determination of activity of membrane-transport proteins can be performed according to techniques such as those described in Gennis, R. B. Pores, Channels and Transporters, in Biomembranes, Molecular Structure and Function, pp. 85-137, 199-234 and 270-322, Springer: Heidelberg (1989).

Example 18

Purification of the Desired Product from Transformed Organisms

Recovery of the desired product from plant material (i.e., *Physcomitrella* patents or *Arabidopsis thaliana*), fungi, algae, ciliates, *C. ghitamicum* cells, or other bacterial cells transformed with the nucleic acid sequences described herein, or the supernatant of the above-described cultures can be performed by various methods well known in the art. If the desired product is not secreted from the cells, can be harvested from the culture by low-speed centrifugation, the cells can be lysed by standard techniques, such as mechanical force or sonification. Organs of plants can be separated mechanically from other tissue or organs. Following homogenization cellular debris is removed by centrifugation, and the supernatant fraction containing the soluble proteins is retained for further purification of the desired compound. If the product is secreted from desired cells, then the cells are removed from the culture by low-speed centrifugation, and the supernate fraction is retained for further purification.

The supernatant fraction from either purification method is subjected to chromatography with a suitable resin, in which the desired molecule is either retained on a chromatography resin while many of the impurities in the sample are not, or where the impurities are retained by the resin while the sample is not. Such chromatography steps may be repeated as necessary, using the same or different chromatography resins. One skilled in the art would be well-versed in the selection of appropriate chromatography resins and in their most efficacious application for a particular molecule to be purified. The purified product may be concentrated by filtration or ultrafiltration, and stored at a temperature at which the stability of the product is maximized.

There is a wide array of purification methods known to the art and the preceding method of purification is not meant to be limiting, Such purification techniques are described, for example, in Bailey, J. E. & Ollis, D. F. Biochemical Engineering Fundamentals, McGraw-Hill: New York (1986). Additionally, the identity and purity of the isolated compounds may be assessed by techniques standard in the art. These include high-performance liquid chromatography (HPLC), spectroscopic methods, staining methods, thin layer chromatography, NIRS, enzymatic assay, or microbiologically. Such analysis methods are reviewed in: Patek et al., 1994 *Appl. Environ. Microbiol.* 60:133-140; Malakhova et al., 1996 *Biotekhnologiya* 11:27-32; and Schmidt et al., 1998 *Bioprocess Engineer.* 19:67-70. Ulmann's Encyclopedia of Industrial Chemistry, (1996) vol. A27, VCH: Weinheim, p. 89-90, p. 521-540, p. 540-547, p. 559-566, 575-581 and p. 581-587; Michal, G. (1999) Biochemical Pathways: An Atlas of Biochemistry and Molecular Biology, John Wiley and Sons; Fallon, A. et al. (1987) Applications of HPLC in Biochemistry in: Laboratory Techniques in Biochemistry and Molecular Biology, vol. 17.

APPENDIX

```
Nucleotide sequence of the partial PK-6 from Physcomitrella patens (SEQ ID NO: 1)
GCACGAGCTCAATCCTCATGTTTCGGACTGTGGACTAGCTGCCCTTGCACCATCTGGTTCTGAACGCCAGGTGTCGGCACAAATGT TGGGCTCTTTCGGTTACAGTGCCCCTGAGTACGCCATGTCTGGAACCTATACCGTGAAGAGTGACGTCTACAGCTTCGGTGTTGTA ATGCTGGAGCTACTCACTGGGCGCAAGCCTTTAGACAGCTCAAGACCACGATCCGAGCAATCTTTGGTACGATGGGCCACACCTCA ATTGCACGACATCGACGCCCTTGCACGAATGGTGGATCCGTCGTTGAAGGGCATCTACCCTGCTAAATCACTCTCTCGGTTTGCTG ATATAGTCGCCCTTTGCGTCCAGCCGGAGCCCGAGTTCCGACCCCCGATGTCTGAAGTGGTGCAGGCACTTGTAAGGCTGATGCAG CGTGCGAGTCTGAGCAAACGCAGATCGGAGTCCGCTGTTGGGAATTGAGTCGAACGAGCCATCTGAGACTTCACCTTTGAGAGTAC TGAAGCGCCCACTAGCCTAATCGTGCATCTTTGGCCATCTCGTTTCTGAGTGGAACACAAAGCTGGGTATATTCTTTGGTGGTTAA GCAACCATTTGTCCCAATTTGAACTTCCGCTGGNGAAGGTCTGTATGTTGAGAAACGATGCAAAGCGTTCGCGTGGTNTGCTTGAA

CTTCAAA

Nucleotide sequence of the partial PK-7 from Physcomitrella patens (SEQ ID NO: 2)
GCACGAGCTCAATCCTCATGTTTCGGACTGTGGACTAGCTGCCCTTGCACCATCTGGTTCTGAACGCCAGGTGTCGGCACAAATGT TGGGCTCTTTCGGTTACAGTGCCCCTGAGTACGCCATGTCTGGAACCTATACCGTGAAGAGTGACGTCTACAGCTTCGGTGTTGTA ATGCTGGAGCTACTCACTGGGCGCAAGCCTTTAGACAGCTCAAGACCACGATCCGAGCAATCTTTGGTACGATGGGCCACACCTCA ATTGCACGACATCGACGCCCTTGCACGAATGGTGGATCCGTCGTTGAAGGGCATCTACCCTGCTAAATCACTCTCTCGGTTTGCTG ATATAGTCGCCCTTTGCGTCCAGCCGGAGCCCGAGTTCCGACCCCCGATGTCTGAAGTGGTGCAGGCACTTGTAAGGCTGATGCAG CGTGCGAGTCTGAGCAAACGCAGATCGGAGTCCGCTGTTGGGAATTGAGTCGAACGAGCCATCTGAGACTTCACCTTTGAGAGTAC TGAAGCGCCCACTAGCCTAATCGTGCATCTTTGGCCATCTCGTTTCTGAGTGGAACACAAAGCTGGGTATATTCTTTGGTGGTTAA GCAACCATTTGTCCCAATTTGAACTTCCGCTGGNGAAGGTCTGTATGTTGAGAAACGATGCAAAGCGTTCGCGTGGTNTGCTTGAA

CTTCAAA

Nucleotide sequence of the partial PK-8 from Physcomitrella patens (SEQ ID NO: 3)
GCACCAGACTATGACAAGCGCACGCCCTTGCACATCGCCGCGTCCCTGGATTGTGTCCCTGTTGCTAAAGTCCTGCTTGCGGAAGG AGCAGAGTTGAATGCAAAAGACAGGTGGGGGAAATCTCCGAGAGGCGAGGCGGAGAGTGCAGGATACATGGAGATGGTAAAGCTGT TGAAGGATTACGGGGCTGAGTCACACGCAGGTGCCCCGAGGGGCCACGTTGAGAGTCTGATTCAGGTTGCCCCTCCGTTGCCTTCT AACCGCGACTGGGAGATCGCTCCGTCGGAGATTGAACTTGATACCAGCGAGCTCATCGGCAAAGGCTCCTTTGGAGAGATTCGGAA GGCGCTTTGGCGCGGCACACCCGTCGCTGTGAAGACAATCAGACCTTCTCTGTCCAACGACAGAATGGTCATCAAGGACTTCCAGC ACGAGGTGCAATTGCTCGTAAAGGTTCGGCACCCAAACATTGTGCAGTTCCTCGGGGCTGTTACCCGTCAAAGACCTCTCATGTTA GTCACCGAGTTTCTGGCAGGGGGGCGATTTGCATCAGTTGCTGAGGAGCACCCTAAATTTGGCTCCTGACCGCATCGTGAAGTATG

CCCTCNACATAGCTCGCGGCATGTCTTACTTCACCATCGGAGCAGCCCA

Nucleotide sequence of the partial PK-9 from Physcomitrella patens (SEQ ID NO: 4)
TCCAGCCCATTTGGTTGGCCACACACAGCTGTTCATGAGTCACCCGCTTCAGGNTGAACTGAAGAAACGTAACTCCGTACGGCTAT TTTACCAAATTTTCAAGCTCGTTGTCCCGCCATGATCCAAATGGAAGCTCAGTTTGCAACATGAAGTACATTGAACACACCTACCG CCCACCAGTCAGAAGCCAGGCCATGACCTTGTCCTTGAATGATCTCGGGTGCTAAGAAATCAGCCATGCCACAGACTGTGAAAGTG CGCTCATCCGACATTTGCTTTGCAAACCGAAAATCAACCAGCTGAAGTCGTCCTTTCCGATCTATCATAAGAACATCGGGAGAGAT GCCACGATATACAACGCCATCCTTGTGCAGAAGTTCGACGGCTAATACCACGTTGGCGACCAGAAAACGAGCTGAGTTCTCGTCTA AAGGTGACCGAAGTAGAAGTTCTAGAGGCCCAGCTAACACACAATTAAGAACGAGTGCCACATTGTCACTGTCAATAGGGGTGGCC AAGAGATGCGGCACGAATGGGAAGGCCTCAGTTGCTTGAAAAGAGTTCTCTCCAATAGGACTTGGCCCTCCCGACCGAGTCTCTG
```

APPENDIX-continued

AACTTTACGTCTCTGGTACCTTTTCATGCTTATGACGTCATCTGATTTCTTGCAGAGCACCACACCGACATCACAGCAATCGGTTG
AATAGACCTGGTGCCGATTCCT

Nucleotide sequence of the partial CK-1 from *Physcomitrella patens* (SEQ ID NO: 5)
TATGCCCATCTTCTCATACTCAGACCAGATCCTCTATTTCAATTACAGAAGAAAGTTGCTTGTGCAACGTATTGAAATCATCACCG
TCATGGGCTTTCCGAGTAAAAATTCTTGTAATGGATAAAGTCATTTCTAGTCTGATCCATACAAGCTACCGACACAATGCTAGAAG
CCTTGATTTACACACTACACACTAGAGAGTCTACAACTCTTTTCCTACACTCTGCTTAGTTGCCTCATCCTCAACTCCATAAACCC
CCATTCACAATCATGTAAGACTTGAGAGAGGGAAACAGTAAGCAACCTTGTGCTATTTTAGTACCAGAGCAGAGGATGAACCACTA
GTCCTCCCAACGTAAGCCCTAATTCGCCGCAACAACCTCACGACGGAACTCCGACTTGGTCAAGGGTGGACAATATGATACATTCG
AAGGTCGATTTTGCAAATGGGACGAAGCAGCGGAATTCTGGCTGCGCACTGATTGCAGAGAGCCATTCTGGGGGAGTTGAGTATAC
ACAGTCCAGTCGTACACATGGTCGAGCTGGAATTTTTTCTGAATGAAAAGATCACGGAACAAGCTTCGGAGGTACAGTAGTCAGGC
TGCTCGTAAAAACCTANACTTCGCGGCGTGGTGCAAAAAGTCGGCAAATTGACTGGGATACCCATCACAAAGCTCCTCCCACAGTG
GGGGTCATCTTGATTTTGTTGTGCATGTACTCGTGTTGCTTCTGGTCAGTGAGGGCGTTGCCCGCCCTTCCCTTGCCATGGCAAAT
TGCCTCTTAGAAAGTACATAAGAATGTAACCCAAGTGATTCTATGTCATCTCTTCTACTGTGCTCGATTCCTCTGTGCTGATTCCT
ACTAGCGTACCGTGCCGTCCCTGTGAAGCTCTTCCTATCTCGGTAAGGGATATGCCTTCGTGTTGCCGGGTCCATGTACTCCTTTG
CCAAGCCAAAATCTATAATGAACACTTGGTTTCCTTGCCGACCGCAGCCCATGAGGAAGTTATCCGGCTTCAGGTCACGGTGAACG
AGCCCTCGAGAATGCACGTATTCCACCCGGTCAATCATTTGGTAACCGAGCATAATCACGGTCTTCAACGAAAACCTTAGCCCACA
CACCTTAAAGAGGTGCAACAGGTTCGGCCCCAATAGGTCTAGCACCATCACATTGTAGTCTTCTGCTGCTTTTCCGAACCATCTCA
TGTTGGGCACTCCCTTCCCACCCCGCAATATGTTGTACAAGCGCGACTCGTGCATTAACTCTCGTGC Nucleotide sequence of the partial CK-2 from *Physcomitrella patens* (SEQ ID NO: 6)
TTTTTTTTTTCCAATAGATTTGCATTACATAACTCCAAGTTATGATATGTACAGGTTAGCAACAAGCTAATGGCTGCAAGCAGTGA
ACATACTACCAAGGGAGAGATTCTCACTCCCTAGACTTCATCCTCGTACGTTACTTGGCAAGGATTATGGTTTAGTGATAAAAAGC
TTCACAAGCCGGCAAGCATGCTGGTTGCTTCTGCTGCAATCTAATGATTATTTCCTTAGGAATCGTATGGCAGAGAGCTACCACAC
AAAGCACTGACAATGGTTTGATGGTAACAAGATAGAGATCCATTCATTCCTAAGTATGAGAGACCTGTAGTCTTAGCACCATTGTA
GGACAGAACCACCGTTTTCCCCTCAATCAGGCTGTTGCCAAATGTAGAGCAACTCTCATCAACATAACAAGAGGGTTTGATAGAAG
ACAGAGCCCGGCTATATAACCACAAGCCCTGCGCCTACCTTATAACGGCTTGGATCCACCTCAACAGAAAGTGATTCAACTCCCTT
GATACCGGCTTTCGTAAATCCTCAAGTTGGCAGATGGCGGTTGTGGATGGCGGCTAGATATCCGCTTTGGGTCCGAAGTAACTGGA
GAGCTCCTCTGCATCCCTGCTGACGACCGTAAGCTGGTGGGACCAAGCTTACTGCTCCCTGTTCGAGAGGAATCTACGACTTCTGC
TGATGCCCCTGAGGGCCTGCTGCTAGATAGGACAGCTCGCCTGGAGGAAGAACCCCCCGAGTTGCATACGAAGATGTATGCATGC
GCTCTGGTTCTGACACAACAGCAAGAGCAGAATCCTTAGCAGATTCATCAAGTCCAGGACTTTTGTGCTTAGATGAGTCCAAAGCA
TTTGCGACCCCGGAGCCATTTGCTCCTCCAGGAAGCCTGCGCCGAGAAGGATCCATTGGTTCGGTGGGCCGCTGCAGGTCTCGGCT
TCCTGTAGCCCCAGTTCCAAGTGCACCACTGGTTTGCCCTGCAGAAGCACCCAGTCGAGTTGAACTGCCACCGGAAATTTGTGACT
GCTGGTACTTCAGAATTGTCCAGTCAAAAACGTAGTCAAATTGAAAACCTGTAAAACTATTTCCAGTTTAGGCAAACAGAAGTGGC
ACTGTAATAAACTGAAAATCATCAAACATTCACAAACTATCTGTTCGTTGATAGAGCATAGTAAAGTCTGCGCTTAGGATCAAGTC
TTGATACATTACAATGCCCAAGCAAGAGTGAAACCTACAAAAGTTACAGTTTTCATACCCTCACGAATAAAGAGGTCACGGAAGAT
TCTTTTCAAATATGCATACTCGGGTTTGTCATCAAAACGCAAGGACCGGCAGTAGTGGAAGTACGCTCGTGCGAATTCTGAAGGAT
AATTTTTACAAAGGACCTCAATGGGCGTGGACATTTGTTTTCTCACTGATCTTCTCGTACTTCTGCTTCTTGGTCCCGCTTTCAG
TCCTTGCCCATGGAAGACTGCCTCTCAGGAAGTACATGAGCACATATCCAAGAGATTCCAAATCATCTCGTCTGCTTTGCTCAATA
CCAAGATGAGTGTTGATGCTTGCATACCGAGCAGTCCCTGTCAGATTTTTGTTCTCCCTGTAGGGAATATGCTGATGCGTGGAAGG
GTCGCGGTACTTCTTGGCAAGACCAAAATCAATAATGTAGACCTGGTTTGCTCGCCTACCAAGCCCCATTAGAAAATTATCAGGCT
TGATGTCTCTATGAAGAAAGCTTTTCGCATGCACATACTCCACTCTGTTGATCAGCTGGTCAGCAAGCATGAGAACAGTCTTTAAA GAGAACTTCCGGCTGCAGAAGTTGAAAAGGTCTTCGAGACTTGGCCCCAACAGATCCAGAACCAAGACATTGTAGTCTCCTTCTAT

CCCGAACCATCCTCGTGC

Nucleotide sequence of the partial CK-3 from *Physcomitrella patens* (SEQ ID NO: 7)
CGGTGGGGCGCTCCCCAATATTTTATCCCCGGGGCTGCAGGGAATCCGGCGACCAGTNTTTGAAGGTGTCAACGCCGTGAATAGTG AGCGTTGCGTTATGAAGATTTTGAAGCCAGTAAAGAAAAAAAAGATCAAAAGAGAGATCAAGATTCTGCAAAACCTTTGTGGAGGG CCCAACATTGTGAAGCTTCTGGACATTGTCCGTGATCAGCAATCGAAGACACCCAGCCTAATTTTTGAGTATGTGAACAATACTGA TTTCAAAGTGCTCTACCCCACTCTTACAGACTTTGATATCCGATACTACATTCATGAGCTGCTCAAGGCTTTGGACTATTGCCATT CTCAAGGGATTATGCACAGGGATGTGAAGCCACACAACGTGATGATTGACCATGAGCAGCGGAAGCTTAGGCTTATTGACTGGGGA CTTGCCGAATTCTATCATCCTGGCAAAGAGTATAATGTGCGTGTTGCCTCTAGGTACTTCAAGGGTCCTGAGCTGCTGGTTGATCT TCAAGATTATGATTACTCTCGACATGTGGAGCTCTGGGGTGCATGTTTGCCGGCATGATATTTCGGAAGGAGCCATTCTTTATG GGCATGACANTTCATGATCAACTTGGTGAAGATCGCTAAGGTGTTGGGAACTTGATGAATTGAATTCCTATCTAACAAATACCGCT

AAGTGGACCCCATTGGAGCACCTGGTGGGGG

Nucleotide sequence of the partial MPK-2 from *Physcomitrella patens* (SEQ ID NO: 8)
GCACGAGGAACTAACGAATTGTCATTCTATAATCCAATAGTGTAATCACACGGGGGGAATAAGTTGCAAAACCATACAACGCCGG GATAGCGTTGTAGCCACCTAAAGAATTGAGAGTAGGCCTTACAACTTGAGATGAAGTGTGAAGTGGTACTGCACCATATCATCAGG ACCTAAGCTGCAATCCAGAGCCTCCCTCCAAATGAGATCCCTGATAGGCTCCTCCGAGATAGAGGGCTCCTCGAAGCCAAACTCGA AGGGAGATACCGAGCCAGGCTCATCGTTGATGTCATGAAGTGAAGCTTAAATAAGGGTGCGCCAAGGCAGCTTCCACTGTGATTCT TTTCGCTGGATCAAAGACCAGCATCTTTTCAACAAGATCAAGAGCAGAACGATTAATGCCTCTGAACTTCTGGGTTAAGGGAATAG GCGACTGTCGAGGCAGGTGCTTGATATACCGCCTAGCATTGTCGCTTCTCAAAAACCCAAGATCCCTATCTTCAGGAGTTCCGATG AGTTCTGTAATTAGGCGGAGCTGATGCACATAGTCTCTCCCAGGGAACAACGCAGATCGGTTAAGCAACTCCATGAAGATGCACCC CACAGACCAAATGTCAATAGCTGCAGTGTATGCTGAACAATTCAGGAGCAGCTCTGGAGCTCTGTACCACCTCGTTACAACATACT CAGTCATGAAATCCGTTTCAGAGAGAGTGCGTGCCAAGCCAAAATCTGCGATTTTCAAATCGCAATTGGCATTGACGAGAAGGTTG GTGGGCTTCAAGTCCCGGTGCAAGACGTTCGCCGAATGGATGTACTTCAAGCCCCGCAAGATTTGATACAGAAAATACTGACAGTG GTCTTCTGTGAGAGCTTGATTTGAACGAATGATCTGGTGTAGGTCCGTATCCATCAACTCGTATACAATGTACACGTCGTTGAAAT

CTCGTGC

Nucleotide sequence of the partial MPK-3 from *Physcomitrella patens* (SEQ ID NO: 9)
CGGCACCAGCCTCGCTGGAGACCGACCATCGAAGCACCTTAAGCTCGTTTTCATTCGGCATTGCTTGCGAGCACTTCGACTTCCTA GAATTTCAATAGACCTAATGGAATCGCCACTCCCTAATCTTTCCGGAGAGGCCTTATCGCCGACGGCAACTGCCGAAGACGAGATT ACTCAGATGATACTAAAAAGTGCCGCAAGGTCCGAATTAGGAATGTATGTTTCGAAGAGACAGGAATTCTATCTTCGAAGAGCGCG GAGGCGGCGTAAGTTTGCGTGGAAGCCGGTTTTGCAGAGCATCTCCGAGATGAAGCCTGTCATGGAATTCCACACTCCGATGGCTT ACCGGGATAGTGGGTCTCCGCCGAAGAACGCCTCTACCCCATCCTTACCTGGCCCGAAGAACATTTCACCGCCACGACAAGTGAGT GTCCCGCAAAGGAGCAGTCCTCCGCCGAAGAACGTCTCACCACCTCCCCAGCCCGGCATTTTGTAGCGCGGACTGCGATCGAAGTA TTCTGCTGCATCTCAGCAAGTTCAACGAAATCGAGGGCAACGCGAAATCTCTTTTATATGGCGTAGTTTGTGTCTCCGACTGGACT CCTATCTATCCCCATCGAGATAACTGATTCGGTGGATAATTTCTCCAAATTTTGGCTAACNCAAGAANCTCAAGGGCGAAT Nucleotide sequence of the partial MPK-4 from *Physcomitrella patens* (SEQ ID NO: 10)
GCACGAGGTTGGTGTAAGTTATTGATAGTGCTGTGCAATTCACAGTTTTGCTACTCCGGTAGGTCCGACCTCTTCAATTGTCAGTT TAAAAACTCTAAAAACATTTGAGAAAAGTGTTGAAAAATCTCCGTGAGGAAATTCCTTGTCGCAAGACGTGAAAAAAAGAAGAAAG AAGATGGAAATATTGTTTTGGGTATCGAAGAAGTGTTCGATGCTGTGCAATAAGGAAAGAAAAAGTGCAGGTAACATAAAAAGCTA GCATGGTGATGATAATATAAGACCCCGATTAACACACTTATGGATTGTTTCATGAGCTGCACGTTCTCAGCGACAAATGGGGCTCA TTGAGAAAACTCCACTTTCTATAAGGTTGGGAAACGAGCGTTTTTTTTTGAAGATGTTTTTTCCGTCAATCTGATTTGATATCGT TCTCAACTTGACCACATATGACTATATAAGGAAAAGGCATTGAGAAAGTGGCGGATTGGCGAGGTAGTTCGACCATGCTTTTGGTA AAGTCCCTTGAAGTTCAGTGGTGGATCAGGCTTGTGGTAGTGACAGTCTCTGCACGCCATGCGAGGCTAACTTTAAGTTACAAAAT APPENDIX-continued

```
CTTGCTCAAATGGTACTCTTCCTCGTTGTACTTTTGCAGGAACGGATGTTTAAGTAAATCAGTAGTTGATGGTCGTTCACTGGGAC

ATTTCCGGATGCAGGATTCAATAAAAGAACAAAATTCGGGGGAGAATTTGTCAGGGGATGCGGCTGCGGGCGTTGATTAACTATA

CATTCCATGAGGATGAAGAAATTTTGCCAACCCTCTTCCATTCCAGCTGGTTTGTATGGGAAGGTACCCAACGCACACTCCAAAG

AGTCAATCCTAAACTCCATAGGTCACTGTCGTATGCATACGAACGCCCCTGAAGGCGTTCTGNCGACATATATGTGCAAGTCCCAA

CGAACGTGTCTCGCTGGGCCAAGGAATGAACCAACACAGCACTGACACCAAAATCAGATATTTTGACCTCACCCTTGTGATTGATG

AGGAGGTTGGAGGGCTTTATATCACGATGTATGATGTGCCTGACTTGGTGTAGGTATTCCAATCCCTTCAGAACTTGACTAGCAAT

GACGGCCAAATACGGCTCAGGTATNTGCTTTCTGGTGC
```

Nucleotide sequence of the partial MPK-5 from *Physcomitrella patens* (SEQ ID NO: 11)
```
TCCCCGGGCTGAGGAATTCGGCACGAGCGGTTGATCCTCACCCTTGGGAAGGACCCTGGAATTGAGTAGCGTGCGGAAGCTGCATC GATCCGGAAGAGACGATGAGTAGGAGAGTGAGAAGGGAGGTCTTCGCGTCGCGGTGCCGAAGCAAGAGACTCCCGTCAGCAAATT TTTGACTGCCAGTGGAACTTTCCAGGATGATGATATCAAGCTCAACCACACCGGGCTTCGCGTCGTCTCTTCAGAACCTAACCTTC CTACGCAGACGCAGTCTAGCTCCCCAGATGGGCAACTGTCAATAGCAGACCTGGAGTTAGTGCGGTTCTTAGGAAAGGGTGCGGGT GGAACCGGTGCAGCTTGGTCCGGCACAAATGGACCAATGTCAATTATGCACTGAAGGCGATACAAATGAATATCAACGAAACAGTG AGGAAGCAGATTGTTCAGGAGCTGAAAATCAACCAAGTGACGCACCAGCAGTGCCCTTATATCGTGGAATGCTTCCACTCCTTCTA CCACAACGGCGTCATATCCATGATCCTAGAGTACATGGACAGGGGCTCGTTGTCCGACATTATTAAGCAACAAAAGCAGATACCTG

AGCCGTATTTGGCCGTCATTGCTAGTC
```

Nucleotide sequence of the partial CPK-1 from *Physcomitrella patens* (SEQ ID NO: 12)
```
GCACCAGCCGAGTCGGGCATTTTTCGTGCGGTGTTGAGGGCTGACCCGAGCTTTGAAGAAGCCCCTTGGCCTTCCATCTCTCCCGA AGCCAAGGATTTCGTGAAGCGTCTCCTGAATAAGGATATGCGGAAACGCATGACTGCTGCACAAGCTTTAACTCATCCATGGATTC GAAGTAACAACGTGAAGATACCTCTGGATATCTTAGTGTACAGACTTGTGAGGAATTATCTTCGTGCATCATCCATGAGAAAGGCT GCTTTGAAGGCCCTGTCAAAGACTTTAACCGAAGACGAGACTTTTTATCTACGTACTCAATTTATGCTGCTAGAACCAAGTAACAA CGGTCGTGTTACTTTTGAGAATTTCAGACAGGCACTGCTGAAAAATTCAACAGAGGCCATGAAAGAGTCACGGGTTTTTGAAATTC TGGAATCGATGGATGGTCTTCATTTCGCACCAGCCGAGTCGGGCATTTTTCGTGCGGTGTTGAGGGCTGACCCGAGCTTTGAAGAA GCCCCTTGGCCTTCCATCTCTCCCGAAGCCAAGGATTTCGTGAAGCGTCTCCTGAATAAGGATATGCGGAAACGCATGACTGCTGC ACAAGCTTTAACTCATCCATGGATTCGAAGTAACAACGTGAAGATACCTCTGGATATCTTAGTGTACAGACTTGTGAGGAATTATC TTCGTGCATCATCCATGAGAAAGGCTGCTTTGAAGGCCCTGTCAAAGACTTTAACCGAAGACGAGACTTTTTATCTACGTACTCAA TTTATGCTGCTAGAACCAAGTAACAACGGTCGTGTTACTTTTGAGAATTTCAGACAGGCACTGCTGAAAAATTCAACAGAGGCCAT GAAAGAGTCACGGGTTTTTGAAATTCTGGAATCGATGGATGGTCTTCATTTCAAGAAAATGGACTTTTCAGAGTTCTGTGCAGCGG

CCATTAGTGTTCTCCAGTTAGAAG
```

Nucleotide sequence of the partial CPK-2 from *Physcomitrella patens* (SEQ ID NO: 13)
```
GCACGAGCTCCTGCATCTCCCCCTCCTTCTCCTCCTCATCATTCTGGAGCCCAGCGAACTGCGATCTGAGATTCCAACTTGGAAGG GCCTCGCGTAAGCACCGGAGCTCGTTTCTTACGCTTTTGCGCCTCGCGATATTTGTACATTGTTTCCTCTGGTTTTATTCGATTCC GCCTCTGAAAATGTGAACGGGCTGCAAGCTTGGTTTTGGAGCAACGTTGGAGCATTGAAGGGTTGCGCTCGTCCCTGCCCATTCCT CGCTTCTGCTCTGGCCTATGTCATGACGACGTGAAGGAGAGGATTTGAGGGTTTTGCAAGTGATATAATCCTCCCCGAGGAGATTT CTGTGAGTTGATTAACTTGGATCAGCGACATGGGGAACACTAGTTCGAGGGGATCGAGGAAGTCCACTCGGCAGGTGAATCAGGGA GTCGGGTCTCAAGCACACCCGAGAGAAGAATGATAGCGTCAATCCAAAGACGAGACAGGGTGGTAGCGTTGGCGCAAACAACTATGG CGGAAAGCACAAGCAGTGGTGCTCAGGCCGGAGAACGATCCACCTCTGCGCCCGCTGCTCTGCCGAGGCCGAAGCCAGCATCGAGG TCAGTATCCGGTGTTTTGGGTAAGCCGCTGTCAGATATTCGTCAATCTTACATCCTGGGACGGGAGCTTGGCCGAGGGCAGTTCGG AGTGACTTACTTGTGTACTGACAAGATGACGAATGAGGCGTACGCGTGCAAGAGCATCGCCAAACGGAAACTGACCAGTAAGGAGG ATATCGAGGATGTTAAGCGGGAGGTTCAGATTATGCATCACCTGTCGGGGACACCCAATATCGTGGTGTTAAAGGATGTGTTCGAG GACAAGCATTCCGTGCATCTTGTGATGGAGCTCTGTGCAGGTGGCGACCTCTTCGATCGCATCATTGCCAAGGGGCATTACAGTGA
```

APPENDIX-continued

```
GCGCGCCGCTGCCGATATGTGCAGAGTCATCGTCAATGTGGTGCACAGATGCCACTCATTAGGGGTCTTCCATCGGGATCTCAAGC
CAGAGAATTTTCTGTTGGCCAGCAAGGCTGAGGATGCGCCTCTGAAGGCCACAGACTTCGGTCTGTCAACTTTCTTTAAGCCAGGA
GATGTGTTCCAGGATATTGTTGGAAGTGCGTATTACGTGGCCCCTGAAGTTTTGAAGAGAAGTTATGGTCCTGAGCTGATGTTTGG
AGTGCAGGCGTGATTGTGTACATTCTGCTGTGTGGTGTACCCCCCTTCTGGGCTGAAACTGAGCAGGGTATCTTTGACGCTGTGCT
CAAAGGGCACATAGACTTCGAGAACGAGTCCATGGCCGAAAATCTCCAACGGGGCTAAGGATTTGGTGAGGAAAATGCTAAACCCT
AACGTGAANAT
```

Nucleotide sequence of the full-length PK-6 from *Physcomitrella patens* (SEQ ID NO: 14)

```
ATCCCGGGTGAGTATCACTTACGGTGGCGAGGGATGGCCTTTGGGGTAGGAGCTGGTATATGCGGAGTCCAACGAAGCTTGTGCA
GGACTCTTGAGTTGTGCGTGCGAGGGCTGAGTGCCGGAAAGGTATTTTCCGACGAAGAGTCAATGTGGGCGTGGACAAACGTTTGA
AGAGATGGGTGTGGATATGAAGGCTCCGGCTAAGCAGTCGCTGGGAGTCGGACTGCTCCTGTGCTCTGTAGTGATCCTCTCGGTGG
TGAGCTCTGTGTATGGCCAAGTTCAGACAGATCCAGTGGATACTACAGGCTTAATTTCCATGTGGTATGACTTAAAACAGAGTCAA
TCTCTCACGGGGTGGACTCAAAATGCTTCTAACCCTTGTGGGCAGCAGTGGTACGGCGTTGTATGTGATGGCTCTTCTGTCACGGA
AATCAAAATTGGAAGTCGGGGTTTGAATGGAAATTTTAATCCTTCGTACTTTCAAAACGCTTTTAAAAAGCTTCGAATTTTTGATG
CTAGTAACAACAACATCGAAGGAAATATTCCTCAACAGTTTCCTACGTCTCTTACTCAAATGATATTGAACAACAATAAATTGACC
GGACGTCTCCCACAGTTTGATCAATTGGGCGCCTTGACAGTCGTAAACTTGAGCAACAACAATCTGACCGGCAACATGAACCCCAA
CTATTTCAATGTGATCGTGAATGTGGAAACCTTCGATGTTTCCTATAACCAACTTGAAGGCACTCTTCCCGACTCCATTCTAAACC
TGGCCAAGCTTCGTTTCTTGAATTTGCAGAACAATAAATTTAATGGTAAACTTCCCGACGATTTCTCTCGGCTGAAGAATTTGCAG
ACTTTCAACATTGAGAACGATCAGTTCACGGGTAATTATCCATCAGGTTTACCCAGTAATAGCAGGGTTGGAGGAAATCGTCTTAC
ATTTCCCCCACCTCCAGCCCCCGGCACACCTGCTCCCAGGACTCCTTCTCCTTCAGGAACATCGAATGGATCATCGTCGCATCTCC
CTCTAGGGGCGATCATTGGAATAGCCGCTGGTGGTGCTGTGCTGCTTTTATTACTAGCACTCGGCATCTGTTTGTGTTGTCGTAAG
CGGTCCAAGAAAGCATTGGGCGATCCAGAGGCCACGACCAGCAGCCCGAAGACCGTGGTTCACACCTCCCCTCTCCGCAAAGAGCC
AGAGTGATCCCAGCAAGAGCATAGACAAAACGACGAAACGCAACATCTTTGGCAGCAGTAAGAGTGAGAAGAAAAGTTCAAAGCAC
AGAGTATTTGAGCCAGCTCCTCTTGACAAAGGAGCAGCCGACGAACCAGTGGTGAAGGCGTCTCCGCCCGTCAAGGTACTGAAGGC
TCCTCCTTCATTTAAGGGTATCAGCGGCCTGGGTGCTGGACATTCGAAAGCAACAATTGGCAAGGTGAACAAGAGCAATATTGCAG
CCACCCCATTCTCTGTAGCGGATCTTCAGGCAGCCACAAACAGCTTCTCCCAGGATAATCTGATTGGAGAAGGGAGCATGGGTCGC
GTGTATCGTGCCGAGTTTCCCAACGGCCAGGTCTTGGCCGTGAAGAAGATCGACAGCAGCGCGTCGATGGTGCAGAATGAGGATGA
CTTCTTGAGTGTAGTAGACAGTTTGGCTCGCCTGCAGCATGCTAATACGGCTGAGCTTGTGGGTTACTGTATTGAACATGACCAAC
GGCTGTTGGTGTACGAGTACGTGAGTCGTGGAACCCTGAACGAATTGCTCCATTTCTCGGGTGAAAACACCAAGGCCCTGTCCTGG
AATGTCCGCATTAAGATTGCTTTGGGATCCGCGCGTGCTCTGGAGTACTTGCACGAAGTCTGTGCACCTCCCGTGGTTCACCACAA
CTTCAAATCTGCCAATATTCTGCTAGACGATGAGCTCAATCCTCATGTTTCGGACTGTGGACTAGCTGCCCTTGCACCATCTGGTT
CTGAACGCCAGGTGTCGGCACAAATGTTGGGCTCTTTCGGTTACAGTGCCCCTGAGTACGCCATGTCTGGAACCTATACCGTGAAG
AGTGACGTCTACAGCTTCGGTGTTGTAATGCTGGAGCTACTCACTGGGCGCAAGTCTTTAGACAGCTCAAGACCACGATCCGAGCA
ATCTTTGGTACGATGGGCCACACCTCAATTGCACGACATCGACGCCCTTGCACGAATGGTGGATCCGTCGTTGAAGGGCATCTACC
CTGCTAAATCACTCTCGGTTTGCTGATATAGTCGCCCTTTGCGTCCAGCCGGAGCCCGAGTTCCGACCCCCGATGTCTGAAGTG
GTGCAGGCACTTGTAAGGCTGATGCAGCGTGCGAGTCTGAGCAAACGCAGATCGGAGTCCGCTGTTGGAATTGAGTCGAACGAGCC
ATCTGAGACTTCACTTTGAGAGTACTGAAGCGCCCACTAGCCTAATCGTGCATCTTTGGCCATCTCGTTTCTGAGTGGAACACAAG
CTGGGTATATTCTTTGGTGGTTAAGCAACATTTTGTCACAATTTGAACTTCAGCTGGAGAAGGGTCTGTAGTGTTGAAGAAAACGA
ATGCAAAGCGTTTCGGCGTGGATGTGCTTTGAGAACTTACAAAACTCATCAAGACTTTGAAGATCTTTGTATTGCATCGAATCCTT
TCAATCAGTCTCGGGTAGGATCAGTTCCTCTGTATCGGATACCCTTTTCATCCTAACATGGGACCCTTTTAATCCAGAGGATGGAG
TGCTTGGAATAGTGACCTTGGTCGAGTTAACGC
```

Nucleotide sequence of the full-length PK-7 from *Physcomitrella patens* (SEQ ID NO: 15)
ATCCCGGGAGTGGGTGGTTGGACTGTAAGGAGCTAGCGTTTTAGAGCTACAGTGCGGTTTGCTGTGTGAGTGAGTGAGTGAGTGAG TGCGTGAGTGAGGATGTCTGTTTCTGGTATGGACAACTATGAGAAGCTGGAGAAGGTAGGAGAGGGGACTTACGGAAAGGTGTATA AGGCCCGTGATAAACGCTCCGGGCAGCTGGTGGCGCTCAAGAAGACTAGGTTGGAGATGGAGGAAGAAGGCGTCCCTTCCACCGCT TTGCGCGAAGTTTCGTTGCTACAAATGCTCTCCCACAGCATGTATATCGTCAGGCTACTTTGCGTGGAGCACGTCGAGAAAGGCAG CAAGCCCATGCTCTACTTGGTCTTTGAATATATGGACACTGATCTTAAGAAGTATATTGACTTGCACGGTCGTGGTCCGAGCGGGA AGCCTCTGCCTCCCAAAGTGGTCCAGAGTTTCATGTATCAATTGTGCACAGGGCTTGCCCACTGTCATGGCCACGGAGTAATGCAC AGGGATCTGAAACCCCAGAATTTGCTCGTCGACAAGCAAACCCGTCGTCTTAAGATTGCCGACCTTGGTCTCGGTCGGGCATTCAC AGTGCCAATGAAGAGTTACACACACGAGATTGTTACTCTATGGTACCGAGCTCCTGAAGTTCTTCTTGGAGCGACCCACTACTCTC TACCTGTGGATATCTGGTCTGTTGGGTGCATCTTCGCTGAACTCGTCCGGAAAATGCCGCTCTTCACTGGAGACTCCGAACTTCAG CAGCTTCTTCACATCTTCAGGTTGCTTGGCACCCCGAATGAGACAATCTGGCCTGGTGTTAGCCAGCACCGTGATTGGCACGAGTT TCCTCAATGGAGACCACAAGATCTGTCCCTTGCTGTTCCCGGACTCAGCGCGGTTGGCTTAGACCTTCTCGCCAAAATGTTGGTAT TCGAGCCCTCAAAGAGAATCTCTGCCAAAGCCGCCTTGAGCCATACTTATTTCGCTGATGTTGATAAGACAGCAACCTAAACACAA

CAGAACAATTCAAGAGAACCAGGTAACCTCTACCTGTCCAAGACGAAGGTTAACGC

Nucleotide sequence of the full-length PK-8 from *Physcomitrella patens* (SEQ ID NO: 16)
ATCCCGGGCAACGAGAAGCATTCGAGATGGCAGATGCGAAGGAGGAACTGGCGCTGCGCACGGAAATGCACTGGGCTGTGAGGAGT AACGACGTGGGGCTGTTAAGGACCATTCTGAAGAAAGACAAGCAGCTCGTGAATGCTGCGGACTATGACAAGCGCACGCCCTTGCA CATCGCCGCGTCCCTGGATTGTGTCCCTGTTGCTAAAGTCCTGCTTGCGGAAGGAGCAGAGTTGAATGCAAAAGACAGGTGGGGGA AATCTCCGAGAGGCGAGGCGGAGAGTGCAGGATACATGGAGATGGTAAAGCTGTTGAAGGATTACGGGGCTGAGTCACACGCAGGT GCCCCGAGGGGCCACGTTGAGAGTCTGATTCAGGTTGCCCCTCCGTTGCCTTCTAACCGCGACTGGGAGATCGCTCCGTCGGAGAT AACTTGATACCAGCGAGCTCATCGGCAAAGGCGCCTTTGGAGAGATTCGGAAGGCGCTTTGGCGCGGCACACCCGTCGCTGTGAAG ACAATCAGACCTTCTCTGTCCAACGACAGAATGGTCATCAAGGACTTCCAGCACGAGGTGCAATTGCTCGTAAAGGTTCGGCACCC AAACATTGTGCAGTTCCTCGGGGCTGTTACCCGTCAAAGACCTCTCATGTTAGTCACCGAGTTTCTGGCAGGGGGCGATTTGCATC AGTTGCTGAGGAGCAACCCTAATTTGGCTCCTGACCGCATCGTGAAGTATGCCCTCGACATACCTCGCGGCATGTCTTACCTTCAC AATCGGAGCAAGCCCATCATCCACCGCGATCTCAAACCCCGAAACATCATAGTGGACGAAGAGCATGAGCTGAAGGTCGGCGACTT CGGACTGAGCAAGCTGATCGACGTAAAGCTTATGCATGATGTGTACAAGATGACGGGGGGGACTGGGAGTTACAGATACATGGCGC CTGAGGTCTTCGAACATCAACCCTACGACAAATCCGTCGACGTGTTTTCCTTTGGAATGATATTATATGAGATGTTTGAAGGCGTC GCTCCGTTTGAGGACAAGGATGCATACGACGCTGCCACACTAGTTGCTAGAGACGATAAGCGGCCAGAGATGAGAGCCCAAACGTA TCCCCCACAAATGAAGGCATTGATCGAGGATTGCTGGTCACCGTATACCCCGAAGCGACCACCTTTCGTCGAAATCGTCAAAAAAC TCGAGGTAATGTATGAGGATTGCTTATTGAGATTGCCCAAAGACCGTCGTCATCTCCCCGACATCTTGCATCTTCGACGCAATCCT GCAGACTCGTGATTGATCGGGCCAACCTTCGAGCTGATCAATCTAAGTAGTCAATGCCTTACTGTGTCAAATTCAGCCTCCGCCGA CAGATTGGCTATGGTTCAAGTGATTGGATTCTCTGCTTCTCCAGAGCCAGAAACGACCCCCGTGCAATTTCTTCTCCGACGACCAC ATTGCGACATGAAGCACCAGACTTTGGATGTAGAAGGCATGGTCTACATGCTTTGCTGTGAGCCTTGCACGTCTCGCAGGTTGATC

TCTTTAACCAGCTTCTAGCCTTTGCAATGGCTGCATCACTTAAGAAATCACCGAGTATCGTGATGCTCGTTAACGC

Nucleotide sequence of the full-length PK-9 from *Physcomitrella patens* (SEQ ID NO: 17)
ATCCCGGGCTGTGATGTCGGTGTGGTGCTCTGCAAGAAATCAGATGACGTCATAAGCATGAAAAGGTACCAGAGACGTAAAGTTCA GAGACTCGGTCGGGAGGGCCAAGTCCTATTGGAGAGAACTCTTTTCAAGCAACTGAGGCCTTCCCCATTCGTGCCGCATCTCTTGG CCACCCCTATTGACAGTGACAATGTGGCACTCGTTCTTAATTGTGTGTTAGCTGGGCCTCTAGAACTTCTACTTCGGTCACCTTTA GACGAGAACTCAGCTCGTTTTCTGGTCGCCAACGTGGTATTAGCCGTCGAACTTCTGCACAAGGATGGCGTTGTATATCGTGGCAT CTCTCCCGATGTTCTTATGATAGATCGGAAAGGACGACTTCAGCTGGTTGATTTTCGGTTTGCAAAGCAAATGTCGGATGAGCGCA CTTTCACAGTCTGTGGCATGGCTGATTTCTTAGCACCCGAGATCATTCAAGGACAAGGTCATGGCCTGGCTTCTGACTGGTGGGCG GTAGGTGTGTTAATGTACTTCATGTTGCAAACTGAGCTTCCATTTGGATCATGGCGGGACAACGAGCTTGAAATTTTTGGTAGAAT
AGCCCGTCGGCAGCTTACGTTTCCTTCAAGTTTCAGCCCTGAAGCGGTTGACCTCATTGACAAGCTGCTGGTGGTGGACCCAACCA
AGAGACTGGGCTGTGACAGCCATGGATCGCTTGCCATAAGGGAACATCCTTGGTTCCGAGGTATAAACTGGGACAAGCACCTCGAT
TGCAGTGTGGAAGTTCCTTCAGAGATCATGACACGCCTTCAGTTGGCCATAGACTTTCTTCCCGTGGATGATAGTTATCAAGTGTT
TGATCTCCAACCCGATGAAGACGATCCACCATGGCTTGATGGCTGGTGATAGCTTGATGGCTCGTAGATCCCCCTTCTCCAAGCAT
CAATGGCACAGTACCGAATGGCTATAACAGAAGATGCACATTAAGTGCTCCATGAACAGATACCGTAGCGCTTAGGATTTTTCGGT
CGTCACAAATGACGGCTCTCTTGTGAGGTTCGAATGTTGTGTCACCCGATGATCTCTACTGGCACAAACCTCCAGGCTGAATCTTA
AGGCCAGCTGTTTTAGGTGAGACGTTTACCTTGGTTCGAACTCACGCTCGTGTTGTTAAGCGCGAGTCGATGATGTATGAAATGAC
GGTGTTCCTTGAAAGTCTTGAAAGGCAATCAATTCGCTTATGTGTGTCCCTTCCATGTGGTCATTAGGGAAGGGAACCGCTGCACT
AGTCAGTAAACGAACATGGCTTCAATTGTATAGCATAGCGGTAGAGGTTTCGTACGAAATGTGGTTGCAGTCGGTGATTATAGGCG
CATTTCTCTGAACATGCACGAGAATCGTGCTCCTGAGTCTCCATCATTCAGTGGTGCGAGCTCGC Nucleotide sequence of the full-length CK-1 from *Physcomitrella patens* (SEQ ID NO: 18)
ATCCCGGGCTCACGTAGTGCACTGAACTCTGTCTGAATTTTAGGGGATGAGAGGTAGATTTGAAGAATACTGGTGTCTAATTTTCT
GTTAATTTTTCACCCTTGAGGTAGCTCATGGATTTGGGAGGTGATCGCATGAGAGCTCCTCAGAGGCAGTCTCGAGAATATCAATA
TAGATCATTGGACGTCTTCACAGAGCAGCACGAGCAGTTGCAAAAGCAGCAGCAGCAAGATGAGTATCAGAGAACAGAATTGAAGC
TCGAGACACTGCCAAAAATGTTAAGCAATGCGACCGTGTCATCTTCCCCTCGAAGCAGTCCGGATGGACGTAGACTACGACAGTC
GCGAATAAGTATGCTGTGGAAGGTATGGTTGGGAGTGGCGCATTCTGCAAGGTGTATCAGGGCTCCGATTTGACGAACCACGAGGT
TGTGGGCATCAAGCTGGAGGATACGAGAACTGAGCACGCTCAGTTAATGCACGAGTCGCGCTTGTACAACATATTGCGGGGTGGGA
AGGGAGTGCCCAACATGAGATGGTTCGGAAAAGAGCAAGACTACAATGTGATGGTGCTAGACCTATTGGGCCGAACCTGTTGCAC
CTCTTTAAGGTGTGTGGGCTAAGGTTTTCGTTGAAGACCGTGATTATGCTCGGTTACCAAATGATTGACCGGGTGGAATACGTGCA
TTCTCGAGGGCTCGTTCACCGTGACCTGAAGCCGGATAACTTCCTCATGGGCTGCGGTCGGCAAGGAAACCAAGTGTTCATTATAG
ATTTTGGCTTGGCAAAGGAGTACATGGACCCGGCAACACGAAGGCATATCCCTTACCGAGATAGGAAGAGCTTCACAGGGACGGCA
CGGTACGCTAGTAGGAATCAGCACAGAGGAATCGAGCACAGTAGAAGAGATGACATAGAATCACTTGGTTACATTCTTATGTACTT
TCTAAGAGGCAATTTGCCATGGCAAGGGAAGGGCGGGCAACGCCTCACTGACCAGAAGCAACACGAGTACATGCACAACAAAATCA
AGATGAACACCACTGTGGAGGAGCTTTGTGATGGGTATCCCAGTCAATTTGCCGACTTTTTGCACCACGCGCGAAGTCTAGGTTTC
TACGAGCAGCCTGACTACTGTTACCTCCGAAGCTTGTTCCGTGATCTTTTCATTCAGAAAAAATTCCAGCTCGACCATGTGTACGA
CTGGACTGTGTATACTCAACTCCCCCAGAATGGCTCTCTGCAATCAGTGCGCAGCCAGAATTCCGCTGCTTCGTCCCATTTGCAAA
ATCGACCTTCGAATGTATCATATTGTCCACCCTTGACCAAGTCGGAGTTCCGTCGTGAGGTTGTTGCGGCGAATTAGGGCTTACGT
TGGGAGGACTAGTGGTTCATCCTCTGCTCTGGTACTAAAATAGCACAAGGTTGCTTACTGTTTCCCTCTCTCAAGTCTTACATGAT
TGTGAATGGGGGTTTATGGAGTTGAGGATGAGGCAACTAAGCAGAGTGTAGGAAAAGAGTTGTAGACTCTCTAGTGTGTAGTGTGT
AAATCAAGGCTTCTAGCATTGTGTCGGTAGCTTGTATGGATCAGACTAGAAATGACTTTATCCATTACAAGAATTTTTACTCGGAA
AGCCCATGACGGTGATGATTTCAATACGTTGCACAAGCAACTTTCTTCTGTAATTGAAATAGAGGATCTGGTCTGAGTATGAGAAG
ATGGGCATGTTAACGC Nucleotide sequence of the full-length CK-2 from *Physcomitrella patens* (SEQ ID NO: 19)
ATCCCGGGTTGTCGAGGACGGAGAGAAGAGAGAGAGAGAGAGAGAGGTGTTGTTTAGGGGAGGCATGCGGGAGCAGGATT
GGTGTTAAGTTCGTAAGGAGAAGGGAGTACATGCAAGTGCGTGCTTGTCGGATATCGGACAGCTGGATTTGTAAATAAGCGGAGAG
GAGGGTCGGTAATCAGGGGCGTACATCGATGGAGCCGCGTGTGGGAAACAAGTATCGGCTGGGACGGAAAATTGGGAGCGGTTCCT
TTGGGGAGATCTATCTTGGGACCAATGTTCAGACCAATGAGGAGGTCGGAATAAAGCTGGAAAGCATCAAGACGAAGCATCCACAA
TTGCTGTACGAGTCCAAGCTCTACCGGATACTACAAGGAGGAACTGGGATTCCCAATATCAGATGGTTCGGGATAGAAGGAGACTA
CAATGTCTTGGTTCTGGATCTGTTGGGGCCAAGTCTCGAAGACCTTTTCAACTTCTGCAGCCGGAAGTTCTCTTTAAAGACTGTTC APPENDIX-continued

```
TCATGCTTGCTGACCAGCTGATCAACAGAGTGGAGTATGTGCATGCGAAAAGCTTTCTTCATAGAGACATCAAGCCTGATAATTTT
CTAATGGGGCTTGGTAGGCGAGCAAACCAGGTCTACATTATTGATTTTGGTCTTGCCAAGAAGTACCGCGACCCTTCCACGCATCA
GCATATTCCCTACAGGGAGAACAAAAATCTGACAGGGACTGCTCGGTATGCAAGCATCAACACTCATCTTGGTATTGAGCAAAGCA
GACGAGATGATTTGGAATCTCTTGGATATGTGCTCATGTACTTCCTGAGAGGCAGTCTTCCATGGCAAGGACTGAAAGCGGGAACC
AAGAAGCAGAAGTACGAGAAGATCAGTGAGAAAAAAATGTCCACGCCCATTGAGGTCCTTTGTAAAAATTATCCTTCAGAATTCGC
CTCGTACTTCCACTACTGCCGGTCCTTGCGTTTTGATGACAAACCCGACTATGCATATTTGAAAAGAATCTTCCGTGACCTCTTTA
TTCGTGAGGGTTTTCAATTTGACTACGTTTTTGACTGGACAATTCTGAAGTACCAGCAGTCACAAATTTCCGGTGGCAGTTCAACT
CGACTGGGTGCTTCTGCAGGGCAAACCAGTGGTGCACTTGGAACTGGGGCTACAGGAAGCCGAGACCTGCAGCGGCCCACCGAACC
AATGGATCCTTCTCGGCGCAGGCTTCCTGGAGGAGCAAATGGCTCCGGGTCGCAAATGCTTTGGACTCATCTAAGCACAAAAGTC
CTGGACTTGATGAATCTGCTAAGGATTCTGCTCTTGCTGTTGTGTCAGAACCAGAGCGCATGCATACATCTTCGTATGCAACTCGG
GGGGGTTCTTCCTCCAGGCGAGCTGTCCTATCTAGCAGCAGGCCCTCAGGGGCATCAGCAGAAGTCGTAGATTCCTCTCGAACAGG
GAGCAGTAAGCTTGGTCCCACCAGCTTACGGTCGTCAGCAGGGATGCAGAGGAGCTCTCCAGTTACTTCGGACCCAAAGCGGATAT
CTAGCCGCCATCCACAACCGCCATCTGCCAACTTGAGGATTTACGAAGCCGCTATCAAGGGAGTTGAATCACTTTCTGTTGAGGTG
GATCAAAGCCGTTATAAGTAGGCCCAGGCTTGTGGTTATATAGCCGGGCTCTGTCTTCTATCAAACCCTCTTGTTATGTAGATGAG
AGTTGCTCTACATTTGGCAACAGCCTGATTGAGGGGAAAACGGTGGTTCTGTCCTACAATGGTGCTAAGACTACAGGTCTCTCATA
CTTAGGAATGAATGGATCTCTATCTTGTTACCATCAAACCATTGTCAGTGCTTTGTGTGGTAGCTCTCTGCCATACGATTCCTAAG
GTTAACGC
```

Nucleotide sequence of the full-length CK-3 from *Physcomitrella patens* (SEQ ID NO: 20)
```
GCGTTAACGGGAGGAAGGTCGGGGGAAGAGACGCTTGAGGCTGCTGAAAGGGGATTCACTCAGCGTCCCCACCCATTCGTCAATCT
GGCGCAGAAGATCGGAAAATCGGTCCGACGGCCAGGTGTTATGTCCAAGGCCCGGGTTTACACAGATGTGAATGTCCAACGTCCGA
AAGATTATTGGGACTACGAGCCCCTCACCGTCCAATGGGGGGACCAAGACGATTACGAGGTAGTGCGTAAGGTGGGGCGAGGGAAA
TACAGTGAGGTTTTTGAAGGTGTCAACGCCGTGAATAGTGAGCGTTGCGTTATGAAGATTTTGAAGCCAGTAAAGAAAAAAAAGAT
CAAAAGAGAGATCAAGATTCTGCAAAACCTTTGTGGAGGGCCCAACATTGTGAAGCTTCTGGACATTGTCCGTGATCAGCAATCGA
AGACACCCAGCCTAATTTTTGAGTATGTGAACAATACTGATTTCAAAGTGCTCTACCCCACTCTTACAGACTTTGATATCCGATAC
TACATTCATGAGCTGCTCAAGGCTTTGGACTATTGCCATTCTCAAGGGATTATGCACAGGGATGTGAAGCCACACAACGTGATGAT
TGACCATGAGCAGCGGAAGCTTAGGCTTATTGACTGGGGACTTGCCGAATTCTATCATCCTGGCAAAGAGTATAATGTGCGTGTTG
CCTCTAGGTACTTCAAGGGTCCTGAGCTGCTGGTTGATCTTCAAGATTATGATTACTCTCGACATGTGGAGCTTGGGGTGCATG
TTTGCCGGCATGATATTTCGGAAGGAGCCATTCTTTTATGGGCATGACAATTATGATCAACTTGTGAAGATTGCTAAGGTGTTGGG
AACTGATGAATTGAATTCCTATCTAAACAAATACCGCCTAGAGCTGGACCCCCATTTGGAAGCACTGGTTGGCAGGCATAGCAGGA
AACCTTGGTCAAAGTTCATCAATGCTGATAATCAGCGTCTGGTTGTTCCAGAGGCTGTGGATTTTTGGATAAGCTTCTACGCTAC
GATCATCAAGACAGGCTGACTGCGAAGGAAGCTATGGCACATCCCTATTTTTATCCCGTGAAGGTGTCGGAGGTTAGCAACCGTCG
CAGTGCTTGATATGAATTGATATATCTCATATGGGCTTTCTTGTGATTACGTCCCACCCGGCTACCAGGTTTCTCAGTTGTGCGAA
GCGCTGAGCTCGC
```

Nucleotide sequence of full-length MPK-2 from *Physcomitrella patens* (SEQ ID NO: 21)
```
ATCCCGGGCGAGCCATGGCGCCACTTGCTTCGGCGAATGGGACTGTTTGACTTCTTCGCTTCGCCCCCGCCTCGCCCTTCACCCTC
CTCTGTTCTTGTCACAGCCTCCTCCTCCGTCTCTGTCTGTTGGCTGGGTAAGTTTTGGGAGTGAGGAGGACGTGGTCATGGAAGAA
GAGCCCCCCTCTTTTGTAGTGGACTGTCGGTAAATTGGACCTGGAGCCTGCCGGCTCATCGCGTTTGCTTAGATTGTGGGCGGGTG
CTGTTGAAATTCCTTGAACTTGCTACTGGTCGGAAACGCTCGAATTGCGACTTTGATTGAAGGTCTGGTTGTTGCTGCGGTCGGGA
TCTTACTCAGTCTCTTCAATAGGACCTCTGAAGCAGTATGGAGACTAGCAGTGGAACTCCAGAATTGAAAGTTATAAGTACTCCGA
CCTACGGAGGTCATTACGTGAAATATGTTGTGGCGGGAACTGATTTCGAAGTCACCGCGAGGTACAAGCCACCACTTCGTCCGATT
GGGCGCGGAGCTTATGGAATCGTCTGTTCACTCTTTGATACCGTTACGGGTGAGGAGGTGGCGGTCAAAAAGATTGGAAACGCCTT
```

APPENDIX-continued

```
CGACAACAGGATCGATGCGAAGCGAACACTGCGTGAAATAAAACTCCTCCGGCATATGGATCATGAAAACGTCGTTGCCATTACAG
ACATCATTCGTCCCCCAACTAGGGAGAATTTCAACGACGTGTACATTGTATACGAGTTGATGGATACGGACCTACACCAGATCATT
CGTTCAAATCAAGCTCTCACAGAAGACCACTGTCAGTATTTTCTGTATCAAATCTTGCGGGCTTGAAGTACATCCATTCGGCGAA
CGTCTTGCACCGGGACTTGAAGCCCACCAACCTTCTCGTCAATGCCAATTGCGATTTGAAAATCGCAGATTTTGGCTTGGCACGCA
CTCTCTCTGAAACGGATTTCATGACTGAGTATGTTGTAACGAGGTGGTACAGAGCTCCAGAGCTGCTCCTGAATTGTTCAGCATAC
ACTGCAGCTATTGACATTTGGTCTGTGGGGTGCATCTTCATGGAGTTGCTTAACCGATCTGCGTTGTTCCCTGGGAGAGACTATGT
GCATCAGCTCCGCCTAATTACAGAACTCATCGGAACTCCTGAAGATAGGGATCTTGGGTTTTTGAGAAGCGACAATGCTAGGCGGT
ATATCAAGCACCTGCCTCGACAGTCGCCTATTCCCTTAACCCAGAAGTTCAGAGGCATTAATCGTTCTGCTCTTGATCTTGTTGAA
AAGATGCTGGTCTTTGATCCAGCGAAAAGAATCACAGTGGAAGCTGCCTTGGCGCACCCTTATTTAGCTTCACTTCATGACATCAA
CGATGAGCCTGCCTCGGTATCTCCCTTCGAGTTTGACTTCGAGGAGCCCCTATCTCGGAGGAGCATATCAAGGATCTCATTTGGA
GGGAGGCTCTGGATTGCAGCTTAGGTCCTGATGATATGGTGCAGTAACTTCACACTTCATCTCAAGTTGTAAGGCCTACTCTCAAT
TCTTTAGGTGGCTACAACGCTATCCCGGCGTTGTATGGTTTTGCAACTTATTCCCCCCGTGTGATTACACTATTGGATTATAGAA
TGACAATTCGTTAGTTCTTTTCCCTGGCGCTATATCTTTGTCTGCACATTTCATCCAGCAGACATTGTTGCTCGGCGTTAACGC
```
Nucleotide sequence of full-length MPK-3 from Physcomitrella patens (SEQ ID NO: 22)
```
ATCCCGGGCTTGTATTGGCTCGGATAATTTATGTTGACAATTGATTTGTGAGGCTTCGTATTGAGTCAGCGAGCAGGCTGAGAGTT
CGGCAGCGAAGTTACACTCGACCTGGCTGAAATTTGGAATTGAAGCGCGTGAAGCTTCATCTGTGATTTTGGAGGTTGTTTGACTG
ATGAGAAGAGGTCTCTGAGCTGAGAATGTTTGCAATTTAGGGGCACCACCGGTTTGTTGGAGTCCCTTGCCACTTATTACAATTGT
TGGTTTACAAGCTCGACGAGTTTCAATCGAACGTAGAGTTTTAGTCGGGTCGAGGATCTATGTATCCGCTCAGCGGAGAAGAGAGC
CTGATGTTGCCGAAGCGATCGTGTGGGATTTGACTAGAAAGAGGTGGACCGCATCAGAACTATTTATTCCTTGTGAGGGAAGGATC
GAGGTTCCAATGGGTCTCACTCCGTTTTCTTGTGTCACGGTTCAAGGTTATGTCCGGGTGGTCTACCCCGACGGCCACGTCGAGAA
TCTGAGCAAATCTTGTAGCGTGCACGATCTTCTTCTGGGTAATCCAGACTACTATGTCTGCGGTAGCACCCCTTACACAATCACCA
ATCGTATGGCAGCGGAAGAGGTGCTCGAGTATGGGGTGACCTACTTCGTTTGCGCAACGCCAAATGCCCAACCTTTCTTAGAACGT
CAGCCGAAGGTAGTACATCGAGGATCCAAGATTTTGCCACGATTTTCCAAACATGGGGTCCATGTGCGGGAGTTGCGAAGCCCGAC
GCATGGGAGCCAACAGTCACGGAAGGTTTTTGATTATCATTCAGTAACGATGCAGCAGCTTGAATCCATACGAAACGAGGGCCCAG
AGCCTCACCTCGCTGGAGACCGACCATCGAAGCACCTTAAGCTCGTTTTCATTCGGCATTGCTTGCGAGCACTTCGACTTCCTAGA
ATTTCAATAGACCTAATGGAATCGCCACTCCCTAATCTTTCCGGAGAGGCCTTATCGCCGACGGCAACTGCCAAAGACGAGATTAC
TCAGATGATACTAAAAAGTGCCGCAAGGTCCGAATTAGGAATGTATGTTTCGAAGAGACAGGAATTCTATCTTCGAAGAGCGCGTA
GGCGGCGTAAGTTTGCGTGGAAGCCGGTTTTGCAGAGCATCTCCGAGATGAAGCCTGTCATGGAATTCCACACTCCGATGGCTTAC
CGGGATAGTGGGTCTCCGCCGAAGAACGCCTCTACCCCATCCTTACCTGGCCCGAAGAACATTTCACCGCCACGACAAGTGAGTGT
CCCGCAAAGGAGCAGTCCTCCGCCGAAGAACGTCTCACCACCTCCCCAGCCCGCATTTGTAGCGCGGACTGCGTCGAAGTATTCTG
CTGCATCTCAGCAAGTTCAACGAAATCGAGGCAACGCGAAATCTCTTTATATGGCGTAGTTTGTGTCTCGACTGAACTCCTATCTA
TTCCCCCATCGAGATAACTGCATTCGTTGGATAAATTTCTCCAACATTTTTTGCTCTTCATCCTCAAGCAGCTCCTCAATGGCCAGT
AATATGTTACGACATTGTGCACAACTCCAATTACGTAGCGTTATTCTGTAACCCACGTTCATCGAGGTATCAAGGAATGGCGCAGT
AAGCACTGCTACTTTGTGCTTTGGTATCCCGTTGTGACGAGATGTCATGTCGCACCGTGCCTATCAGTGGGATTTTCTTGAGCGCA
GATCTTGCTTCCGCAGTTTGTTTCATAACGTTTTGGTTCGTAGGGGCCTAGACGGTACTATCAAGCAATGAGAAGTGTGCTGGTG
TGGATTTGACAGCAATCTTTTGGAGGATTGTCTTTCCTATGTAGAACATAGCGAGGACACTTGCGCCTGGTGGGCACATCCCATAG
AACATAGTGCTTCACTTCTGGGTTGTTCACCACTAGGATCATATGACCTTCTCATCTATTTTCGGGCTTTGTTTCGAGCTCATGTA
CCATCGACTAGCGTCACTTTGACTGCGGTGATAATCGTTTGTCAATTTAGTGGAGCTTTGTAGATGATAGATGCCATTTGTACAGT
AGCTTGGATGCTGTTTACAAGATAGCGGCAGCTAGAAGCCTTAAACCCTTTAGCTACCATGTATTATTTAAACCTATATGAAGTGAA
CGGCTGTGCAGATATTGCCGTTAACGC
```

APPENDIX-continued

Nucleotide sequence of full-length MPK-4 from *Physcomitrella patens* (SEQ ID NO: 23)
ATCCCGGGCGGTCGAGTCGTATTAGGTGTTGTTTCATTGTAAGGGTTCGGAAGCACGGGCACGGCGTATATACCGTTCCCCTTGA ACGTTGATCTCACCTTTGGAAGACCTGAATTGAGTAGCGTGCGGAAGCTGCATCGATCCGGAAGAGACGATGAGTAGGAGAGTGAG AAGGGGAGGTCTTCGCGTCGCGGTGCCGAAGCAAGAGACTCCCGTCAGCAAATTTTTGACTGCCAGTGGAACTTTCCAGGATGATG ATATCAAGCTCAACCACACCGGGCTTCGCGTCGTCTCTTCAGAACCTAACCTTCCTACGCAGACGCAGTCTAGCTCCCCAGATGGG CAACTGTCAATAGCAGACCTGGAGTTAGTGCGGTTCTTGGGAAAGGGTGCGGGTGGAACCGTGCAGCTTGTCCGGCACAAATGGAC CAATGTCAATTATGCACTGAAGGCGATACAAATGAATATCAACGAAACAGTGAGGAAGCAGATTGTTCAGGAGCTGAAAATCAACC AAGTGACGCACCAGCAGTGCCCTTATATCGTGGAATGCTTCCACTCCTTCTACCACAACGGCGTCATATCCATGATCCTAGAGTAC ATGGACAGGGGCTCGTTGTCCGACATTATTAAGCAACAAAAGCAGATACCTGAGCCGTATTTGGCCGTCATTGCTAGTCAAGTTCT GAAGGGATTGGAATACCTACACCAAGTCAGGCACATCATACATCGTGATATAAAGCCCTCCAACCTCCTCATCAATCACAAGGGTG AGGTCAAAATATCTGATTTTGGTGTCAGTGCTGTGTTGGTTCATTCCTTGGCCCAGCGAGACACGTTCGTTGGGACTTGCACATAT ATGTCGCCAGAACGCCTTCAGGGGCGTTCGTATGCATACGACAGTGACCTATGGAGTTTAGGATTGACTCTTTTGGAGTGTGCGTT GGGTACCTTCCCATACAAACCAGCTGGAATGGAAGAGGGTTGGCAAAATTTCTTCATCCTCATGGAATGTATAGTTAATCAACCCC CCGCAGCCGCATCCCCTGACAAATTCTCCCCCGAATTTTGTTCTTTTATTGAATCCTGCATCCGGAAATGTCCCAGTGAACGACCA TCAACTACTGATTTACTTAAACATCCGTTCCTGCAAAAGTACAACGAGGAAGAGTACCATTTGAGCAAGATTTTGTAACTTAAAGT TAGCCTCGCATGGCGTGCAGAGACTGTCACTACCACAAGCCTGATCCACCACTGAACTTCAAGGGACTTTACCAAAAGCATGGTCG AACTACCTCGCCAATCCGCCACTTTCTCAATGCCTTTTCCTTATATAGTCATATGTGGTCAAGTTGAGAACGATATCAAATCAGAT TGACGGAAAAAACATCTTCAACGCCGTTTCCCAACCTTATAGAAAGTGGAGTTTTCTCAATGAGCCCCATTTGTCGCTGAGAACGT GCAGCTCATGAAACAATCCATAAGTGTGTTAATCGGGGTCTTATATTATCATCACCATGCTAGCTTTTTATGTTACCTGCACTTTT TCTTTCCTTATTGCACAGCATCGAACACTTCTTCGATACCCAAAACAATATTTCCATCTTCTTTCTTCTTTTTTTCACGTCTTGCG ACAAGGAATTTCCTCACGGAGATTTTTCAACACTTTTCTCAAATGTTTTTAGAGTTTTTAAACTGACAATTGAAGAGGTCGGACCT

ACCGGACTCGC

Nucleotide sequence of full-length MPK-5 from *Physcomitrella patens* (SEQ ID NO: 24)
ATCCCGGGAGAGGCTGATCTGATGCTACAGTTTCGTGTGCAGCTAGTCTTTAGAGATTCGGGCAACGCACTTGTTGAAGATCGGAA ACTTTCAAAATCGGTCGAGTCGTATTAGGTGTTGTTTCATTGTAAGGGTTCGGAAGCACGGGCACGGCGTATATACCGTTCCCCT TGAACGTTGATCTCACCTTTGGAAGACCTGAATTGAGTAGCGTGCGGAAGCTGCATCGATCCGGAAGAGACGATGAGTAGGAGAGT GAGAAGGGGAGGTCTTCGCGTCGCGGTGCCGAAGCAAGAGACTCCCGTCAGCAAATTTTTGACTGCCAGTGGAACTTTCCAGGATGA TGATATCAAGCTCAACCACACCGGGCTTCGCGTCGTCTCTTCAGAACCTAACCTTCCTACGCAGACGCAGTCTAGCTCCCCAGATG GGCAACTGTCAATAGCAGACCTGGAGTTAGTGCGGTTCTTAGGAAAGGGTGCGGGTGGAACCGTGCAGCTTGTCCGGCACAAATGG ACCAATGTCAATTATGCACTGAAGGCGATACAAATGAATATCAACGAAACAGTGAGGAAGCAGATTGTTCAGGAGCTGAAAATCAA CCAAGTGACGCACCAGCAGTGCCCTTATATCGTGGAATGCTTCCACTCCTTCTACCACAACGGCGTCATATCCATGATCCTAGAGT ACATGGACAGGGGCTCGTTGTCCGACATTATTAAGCAACAAAAGCAGATACCTGAGCCGTATCTGGCCGTCATTGCTAGTCAAGTT CTGAAGGGATTGGAATACCTACACCAAGTCAGGCACATCATACATCGTGATATAAAGCCCTCCAACCTCCTCATCAATCACAAGGG TGAGGTCAAAATATCTGATTTTGGTGTCAGTGCTGTGTTGGTTCATTCCTTGGCCCAGCGAGACACGTTCGTTGGGACTTGCACAT ATATGTCGCCAGAACGCCTTCAGGGGCGTTCGTATGCATACGACAGTGACCTATGGAGTTTAGGATTGACTCTTTTGGAGTGTGCG TTGGGTACCTTCCCATACAAACCAGCTGGAATGGAAGAGGGTTGGCAAAATTTCTTCATCCTCATGGAATGTATAGTTAATCAACC CCCGCAGCCGCATCCCCTGACAAATTCTCCCCCGAATTTTGTTCTTTTATTGAATCCTGCATCCGGAAATGTCCCAGTGAACGAC CATCAACTACTGATTTACTTAAACATCCGTTCCTGCAAAAGTACAACGAGGAAGAGTACCATTTGAGCAAGATTTTGTAACTTAAA GTTAGCCTCGCATGGCGTGCAGAGACTGTCACTACCACAAGCCTGATCCACCACTGAACTTCAAGGGACTTTACCAAAAGCATGGT

CGAACTACCTCGCCAATCCGCCAGAGCTCA

APPENDIX-continued

Nucleotide sequence of full-length CPK-1 from *Physcomitrella patens* (SEQ ID NO: 25)
ATCCCGGGTGTAGGCGGGCGAGGTTCGATGCAATGGGGCAGTGTTATGGAAAGTTTGATGATGGAGGCGAAGGGGAGGATTTGTTT GAGCGGCAGAAAGTGCAGGTTTCTAGGACGCCAAAGCATGGATCGTGGAGCAATAGCAACCGAGGGAGCTTCAACAATGGCGGGGG GGCCTCGCCTATGAGAGCCAAGACGTCGTTCGGGAGCAGCCATCCGTCCCCGCGGCATCCCTCAGCTAGTCCGCTCCCTCACTACA CGAGCTCCCCAGCGCCTTCGACCCCGCGACGGAACATTTTCAAAAGGCCTTTTCCTCCTCCTTCTCCCGCGAAGCACATTCAGTCC AGTCTCGTGAAACGGCATGGCGCGAAGCCGAAAGAAGGAGGGGCGATCCCTGAGGCTGTCGATGGTGAGAAGCCCTTGGATAAGCA TTTCGGCTATCACAAGAACTTCGCTACTAAGTATGAGCTGGGGCATGAAGTCGGTCGCGGGCACTTCGGTCACACATGTTACGCGA AAGTACGGAAGGGCGAGCATAAGGGACAAGCCGTGGCAGTGAAGATAATCTCGAAAGCGAAGATGACGACTGCTATTGCGATCGAG GACGTGGGACGAGAAGTGAAAATTTTGAAGGCTCTGACGGGACACCAGAATTTGGTTCGATTCTACGATTCCTGCGAGGACCATCT AAATGTGTACATTGTTATGGAATTATGTGAAGGAGGTGAATTATTGGATCGAATTTTGTCTCGGGGAGGGAAGTACTCGGAGGAAG ACGCCAAGGTTGTTGTGCGGCAGATTTTGAGCGTTGTTGCGTTTTGTCACCTGCAAGGCGTTGTTCACCGAGATCTTAAGCCTGAG AATTTTCTGTTTACCACGAAGGATGAATATGCTCAGCTTAAGGCCATTGATTTTGGATTGTCAGATTTCATCAAACCCGATGAAAG ACTGAACGATATCGTTGGAAGCGCATACTACGTTGCGCCGGAGGTATTGCATAGGTTATATTCAATGGAAGCTGACGTATGGAGCA TTGGAGTCATCACGTACATTTTGTTATGTGGTAGTCGACCGTTTTGGGCGCGGACCGAGTCGGGCATTTTTCGTGCGGTGTTGAGG GCTGACCCGAGCTTTGAAGAAGCCCCTTGGCCTTCCATCTCTCCCGAAGCCAAGGATTTCGTGAAGCGTCTCCTGAATAAGGATAT GCGGAAACGCATGACTGCTGCACAAGCTTTAACTCATCCATGGATTCGAAGTAACAACGTGAAGATACCTCTGGATATCTTAGTGT ACAGACTTGTGAGGAATTATCTTCGTGCATCATCCATGAGAAAGGCTGCTTTGAAGGCCCTGTCAAAGACTTTAACCGAAGACGAG ACTTTTTATCTACGTACTCAATTTATGCTGCTAGAACCAAGTAACAACGGTCGTGTTACTTTTGAGAATTTCAGACAGGCACTGCT GAAAAATTCAACAGAGGCCATGAAAGAGTCACGGGTTTTTGAAATTCTGGAATCGATGGATGGTCTTCATTTCAAGAAAATGGACT TTTCAGAGTTCTGTGCAGCGGCCATTAGTGTTCTCCAGTTAGAAGCCACAGAACGATGGGAGCAGCATGCTCGCGCAGCTTACGAC ATATTTGAGAAAGAGGGTAACCGAGTCATTTATCCTGATGAACTTGCGAAAGAGATGGGACTAGCACCAAATGTACCAGCCCAAGT GTTTCTAGATTGGATTAGACAGTCTGATGGTCGGCTGAGTTTCACTGGGTTCACCAAGCTGCTACATGGAATTTCCAGCCGTGCTA TCAAAAATCTCCAGCAGTGATTCTTTGCATCGTACAGTTCGGAATGGAGTTTTTAAGCTCTTTTAGTTTCACTTCCGTCTTCAACT GCTGCTTCGCCTCGTCTCTGAGCTGTGATAGCGTATCTCAAGCATATGCACAACTCGCATTTTTGCTGAAGTGATTTGTCACCTCA CATTAGTCGGGCCTCTGGAACTTTCACTTATTTGGATTATTTATGTAGAAGTCCAGATCAAAAAGCGAAAAGGAATGGCTAGATAT TGTCACAAGAAGTAACATAGTCAAATTCAGGAGCACTTAAGCACACATTGAGTGCTTTTTATTGGAATTCTTAGATATGGAACTGA TGTTTCCAAGGGAAGGGTCTATGAGGCAGAGAGTGGAATGTATAGACTGGCATATGGTTAAGTGATCATTGGACTGCCGTTCTACT

CCGGTTGTCGTTAACGC

Nucleotide sequence of full-length CPK-2 from *Physcomitrella patens* (SEQ ID NO: 26)
ATCCCGGGCGAACTGCGATCTGAGATTCCAACTTGGAAGGGCCTCGCGTAAGACCGGATCTCGTTTCTTACGCTTTTGCGCCTCGC GATATTTGTACATTGTTTCCTCTGGTTTTATTCGATTCCGCCTCTGAAAATGTGAACGGGCTGCAAGCTTGGTTTTGGAGCAACGT TGGAGCATTGAAGGGTTGCGCTCGTCCCTGCCCATTCCTCGCTTCTGCTCTGGCCTATGTCATGACGACGTGAAGGAGAGGATTTG AGGGTTTTGTAAGTGATATAATCCTCCCCGAGGAGATTTCTGTGAGTTGATTAACTTGGATCAGCGACATGGGAACACTAGTTCG AGGGGATCGAGGAAGTCCACTCGGCAGGTGAATCAGGGAGTCGGGTCTCAAGACACCCGAGAGAAGAATGATAGCGTCAATCCAAA GACGAGACAGGGTGGTAGCGTTGGCGCAAACAACTATGGCGGAAAGCCAAGCAGTGGTGCTCAGGCCGGAGAACGATCCACCTCTG CGCCCGCTGCTCTGCCGAGGCCGAAGCCAGCATCGAGGTCAGTATCCGGTGTTTTGGGTAAGCCGCTGTCAGATATTCGTCAATCT TACATCCTGGGACGGGAGCTTGGCCGAGGGCAGTTCGGAGTGACTTACTTGTGTACTGACAAGATGACGAATGAGGCGTACGCGTG CAAGAGCATCGCCAAACGGAAACTGACCAGTAAGGAGGATATCGAGGATGTTAAGCGGGAGGTTCAGATTATGCATCACCTGTCGG GGACACCCAATATCGTGGTGTTAAAGGATGTGTTCGAGGACAAGCATTCCGTGCATCTTGTGATGGAGCTCTGTGCAGGTGGCGAG CTCTTCGATCGCATCATTGCCAAGGGGCATTACAGTGAGCGCGCCGCTGCCGATATGTGCAGAGTCATCGTCAATGTGGTGCACAG ATGCCACTCATTAGGGGTCTTCCATCGGGATCTCAAGCCAGAGAATTTTCTGTTGGCCAGCAAGGCTGAGGATGCGCCTCTGAAGG APPENDIX-continued

```
CCACAGACTTCGGTCTGTCAACTTTCTTTAAGCCAGGAGATGTGTTCCAGGATATTGTTGGAAGTGCGTATTACGTGGCCCCTGAA
GTTTTGAAGAGAAGTTATGGTCCTGAAGCTGATGTTTGGAGTGCAGGCGTGATTGTGTACATTCTGCTGTGTGGTGTACCCCCCTT
CTGGGCTGAAACTGAGCAGGGTATCTTTGACGCTGTGCTCAAAGGGCACATAGACTTCGAGAACGATCCATGGCCGAAAATCTCCA
ACGGGGCTAAGGATTTGGTGAGGAAAATGCTAAACCCTAACGTGAAGATACGTCTGACGGCACAGCAGGTGTTGAACCATCCATGG
ATGAAGGAAGATGGTGATGCTCCAGACGTGCCACTCGACAATGCGGTGTTGACCAGACTGAAAAATTTCTCAGCCGCCAACAAGAT
GAAAAAGCTGGCGCTGAAGGTGATTGCAGAGAGTCTGTCGGAGGAAGAGATCGTGGGGTTGAGGGAGATGTTCAAATCCATAGATA
CAGACAACAGCGGCACGGTGACGTTCGAGGAGCTTAAGGAAGGGTTGCTGAAGCAGGGCTCAAAACTTAATGAATCGGACATCAGG
AAACTAATGGAAGCTGCAGATGTCGATGGAAACGGCAAGATCGACTTCAACGAGTTCATATCGGCAACAATGCACATGAACAAGAC
GGAGAAAGAGGATCACCTTTGGGCAGCATTCATGCATTTCGACACGGACAATAGCGGGTATATCACCATCGACGAGCTTCAGGAAG
CAATGGAGAAGAATGGAATGGGAGATCCTGAGACCATCCAAGAGATCATCAGCGAGGTGGACACAGACAACGACGGAAGAATAGAC
TACGACGAGTTCGTAGCCATGATGCGCAAGGGCAATCCTGGCGCTGAAAACGGAGGAACGGTGAACAAGCCCAGACACAGGTAGTA
GCTCCTGGTTGCCAATTTGACGACGGGTTTGGCAAGGCAACAGTAGTTGTTGTTAGCTTTCAGATTCAGGTTCGGTATTGTTCATG
CCCTCCTTTGTCTCGAACAATGGACTCTAGGCCTTTCCAATGGAAAAGCTATTCCAACAGGGTTTGCATAACGTGTAGTAGAATGA
AGCATTGCCTGGGGGGTGTACAGTGCCTGTGATCTTGTGGAGTTCTCGTAGGATGGCTTCGGTTGGATCTCGTTAACGC
```

Deduced amino acid sequence of PK-6 from *Physcomitrella patens* (SEQ ID NO: 27)
MGVDMKAPAKQSLGVGLLLCSVVILSVVSSVYGQVQTDPVDTTGLISMWYDLKQSQSLTGWTQNASNPCGQQWYGVVCDGSSVTEI
KIGSRGLNGNFNPSYFQNAFKKLRIFDASNNNIEGNIPQQFPTSLTQMILNNNKLTGGLPQFDQLGALTVVNLSNNNLTGNMNPNY
FNVIVNVETFDVSYNQLEGTLPDSILNLAKLRFLNLQNNKFNGKLPDDFSRLKNLQTFNIENDQFTGNYPSGLPSNSRVGGNRLTF
PPPPAPGTPAPRTPSPSGTSNGSSSHLPLGAIIGIAAGGAVLLLLLALGICLCCRKRSKKALGDPEATTSSRRPWFTPPLSAKSQS
DPSKSIDKTTKRNIFGSSKSEKKSSKHRVFEPAPLDKGAADEPVVKASPPVKVLKAPPSFKGISGLGAGHSKATIGKVNKSNIAAT
PFSVADLQAATNSFSQDNLIGEGSMGRVYRAEFPNGQVLAVKKIDSSASMVQNEDDFLSVVDSLARLQHANTAELVGYCIEHDQRL
LVYEYVSRGTLNELLHFSGENTKALSWNVRIKIALGSARALEYLHEVCAPPVVHHNFKSANILLDDELNPHVSDCGLAALAPSGSE
RQVSAQMLGSFGYSAPEYAMSGTYTVKSDVYSFGVVMLELLTGRKSLDSSRPRSEQSLVRWATPQLHDIDALARMVDPSLKGIYPA
KSLSRFADIVALCVQPEPEFRPPMSEVVQALVRLMQRASLSKRRSESAVGIESNEPSETSL Deduced amino acid sequence of PK-7 from *Physcomitrella patens* (SEQ ID NO: 28)
MSVSGMDNYEKLEKVGEGTYGKVYKARDKRSGQLVALKKTRLEMEEEGVPSTALREVSLLQMLSHSMYIVRLLCVEHVEKGSKPML
YLVFEYMDTDLKKYIDLHGRGPSGKPLPPKVVQSFMYQLCTGLAHCHGHGVMHRDLKPQNLLVDKQTRRLKIADLGLGRAFTVPMK
SYTHEIVTLWYRAPEVLLGATHYSLPVDIWSVGCIFAELVRKMPLFTGDSELQQLLHIFRLLGTPNETIWPGVSQHRDWHEFPQWR
PQDLSLAVPGLSAVGLDLLAKMLVFEPSKRISAKAALSHTYFADVDKTAT Deduced amino acid sequence of PK-8 from *Physcomitrella patens* (SEQ ID NO: 29)
MADAKEELALRTEMHWAVRSNDVGLLRTILKKDKQLVNAADYDKRTPLHIAASLDCVPVAKVLLAEGAELNAKDRWGKSPRGEAES
AGYMEMVKLLKDYGAESHAGAPRGHVESLIQVAPPLPSNRDWEIAPSEIELDTSELIGKGAFGEIRKALWRGTPVAVKTIRPSLSN
DRMVIKDFQHEVQLLVKVRHPNIVQFLGAVTRQRPLMLVTEFLAGGDLHQLLRSNPNLAPDRIVKYALDIARGMSYLHNRSKPIIH
RDLKPRNIIVDEEHELKVGDFGLSKLIDVKLMHDVYKMTGGTGSYRYMAPEVFEHQPYDKSVDVFSFGMILYEMFEGVAPFEDKDA
YDAATLVARDDKRPEMRAQTYPPQMKALIEDCWSPYTPKRPPFVEIVKKLEVMYEDCLLRLPKDRRHLRDILHLRRNPADS Deduced amino acid sequence of PK-9 from *Physcomitrella patens* (SEQ ID NO: 30)
MKRYQRRKVQRLGREGQVLLERTLFKQLRPSPFVPHLLATPIDSDNVALVLNCVLAGPLELLLRSPLDENSARFLVANVVLAVELL
HKDGVVYRGISPDVLMIDRKGRLQLVDFRFAKQMSDERTFTVCGMADFLAPEIIQGQGHGLASDWWAVGVLMYFMLQTELPFGSWR
DNELEIFGRIARRQLTFPSSFSPEAVDLIDKLLVVDPTKRLGCDSHGSLAIREHPWFRGINWDKHLDCSVEVPSEIMTRLQLAIDF
LPVDDSYQVFDLQPDEDDPPWLDGW Deduced amino acid sequence of CK-1 from *Physcomitrella patens* (SEQ ID NO: 31)
MDLGGDRMRAPQRQSREYQYRSLDVFTEQHEQLQKQQQQDEYQRTELKLETLPKMLSNATVSSSPRSSPDGRRLRTVANKYAVEGM APPENDIX-continued

```
VGSGAFCKVYQGSDLTNHEVVGIKLEDTRTEHAQLMHESRLYNILRGGKGVPNMRWFGKEQDYNVMVLDLLGPNLLHLFKVCGLRF

SLKTVIMLGYQMIDRVEYVHSRGLVHRDLKPDNFLMGCGRQGNQVFIIDFGLAKEYMDPATRRHIPYRDRKSFTGTARYASRNQHR

GIEHSRRDDIESLGYILMYFLRGNLPWQGKGGQRLTDQKQHEYMHNKIKMNTTVEELCDGYPSQFADFLHHARSLGFYEQPDYCYL

RSLFRDLFIQKKFQLDHVYDWTVYTQLPQNGSLQSVRSQNSAASSHLQNRPSNVSYCPPLTKSEFRREVVAAN

Deduced amino acid sequence of CK-2 from Physcomitrella patens (SEQ ID NO: 32)
MEPRVGNKYRLGRKIGSGSFGEIYLGTNVQTNEEVGIKLESIKTKHPQLLYESKLYRILQGGTGIPNIRWFGIEGDYNVLVLDLLG PSLEDLFNFCSRKFSLKTVLMLADQLINRVEYVHAKSFLHRDIKPDNFLMGLGRRANQVYIIDFGLAKKYRDPSTHQHIPYRENKN LTGTARYASINTHLGIEQSRRDDLESLGYVLMYFLRGSLPWQGLKAGTKKQKYEKISEKKMSTPIEVLCKNYPSEFASYFHYCRSL RFDDKPDYAYLKRIFRDLFIREGFQFDYVFDWTILKYQQSQISGGSSTRLGASAGQTSGALGTGATGSRDLQRPTEPMDPSRRRLP GGANGSGVANALDSSKHKSPGLDESAKDSALAVVSEPERMHTSSYATRGGSSSRRAVLSSSRPSGASAEVVDSSRTGSSKLGPTSL

RSSAGMQRSSPVTSDPKRISSRHPQPPSANLRIYEAAIKGVESLSVEVDQSRYK

Deduced amino acid sequence of CK-3 from Physcomitrella patens (SEQ ID NO: 33)
MSKARVYTDVNVQRPKDYWDYEALTVQWGDQDDYEVVRKVGRGKYSEVFEGVNAVNSERCVMKILKPVKKKKIKREIKILQNLCGG PNIVKLLDIVRDQQSKTPSLIFEYVNNTDFKVLYPTLTDFDIRYYIHELLKALDYCHSQGIMHRDVKPHNVMIDHEQRKLRLIDWG LAEFYHPGKEYNVRVASRYFKGPELLVDLQDYDYSLDMWSLGCMFAGMIFRKEPFFYGHDNYDQLVKIAKVLGTDELNSYLNKYRL

ELDPHLEALVGRHSRKPWSKFINADNQRLVVPEAVDFLDKLLRYDHQDRLTAKEAMAHPYFYPVKVSEVSNRRSA

Deduced amino acid sequence of MPK-2 from Physcomitrella patens (SEQ ID NO: 34)
METSSGTPELKVISTPTYGGHYVKYVVAGTDFEVTARYKPPLRPIGRGAYGIVCSLFDTVTGEEVAVKKIGNAFDNRIDAKRTLRE IKLLRHMDHENVVAITDIIRPPTRENFNDVYIVYELMDTDLHQIIRSNQALTEDHCQYFLYQILRGLKYIHSANVLHRDLKPTNLL VNANCDLKIADFGLARTLSETDFMTEYVVTRWYRAPELLLNCSAYTAAIDIWSVGCIFMELLNRSALFPGRDYVHQLRLITELIGT PEDRDLGFLRSDNARRYIKHLPRQSPIPLTQKFRGINRSALDLVEKMLVFDPAKRITVEAALAHPYLASLHDINDEPASVSPFEFD

FEEPPISEEHIKDLIWREALDCSLGPDDMVQ

Deduced amino acid sequence of MPK-3 from Physcomitrella patens (SEQ ID NO: 35)
MGLTPFSCVTVQGYVRVVYPDGHVENLSKSCSVHDLLLGNPDYYVCGSTPYTITNRMAAEEVLEYGVTYFVCATPNAQPFLERQPK VVHRGSKILPRFSKHGVHVRELRSPTHGSQQSRKVFDYHSVTMQQLESIRNEGPEPHLAGDRPSKHLKLVFIRHCLRALRLPRISI DLMESPLPNLSGEALSPTATAKDEITQMILKSAARSELGMYVSKRQEFYLRRARRRRKFAWKPVLQSISEMKPVMEFHTPMAYRDS

GSPPKNASTPSLPGPKNISPPRQVSVPQRSSPPPKNVSPPPQPAFVARTASKYSAASQQVQRNRGNAKSLYMA

Deduced amino acid sequence of MPK-4 from Physcomitrella patens (SEQ ID NO: 36)
MSRRVRRGGLRVAVPKQETPVSKFLTASGTFQDDDIKLNHTGLRVVSSEPNLPTQTQSSSPDGQLSIADLELVRFLGKGAGGTVQL VRHKWTNVNYALKAIQMNINETVRKQIVQELKINQVTHQQCPYIVECFHSFYHNGVISMILEYMDRGSLSDIIKQQKQIPEPYLAV IASQVLKGLEYLHQVRHIIHRDIKPSNLLINHKGEVKISDFGVSAVLVHSLAQRDTFVGTCTYMSPERLQGRSYAYDSDLWSLGLT LLECALGTFPYKPAGMEEGWQNFFILMECIVNQPPAAASPDKFSPEFCSFIESCIRKCPSERPSTTDLLKHPFLQKYNEEEYHLSK

IL

Deduced amino acid sequence of MPK-5 from Physcomitrella patens (SEQ ID NO: 37)
MSRRVRRGGLRVAVPKQETPVSKFLTASGTFQDDDIKLNHTGLRVVSSEPNLPTQTQSSSPDGQLSIADLELVRFLGKGAGGTVQL VRHKWTNVNYALKAIQMNINETVRKQIVQELKINQVTHQQCPYTVECFHSFYHNGVISMILEYMDRGSLSDIIKQQKQIPEPYLAV IASQVLKGLEYLHQVRHIIHRDIKPSNLLINHKGEVKISDFGVSAVLVHSLAQRDTFVGTCTYMSPERLQGRSYAYDSDLWSLGLT LLECALGTFPYKPAGMEEGWQNFFILMECIVNQPPAAASPDKFSPEFCSFIESCIRKCPSERPSTTDLLKHPFLQKYNEEEYHLSK

IL

Deduced amino acid sequence of CPK-1 from Physcomitrella patens (SEQ ID NO: 38)
MGQCYGKFDDGGEGEDLFERQKVQVSRTPKHGSWSNSNRGSFNNGGGASPMRAKTSFGSSHPSPRHPSASPLPHYTSSPAPSTPRR NIFKRPFPPPSPAKHIQSSLVKRHGAKPKEGGAIPEAVDGEKPLDKHFGYHKNFATKYELGHEVGRGHFGHTCYAKVRKGEHKGQA VAVKIISKAKMTTAIAIEDVGREVKILKALTGHQNLVRFYDSCEDHLNVYIVMELCEGGELLDRILSRGGKYSEEDAKVVVRQILS
```

APPENDIX-continued

```
VVAFCHLQGVVHRDLKPENFLFTTKDEYAQLKAIDFGLSDFIKPDERLNDIVGSAYYVAPEVLHRLYSMEADVWSIGVITYILLCG

SRPFWARTESGIFRAVLRADPSFEEAPWPSISPEAKDFVKRLLNKDMRKRMTAAQALTHPWIRSNNVKIPLDILVYRLVRNYLRAS

SMRKAALKALSKTLTEDETFYLRTQFMLLEPSNNGRVTFENFRQALLKNSTEAMKESRVFEILESMDGLHFKKMDFSEFCAAAISV

LQLEATERWEQHARAAYDIFEKEGNRVIYPDELAKEMGLAPNVPAQVFLDWIRQSDGRLSFTGFTKLLHGISSRAIKNLQQ

Deduced amino acid sequence of CPK-2 from Physcomitrella patens (SEQ ID NO: 39)
MGNTSSRGSRKSTRQVNQGVGSQDTREKNDSVNPKTRQGGSVGANNYGGKPSSGAQAGERSTSAPAALPRPKPASRSVSGVLGKPL SDIRQSYILGRELGRGQFGVTYLCTDKMTNEAYACKSIAKRKLTSKEDIEDVKREVQIMHHLSGTPNIVVLKDVFEDKHSVHLVME LCAGGELFDRIINKGHYSERAAADMCRVIVNVVHRCHSLGVFHRDLKPENFLLASKAEDAPLKATDFGLSTFFKPGDVFQDIVGSA YYVAPEVLKRSYGPEADVWSAGVIVYILLCGVPPFWAETEQGIFDAVLKGHIDFENDPWPKISNGAKDLVRKMLNPNVKIRLTAQQ VLNHPWMKEDGDAPDVPLDNAVLTRLKNFSAANKMKKLALKVIAESLSEEEIVGLREMFKSIDTDNSGTVTFEELKEGLLKQGSKL NESDIRKLMEAADVDGNGKIDFNEFISATMHMNKTEKEDHLWAAFMHFDTDNSGYITIDELQEAMEKNGMGDPETIQEIISEVDTD

NDGRIDYDEFVAMMRKGNPGAENGGTVNKPRHR
```

The invention claimed is:

1. A transgenic plant cell transformed with an expression vector comprising an isolated polynucleotide selected from the group consisting of:
   a) a polynucleotide having a sequence comprising nucleotides 1 to 1088 of SEQ ID NO:15; and
   b) a polynucleotide encoding a polypeptide having a sequence comprising amino acids 1 to 308 of SEQ ID NO:28.

2. The plant cell of claim 1, wherein the polynucleotide has the sequence comprising nucleotides 1 to 1088 of SEQ ID NO:15.

3. The plant cell of claim 1, wherein the polynucleotide encodes the polypeptide having the sequence comprising amino acids 1 to 308 of SEQ ID NO:28.

4. A transgenic plant transformed with an expression cassette comprising an isolated polynucleotide selected from the group consisting of:
   a) a polynucleotide having a sequence comprising nucleotides 1 to 1088 of SEQ ID NO:15; and
   b) a polynucleotide encoding a polypeptide having a sequence comprising amino acids 1 to 308 of SEQ ID NO:28.

5. The plant of claim 4, wherein the polynucleotide has the sequence comprising nucleotides 1 to 1088 of SEQ ID NO:15.

6. The plant of claim 4, wherein the polynucleotide encodes the polypeptide having the sequence comprising amino acids 1 to 308 of SEQ ID NO:28.

7. The plant of claim 4, further described as a monocot.

8. The plant of claim 5, further described as a dicot.

9. The plant of claim 4, wherein the plant is selected from the group consisting of maize, wheat, lye, oat, triticale, rice, barley, soybean, peanut, cotton, rapeseed, canola, *manihot*, pepper, sunflower, tagetes, potato, tobacco, eggplant, tomato, *Vicia* species, pea, alfalfa, coffee, cacao, tea, *Salix* species, oil palm, coconut, perennial grasses, and a forage crop plant.

10. The plant of claim 9, which is maize.

11. The plant of claim 9, which is soybean.

12. The plant of claim 9, which is rapeseed or canola.

13. The plant of claim 9, which is cotton.

14. A seed which is true breeding for a transgene comprising a polynucleotide selected from the group consisting of:
   a) a polynucleotide having a sequence comprising nucleotides 1 to 1088 of SEQ ID NO:15; and
   b) a polynucleotide encoding a polypeptide having a sequence comprising amino acids 1 to 308 of SEQ ID NO:28.

15. The seed of claim 14, wherein the polynucleotide has the sequence comprising nucleotides 1 to 1088 of SEQ ID NO:15.

16. The seed of claim 14, wherein the polynucleotide encodes the polypeptide having the sequence comprising amino acids 1 to 308 of SEQ ID NO:28.

17. An isolated nucleic acid comprising a polynucleotide selected from the group consisting of:
   a) a polynucleotide having a sequence comprising nucleotides 1 to 1088 of SEQ ID NO:15; and
   b) a polynucleotide encoding a polypeptide having a sequence comprising amino acids 1 to 308 of SEQ ID NO:28.

18. The isolated nucleic acid of claim 17, wherein the polynucleotide has the sequence comprising nucleotides 1 to 1088 of SEQ ID NO:15.

19. The isolated nucleic acid of claim 17, wherein the polynucleotide encodes the polypeptide having the sequence comprising amino acids 1 to 308 of SEQ ID NO:28.

20. A method of producing a drought-tolerant transgenic plant, the method comprising the steps of:
   a) transforming a plant cell with an expression vector comprising a polynucleotide selected from the group consisting of:
      a) a polynucleotide having a sequence comprising nucleotides 1 to 1088 of SEQ ID NO:15; and
      b) a polynucleotide encoding a polypeptide having a sequence comprising amino acids 1 to 308 of SEQ ID NO:28.

21. The method of claim 20, wherein the polynucleotide has the sequence comprising nucleotides 1 to 1088 of SEQ ID NO:15.

22. The method of claim 20, wherein the polynucleotide encodes the polypeptide having the sequence comprising amino acids 1 to 308 of SEQ ID NO:28.

* * * * *

SEQUENCE LISTING

<160> NUMBER OF SEQ ID NOS: 128

<210> SEQ ID NO 1
<211> LENGTH: 695
<212> TYPE: DNA
<213> ORGANISM: Physcomitrella patens
<220> FEATURE:
<221> NAME/KEY: modified_base
<222> LOCATION: (636)
<223> OTHER INFORMATION: a, t, c, g, other or unknown
<220> FEATURE:
<221> NAME/KEY: modified_base
<222> LOCATION: (680)
<223> OTHER INFORMATION: a, t, c, g, other or unknown

<400> SEQUENCE: 1

```
gcacgagctc aatcctcatg tttcggactg tggactagct gcccttgcac catctggttc      60
tgaacgccag gtgtcggcac aaatgttggg ctctttcggt tacagtgccc ctgagtacgc     120
catgtctgga acctataccg tgaagagtga cgtctacagc ttcggtgttg taatgctgga     180
gctactcact gggcgcaagc ctttagacag ctcaagacca cgatccgagc aatctttggt     240
acgatgggcc acacctcaat tgcacgacat cgacgcccct gcacgaatgg tggatccgtc     300
gttgaagggc atctaccctg ctaaatcact ctctcggttt gctgatatag tcgcccttg      360 cgtccagccg gagcccgagt tccgaccccc gatgtctgaa gtggtgcagg cacttgtaag     420
gctgatgcag cgtgcgagtc tgagcaaacg cagatcggag tccgctgttg ggaattgagt     480
cgaacgagcc atctgagact tcacctttga gagtactgaa gcgcccacta gcctaatcgt     540
gcatctttgg ccatctcgtt tctgagtgga acacaaagct gggtatattc tttggtggtt     600
aagcaaccat ttgtcccaat ttgaacttcc gctggngaag gtctgtatgt tgagaaacga     660
tgcaaagcgt tcgcgtggtn tgcttgaact tcaaa                                 695
```

<210> SEQ ID NO 2
<211> LENGTH: 512
<212> TYPE: DNA
<213> ORGANISM: Physcomitrella patens -continued

```
<400> SEQUENCE: 2
ggcacgagcc gaacttcagc agcttcttca catcttcagg ttgcttggca ccccgaatga    60
gacaatctgg cctggtgtta gccagcaccg tgattggcac gagtttcctc aatggagacc   120
acaagatctg tcccttgctg ttcccggact cagcgcggtt ggcttagacc ttctcgccaa   180
aatgttggta ttcgagccct caaagagaat ctctgccaaa gccgccttga gccatactta   240
tttcgctgat gttgataaga cagcaaccta aacacaacag aacaattcaa gagaaccagg   300
taacctctac ctgtccaaga cgaaggacat ctaactcttc agtcaaactt ggccaatcat   360
gctgattggg aattgaacca caggaacgag gtgggcaccg tggttcgctg tagcatacaa   420
agtagtctgg aagacttgac atcgttagct ggcaatgcag tattttggaa atacaatttt   480
tcattaaaaa tctcctaaag attcaatatt tg                                  512

<210> SEQ ID NO 3
<211> LENGTH: 651
<212> TYPE: DNA
<213> ORGANISM: Physcomitrella patens
<220> FEATURE:
<221> NAME/KEY: modified_base
<222> LOCATION: (608)
<223> OTHER INFORMATION: a, t, c, g, other or unknown

<400> SEQUENCE: 3
gcaccagact atgacaagcg cacgcccttg cacatcgccg cgtccctgga ttgtgtccct    60
gttgctaaag tcctgcttgc ggaaggagca gagttgaatg caaaagacag gtggggaaa    120 tctccgagag gcgaggcgga gagtgcagga tacatggaga tggtaaagct gttgaaggat   180
tacggggctg agtcacacgc aggtgcccccg agggccacg ttgagagtct gattcaggtt   240
gcccctccgt tgccttctaa ccgcgactgg gagatcgctc cgtcggagat tgaacttgat   300
accagcgagc tcatcggcaa aggctccttt ggagagattc ggaaggcgct ttggcgcggc   360
acacccgtcg ctgtgaagac aatcagacct tctctgtcca acgacagaat ggtcatcaag   420
gacttccagc acgaggtgca attgctcgta aaggttcggc acccaaacat tgtgcagttc   480
ctcggggctg ttacccgtca aagacctctc atgttagtca ccgagtttct ggcagggggg   540
cgatttgcat cagttgctga ggagcaccct aaatttggct cctgaccgca tcgtgaagta   600
tgccctcnac atagctcgcg gcatgtctta cttcaccatc ggagcagccc a            651

<210> SEQ ID NO 4
<211> LENGTH: 710
<212> TYPE: DNA
<213> ORGANISM: Physcomitrella patens
<220> FEATURE:
<221> NAME/KEY: modified_base
<222> LOCATION: (54)
<223> OTHER INFORMATION: a, t, c, g, other or unknown

<400> SEQUENCE: 4
tccagcccat ttggttggcc acacacagct gttcatgagt cacccgcttc aggntgaact    60
gaagaaacgt aactccgtac ggctatttta ccaaattttc aagctcgttg tcccgccatg   120
atccaaatgg aagctcagtt tgcaacatga agtacattga acacacctac cgcccaccag   180
tcagaagcca ggccatgacc ttgtccttga atgatctcgg gtgctaagaa tcagccatg   240 ccacagactg tgaaagtgcg ctcatccgac atttgctttg caaaccgaaa atcaaccagc   300
tgaagtcgtc ctttccgatc tatcataaga acatcgggag agatgccacg atatacaacg   360
ccatccttgt gcagaagttc gacggctaat accacgttgg cgaccagaaa acgagctgag   420
```

| | |
|---|---|
| ttctcgtcta aaggtgaccg aagtagaagt tctagaggcc cagctaacac acaattaaga | 480 |
| acgagtgcca cattgtcact gtcaataggg gtggccaaga gatgcggcac gaatggggaa | 540 |
| ggcctcagtt gcttgaaaag agttctctcc aataggactt ggccctcccg accgagtctc | 600 |
| tgaactttac gtctctggta cctttcatg cttatgacgt catctgattt cttgcagagc | 660 |
| accacaccga catcacagca atcggttgaa tagacctggt gccgattcct | 710 |

```
<210> SEQ ID NO 5
<211> LENGTH: 1271
<212> TYPE: DNA
<213> ORGANISM: Physcomitrella patens
<220> FEATURE:
<221> NAME/KEY: modified_base
<222> LOCATION: (619)
<223> OTHER INFORMATION: a, t, c, g, other or unknown

<400> SEQUENCE: 5
```

| | |
|---|---|
| tatgcccatc ttctcatact cagaccagat cctctatttc aattacagaa gaaagttgct | 60 |
| tgtgcaacgt attgaaatca tcaccgtcat gggctttccg agtaaaaatt cttgtaatgg | 120 |
| ataaagtcat ttctagtctg atccatacaa gctaccgaca caatgctaga agccttgatt | 180 |
| tacacactac acactagaga gtctacaact cttttcctac actctgctta gttgcctcat | 240 |
| cctcaactcc ataaaccccc attcacaatc atgtaagact tgagagaggg aaacagtaag | 300 |
| caaccttgtg ctattttagt accagagcag aggatgaacc actagtcctc ccaacgtaag | 360 |
| ccctaattcg ccgcaacaac ctcacgacgg aactccgact tggtcaaggg tggacaatat | 420 |
| gatacattcg aaggtcgatt ttgcaaatgg gacgaagcag cggaattctg gctgcgcact | 480 |
| gattgcagag agccattctg ggggagttga gtatacacag tccagtcgta cacatggtcg | 540 |
| agctggaatt ttttctgaat gaaaagatca cggaacaagc ttcggaggta cagtagtcag | 600 |
| gctgctcgta aaaacctana cttcgcggcg tggtgcaaaa agtcggcaaa ttgactggga | 660 |
| tacccatcac aaagctcctc ccacagtggg ggtcatcttg attttgttgt gcatgtactc | 720 |
| gtgttgcttc tggtcagtga gggcgttgcc cgcccttccc ttgccatggc aaattgcctc | 780 |
| ttagaaagta cataagaatg taacccaagt gattctatgt catctcttct actgtgctcg | 840 |
| attcctctgt gctgattcct actagcgtac cgtgccgtcc ctgtgaagct cttcctatct | 900 |
| cggtaaggga tatgccttcg tgttgccggg tccatgtact cctttgccaa gccaaaatct | 960 |
| ataatgaaca cttggtttcc ttgccgaccg cagcccatga ggaagttatc cggcttcagg | 1020 |
| tcacggtgaa cgagccctcg agaatgcacg tattccaccc ggtcaatcat ttggtaaccg | 1080 |
| agcataatca cggtcttcaa cgaaaacctt agcccacaca ccttaaagag gtgcaacagg | 1140 |
| ttcggcccca ataggtctag caccatcaca ttgtagtctt ctgctgcttt tccgaaccat | 1200 |
| ctcatgttgg gcactccctt cccaccccgc aatatgttgt acaagcgcga ctcgtgcatt | 1260 |
| aactctcgtg c | 1271 |

```
<210> SEQ ID NO 6
<211> LENGTH: 1910
<212> TYPE: DNA
<213> ORGANISM: Physcomitrella patens

<400> SEQUENCE: 6
```

| | |
|---|---|
| ttttttttt ccaatagatt tgcattacat aactccaagt tatgatatgt acaggttagc | 60 |
| aacaagctaa tggctgcaag cagtgaacat actaccaagg gagagattct cactccctag | 120 |

-continued

```
acttcatcct cgtacgttac ttggcaagga ttatggttta gtgataaaaa gcttcacaag      180
ccggcaagca tgctggttgc ttctgctgca atctaatgat tatttcctta ggaatcgtat      240
ggcagagagc taccacacaa agcactgaca atggtttgat ggtaacaaga tagagatcca      300
ttcattccta agtatgagag acctgtagtc ttagcaccat tgtaggacag aaccaccgtt      360
ttcccctcaa tcaggctgtt gccaaatgta gagcaactct catcaacata caagagggt       420 ttgatagaag acagagcccg gctatataac cacaagccct cgcctacct tataacggct       480 tggatccacc tcaacagaaa gtgattcaac tcccttgata ccggctttcg taaatcctca      540
agttggcaga tggcggttgt ggatggcggc tagatatccg ctttgggtcc gaagtaactg      600
gagagctcct ctgcatccct gctgacgacc gtaagctggt gggaccaagc ttactgctcc      660
ctgttcgaga ggaatctacg acttctgctg atgcccctga gggcctgctg ctagatagga      720
cagctcgcct ggaggaagaa ccccccgag ttgcatacga agatgtatgc atgcgctctg       780
gttctgacac aacagcaaga gcagaatcct tagcagattc atcaagtcca ggacttttgt      840
gcttagatga gtccaaagca tttgcgaccc cggagccatt tgctcctcca ggaagcctgc      900
gccgagaagg atccattggt tcggtgggcc gctgcaggtc tcggcttcct gtagccccag      960
ttccaagtgc accactggtt tgccctgcag aagcacccag tcgagttgaa ctgccaccgg     1020
aaatttgtga ctgctggtac ttcagaattg tccagtcaaa aacgtagtca aattgaaaac     1080
ctgtaaaact atttccagtt taggcaaaca gaagtggcac tgtaataaac tgaaaatcat     1140
caaacattca caaactatct gttcgttgat agagcatagt aaagtctgcg cttaggatca     1200
agtcttgata cattacaatg cccaagcaag agtgaaacct acaaaagtta cagttttcat     1260
accctcacga ataaagaggt cacggaagat tcttttcaaa tatgcatagt cgggtttgtc     1320
atcaaaacgc aaggaccggc agtagtggaa gtacgctcgt gcgaattctg aaggataatt     1380
tttacaaagg acctcaatgg gcgtggacat ttgttttctc actgatcttc tcgtacttct     1440
gcttcttggt tcccgctttc agtccttgcc catggaagac tgcctctcag gaagtacatg     1500
agcacatatc caagagattc caaatcatct cgtctgcttt gctcaatacc aagatgagtg     1560
ttgatgcttg cataccgagc agtccctgtc agatttttgt tctccctgta gggaatatgc     1620
tgatgcgtgg aagggtcgcg gtacttcttg gcaagaccaa aatcaataat gtagacctgg     1680
tttgctcgcc taccaagccc cattagaaaa ttatcaggct tgatgtctct atgaagaaag     1740
cttttcgcat gcacatactc cactctgttg atcagctggt cagcaagcat gagaacagtc     1800
tttaaagaga acttccggct gcagaagttg aaaaggtctt cgagacttgg ccccaacaga     1860
tccagaacca agacattgta gtctccttct atcccgaacc atcctcgtgc                1910
```

<210> SEQ ID NO 7  
<211> LENGTH: 720  
<212> TYPE: DNA  
<213> ORGANISM: Physcomitrella patens  
<220> FEATURE:  
<221> NAME/KEY: modified_base  
<222> LOCATION: (58)  
<223> OTHER INFORMATION: a, t, c, g, other or unknown  
<220> FEATURE:  
<221> NAME/KEY: modified_base  
<222> LOCATION: (613)  
<223> OTHER INFORMATION: a, t, c, g, other or unknown

<400> SEQUENCE: 7

```
cggtggggcg ctccccaata ttttatcccc ggggctgcag ggaatccggc gaccagtntt       60
tgaaggtgtc aacgccgtga atagtgagcg ttgcgttatg aagattttga agccagtaaa      120
```

```
gaaaaaaaag atcaaaagag agatcaagat tctgcaaaac ctttgtggag ggcccaacat        180
tgtgaagctt ctggacattg tccgtgatca gcaatcgaag acacccagcc taattttga         240 gtatgtgaac aatactgatt tcaaagtgct ctaccccact cttacagact ttgatatccg        300
atactacatt catgagctgc tcaaggcttt ggactattgc cattctcaag ggattatgca        360
cagggatgtg aagccacaca acgtgatgat tgaccatgag cagcggaagc ttaggcttat        420
tgactgggga cttgccgaat tctatcatcc tggcaaagag tataatgtgc gtgttgcctc        480
taggtacttc aagggtcctg agctgctggt tgatcttcaa gattatgatt actctctcga        540
catgtggagc tctggggtgc atgtttgccg gcatgatatt tcggaaggag ccattctttt        600
atgggcatga canttcatga tcaacttggt gaagatcgct aaggtgttgg gaacttgatg        660
aattgaattc ctatctaaca aataccgcta agtggacccc attggagcac ctggtggggg        720
```

<210> SEQ ID NO 8
<211> LENGTH: 953
<212> TYPE: DNA
<213> ORGANISM: Physcomitrella patens

<400> SEQUENCE: 8

```
gcacgaggaa ctaacgaatt gtcattctat aatccaatag tgtaatcaca cgggggggaa         60
taagttgcaa aaccatacaa cgccgggata gcgttgtagc cacctaaaga attgagagta        120
ggccttacaa cttgagatga agtgtgaagt ggtactgcac catatcatca ggacctaagc        180
tgcaatccag agcctccctc caatgagat ccctgatagg ctcctccgag atagagggct         240
cctcgaagcc aaactcgaag ggagataccg agccaggctc atcgttgatg tcatgaagtg        300
aagcttaaat aagggtgcgc caaggcagct tccactgtga ttcttttcgc tggatcaaag        360
accagcatct tttcaacaag atcaagagca gaacgattaa tgcctctgaa cttctgggtt        420
aagggaatag gcgactgtcg aggcaggtgc ttgatatacc gcctagcatt gtcgcttctc        480
aaaaacccaa gatccctatc ttcaggagtt ccgatgagtt ctgtaattag gcggagctga        540
tgcacatagt ctctcccagg gaacaacgca gatcggttaa gcaactccat gaagatgcac        600
cccacagacc aaatgtcaat agctgcagtg tatgctgaac aattcaggag cagctctgga        660
gctctgtacc acctcgttac aacatactca gtcatgaaat ccgtttcaga gagagtgcgt        720
gccaagccaa aatctgcgat tttcaaatcg caattggcat tgacgagaag gttggtgggc        780
ttcaagtccc ggtgcaagac gttcgccgaa tggatgtact tcaagccccg caagatttga        840
tacagaaaat actgacagtg gtcttctgtg agagcttgat ttgaacgaat gatctggtgt        900
aggtccgtat ccatcaactc gtatacaatg tacacgtcgt tgaaatctcg tgc              953
```

<210> SEQ ID NO 9
<211> LENGTH: 683
<212> TYPE: DNA
<213> ORGANISM: Physcomitrella patens
<220> FEATURE:
<221> NAME/KEY: modified_base
<222> LOCATION: (663)
<223> OTHER INFORMATION: a, t, c, g, other or unknown
<220> FEATURE:
<221> NAME/KEY: modified_base
<222> LOCATION: (670)
<223> OTHER INFORMATION: a, t, c, g, other or unknown

<400> SEQUENCE: 9

```
cggcaccagc ctcgctggag accgaccatc gaagcacctt aagctcgttt tcattcggca         60
```

-continued

| | |
|---|---|
| ttgcttgcga gcacttcgac ttcctagaat ttcaatagac ctaatggaat cgccactccc | 120 |
| taatctttcc ggagaggcct tatcgccgac ggcaactgcc gaagacgaga ttactcagat | 180 |
| gatactaaaa agtgccgcaa ggtccgaatt aggaatgtat gtttcgaaga gacaggaatt | 240 |
| ctatcttcga agagcgcgga ggcggcgtaa gtttgcgtgg aagccggttt tgcagagcat | 300 |
| ctccgagatg aagcctgtca tggaattcca cactccgatg gcttaccggg atagtgggtc | 360 |
| tccgccgaag aacgcctcta ccccatcctt acctggcccg aagaacattt caccgccacg | 420 |
| acaagtgagt gtcccgcaaa ggagcagtcc tccgccgaag aacgtctcac cacctcccca | 480 |
| gcccggcatt ttgtagcgcg gactgcgatc gaagtattct gctgcatctc agcaagttca | 540 |
| acgaaatcga gggcaacgcg aaatctcttt tatatggcgt agtttgtgtc tccgactgga | 600 |
| ctcctatcta tccccatcga gataactgat tcggtggata atttctccaa attttggcta | 660 |
| acncaagaan ctcaagggcg aat | 683 |

<210> SEQ ID NO 10
<211> LENGTH: 1156
<212> TYPE: DNA
<213> ORGANISM: Physcomitrella patens
<220> FEATURE:
<221> NAME/KEY: modified_base
<222> LOCATION: (923)
<223> OTHER INFORMATION: a, t, c, g, other or unknown
<220> FEATURE:
<221> NAME/KEY: modified_base
<222> LOCATION: (1143)
<223> OTHER INFORMATION: a, t, c, g, other or unknown

<400> SEQUENCE: 10

| | |
|---|---|
| gcacgaggtt ggtgtaagtt attgatagtg ctgtgcaatt cacagttttg ctactccggt | 60 |
| aggtccgacc tcttcaattg tcagtttaaa aactctaaaa acatttgaga aaagtgttga | 120 |
| aaaatctccg tgaggaaatt ccttgtcgca agacgtgaaa aaaagaagaa agaagatgga | 180 |
| aatattgttt tgggtatcga agaagtgttc gatgctgtgc aataaggaaa gaaaaagtgc | 240 |
| aggtaacata aaaagctagc atggtgatga taatataaga ccccgattaa cacacttatg | 300 |
| gattgtttca tgagctgcac gttctcagcg acaaatgggg ctcattgaga aaactccact | 360 |
| ttctataagg ttgggaaacg agcgtttttt ttttgaagat gttttttccg tcaatctgat | 420 |
| ttgatatcgt tctcaacttg accacatatg actatataag gaaaaggcat tgagaaagtg | 480 |
| gcggattggc gaggtagttc gaccatgctt ttggtaaagt cccttgaagt tcagtggtgg | 540 |
| atcaggcttg tggtagtgac agtctctgca cgccatgcga ggctaacttt aagttacaaa | 600 |
| atcttgctca aatggtactc ttcctcgttg tacttttgca ggaacggatg tttaagtaaa | 660 |
| tcagtagttg atggtcgttc actgggacat ttccggatgc aggattcaat aaaagaacaa | 720 |
| aattcggggg agaatttgtc aggggatgcg gctgcggggg gttgattaac tatacattcc | 780 |
| atgaggatga agaaatttg ccaaccctct tccattccag ctggtttgta tgggaaggta | 840 |
| cccaacgcac actccaaaag agtcaatcct aaactccata ggtcactgtc gtatgcatac | 900 |
| gaacgcccct gaaggcgttc tgncgacata tatgtgcaag tcccaacgaa cgtgtctcgc | 960 |
| tgggccaagg aatgaaccaa cacagcactg acaccaaaat cagatatttt gacctcaccc | 1020 |
| ttgtgattga tgaggaggtt ggagggcttt atatcacgat gtatgatgtg cctgacttgg | 1080 |
| tgtaggtatt ccaatcccctt cagaacttga ctagcaatga cggccaaata cggctcaggt | 1140 |
| atntgctttc tggtgc | 1156 |

<210> SEQ ID NO 11
<211> LENGTH: 629
<212> TYPE: DNA
<213> ORGANISM: Physcomitrella patens

<400> SEQUENCE: 11

```
tccccgggct gaggaattcg gcacgagcgg ttgatcctca cccttgggaa ggaccctgga      60
attgagtagc gtgcggaagc tgcatcgatc cggaagagac gatgagtagg agagtgagaa     120
ggggaggtct tcgcgtcgcg gtgccgaagc aagagactcc cgtcagcaaa ttttttgactg    180
ccagtggaac tttccaggat gatgatatca agctcaacca caccgggctt cgcgtcgtct    240
cttcagaacc taaccttcct acgcagacgc agtctagctc cccagatggg caactgtcaa    300
tagcagacct ggagttagtg cggttcttag gaaagggtgc gggtggaacc ggtgcagctt    360
ggtccggcac aaatggacca atgtcaatta tgcactgaag gcgatacaaa tgaatatcaa    420
cgaaacagtg aggaagcaga ttgttcagga gctgaaaatc aaccaagtga cgcaccagca    480
gtgcccttat atcgtggaat gcttccactc cttctaccac aacggcgtca tatccatgat    540
cctagagtac atggacaggg gctcgttgtc cgacattatt aagcaacaaa agcagatacc    600
tgagccgtat ttggccgtca ttgctagtc                                      629
```

<210> SEQ ID NO 12
<211> LENGTH: 514
<212> TYPE: DNA
<213> ORGANISM: Physcomitrella patens

<400> SEQUENCE: 12

```
gcaccagccg agtcgggcat ttttcgtgcg gtgttgaggg ctgacccgag ctttgaagaa     60
gcccccttggc cttccatctc tcccgaagcc aaggatttcg tgaagcgtct cctgaataag   120
gatatgcgga aacgcatgac tgctgcacaa gctttaactc atccatggat tcgaagtaac   180
aacgtgaaga tacctctgga tatcttagtg tacagacttg tgaggaatta tcttcgtgca   240
tcatccatga gaaaggctgc tttgaaggcc ctgtcaaaga ctttaaccga agacgagact   300
ttttatctac gtactcaatt tatgctgcta gaaccaagta acaacggtcg tgttactttt   360
gagaatttca gacaggcact gctgaaaaat tcaacagagg ccatgaaaga gtcacgggtt   420
tttgaaattc tggaatcgat ggatggtctt catttcaaga aaatggactt ttcagagttc   480
tgtgcagcgg ccattagtgt tctccagtta gaag                               514
```

<210> SEQ ID NO 13
<211> LENGTH: 1387
<212> TYPE: DNA
<213> ORGANISM: Physcomitrella patens
<220> FEATURE:
<221> NAME/KEY: modified_base
<222> LOCATION: (1385)
<223> OTHER INFORMATION: a, t, c, g, other or unknown

<400> SEQUENCE: 13

```
gcacgagctc ctgcatctcc ccctccttct cctcctcatc attctggagc ccagcgaact      60
gcgatctgag attccaactt ggaagggcct cgcgtaagca ccggagctcg tttcttacgc    120
ttttgcgcct cgcgatattt gtacattgtt cctctggtt ttattcgatt ccgcctctga    180
aaatgtgaac gggctgcaag cttggttttg gagcaacgtt ggagcattga agggttgcgc   240
tcgtccctgc ccattcctcg cttctgctct ggcctatgtc atgacgacgt gaaggagagg   300
atttgagggt tttgcaagtg atataatcct ccccgaggag atttctgtga gttgattaac   360
```

```
ttggatcagc gacatgggga acactagttc gaggggatcg aggaagtcca ctcggcaggt      420
gaatcaggga gtcgggtctc aagacacccg agagaagaat gatagcgtca atccaaagac      480 gagacaggt ggtagcgttg cgcaaacaa ctatggcgga aagcacaagc agtggtgctc        540
aggccggaga acgatccacc tctgcgcccg ctgctctgcc gaggccgaag ccagcatcga      600
ggtcagtatc cggtgttttg ggtaagccgc tgtcagatat tcgtcaatct tacatcctgg      660
gacgggagct tggccgaggg cagttcggag tgacttactt gtgtactgac aagatgacga      720
atgaggcgta cgcgtgcaag agcatcgcca acggaaaact gaccagtaag gaggatatcg      780
aggatgttaa gcgggaggtt cagattatgc atcacctgtc ggggacaccc aatatcgtgg      840
tgttaaagga tgtgttcgag acaagcatt ccgtgcatct tgtgatggag ctctgtgcag       900
gtggcgagct cttcgatcgc atcattgcca agggcatta cagtgagcgc gccgctgccg       960
atatgtgcag agtcatcgtc aatgtggtgc acagatgcca ctcattaggg gtcttccatc      1020
gggatctcaa gccagagaat tttctgttgg ccagcaaggc tgaggatgcg cctctgaagg      1080
ccacagactt cggtctgtca acttctttta agccaggaga tgtgttccag gatattgttg      1140
gaagtgcgta ttacgtggcc cctgaagttt tgaagagaag ttatggtcct gagctgatgt      1200
ttggagtgca ggcgtgattg tgtacattct gctgtgtggt gtaccccct tctgggctga      1260 aactgagcag ggtatctttg acgctgtgct caaagggcac atagacttcg agaacgagtc      1320
catggccgaa aatctccaac ggggctaagg atttggtgag gaaaatgcta aaccctaacg      1380 tgaanat                                                              1387
```

<210> SEQ ID NO 14
<211> LENGTH: 2784
<212> TYPE: DNA
<213> ORGANISM: Physcomitrella patens

<400> SEQUENCE: 14

```
atcccgggtg agtatcactt acggtggcga gggatggcct ttggggtagg agctggtata       60
tgcggagtcc aacagaagct tgtgcaggac tcttgagttg tgcgtgcgag ggctgagtgc      120
cggaaaggta ttttccgacg aagagtcaat gtgggcgtgg acaaacgttt gaagagatgg      180
gtgtggatat gaaggctccg gctaagcagt cgctgggagt cggactgctc ctgtgctctg      240
tagtgatcct ctcggtggtg agctctgtgt atggccaagt tcagacagat ccagtggata      300
ctacaggctt aatttccatg tggtatgact taaaacagag tcaatctctc acggggtgga      360
ctcaaaatgc ttctaacct tgtgggcagc agtggtacgg cgttgtatgt gatggctctt       420
ctgtcacgga atcaaaatt ggaagtcggg gtttgaatgg aaattttaat ccttcgtact       480
ttcaaaacgc ttttaaaaag cttcgaattt ttgatgctag taacaacaac atcgaaggaa      540
atattcctca acagtttcct acgtctctta ctcaaatgat attgaacaac aataaattga      600
ccggaggtct cccacagttt gatcaattgg gcgccttgac agtcgtaaac ttgagcaaca      660
acaatctgac cggcaacatg aacccccaact atttcaatgt gatcgtgaat gtggaaacct     720
tcgatgtttc ctataaccaa cttgaaggca ctcttcccga ctccattcta aacctggcca      780
agcttcgttt cttgaatttg cagaacaata aatttaatgg taaacttccc gacgatttct      840
ctcggctgaa gaatttgcag actttcaaca ttgagaacga tcagttcacg ggtaattatc      900
catcaggttt acccagtaat agcagggttg gaggaaatcg tcttacattt cccccacctc      960 cagccccgg cacacctgct cccaggactc cttctccttc aggaacatcg aatgggatcat     1020 cgtcgcatct ccctctaggg gcgatcattg gaatagccgc tggtggtgct gtgctgcttt     1080
```

-continued

| | |
|---|---|
| tattactagc actcggcatc tgtttgtgtt gtcgtaagcg gtccaagaaa gcattgggcg | 1140 |
| atccagaggc cacgaccagc agccgaagac cgtggttcac acctcccctc tccgcaaaga | 1200 |
| gccagagtga tcccagcaag agcatagaca aaacgacgaa acgcaacatc tttggcagca | 1260 |
| gtaagagtga aagaaaagt tcaaagcaca gagtatttga gccagctcct cttgacaaag | 1320 |
| gagcagccga cgaaccagtg gtgaaggcgt ctccgcccgt caaggtactg aaggctcctc | 1380 |
| cttcatttaa gggtatcagc ggcctgggtg ctggacattc gaaagcaaca attggcaagg | 1440 |
| tgaacaagag caatattgca gccacccat tctctgtagc ggatcttcag gcagccacaa | 1500 |
| acagcttctc ccaggataat ctgattggag aagggagcat gggtcgcgtg tatcgtgccg | 1560 |
| agtttcccaa cggccaggtc ttggccgtga agaagatcga cagcagcgcg tcgatggtgc | 1620 |
| agaatgagga tgacttcttg agtgtagtag acagtttggc tcgcctgcag catgctaata | 1680 |
| cggctgagct tgtgggttac tgtattgaac atgaccaacg gctgttggtg tacgagtacg | 1740 |
| tgagtcgtgg aaccctgaac gaattgctcc atttctcggg tgaaaacacc aaggccctgt | 1800 |
| cctggaatgt ccgcattaag attgcttttgg gatccgcgcg tgctctggag tacttgcacg | 1860 |
| aagtctgtgc acctcccgtg gttcaccaca acttcaaatc tgccaatatt ctgctagacg | 1920 |
| atgagctcaa tcctcatgtt tcggactgtg gactagctgc ccttgcacca tctggttctg | 1980 |
| aacgccaggt gtcggcacaa atgttgggct ctttcggtta cagtgcccct gagtacgcca | 2040 |
| tgtctggaac ctataccgtg aagagtgacg tctacagctt cggtgttgta atgctggagc | 2100 |
| tactcactgg gcgcaagtct ttagacagct caagaccacg atccgagcaa tctttggtac | 2160 |
| gatgggccac acctcaattg cacgacatcg acgcccttgc acgaatggtg gatccgtcgt | 2220 |
| tgaagggcat ctaccctgct aaatcactct ctcggtttgc tgatatagtc gccctttgcg | 2280 |
| tccagccgga gcccgagttc cgaccccga tgtctgaagt ggtgcaggca cttgtaaggc | 2340 |
| tgatgcagcg tgcgagtctg agcaaacgca gatcggagtc cgctgttgga attgagtcga | 2400 |
| acgagccatc tgagacttca ctttgagagt actgaagcgc ccactagcct aatcgtgcat | 2460 |
| cttttggccat ctcgtttctg agtggaacac aagctgggta tattctttgg tggttaagca | 2520 |
| acattttgtc acaatttgaa cttcagctgg agaagggtct gtagtgttga agaaaacgaa | 2580 |
| tgcaaagcgt ttcggcgtgg atgtgctttg agaacttaca aaactcatca agactttgaa | 2640 |
| gatctttgta ttgcatcgaa tcctttcaat cagtctcggg taggatcagt tcctctgtat | 2700 |
| cggatacccct tttcatccta acatgggacc cttttaatcc agaggatgga gtgcttggaa | 2760 |
| tagtgacctt ggtcgagtta acgc | 2784 |

<210> SEQ ID NO 15
<211> LENGTH: 1088
<212> TYPE: DNA
<213> ORGANISM: Physcomitrella patens

<400> SEQUENCE: 15

| | |
|---|---|
| atcccgggag tgggtggttg gactgtaagg agctagcgtt ttagagctac agtgcggttt | 60 |
| gctgtgtgag tgagtgagtg agtgagtgcg tgagtgagga tgtctgtttc tggtatggac | 120 |
| aactatgaga agctggagaa ggtaggagag gggacttacg gaaaggtgta taaggcccgt | 180 |
| gataaacgct ccgggcagct ggtggcgctc aagaagacta ggttggagat ggaggaagaa | 240 |
| ggcgtccctt ccaccgcttt gcgcgaagtt tcgttgctac aaatgctctc ccacagcatg | 300 |
| tatatcgtca ggctactttg cgtggagcac gtcgagaaag gcagcaagcc catgctctac | 360 |

-continued

```
ttggtctttg aatatatgga cactgatctt aagaagtata ttgacttgca cggtcgtggt      420
ccgagcggga agcctctgcc tcccaaagtg gtccagagtt tcatgtatca attgtgcaca      480
gggcttgccc actgtcatgg ccacggagta atgcacaggg atctgaaacc ccagaatttg      540
ctcgtcgaca agcaaacccg tcgtcttaag attgccgacc ttggtctcgg tcgggcattc      600
acagtgccaa tgaagagtta cacacacgag attgttactc tatggtaccg agctcctgaa      660
gttcttcttg gagcgaccca ctactctcta cctgtggata tctggtctgt tgggtgcatc      720
ttcgctgaac tcgtccggaa aatgccgctc ttcactggag actccgaact tcagcagctt      780
cttcacatct tcaggttgct tggcaccccg aatgagacaa tctggcctgg tgttagccag      840
caccgtgatt ggcacgagtt tcctcaatgg agaccacaag atctgtccct tgctgttccc      900
ggactcagcg cggttggctt agaccttctc gccaaaatgt tggtattcga gcccctcaaag     960 agaatctctg ccaaagccgc cttgagccat acttatttcg ctgatgttga taagacagca     1020
acctaaacac aacagaacaa ttcaagagaa ccaggtaacc tctacctgtc caagacgaag     1080
gttaacgc                                                              1088
```

<210> SEQ ID NO 16
<211> LENGTH: 1627
<212> TYPE: DNA
<213> ORGANISM: Physcomitrella patens

<400> SEQUENCE: 16

```
atcccgggca acgagaagca ttcgagatgg cagatgcgaa ggaggaactg gcgctgcgca       60
cggaaatgca ctgggctgtg aggagtaacg acgtggggct gttaaggacc attctgaaga      120
aagacaagca gctcgtgaat gctgcggact atgacaagcg cacgcccttg cacatcgccg      180
cgtccctgga ttgtgtccct gttgctaaag tcctgcttgc ggaaggagca gagttgaatg      240
caaaagacag gtgggggaaa tctccgagag gcgaggcgga gagtgcagga tacatggaga      300
tggtaaagct gttgaaggat tacggggctg agtcacacgc aggtgccccg aggggccacg      360
ttgagagtct gattcaggtt gccccctccgt tgccttctaa ccgcgactgg gagatcgctc      420
cgtcggagat tgaacttgat accagcgagc tcatcggcaa aggcgccttt ggagagattc      480
ggaaggcgct ttggcgcggc acacccgtcg ctgtgaagac aatcagacct tctctgtcca      540
acgacagaat ggtcatcaag gacttccagc acgaggtgca attgctcgta aaggttcggc      600
acccaaacat tgtgcagttc ctcggggctg ttacccgtca aagacctctc atgttagtca      660
ccgagtttct ggcaggggc gatttgcatc agttgctgag gagcaaccct aatttggctc      720
ctgaccgcat cgtgaagtat gcccctcgaca tagctcgcgg catgtcttac cttcacaatc      780
ggagcaagcc catcatccac cgcgatctca aaccccgaaa catcatagtg gacgaagagc      840
atgagctgaa ggtcggcgac ttcggactga gcaagctgat cgacgtaaag cttatgcatg      900
atgtgtacaa gatgacgggg gggactggga gttacagata catggcgcct gaggtcttcg      960
aacatcaacc ctacgacaaa tccgtcgacg tgttttcctt tggaatgata ttatatgaga     1020
tgtttgaagg cgtcgctccg tttgaggaca aggatgcata cgacgctgcc acactagttg     1080
ctagagacga taagcggcca gagatgagag cccaaacgta tcccccacaa atgaaggcat     1140
tgatcgagga ttgctggtca ccgtataccc cgaagcgacc acctttcgtc gaaatcgtca     1200
aaaaactcga ggtaatgtat gaggattgct tattgagatt gcccaaagac cgtcgtcatc     1260
tccgcgacat cttgcatctt cgacgcaatc ctgcagactc gtgattgatc gggccaacct     1320
tcgagctgat caatctaagt agtcaatgcc ttactgtgtc aaattcagcc tccgccgaca     1380
```

```
gattggctat ggttcaagtg attggattct ctgcttctcc agagccagaa acgaccccg      1440 tgcaatttct tctccgacga ccacattgcg acatgaagca ccagactttg gatgtagaag      1500
gcatggtcta catgctttgc tgtgagcctt gcacgtctcg caggttgatc tctttaacca      1560
gcttctagcc tttcgcaatg gctgcatcac ttaagaaatc accgagtatc gtgatgctcg      1620
ttaacgc                                                                1627

<210> SEQ ID NO 17
<211> LENGTH: 1441
<212> TYPE: DNA
<213> ORGANISM: Physcomitrella patens

<400> SEQUENCE: 17
atcccgggct gtgatgtcgg tgtggtgctc tgcaagaaat cagatgacgt cataagcatg        60
aaaaggtacc agagacgtaa agttcagaga ctcggtcggg agggccaagt cctattggag       120
agaactcttt tcaagcaact gaggccttcc ccattcgtgc cgcatctctt ggccacccct       180
attgacagtg acaatgtggc actcgttctt aattgtgtgt tagctgggcc tctagaactt       240
ctacttcggt cacctttaga cgagaactca gctcgttttc tggtcgccaa cgtggtatta       300
gccgtcgaac ttctgcacaa ggatggcgtt gtatatcgtg gcatctctcc cgatgttctt       360
atgatagatc ggaaaggacg acttcagctg gttgattttc ggtttgcaaa gcaaatgtcg       420
gatgagcgca ctttcacagt ctgtggcatg gctgatttct tagcacccga gatcattcaa       480
ggacaaggtc atggcctggc ttctgactgg tgggcgtag tgtgttaat gtacttcatg         540 ttgcaaactg agcttccatt tggatcatgg cgggacaacg agcttgaaat ttttggtaga       600
atagcccgtc ggcagcttac gtttccttca gtttcagcc tgaagcggt tgacctcatt         660 gacaagctgc tggtggtgga cccaaccaag agactgggct gtgacagcca tggatcgctt       720
gccataaggg aacatccttg gttccgaggt ataaactggg acaagcacct cgattgcagt       780
gtggaagttc cttcagagat catgacacgc cttcagttgg ccatagactt tcttcccgtg       840
gatgatagtt atcaagtgtt tgatctccaa cccgatgaag acgatccacc atggcttgat       900
ggctggtgat agcttgatgg ctcgtagatc cccttctcc aagcatcaat ggcacagtac        960
cgaatggcta taacagaaga tgcacattaa gtgctccatg aacagatacc gtagcgctta      1020
ggatttttcg gtcgtcacaa atgacggctc tcttgtgagg ttcgaatgtt gtgtcacccg      1080
atgatctcta ctggcacaaa cctccaggct gaatcttaag gccagctgtt ttaggtgaga      1140
cgtttacctt ggttcgaact cacgctcgtg ttgttaagcg cgagtcgatg atgtatgaaa      1200
tgacggtgtt ccttgaaagt cttgaaaggc aatcaattcg cttatgtgtg tcccttccat      1260
gtggtcatta gggaagggaa ccgctgcact agtcagtaaa cgaacatggc ttcaattgta      1320
tagcatagcg gtagaggttt cgtacgaaat gtggttgcag tcggtgatta taggcgcatt      1380
tctctgaaca tgcacgagaa tcgtgctcct gagtctccat cattcagtgg tgcgagctcg      1440
c                                                                      1441

<210> SEQ ID NO 18
<211> LENGTH: 1736
<212> TYPE: DNA
<213> ORGANISM: Physcomitrella patens

<400> SEQUENCE: 18
atcccgggct cacgtagtgc actgaactct gtctgaattt tagggatga gaggtagatt         60
```

```
tgaagaatac tggtgtctaa ttttctgtta attttcacc cttgaggtag ctcatggatt    120
tgggaggtga tcgcatgaga gctcctcaga ggcagtctcg agaatatcaa tatagatcat    180
tggacgtctt cacagagcag cacgagcagt tgcaaaagca gcagcagcaa gatgagtatc    240
agagaacaga attgaagctc gagacactgc caaaaatgtt aagcaatgcg accgtgtcat    300
cttcccctcg aagcagtccg gatgacgta gactacgtac agtcgcgaat aagtatgctg    360
tggaaggtat ggttgggagt ggcgcattct gcaaggtgta tcagggctcc gatttgacga    420
accacgaggt tgtgggcatc aagctggagg atacgagaac tgagcacgct cagttaatgc    480
acgagtcgcg cttgtacaac atattgcggg gtgggaaggg agtgcccaac atgagatggt    540
tcggaaaaga gcaagactac aatgtgatgg tgctagacct attggggccg aacctgttgc    600
acctctttaa ggtgtgtggg ctaaggtttt cgttgaagac cgttgattatg ctcgttacc    660 aaatgattga ccgggtggaa tacgtgcatt ctcgagggct cgttcaccgt gacctgaagc    720
cggataactt cctcatgggc tgcggtcggc aaggaaacca agtgttcatt atagattttg    780
gcttggcaaa ggagtacatg gacccggcaa cacgaaggca tatcccttac cgagatagga    840
agagcttcac agggacggca cggtacgcta gtaggaatca gcacagagga atcgagcaca    900
gtagaagaga tgacatagaa tcacttggtt acattcttat gtactttcta agaggcaatt    960
tgccatggca agggaagggc gggcaacgcc tcactgacca gaagcaacac gagtacatgc   1020
acaacaaaat caagatgaac accactgtgg aggagctttg tgatgggtat cccagtcaat   1080
ttgccgactt tttgcaccac gcgcgaagtc taggtttcta cgagcagcct gactactgtt   1140
acctccgaag cttgttccgt gatcttttca ttcagaaaaa attccagctc gaccatgtgt   1200
acgactggac tgtgtatact caactccccc agaatggctc tctgcaatca gtgcgcagcc   1260
agaattccgc tgcttcgtcc catttgcaaa atcgaccttc gaatgtatca tattgtccac   1320
ccttgaccaa gtcggagttc cgtcgtgagg ttgttgcggc gaattagggc ttacgttggg   1380
aggactagtg gttcatcctc tgctctggta ctaaaatagc acaaggttgc ttactgtttc   1440
cctctctcaa gtcttacatg attgtgaatg ggggtttatg gagttgagga tgaggcaact   1500
aagcagagtg taggaaaaga gttgtagact ctctagtgtg tagtgtgtaa atcaaggctt   1560
ctagcattgt gtcggtagct tgtatggatc agactagaaa tgactttatc cattacaaga   1620 attttactc ggaaagccca tgacggtgat gatttcaata cgttgcacaa gcaactttct   1680
tctgtaattg aaatagagga tctggtctga gtatgagaag atgggcatgt taacgc       1736
```

<210> SEQ ID NO 19
<211> LENGTH: 1900
<212> TYPE: DNA
<213> ORGANISM: Physcomitrella patens

<400> SEQUENCE: 19

```
atcccgggtt gtcgaggacg gagagagaag agagagagag agagagagag aggtgttgtt     60
taggggaggc atgcgggagc aggattggtg ttaagttcgt aaggagaagg gagtacatgc    120
aagtgcgtgc ttgtcggata tcggacagct ggatttgtaa ataagcggag aggagggtcg    180
gtaatcaggg gcgtacatcg atggagccgc gtgtgggaaa caagtatcgg ctgggacgga    240
aaattgggag cggttccttt ggggagatct atcttggac caatgttcag accaatgagg    300
aggtcggaat aaagctggaa agcatcaaga cgaagcatcc acaattgctg tacgagtcca    360
agctctaccg gatactacaa ggaggaactg ggattcccaa tatcagatgg ttcgggatag    420
aaggagacta caatgtcttg gttctggatc tgttggggcc aagtctcgaa gacctttca    480
```

```
acttctgcag ccggaagttc tctttaaaga ctgttctcat gcttgctgac cagctgatca    540
acagagtgga gtatgtgcat gcgaaaagct ttcttcatag agacatcaag cctgataatt    600
ttctaatggg gcttggtagg cgagcaaacc aggtctacat tattgatttt ggtcttgcca    660
agaagtaccg cgacccttcc acgcatcagc atattcccta cagggagaac aaaaatctga    720
cagggactgc tcggtatgca agcatcaaca ctcatcttgg tattgagcaa agcagacgag    780
atgatttgga atctcttgga tatgtgctca tgtacttcct gagaggcagt cttccatggc    840
aaggactgaa agcgggaacc aagaagcaga agtacgagaa gatcagtgag aaaaaaatgt    900
ccacgcccat tgaggtcctt tgtaaaaatt atccttcaga attcgcctcg tacttccact    960
actgccggtc cttgcgtttt gatgacaaac ccgactatgc atatttgaaa agaatcttcc   1020
gtgacctctt tattcgtgag ggttttcaat ttgactacgt ttttgactgg acaattctga   1080
agtaccagca gtcacaaatt tccggtggca gttcaactcg actgggtgct tctgcagggc   1140
aaaccagtgg tgcacttgga actggggcta caggaagccg agacctgcag cggcccaccg   1200
aaccaatgga tccttctcgg cgcaggcttc tggaggagc aaatggctcc ggggtcgcaa   1260
atgctttgga ctcatctaag cacaaaagtc ctggacttga tgaatctgct aaggattctg   1320
ctcttgctgt tgtgtcagaa ccagagcgca tgcatacatc ttcgtatgca actcgggggg   1380
gttcttcctc caggcgagct gtcctatcta gcagcaggcc ctcagggca tcagcagaag   1440 tcgtagattc ctctcgaaca gggagcagta agcttggtcc caccagctta cggtcgtcag   1500
cagggatgca gaggagctct ccagttactt cggacccaaa gcggatatct agccgccatc   1560
cacaaccgcc atctgccaac ttgaggattt acgaagccgc tatcaaggga gttgaatcac   1620
tttctgttga ggtggatcaa agccgttata agtaggccca ggcttgtggt tatatagccg   1680
ggctctgtct tctatcaaac cctcttgtta tgtagatgag agttgctcta catttggcaa   1740
cagcctgatt gaggggaaaa cggtggttct gtcctacaat ggtgctaaga ctacaggtct   1800
ctcatactta ggaatgaatg gatctctatc ttgttaccat caaaccattg tcagtgcttt   1860
gtgtggtagc tctctgccat acgattccta aggttaacgc                        1900
```

<210> SEQ ID NO 20
<211> LENGTH: 1217
<212> TYPE: DNA
<213> ORGANISM: Physcomitrella patens

<400> SEQUENCE: 20

```
gcgttaacgg gaggaaggtc gggggaagag acgcttgagg ctgctgaaag gggattcact     60
cagcgtcccc acccattcgt caatctggcg cagaagatcg gaaaatcggt ccgacggcca    120
ggtgttatgt ccaaggcccg ggtttacaca gatgtgaatg tccaacgtcc gaaagattat    180
tgggactacg aggccctcac cgtccaatgg ggggaccaag acgattacga ggtagtgcgt    240
aaggtggggc gagggaaata cagtgaggtt tttgaaggtg tcaacgccgt gaatagtgag    300
cgttgcgtta tgaagatttt gaagccagta aagaaaaaaa agatcaaaag agagatcaag    360
attctgcaaa acctttgtgg agggcccaac attgtgaagc ttctggacat tgtccgtgat    420
cagcaatcga agacacccag cctaatttt gagtatgtga acaatactga tttcaaagtg    480
ctctacccca ctcttacaga ctttgatatc cgatactaca ttcatgagct gctcaaggct    540
ttggactatt gccattctca agggattatg cacaggatg tgaagccaca caacgtgatg    600
attgaccatg agcagcggaa gcttaggctt attgactggg gacttgccga attctatcat    660
```

-continued

| | |
|---|---|
| cctggcaaag agtataatgt gcgtgttgcc tctaggtact tcaagggtcc tgagctgctg | 720 |
| gttgatcttc aagattatga ttactctctc gacatgtgga gcttggggtg catgtttgcc | 780 |
| ggcatgatat ttcggaagga gccattcttt tatgggcatg acaattatga tcaacttgtg | 840 |
| aagattgcta aggtgttggg aactgatgaa ttgaattcct atctaaacaa ataccgccta | 900 |
| gagctggacc cccatttgga agcactggtt ggcaggcata gcaggaaacc ttggtcaaag | 960 |
| ttcatcaatg ctgataatca gcgtctggtt gttccagagg ctgtggattt tttggataag | 1020 |
| cttctacgct acgatcatca agacaggctg actgcgaagg aagctatggc acatccctat | 1080 |
| ttttatcccg tgaaggtgtc ggaggttagc aaccgtcgca gtgcttgata tgaattgata | 1140 |
| tatctcatat gggctttctt gtgattacgt cccacccggc taccaggttt ctcagttgtg | 1200 |
| cgaagcgctg agctcgc | 1217 |

<210> SEQ ID NO 21
<211> LENGTH: 1718
<212> TYPE: DNA
<213> ORGANISM: Physcomitrella patens

<400> SEQUENCE: 21

| | |
|---|---|
| atcccgggcg agccatggcg ccacttgctt cggcgaatgg gactgtttga cttcttcgct | 60 |
| tcgccccgc ctcgcccttc accctcctct gttcttgtca cagcctcctc ctccgtctct | 120 |
| gtctgttggc tgggtaagtt ttgggagtga ggaggacgtg gtcatggaag aagagccccc | 180 |
| ctcttttgta gtggactgtc ggtaaattgg acctggagcc tgccggctca tcgcgtttgc | 240 |
| ttagattgtg ggcgggtgct gttgaaattc cttgaacttg ctactggtcg gaaacgctcg | 300 |
| aattgcgact ttgattgaag gtctggttgt tgctgcggtc gggatcttac tcagtctctt | 360 |
| caataggacc tctgaagcag tatggagact agcagtggaa ctccagaatt gaaagttata | 420 |
| agtactccga cctacggagg tcattacgtg aaatatgttg tggcgggaac tgatttcgaa | 480 |
| gtcaccgcga ggtacaagcc accacttcgt ccgattgggc gcggagctta tggaatcgtc | 540 |
| tgttcactct tgataccgt tacgggtgag gaggtggcgg tcaaaaagat tggaaacgcc | 600 |
| ttcgacaaca ggatcgatgc gaagcgaaca ctgcgtgaaa taaaactcct ccggcatatg | 660 |
| gatcatgaaa acgtcgttgc cattacagac atcattcgtc ccccaactag ggagaatttc | 720 |
| aacgacgtgt acattgtata cgagttgatg gatacggacc tacaccagat cattcgttca | 780 |
| aatcaagctc tcacagaaga ccactgtcag tattttctgt atcaaatctt gcggggcttg | 840 |
| aagtacatcc attcggcgaa cgtcttgcac cgggacttga agcccaccaa ccttctcgtc | 900 |
| aatgccaatt gcgatttgaa aatcgcagat tttggcttgg cacgcactct ctctgaaacg | 960 |
| gatttctga ctgagtatgt tgtaacgagg tggtacagag ctccagagct gctcctgaat | 1020 |
| tgttcagcat acactgcagc tattgacatt tggtctgtgg ggtgcatctt catggagttg | 1080 |
| cttaaccgat ctgcgttgtt ccctgggaga gactatgtgc atcagctccg cctaattaca | 1140 |
| gaactcatcg gaactcctga agataggggat cttgggtttt tgagaagcga caatgctagg | 1200 |
| cggtatatca agcacctgcc tcgacagtcg cctattccct taacccagaa gttcagaggc | 1260 |
| attaatcgtt ctgctcttga tcttgttgaa aagatgctgg tctttgatcc agcgaaaaga | 1320 |
| atcacagtgg aagctgcctt ggcgcaccct tatttagctt cacttcatga catcaacgat | 1380 |
| gagcctgcct cggtatctcc cttcgagttt gacttcgagg agcccctat ctcggaggag | 1440 |
| catatcaagg atctcatttg gagggaggct ctggattgca gcttaggtcc tgatgatatg | 1500 |
| gtgcagtaac ttcacacttc atctcaagtt gtaaggccta ctctcaattc tttaggtggc | 1560 |

```
tacaacgcta tcccggcgtt gtatggtttt gcaacttatt ccccccgtg tgattacact    1620 attggattat agaatgacaa ttcgttagtt ctttcccctg gcgctatatc tttgtctgca    1680
catttcatcc agcagacatt gttgctcggc gttaacgc                            1718

<210> SEQ ID NO 22
<211> LENGTH: 2177
<212> TYPE: DNA
<213> ORGANISM: Physcomitrella patens

<400> SEQUENCE: 22
atcccgggct tgtattggct cggataattt atgttgacaa ttgatttgtg aggcttcgta      60
ttgagtcagc gagcaggctg agagttcggc agcgaagtta cactcgacct ggctgaaatt    120
tggaattgaa gcgcgtgaag cttcatctgt gattttggag gttgtttgac tgatgagaag    180
aggtctctga gctgagaatg tttgcaattt aggggcacca ccggtttgtt ggagtccctt    240
gccacttatt acaattgttg gtttacaagc tcgacgagtt tcaatcgaac gtagagtttt    300
agtcgggtcg aggatctatg tatccgctca gcggagaaga gagcctgatg ttgccgaagc    360
gatcgtgtgg gatttgacta gaaagaggtg gaccgcatca gaactattta ttccttgtga    420
gggaaggatc gaggttccaa tgggtctcac tccgttttct tgtgtcacgg ttcaaggtta    480
tgtccgggtg gtctaccccg acggccacgt cgagaatctg agcaaatctt gtagcgtgca    540
cgatcttctt ctgggtaatc cagactacta tgtctgcggt agcaccccctt acacaatcac    600 caatcgtatg gcagcggaag aggtgctcga gtatggggtg acctacttcg tttgcgcaac    660
gccaaatgcc caacctttct tagaacgtca gccgaaggta gtacatcgag gatccaagat    720
tttgccacga ttttccaaac atgggggtcca tgtgcgggag ttgcgaagcc cgacgcatgg    780
gagccaacag tcacggaagg ttttttgatta tcattcagta acgatgcagc agcttgaatc    840
catacgaaac gagggcccag agcctcacct cgctggagac cgaccatcga agcaccttaa    900
gctcgttttc attcggcatt gcttgcgagc acttcgactt cctagaattt caatagacct    960
aatggaatcg ccactcccta atctttccgg agaggcctta tcgccgacgg caactgccaa   1020
agacgagatt actcagatga tactaaaaag tgccgcaagg tccgaattag gaatgtatgt   1080
ttcgaagaga caggaattct atcttccgaag agcgcgtagg cggcgtaagt ttgcgtggaa   1140
gccggttttg cagagcatct ccgagatgaa gcctgtcatg gaattccaca ctccgatggc   1200
ttaccgggat agtgggtctc cgccgaagaa cgcctctacc ccatccttac ctggcccgaa   1260
gaacatttca ccgccacgac aagtgagtgt cccgcaaagg agcagtcctc cgccgaagaa   1320
cgtctcacca cctccccagc ccgcatttgt agcgcggact gcgtcgaagt attctgctgc   1380
atctcagcaa gttcaacgaa atcgaggcaa cgcgaaatct ctttatatgg cgtagtttgt   1440
gtctcgactg aactcctatc tattccccca tcgagataac tgcattcgtt ggataaattt   1500
ctccaacatt tttgctcttc atcctcaagc agctcctcaa tggccagtaa tatgttacga   1560
cattgtgcac aactccaatt acgtagcgtt attctgtaac ccacgttcat cgaggtatca   1620
aggaatggcg cagtaagcac tgctactttg tgctttggta tcccgttgtg acgagatgtc   1680
atgtcgcacc gtgcctatca gtgggatttt cttgagcgca gatcttgctt ccgcagtttg   1740
tttcataacg ttttggttcg taggggggcct agacggtact atcaagcaat gagaagtgtg   1800
ctggtgtgga tttgacagca atcttttgga ggattgtctt tcctatgtag aacatagcga   1860
ggacacttgc gcctggtggg cacatcccat agaacatagt gcttcacttc tgggttgttc   1920
```

```
accactagga tcatatgacc ttctcatcta ttttcgggct tgtttcgag ctcatgtacc    1980 atcgactagc gtcactttga ctgcggtgat aatcgtttgt caatttagtg gagctttgta    2040
gatgatagat gccatttgta cagtagcttg gatgctgttt acaagatagc ggcagctaga    2100
agccttaaac ctttagctac catgtattat ttaaacctat atgaagtgaa cggctgtgca    2160
gatattgccg ttaacgc                                                    2177

<210> SEQ ID NO 23
<211> LENGTH: 1731
<212> TYPE: DNA
<213> ORGANISM: Physcomitrella patens

<400> SEQUENCE: 23
atcccgggcg gtcgagtcgt attaggtgtt gtttcattgt aagggttcgg aagcacgggg      60
cacggcgtat ataccgttcc ccttgaacgt tgatctcacc tttggaagac ctgaattgag     120
tagcgtgcgg aagctgcatc gatccggaag agacgatgag taggagagtg agaaggggag     180
gtcttcgcgt cgcggtgccg aagcaagaga ctcccgtcag caaattttg  actgccagtg     240 gaactttcca ggatgatgat atcaagctca accacaccgg gcttcgcgtc gtctcttcag     300
aacctaacct tcctacgcag acgcagtcta gctccccaga tgggcaactg tcaatagcag     360
acctggagtt agtgcggttc ttgggaaagg gtgcgggtgg aaccgtgcag cttgtccggc     420
acaaatggac caatgtcaat tatgcactga aggcgataca aatgaatatc aacgaaacag     480
tgaggaagca gattgttcag gagctgaaaa tcaaccaagt gacgcaccag cagtgccctt     540
atatcgtgga atgcttccac tccttctacc acaacggcgt catatccatg atcctagagt     600
acatggacag gggctcgttg tccgacatta ttaagcaaca aaagcagata cctgagccgt     660
atttggccgt cattgctagt caagttctga agggattgga atacctacac caagtcaggc     720
acatcataca tcgtgatata aagccctcca acctcctcat caatcacaag ggtgaggtca     780
aaatatctga ttttggtgtc agtgctgtgt tggttcattc cttggcccag cgagacacgt     840
tcgttgggac ttgcacatat atgtcgccag aacgccttca ggggcgttcg tatgcatacg     900
acagtgacct atggagttta ggattgactc ttttggagtg tgcgttgggt accttcccat     960
acaaaccagc tggaatggaa gagggttggc aaaatttctt catcctcatg gaatgtatag    1020
ttaatcaacc ccccgcagcc gcatcccctg acaaattctc ccccgaattt tgttctttta    1080
ttgaatcctg catccggaaa tgtcccagtg aacgaccatc aactactgat ttacttaaac    1140
atccgttcct gcaaaagtac aacgaggaag agtaccattt gagcaagatt ttgtaactta    1200
aagttagcct cgcatggcgt gcagagactg tcactaccac aagcctgatc caccactgaa    1260
cttcaaggga ctttaccaaa agcatggtcg aactacctcg ccaatccgcc actttctcaa    1320
tgccttttcc ttatatagtc atatgtggtc aagttgagaa cgatatcaaa tcagattgac    1380
ggaaaaaaca tcttcaacgc cgtttcccaa ccttatagaa agtggagttt ctcaatgag     1440 ccccatttgt cgctgagaac gtgcagctca tgaaacaatc cataagtgtg ttaatcgggg    1500
tcttatatta tcatccaccat gctagctttt tatgttacct gcacttttc tttccttatt    1560 gcacagcatc gaacacttct tcgatacccca aaacaatatt tccatcttct ttcttctttt    1620
tttcacgtct tgcgacaagg aatttcctca cggagatttt tcaacacttt tctcaaatgt    1680
ttttagagtt tttaaactga caattgaaga ggtcggacct accggactcg c              1731

<210> SEQ ID NO 24
<211> LENGTH: 1407
```

```
<212> TYPE: DNA
<213> ORGANISM: Physcomitrella patens

<400> SEQUENCE: 24
atcccgggag aggctgatct gatgctacag tttcgtgtgc agctagtctt tagagattcg      60
ggcaacgcac ttgttgaaga tcggaaactt tcaaaatcgg tcgagtcgta ttaggtgttg     120
tttcattgta agggttcgga agcacggggc acggcgtata taccgttccc cttgaacgtt     180
gatctcacct ttggaagacc tgaattgagt agcgtgcgga agctgcatcg atccggaaga     240
gacgatgagt aggagagtga aaggggagg tcttcgcgtc gcggtgccga agcaagagac      300
tcccgtcagc aaattttga ctgccagtgg aactttccag gatgatgata tcaagctcaa      360
ccacaccggg cttcgcgtcg tctcttcaga acctaacctt cctacgcaga cgcagtctag     420
ctccccagat gggcaactgt caatagcaga cctggagtta gtgcggttct taggaaaggg     480
tgcgggtgga accgtgcagc ttgtccggca caaatggacc aatgtcaatt atgcactgaa     540
ggcgatacaa atgaatatca acgaaacagt gaggaagcag attgttcagg agctgaaaat     600
caaccaagtg acgcaccagc agtgcccttta tatcgtggaa tgcttccact ccttctacca    660
caacggcgtc atatccatga tcctagagta catggacagg ggctcgttgt ccgacattat    720
taagcaacaa aagcagatac ctgagccgta tctggccgtc attgctagtc aagttctgaa    780
gggattggaa tacctacacc aagtcaggca catcatacat cgtgatataa agccctccaa    840
cctcctcatc aatcacaagg gtgaggtcaa aatatctgat tttggtgtca gtgctgtgtt    900
ggttcattcc ttggcccagc gagacacgtt cgttgggact tgcacatata tgtcgccaga    960
acgccttcag gggcgttcgt atgcatacga cagtgaccta tggagtttag gattgactct   1020
tttggagtgt gcgttgggta ccttcccata caaaccagct ggaatggaag agggttggca   1080
aaatttcttc atcctcatgg aatgtatagt taatcaaccc cccgcagccg catcccctga   1140
caaattctcc cccgaatttt gttctttat tgaatcctgc atccggaaat gtcccagtga    1200
acgaccatca actactgatt tacttaaaca tccgttcctg caaaagtaca acgaggaaga   1260
gtaccatttg agcaagattt tgtaacttaa agttagcctc gcatggcgtg cagagactgt   1320
cactaccaca agcctgatcc accactgaac ttcaagggac tttaccaaaa gcatggtcga   1380
actacctcgc caatccgcca gagctca                                       1407

<210> SEQ ID NO 25
<211> LENGTH: 2253
<212> TYPE: DNA
<213> ORGANISM: Physcomitrella patens

<400> SEQUENCE: 25
atcccgggtg taggcgggcg aggttcgatg caatggggca gtgttatgga aagtttgatg     60
atggaggcga aggggaggat ttgtttgagc ggcagaaagt gcaggtttct aggacgccaa    120
agcatggatc gtggagcaat agcaaccgag ggagcttcaa caatggcggg ggggcctcgc    180
ctatgagagc caagacgtcg ttcgggagca gccatccgtc cccgcggcat ccctcagcta    240
gtccgctccc tcactacacg agctccccag cgccttcgac cccgcgacgg aacattttca    300
aaaggccttt tcctcctcct tctcccgcga agcacattca gtccagtctc gtgaaacggc    360
atggcgcgaa gccgaaagaa ggagggggcga tccctgaggc tgtcgatggt gagaagccct    420
tggataagca tttcggctat cacaagaact tcgctactaa gtatgagctg ggcatgaag     480
tcggtcgcgg gcacttcggt cacacatgtt acgcgaaagt acggaagggc gagcataagg    540
```

```
gacaagccgt ggcagtgaag ataatctcga aagcgaagat gacgactgct attgcgatcg      600
aggacgtggg acgagaagtg aaaattttga aggctctgac gggacaccag aatttggttc      660
gattctacga ttcctgcgag gaccatctaa atgtgtacat tgttatggaa ttatgtgaag      720
gaggtgaatt attggatcga attttgtctc ggggagggaa gtactcggag gaagacgcca      780
aggttgttgt gcggcagatt ttgagcgttg ttgcgttttg tcacctgcaa ggcgttgttc      840
accgagatct taagcctgag aattttctgt ttaccacgaa ggatgaatat gctcagctta      900
aggccattga ttttggattg tcagatttca tcaaacccga tgaaagactg aacgatatcg      960
ttggaagcgc atactacgtt gcgccggagg tattgcatag gttatattca atggaagctg     1020
acgtatggag cattggagtc atcacgtaca ttttgttatg tggtagtcga ccgttttggg     1080
cgcggaccga gtcgggcatt tttcgtgcgg tgttgagggc tgacccgagc tttgaagaag     1140
cccttggcc ttccatctct cccgaagcca aggatttcgt gaagcgtctc ctgaataagg      1200
atatgcggaa acgcatgact gctgcacaag ctttaactca tccatggatt cgaagtaaca     1260
acgtgaagat acctctggat atcttagtgt acagacttgt gaggaattat cttcgtgcat     1320
catccatgag aaaggctgct tgaaggccc tgtcaaagac tttaaccgaa gacgagactt      1380
tttatctacg tactcaattt atgctgctag aaccaagtaa caacggtcgt gttacttttg     1440
agaatttcag acaggcactg ctgaaaaatt caacagaggc catgaaagag tcacgggttt     1500
ttgaaattct ggaatcgatg gatggtcttc atttcaagaa aatggacttt tcagagttct     1560
gtgcagcggc cattagtgtt ctccagttag aagccacaga acgatgggag cagcatgctc     1620
gcgcagctta cgacatattt gagaaagagg gtaaccgagt catttatcct gatgaacttg     1680
cgaaagagat gggactagca ccaaatgtac cagcccaagt gtttctagat tggattagac     1740
agtctgatgg tcggctgagt ttcactgggt tcaccaagct gctacatgga atttccagcc     1800
gtgctatcaa aaatctccag cagtgattct ttgcatcgta cagttcggaa tggagttttt     1860
aagctctttt agtttcactt ccgtcttcaa ctgctgcttc gcctcgtctc tgagctgtga     1920
tagcgtatct caagcatatg cacaactcgc attttttgctg aagtgatttg tcacctcaca     1980
ttagtcgggc ctctggaact ttcacttatt tggattattt atgtagaagt ccagatcaaa     2040
aagcgaaaag gaatggctag atattgtcac aagaagtaac atagtcaaat tcaggagcac     2100
ttaagcacac attgagtgct ttttattgga attcttagat atggaactga tgtttccaag     2160
ggaagggtct atgaggcaga gagtggaatg tatagactgg catatggtta agtgatcatt     2220
ggactgccgt tctactccgg ttgtcgttaa cgc                                  2253

<210> SEQ ID NO 26
<211> LENGTH: 2230
<212> TYPE: DNA
<213> ORGANISM: Physcomitrella patens

<400> SEQUENCE: 26
atcccgggcg aactgcgatc tgagattcca acttggaagg gcctcgcgta agaccggatc       60
tcgtttctta cgcttttgcg cctcgcgata tttgtacatt gtttcctctg gttttattcg      120
attccgcctc tgaaaatgtg aacgggctgc aagcttggtt ttggagcaac gttggagcat      180
tgaagggttg cgctcgtccc tgcccattcc tcgcttctgc tctggcctat gtcatgacga      240
cgtgaaggag aggatttgag ggttttgtaa gtgatataat cctccccgag gagatttctg      300
tgagttgatt aacttggatc agcgacatgg ggaacactag ttcgagggga tcgaggaagt      360
ccactcggca ggtgaatcag ggagtcgggt ctcaagacac ccgagagaag aatgatagcg      420
```

```
tcaatccaaa gacgagacag ggtggtagcg ttggcgcaaa caactatggc ggaaagccaa      480
gcagtggtgc tcaggccgga gaacgatcca cctctgcgcc cgctgctctg ccgaggccga      540
agccagcatc gaggtcagta tccggtgttt tgggtaagcc gctgtcagat attcgtcaat      600
cttacatcct gggacgggag cttggccgag gcagttcgg agtgacttac ttgtgtactg       660
acaagatgac gaatgaggcg tacgcgtgca agagcatcgc caaacggaaa ctgaccagta      720
aggaggatat cgaggatgtt aagcgggagg ttcagattat gcatcacctg tcggggacac      780
ccaatatcgt ggtgttaaag gatgtgttcg aggacaagca ttccgtgcat cttgtgatgg      840
agctctgtgc aggtggcgag ctcttcgatc gcatcattgc caaggggcat tacagtgagc      900
gcgccgctgc cgatatgtgc agagtcatcg tcaatgtggt gcacagatgc cactcattag      960
gggtcttcca tcgggatctc aagccagaga atttctgtt ggccagcaag gctgaggatg     1020
cgcctctgaa ggccacagac ttcggtctgt caactttctt taagccagga gatgtgttcc     1080
aggatattgt tggaagtgcg tattacgtgg cccctgaagt tttgaagaga agttatggtc     1140
ctgaagctga tgtttggagt gcaggcgtga ttgtgtacat tctgctgtgt ggtgtacccc     1200
ccttctgggc tgaaactgag cagggtatct ttgacgctgt gctcaaaggg cacatagact     1260
tcgagaacga tccatggccg aaaatctcca acggggctaa ggatttggtg aggaaaatgc     1320
taaaccctaa cgtgaagata cgtctgacgg cacagcaggt gttgaaccat ccatggatga     1380
aggaagatgg tgatgctcca gacgtgccac tcgacaatgc ggtgttgacc agactgaaaa     1440
atttctcagc cgccaacaag atgaaaaagc tggcgctgaa ggtgattgca gagagtctgt     1500
cggaggaaga gatcgtgggg ttgagggaga tgttcaaatc catagataca gacaacagcg     1560
gcacggtgac gttcgaggag cttaaggaag ggttgctgaa gcagggctca aaacttaatg     1620
aatcggacat caggaaaacta atggaagctg cagatgtcga tggaaacggc aagatcgact     1680
tcaacgagtt catatcggca acaatgcaca tgaacaagac ggagaaagag gatcaccttt     1740
gggcagcatt catgcatttc gacacggaca atagcgggta tatcaccatc gacgagcttc     1800
aggaagcaat ggagaagaat ggaatgggag atcctgagac catccaagag atcatcagcg     1860
aggtggacac agacaacgac ggaagaatag actacgacga gttcgtagcc atgatgcgca     1920
agggcaatcc tggcgctgaa aacgaggaa cggtgaacaa gcccagacac aggtagtagc      1980
tcctggttgc caatttgacg acgggtttgg caaggcaaca gtagttgttg ttagctttca     2040
gattcaggtt cggtattgtt catgccctcc tttgtctcga acaatggact ctaggccttt     2100
ccaatggaaa agctattcca acagggtttg cataacgtgt agtagaatga aagcattgcc     2160 tgggggggtgt acagtgcctg tgatcttgtg gagttctcgt aggatggctt cggttggatc     2220
tcgttaacgc                                                            2230
```

<210> SEQ ID NO 27
<211> LENGTH: 749
<212> TYPE: PRT
<213> ORGANISM: Physcomitrella patens

<400> SEQUENCE: 27

Met Gly Val Asp Met Lys Ala Pro Ala Lys Gln Ser Leu Gly Val Gly
1               5                   10                  15

Leu Leu Leu Cys Ser Val Val Ile Leu Ser Val Val Ser Ser Val Tyr
            20                  25                  30

Gly Gln Val Gln Thr Asp Pro Val Asp Thr Thr Gly Leu Ile Ser Met
        35                  40                  45

```
Trp Tyr Asp Leu Lys Gln Ser Gln Ser Leu Thr Gly Trp Thr Gln Asn
 50                  55                  60

Ala Ser Asn Pro Cys Gly Gln Gln Trp Tyr Gly Val Val Cys Asp Gly
 65                  70                  75                  80

Ser Ser Val Thr Glu Ile Lys Ile Gly Ser Arg Gly Leu Asn Gly Asn
                 85                  90                  95

Phe Asn Pro Ser Tyr Phe Gln Asn Ala Phe Lys Lys Leu Arg Ile Phe
            100                 105                 110

Asp Ala Ser Asn Asn Asn Ile Glu Gly Asn Ile Pro Gln Gln Phe Pro
            115                 120                 125

Thr Ser Leu Thr Gln Met Ile Leu Asn Asn Lys Leu Thr Gly Gly
130                 135                 140

Leu Pro Gln Phe Asp Gln Leu Gly Ala Leu Thr Val Val Asn Leu Ser
145                 150                 155                 160

Asn Asn Asn Leu Thr Gly Asn Met Asn Pro Asn Tyr Phe Asn Val Ile
                165                 170                 175

Val Asn Val Glu Thr Phe Asp Val Ser Tyr Asn Gln Leu Glu Gly Thr
            180                 185                 190

Leu Pro Asp Ser Ile Leu Asn Leu Ala Lys Leu Arg Phe Leu Asn Leu
            195                 200                 205

Gln Asn Asn Lys Phe Asn Gly Lys Leu Pro Asp Asp Phe Ser Arg Leu
210                 215                 220

Lys Asn Leu Gln Thr Phe Asn Ile Glu Asn Asp Gln Phe Thr Gly Asn
225                 230                 235                 240

Tyr Pro Ser Gly Leu Pro Ser Asn Ser Arg Val Gly Asn Arg Leu
                245                 250                 255

Thr Phe Pro Pro Pro Ala Pro Gly Thr Pro Ala Pro Arg Thr Pro
            260                 265                 270

Ser Pro Ser Gly Thr Ser Asn Gly Ser Ser Ser His Leu Pro Leu Gly
            275                 280                 285

Ala Ile Ile Gly Ile Ala Ala Gly Gly Ala Val Leu Leu Leu Leu
290                 295                 300

Ala Leu Gly Ile Cys Leu Cys Cys Arg Lys Arg Ser Lys Lys Ala Leu
305                 310                 315                 320

Gly Asp Pro Glu Ala Thr Thr Ser Ser Arg Arg Pro Trp Phe Thr Pro
            325                 330                 335

Pro Leu Ser Ala Lys Ser Gln Ser Asp Pro Ser Lys Ser Ile Asp Lys
            340                 345                 350

Thr Thr Lys Arg Asn Ile Phe Gly Ser Ser Lys Ser Glu Lys Lys Ser
            355                 360                 365

Ser Lys His Arg Val Phe Glu Pro Ala Pro Leu Asp Lys Gly Ala Ala
            370                 375                 380

Asp Glu Pro Val Val Lys Ala Ser Pro Val Lys Val Leu Lys Ala
385                 390                 395                 400

Pro Pro Ser Phe Lys Gly Ile Ser Gly Leu Gly Ala Gly His Ser Lys
            405                 410                 415

Ala Thr Ile Gly Lys Val Asn Lys Ser Asn Ile Ala Ala Thr Pro Phe
            420                 425                 430

Ser Val Ala Asp Leu Gln Ala Ala Thr Asn Ser Phe Ser Gln Asp Asn
            435                 440                 445

Leu Ile Gly Glu Gly Ser Met Gly Arg Val Tyr Arg Ala Glu Phe Pro
450                 455                 460
```

Asn Gly Gln Val Leu Ala Val Lys Lys Ile Asp Ser Ser Ala Ser Met
465                 470                 475                 480

Val Gln Asn Glu Asp Asp Phe Leu Ser Val Val Asp Ser Leu Ala Arg
            485                 490                 495

Leu Gln His Ala Asn Thr Ala Glu Leu Val Gly Tyr Cys Ile Glu His
            500                 505                 510

Asp Gln Arg Leu Leu Val Tyr Glu Tyr Val Ser Arg Gly Thr Leu Asn
            515                 520                 525

Glu Leu Leu His Phe Ser Gly Glu Asn Thr Lys Ala Leu Ser Trp Asn
    530                 535                 540

Val Arg Ile Lys Ile Ala Leu Gly Ser Ala Arg Ala Leu Glu Tyr Leu
545                 550                 555                 560

His Glu Val Cys Ala Pro Val Val His His Asn Phe Lys Ser Ala
                565                 570                 575

Asn Ile Leu Leu Asp Asp Glu Leu Asn Pro His Val Ser Asp Cys Gly
            580                 585                 590

Leu Ala Ala Leu Ala Pro Ser Gly Ser Glu Arg Gln Val Ser Ala Gln
            595                 600                 605

Met Leu Gly Ser Phe Gly Tyr Ser Ala Pro Glu Tyr Ala Met Ser Gly
    610                 615                 620

Thr Tyr Thr Val Lys Ser Asp Val Tyr Ser Phe Gly Val Val Met Leu
625                 630                 635                 640

Glu Leu Leu Thr Gly Arg Lys Ser Leu Asp Ser Ser Arg Pro Arg Ser
                645                 650                 655

Glu Gln Ser Leu Val Arg Trp Ala Thr Pro Gln Leu His Asp Ile Asp
            660                 665                 670

Ala Leu Ala Arg Met Val Asp Pro Ser Leu Lys Gly Ile Tyr Pro Ala
            675                 680                 685

Lys Ser Leu Ser Arg Phe Ala Asp Ile Val Ala Leu Cys Val Gln Pro
    690                 695                 700

Glu Pro Glu Phe Arg Pro Pro Met Ser Glu Val Val Gln Ala Leu Val
705                 710                 715                 720

Arg Leu Met Gln Arg Ala Ser Leu Ser Lys Arg Ser Glu Ser Ala
                725                 730                 735

Val Gly Ile Glu Ser Asn Glu Pro Ser Glu Thr Ser Leu
            740                 745

<210> SEQ ID NO 28
<211> LENGTH: 308
<212> TYPE: PRT
<213> ORGANISM: Physcomitrella patens

<400> SEQUENCE: 28

Met Ser Val Ser Gly Met Asp Asn Tyr Glu Lys Leu Glu Lys Val Gly
1               5                   10                  15

Glu Gly Thr Tyr Gly Lys Val Tyr Lys Ala Arg Asp Lys Arg Ser Gly
            20                  25                  30

Gln Leu Val Ala Leu Lys Lys Thr Arg Leu Glu Met Glu Glu Glu Gly
        35                  40                  45

Val Pro Ser Thr Ala Leu Arg Glu Val Ser Leu Leu Gln Met Leu Ser
    50                  55                  60

His Ser Met Tyr Ile Val Arg Leu Leu Cys Val Glu His Val Glu Lys
65                  70                  75                  80

Gly Ser Lys Pro Met Leu Tyr Leu Val Phe Glu Tyr Met Asp Thr Asp
                85                  90                  95

Leu Lys Lys Tyr Ile Asp Leu His Gly Arg Gly Pro Ser Gly Lys Pro
            100                 105                 110

Leu Pro Pro Lys Val Val Gln Ser Phe Met Tyr Gln Leu Cys Thr Gly
            115                 120                 125

Leu Ala His Cys His Gly His Gly Val Met His Arg Asp Leu Lys Pro
            130                 135                 140

Gln Asn Leu Leu Val Asp Lys Gln Thr Arg Arg Leu Lys Ile Ala Asp
145                 150                 155                 160

Leu Gly Leu Gly Arg Ala Phe Thr Val Pro Met Lys Ser Tyr Thr His
                165                 170                 175

Glu Ile Val Thr Leu Trp Tyr Arg Ala Pro Glu Val Leu Leu Gly Ala
                180                 185                 190

Thr His Tyr Ser Leu Pro Val Asp Ile Trp Ser Val Gly Cys Ile Phe
                195                 200                 205

Ala Glu Leu Val Arg Lys Met Pro Leu Phe Thr Gly Asp Ser Glu Leu
            210                 215                 220

Gln Gln Leu Leu His Ile Phe Arg Leu Leu Gly Thr Pro Asn Glu Thr
225                 230                 235                 240

Ile Trp Pro Gly Val Ser Gln His Arg Asp Trp His Glu Phe Pro Gln
                245                 250                 255

Trp Arg Pro Gln Asp Leu Ser Leu Ala Val Pro Gly Leu Ser Ala Val
                260                 265                 270

Gly Leu Asp Leu Leu Ala Lys Met Leu Val Phe Glu Pro Ser Lys Arg
            275                 280                 285

Ile Ser Ala Lys Ala Ala Leu Ser His Thr Tyr Phe Ala Asp Val Asp
            290                 295                 300

Lys Thr Ala Thr
305

<210> SEQ ID NO 29
<211> LENGTH: 425
<212> TYPE: PRT
<213> ORGANISM: Physcomitrella patens

<400> SEQUENCE: 29

Met Ala Asp Ala Lys Glu Glu Leu Ala Leu Arg Thr Glu Met His Trp
  1                 5                  10                  15

Ala Val Arg Ser Asn Asp Val Gly Leu Leu Arg Thr Ile Leu Lys Lys
                20                  25                  30

Asp Lys Gln Leu Val Asn Ala Ala Asp Tyr Asp Lys Arg Thr Pro Leu
            35                  40                  45

His Ile Ala Ala Ser Leu Asp Cys Val Pro Val Ala Lys Val Leu Leu
        50                  55                  60

Ala Glu Gly Ala Glu Leu Asn Ala Lys Asp Arg Trp Gly Lys Ser Pro
65                  70                  75                  80

Arg Gly Glu Ala Glu Ser Ala Gly Tyr Met Glu Met Val Lys Leu Leu
                85                  90                  95

Lys Asp Tyr Gly Ala Glu Ser His Ala Gly Ala Pro Arg Gly His Val
            100                 105                 110

Glu Ser Leu Ile Gln Val Ala Pro Pro Leu Pro Ser Asn Arg Asp Trp
            115                 120                 125

Glu Ile Ala Pro Ser Glu Ile Glu Leu Asp Thr Ser Glu Leu Ile Gly
            130                 135                 140

Lys Gly Ala Phe Gly Glu Ile Arg Lys Ala Leu Trp Arg Gly Thr Pro

```
                145                 150                 155                 160
Val Ala Val Lys Thr Ile Arg Pro Ser Leu Ser Asn Asp Arg Met Val
                    165                 170                 175

Ile Lys Asp Phe Gln His Glu Val Gln Leu Leu Val Lys Val Arg His
                180                 185                 190

Pro Asn Ile Val Gln Phe Leu Gly Ala Val Thr Arg Gln Arg Pro Leu
                195                 200                 205

Met Leu Val Thr Glu Phe Leu Ala Gly Gly Asp Leu His Gln Leu Leu
            210                 215                 220

Arg Ser Asn Pro Asn Leu Ala Pro Asp Arg Ile Val Lys Tyr Ala Leu
225                 230                 235                 240

Asp Ile Ala Arg Gly Met Ser Tyr Leu His Asn Arg Ser Lys Pro Ile
                245                 250                 255

Ile His Arg Asp Leu Lys Pro Arg Asn Ile Ile Val Asp Glu Glu His
                260                 265                 270

Glu Leu Lys Val Gly Asp Phe Gly Leu Ser Lys Leu Ile Asp Val Lys
                275                 280                 285

Leu Met His Asp Val Tyr Lys Met Thr Gly Gly Thr Gly Ser Tyr Arg
            290                 295                 300

Tyr Met Ala Pro Glu Val Phe Glu His Gln Pro Tyr Asp Lys Ser Val
305                 310                 315                 320

Asp Val Phe Ser Phe Gly Met Ile Leu Tyr Glu Met Phe Glu Gly Val
                325                 330                 335

Ala Pro Phe Glu Asp Lys Asp Ala Tyr Asp Ala Ala Thr Leu Val Ala
                340                 345                 350

Arg Asp Asp Lys Arg Pro Glu Met Arg Ala Gln Thr Tyr Pro Pro Gln
                355                 360                 365

Met Lys Ala Leu Ile Glu Asp Cys Trp Ser Pro Tyr Thr Pro Lys Arg
            370                 375                 380

Pro Pro Phe Val Glu Ile Val Lys Lys Leu Glu Val Met Tyr Glu Asp
385                 390                 395                 400

Cys Leu Leu Arg Leu Pro Lys Asp Arg Arg His Leu Arg Asp Ile Leu
                405                 410                 415

His Leu Arg Arg Asn Pro Ala Asp Ser
            420                 425

<210> SEQ ID NO 30
<211> LENGTH: 283
<212> TYPE: PRT
<213> ORGANISM: Physcomitrella patens

<400> SEQUENCE: 30

Met Lys Arg Tyr Gln Arg Arg Lys Val Gln Arg Leu Gly Arg Glu Gly
1               5                   10                  15

Gln Val Leu Leu Glu Arg Thr Leu Phe Lys Gln Leu Arg Pro Ser Pro
                20                  25                  30

Phe Val Pro His Leu Leu Ala Thr Pro Ile Asp Ser Asp Asn Val Ala
            35                  40                  45

Leu Val Leu Asn Cys Val Leu Ala Gly Pro Leu Glu Leu Leu Leu Arg
        50                  55                  60

Ser Pro Leu Asp Glu Asn Ser Ala Arg Phe Leu Val Ala Asn Val Val
65                  70                  75                  80

Leu Ala Val Glu Leu Leu His Lys Asp Gly Val Val Tyr Arg Gly Ile
                85                  90                  95
```

```
Ser Pro Asp Val Leu Met Ile Asp Arg Lys Gly Arg Leu Gln Leu Val
            100                 105                 110

Asp Phe Arg Phe Ala Lys Gln Met Ser Asp Glu Arg Thr Phe Thr Val
            115                 120                 125

Cys Gly Met Ala Asp Phe Leu Ala Pro Glu Ile Ile Gln Gly Gln Gly
        130                 135                 140

His Gly Leu Ala Ser Asp Trp Trp Ala Val Gly Val Leu Met Tyr Phe
145                 150                 155                 160

Met Leu Gln Thr Glu Leu Pro Phe Gly Ser Trp Arg Asp Asn Glu Leu
                165                 170                 175

Glu Ile Phe Gly Arg Ile Ala Arg Arg Gln Leu Thr Phe Pro Ser Ser
            180                 185                 190

Phe Ser Pro Glu Ala Val Asp Leu Ile Asp Lys Leu Leu Val Val Asp
            195                 200                 205

Pro Thr Lys Arg Leu Gly Cys Asp Ser His Gly Ser Leu Ala Ile Arg
        210                 215                 220

Glu His Pro Trp Phe Arg Gly Ile Asn Trp Asp Lys His Leu Asp Cys
225                 230                 235                 240

Ser Val Glu Val Pro Ser Glu Ile Met Thr Arg Leu Gln Leu Ala Ile
                245                 250                 255

Asp Phe Leu Pro Val Asp Asp Ser Tyr Gln Val Phe Asp Leu Gln Pro
            260                 265                 270

Asp Glu Asp Asp Pro Pro Trp Leu Asp Gly Trp
        275                 280

<210> SEQ ID NO 31
<211> LENGTH: 417
<212> TYPE: PRT
<213> ORGANISM: Physcomitrella patens

<400> SEQUENCE: 31

Met Asp Leu Gly Gly Asp Arg Met Arg Ala Pro Gln Arg Gln Ser Arg
 1               5                  10                  15

Glu Tyr Gln Tyr Arg Ser Leu Asp Val Phe Thr Glu Gln His Glu Gln
            20                  25                  30

Leu Gln Lys Gln Gln Gln Asp Glu Tyr Gln Arg Thr Glu Leu Lys
        35                  40                  45

Leu Glu Thr Leu Pro Lys Met Leu Ser Asn Ala Thr Val Ser Ser Ser
    50                  55                  60

Pro Arg Ser Ser Pro Asp Gly Arg Leu Arg Thr Val Ala Asn Lys
65                  70                  75                  80

Tyr Ala Val Glu Gly Met Val Gly Ser Gly Ala Phe Cys Lys Val Tyr
                85                  90                  95

Gln Gly Ser Asp Leu Thr Asn His Glu Val Val Gly Ile Lys Leu Glu
            100                 105                 110

Asp Thr Arg Thr Glu His Ala Gln Leu Met His Glu Ser Arg Leu Tyr
        115                 120                 125

Asn Ile Leu Arg Gly Gly Lys Gly Val Pro Asn Met Arg Trp Phe Gly
    130                 135                 140

Lys Glu Gln Asp Tyr Asn Val Met Val Leu Asp Leu Leu Gly Pro Asn
145                 150                 155                 160

Leu Leu His Leu Phe Lys Val Cys Gly Leu Arg Phe Ser Leu Lys Thr
                165                 170                 175

Val Ile Met Leu Gly Tyr Gln Met Ile Asp Arg Val Glu Tyr Val His
            180                 185                 190
```

-continued

Ser Arg Gly Leu Val His Arg Asp Leu Lys Pro Asp Asn Phe Leu Met
            195                 200                 205

Gly Cys Gly Arg Gln Gly Asn Gln Val Phe Ile Ile Asp Phe Gly Leu
        210                 215                 220

Ala Lys Glu Tyr Met Asp Pro Ala Thr Arg Arg His Ile Pro Tyr Arg
225                 230                 235                 240

Asp Arg Lys Ser Phe Thr Gly Thr Ala Arg Tyr Ala Ser Arg Asn Gln
                245                 250                 255

His Arg Gly Ile Glu His Ser Arg Arg Asp Asp Ile Glu Ser Leu Gly
            260                 265                 270

Tyr Ile Leu Met Tyr Phe Leu Arg Gly Asn Leu Pro Trp Gln Gly Lys
        275                 280                 285

Gly Gly Gln Arg Leu Thr Asp Gln Lys Gln His Glu Tyr Met His Asn
        290                 295                 300

Lys Ile Lys Met Asn Thr Thr Val Glu Glu Leu Cys Asp Gly Tyr Pro
305                 310                 315                 320

Ser Gln Phe Ala Asp Phe Leu His His Ala Arg Ser Leu Gly Phe Tyr
                325                 330                 335

Glu Gln Pro Asp Tyr Cys Tyr Leu Arg Ser Leu Phe Arg Asp Leu Phe
            340                 345                 350

Ile Gln Lys Lys Phe Gln Leu Asp His Val Tyr Asp Trp Thr Val Tyr
        355                 360                 365

Thr Gln Leu Pro Gln Asn Gly Ser Leu Gln Ser Val Arg Ser Gln Asn
        370                 375                 380

Ser Ala Ala Ser Ser His Leu Gln Asn Arg Pro Ser Asn Val Ser Tyr
385                 390                 395                 400

Cys Pro Pro Leu Thr Lys Ser Glu Phe Arg Arg Glu Val Val Ala Ala
                405                 410                 415

Asn

<210> SEQ ID NO 32
<211> LENGTH: 484
<212> TYPE: PRT
<213> ORGANISM: Physcomitrella patens

<400> SEQUENCE: 32

Met Glu Pro Arg Val Gly Asn Lys Tyr Arg Leu Gly Arg Lys Ile Gly
1               5                   10                  15

Ser Gly Ser Phe Gly Glu Ile Tyr Leu Gly Thr Asn Val Gln Thr Asn
            20                  25                  30

Glu Glu Val Gly Ile Lys Leu Glu Ser Ile Lys Thr Lys His Pro Gln
        35                  40                  45

Leu Leu Tyr Glu Ser Lys Leu Tyr Arg Ile Leu Gln Gly Gly Thr Gly
    50                  55                  60

Ile Pro Asn Ile Arg Trp Phe Gly Ile Glu Gly Asp Tyr Asn Val Leu
65              70                  75                  80

Val Leu Asp Leu Leu Gly Pro Ser Leu Glu Asp Leu Phe Asn Phe Cys
                85                  90                  95

Ser Arg Lys Phe Ser Leu Lys Thr Val Leu Met Leu Ala Asp Gln Leu
            100                 105                 110

Ile Asn Arg Val Glu Tyr Val His Ala Lys Ser Phe Leu His Arg Asp
        115                 120                 125

Ile Lys Pro Asp Asn Phe Leu Met Gly Leu Gly Arg Arg Ala Asn Gln
    130                 135                 140

Val Tyr Ile Ile Asp Phe Gly Leu Ala Lys Lys Tyr Arg Asp Pro Ser
145                 150                 155                 160

Thr His Gln His Ile Pro Tyr Arg Glu Asn Lys Asn Leu Thr Gly Thr
                165                 170                 175

Ala Arg Tyr Ala Ser Ile Asn Thr His Leu Gly Ile Glu Gln Ser Arg
            180                 185                 190

Arg Asp Asp Leu Glu Ser Leu Gly Tyr Val Leu Met Tyr Phe Leu Arg
        195                 200                 205

Gly Ser Leu Pro Trp Gln Gly Leu Lys Ala Gly Thr Lys Lys Gln Lys
    210                 215                 220

Tyr Glu Lys Ile Ser Glu Lys Met Ser Thr Pro Ile Glu Val Leu
225                 230                 235                 240

Cys Lys Asn Tyr Pro Ser Glu Phe Ala Ser Tyr Phe His Tyr Cys Arg
                245                 250                 255

Ser Leu Arg Phe Asp Asp Lys Pro Asp Tyr Ala Tyr Leu Lys Arg Ile
            260                 265                 270

Phe Arg Asp Leu Phe Ile Arg Glu Gly Phe Gln Phe Asp Tyr Val Phe
        275                 280                 285

Asp Trp Thr Ile Leu Lys Tyr Gln Gln Ser Gln Ile Ser Gly Gly Ser
    290                 295                 300

Ser Thr Arg Leu Gly Ala Ser Ala Gly Gln Thr Ser Gly Ala Leu Gly
305                 310                 315                 320

Thr Gly Ala Thr Gly Ser Arg Asp Leu Gln Arg Pro Thr Glu Pro Met
                325                 330                 335

Asp Pro Ser Arg Arg Leu Pro Gly Gly Ala Asn Gly Ser Gly Val
            340                 345                 350

Ala Asn Ala Leu Asp Ser Ser Lys His Lys Ser Pro Gly Leu Asp Glu
        355                 360                 365

Ser Ala Lys Asp Ser Ala Leu Ala Val Val Ser Glu Pro Glu Arg Met
    370                 375                 380

His Thr Ser Ser Tyr Ala Thr Arg Gly Gly Ser Ser Arg Arg Ala
385                 390                 395                 400

Val Leu Ser Ser Arg Pro Ser Gly Ala Ser Ala Glu Val Val Asp
                405                 410                 415

Ser Ser Arg Thr Gly Ser Ser Lys Leu Gly Pro Thr Ser Leu Arg Ser
            420                 425                 430

Ser Ala Gly Met Gln Arg Ser Pro Val Thr Ser Asp Pro Lys Arg
        435                 440                 445

Ile Ser Ser Arg His Pro Gln Pro Pro Ser Ala Asn Leu Arg Ile Tyr
    450                 455                 460

Glu Ala Ala Ile Lys Gly Val Glu Ser Leu Ser Val Glu Val Asp Gln
465                 470                 475                 480

Ser Arg Tyr Lys

<210> SEQ ID NO 33
<211> LENGTH: 333
<212> TYPE: PRT
<213> ORGANISM: Physcomitrella patens

<400> SEQUENCE: 33

Met Ser Lys Ala Arg Val Tyr Thr Asp Val Asn Val Gln Arg Pro Lys
1               5                   10                  15

Asp Tyr Trp Asp Tyr Glu Ala Leu Thr Val Gln Trp Gly Asp Gln Asp
            20                  25                  30

```
Asp Tyr Glu Val Val Arg Lys Val Gly Arg Gly Lys Tyr Ser Glu Val
         35                  40                  45

Phe Glu Gly Val Asn Ala Val Asn Ser Glu Arg Cys Val Met Lys Ile
 50                  55                  60

Leu Lys Pro Val Lys Lys Lys Ile Lys Arg Glu Ile Lys Ile Leu
 65              70                  75                  80

Gln Asn Leu Cys Gly Gly Pro Asn Ile Val Lys Leu Leu Asp Ile Val
                 85                  90                  95

Arg Asp Gln Gln Ser Lys Thr Pro Ser Leu Ile Phe Glu Tyr Val Asn
             100                 105                 110

Asn Thr Asp Phe Lys Val Leu Tyr Pro Thr Leu Thr Asp Phe Asp Ile
         115                 120                 125

Arg Tyr Tyr Ile His Glu Leu Leu Lys Ala Leu Asp Tyr Cys His Ser
     130                 135                 140

Gln Gly Ile Met His Arg Asp Val Lys Pro His Asn Val Met Ile Asp
145                 150                 155                 160

His Glu Gln Arg Lys Leu Arg Leu Ile Asp Trp Gly Leu Ala Glu Phe
                 165                 170                 175

Tyr His Pro Gly Lys Glu Tyr Asn Val Arg Val Ala Ser Arg Tyr Phe
             180                 185                 190

Lys Gly Pro Glu Leu Leu Val Asp Leu Gln Asp Tyr Asp Tyr Ser Leu
         195                 200                 205

Asp Met Trp Ser Leu Gly Cys Met Phe Ala Gly Met Ile Phe Arg Lys
     210                 215                 220

Glu Pro Phe Phe Tyr Gly His Asp Asn Tyr Asp Gln Leu Val Lys Ile
225                 230                 235                 240

Ala Lys Val Leu Gly Thr Asp Glu Leu Asn Ser Tyr Leu Asn Lys Tyr
                 245                 250                 255

Arg Leu Glu Leu Asp Pro His Leu Glu Ala Leu Val Gly Arg His Ser
             260                 265                 270

Arg Lys Pro Trp Ser Lys Phe Ile Asn Ala Asp Asn Gln Arg Leu Val
         275                 280                 285

Val Pro Glu Ala Val Asp Phe Leu Asp Lys Leu Leu Arg Tyr Asp His
     290                 295                 300

Gln Asp Arg Leu Thr Ala Lys Glu Ala Met Ala His Pro Tyr Phe Tyr
305                 310                 315                 320

Pro Val Lys Val Ser Glu Val Ser Asn Arg Arg Ser Ala
                 325                 330

<210> SEQ ID NO 34
<211> LENGTH: 375
<212> TYPE: PRT
<213> ORGANISM: Physcomitrella patens

<400> SEQUENCE: 34

Met Glu Thr Ser Ser Gly Thr Pro Glu Leu Lys Val Ile Ser Thr Pro
 1               5                  10                  15

Thr Tyr Gly Gly His Tyr Val Lys Tyr Val Val Ala Gly Thr Asp Phe
             20                  25                  30

Glu Val Thr Ala Arg Tyr Lys Pro Pro Leu Arg Pro Ile Gly Arg Gly
         35                  40                  45

Ala Tyr Gly Ile Val Cys Ser Leu Phe Asp Thr Val Thr Gly Glu Glu
     50                  55                  60

Val Ala Val Lys Lys Ile Gly Asn Ala Phe Asp Asn Arg Ile Asp Ala
```

```
                65                  70                  75                  80
Lys Arg Thr Leu Arg Glu Ile Lys Leu Leu Arg His Met Asp His Glu
                    85                  90                  95

Asn Val Val Ala Ile Thr Asp Ile Ile Arg Pro Pro Thr Arg Glu Asn
                100                 105                 110

Phe Asn Asp Val Tyr Ile Val Tyr Glu Leu Met Asp Thr Asp Leu His
                115                 120                 125

Gln Ile Ile Arg Ser Asn Gln Ala Leu Thr Glu Asp His Cys Gln Tyr
            130                 135                 140

Phe Leu Tyr Gln Ile Leu Arg Gly Leu Lys Tyr Ile His Ser Ala Asn
145                 150                 155                 160

Val Leu His Arg Asp Leu Lys Pro Thr Asn Leu Leu Val Asn Ala Asn
                165                 170                 175

Cys Asp Leu Lys Ile Ala Asp Phe Gly Leu Ala Arg Thr Leu Ser Glu
                180                 185                 190

Thr Asp Phe Met Thr Glu Tyr Val Val Thr Arg Trp Tyr Arg Ala Pro
                195                 200                 205

Glu Leu Leu Leu Asn Cys Ser Ala Tyr Thr Ala Ala Ile Asp Ile Trp
            210                 215                 220

Ser Val Gly Cys Ile Phe Met Glu Leu Leu Asn Arg Ser Ala Leu Phe
225                 230                 235                 240

Pro Gly Arg Asp Tyr Val His Gln Leu Arg Leu Ile Thr Glu Leu Ile
                245                 250                 255

Gly Thr Pro Glu Asp Arg Asp Leu Gly Phe Leu Arg Ser Asp Asn Ala
                260                 265                 270

Arg Arg Tyr Ile Lys His Leu Pro Arg Gln Ser Pro Ile Pro Leu Thr
            275                 280                 285

Gln Lys Phe Arg Gly Ile Asn Arg Ser Ala Leu Asp Leu Val Glu Lys
290                 295                 300

Met Leu Val Phe Asp Pro Ala Lys Arg Ile Thr Val Glu Ala Ala Leu
305                 310                 315                 320

Ala His Pro Tyr Leu Ala Ser Leu His Asp Ile Asn Asp Glu Pro Ala
                325                 330                 335

Ser Val Ser Pro Phe Glu Phe Asp Phe Glu Glu Pro Pro Ile Ser Glu
                340                 345                 350

Glu His Ile Lys Asp Leu Ile Trp Arg Glu Ala Leu Asp Cys Ser Leu
            355                 360                 365

Gly Pro Asp Asp Met Val Gln
        370                 375

<210> SEQ ID NO 35
<211> LENGTH: 331
<212> TYPE: PRT
<213> ORGANISM: Physcomitrella patens

<400> SEQUENCE: 35

Met Gly Leu Thr Pro Phe Ser Cys Val Thr Val Gln Gly Tyr Val Arg
 1               5                  10                  15

Val Val Tyr Pro Asp Gly His Val Glu Asn Leu Ser Lys Ser Cys Ser
                20                  25                  30

Val His Asp Leu Leu Gly Asn Pro Asp Tyr Tyr Val Cys Gly Ser
            35                  40                  45

Thr Pro Tyr Thr Ile Thr Asn Arg Met Ala Ala Glu Glu Val Leu Glu
50                  55                  60
```

```
Tyr Gly Val Thr Tyr Phe Val Cys Ala Thr Pro Asn Ala Gln Pro Phe
 65                  70                  75                  80

Leu Glu Arg Gln Pro Lys Val Val His Arg Gly Ser Lys Ile Leu Pro
                 85                  90                  95

Arg Phe Ser Lys His Gly Val His Val Arg Glu Leu Arg Ser Pro Thr
            100                 105                 110

His Gly Ser Gln Gln Ser Arg Lys Val Phe Asp Tyr His Ser Val Thr
        115                 120                 125

Met Gln Gln Leu Glu Ser Ile Arg Asn Glu Gly Pro Glu Pro His Leu
    130                 135                 140

Ala Gly Asp Arg Pro Ser Lys His Leu Lys Leu Val Phe Ile Arg His
145                 150                 155                 160

Cys Leu Arg Ala Leu Arg Leu Pro Arg Ile Ser Ile Asp Leu Met Glu
                165                 170                 175

Ser Pro Leu Pro Asn Leu Ser Gly Glu Ala Leu Ser Pro Thr Ala Thr
            180                 185                 190

Ala Lys Asp Glu Ile Thr Gln Met Ile Leu Lys Ser Ala Ala Arg Ser
        195                 200                 205

Glu Leu Gly Met Tyr Val Ser Lys Arg Gln Glu Phe Tyr Leu Arg Arg
    210                 215                 220

Ala Arg Arg Arg Lys Phe Ala Trp Lys Pro Val Leu Gln Ser Ile
225                 230                 235                 240

Ser Glu Met Lys Pro Val Met Glu Phe His Thr Pro Met Ala Tyr Arg
                245                 250                 255

Asp Ser Gly Ser Pro Pro Lys Asn Ala Ser Thr Pro Ser Leu Pro Gly
            260                 265                 270

Pro Lys Asn Ile Ser Pro Pro Arg Gln Val Ser Val Pro Gln Arg Ser
        275                 280                 285

Ser Pro Pro Pro Lys Asn Val Ser Pro Pro Gln Pro Ala Phe Val
    290                 295                 300

Ala Arg Thr Ala Ser Lys Tyr Ser Ala Ala Ser Gln Gln Val Gln Arg
305                 310                 315                 320

Asn Arg Gly Asn Ala Lys Ser Leu Tyr Met Ala
                325                 330

<210> SEQ ID NO 36
<211> LENGTH: 346
<212> TYPE: PRT
<213> ORGANISM: Physcomitrella patens

<400> SEQUENCE: 36

Met Ser Arg Arg Val Arg Arg Gly Gly Leu Arg Val Ala Val Pro Lys
  1               5                  10                  15

Gln Glu Thr Pro Val Ser Lys Phe Leu Thr Ala Ser Gly Thr Phe Gln
                 20                  25                  30

Asp Asp Asp Ile Lys Leu Asn His Thr Gly Leu Arg Val Val Ser Ser
            35                  40                  45

Glu Pro Asn Leu Pro Thr Gln Thr Gln Ser Ser Ser Pro Asp Gly Gln
        50                  55                  60

Leu Ser Ile Ala Asp Leu Glu Leu Val Arg Phe Leu Gly Lys Gly Ala
 65                  70                  75                  80

Gly Gly Thr Val Gln Leu Val Arg His Lys Trp Thr Asn Val Asn Tyr
                 85                  90                  95

Ala Leu Lys Ala Ile Gln Met Asn Ile Asn Glu Thr Val Arg Lys Gln
            100                 105                 110
```

```
Ile Val Gln Glu Leu Lys Ile Asn Gln Val Thr His Gln Gln Cys Pro
            115                 120                 125

Tyr Ile Val Glu Cys Phe His Ser Phe Tyr His Asn Gly Val Ile Ser
            130                 135                 140

Met Ile Leu Glu Tyr Met Asp Arg Gly Ser Leu Ser Asp Ile Ile Lys
145                 150                 155                 160

Gln Gln Lys Gln Ile Pro Glu Pro Tyr Leu Ala Val Ile Ala Ser Gln
            165                 170                 175

Val Leu Lys Gly Leu Glu Tyr Leu His Gln Val Arg His Ile Ile His
            180                 185                 190

Arg Asp Ile Lys Pro Ser Asn Leu Leu Ile Asn His Lys Gly Glu Val
            195                 200                 205

Lys Ile Ser Asp Phe Gly Val Ser Ala Val Leu Val His Ser Leu Ala
210                 215                 220

Gln Arg Asp Thr Phe Val Gly Thr Cys Thr Tyr Met Ser Pro Glu Arg
225                 230                 235                 240

Leu Gln Gly Arg Ser Tyr Ala Tyr Asp Ser Asp Leu Trp Ser Leu Gly
            245                 250                 255

Leu Thr Leu Leu Glu Cys Ala Leu Gly Thr Phe Pro Tyr Lys Pro Ala
            260                 265                 270

Gly Met Glu Glu Gly Trp Gln Asn Phe Phe Ile Leu Met Glu Cys Ile
            275                 280                 285

Val Asn Gln Pro Pro Ala Ala Ala Ser Pro Asp Lys Phe Ser Pro Glu
290                 295                 300

Phe Cys Ser Phe Ile Glu Ser Cys Ile Arg Lys Cys Pro Ser Glu Arg
305                 310                 315                 320

Pro Ser Thr Thr Asp Leu Leu Lys His Pro Phe Leu Gln Lys Tyr Asn
            325                 330                 335

Glu Glu Glu Tyr His Leu Ser Lys Ile Leu
            340                 345

<210> SEQ ID NO 37
<211> LENGTH: 346
<212> TYPE: PRT
<213> ORGANISM: Physcomitrella patens

<400> SEQUENCE: 37

Met Ser Arg Arg Val Arg Arg Gly Gly Leu Arg Val Ala Val Pro Lys
1               5                   10                  15

Gln Glu Thr Pro Val Ser Lys Phe Leu Thr Ala Ser Gly Thr Phe Gln
            20                  25                  30

Asp Asp Asp Ile Lys Leu Asn His Thr Gly Leu Arg Val Val Ser Ser
            35                  40                  45

Glu Pro Asn Leu Pro Thr Gln Thr Gln Ser Ser Pro Asp Gly Gln
            50                  55                  60

Leu Ser Ile Ala Asp Leu Glu Leu Val Arg Phe Leu Gly Lys Gly Ala
65                  70                  75                  80

Gly Gly Thr Val Gln Leu Val Arg His Lys Trp Thr Asn Val Asn Tyr
            85                  90                  95

Ala Leu Lys Ala Ile Gln Met Asn Ile Asn Glu Thr Val Arg Lys Gln
            100                 105                 110

Ile Val Gln Glu Leu Lys Ile Asn Gln Val Thr His Gln Gln Cys Pro
            115                 120                 125

Tyr Ile Val Glu Cys Phe His Ser Phe Tyr His Asn Gly Val Ile Ser
            130                 135                 140
```

```
                130                 135                 140
Met Ile Leu Glu Tyr Met Asp Arg Gly Ser Leu Ser Asp Ile Ile Lys
145                 150                 155                 160

Gln Gln Lys Gln Ile Pro Glu Pro Tyr Leu Ala Val Ile Ala Ser Gln
                165                 170                 175

Val Leu Lys Gly Leu Glu Tyr Leu His Gln Val Arg His Ile Ile His
            180                 185                 190

Arg Asp Ile Lys Pro Ser Asn Leu Leu Ile Asn His Lys Gly Glu Val
            195                 200                 205

Lys Ile Ser Asp Phe Gly Val Ser Ala Val Leu Val His Ser Leu Ala
210                 215                 220

Gln Arg Asp Thr Phe Val Gly Thr Cys Thr Tyr Met Ser Pro Glu Arg
225                 230                 235                 240

Leu Gln Gly Arg Ser Tyr Ala Tyr Asp Ser Asp Leu Trp Ser Leu Gly
                245                 250                 255

Leu Thr Leu Leu Glu Cys Ala Leu Gly Thr Phe Pro Tyr Lys Pro Ala
            260                 265                 270

Gly Met Glu Glu Gly Trp Gln Asn Phe Phe Ile Leu Met Glu Cys Ile
            275                 280                 285

Val Asn Gln Pro Pro Ala Ala Ala Ser Pro Asp Lys Phe Ser Pro Glu
290                 295                 300

Phe Cys Ser Phe Ile Glu Ser Cys Ile Arg Lys Cys Pro Ser Glu Arg
305                 310                 315                 320

Pro Ser Thr Thr Asp Leu Leu Lys His Pro Phe Leu Gln Lys Tyr Asn
                325                 330                 335

Glu Glu Glu Tyr His Leu Ser Lys Ile Leu
            340                 345

<210> SEQ ID NO 38
<211> LENGTH: 597
<212> TYPE: PRT
<213> ORGANISM: Physcomitrella patens

<400> SEQUENCE: 38

Met Gly Gln Cys Tyr Gly Lys Phe Asp Asp Gly Gly Glu Gly Glu Asp
1               5                   10                  15

Leu Phe Glu Arg Gln Lys Val Gln Val Ser Arg Thr Pro Lys His Gly
                20                  25                  30

Ser Trp Ser Asn Ser Asn Arg Gly Ser Phe Asn Asn Gly Gly Gly Ala
            35                  40                  45

Ser Pro Met Arg Ala Lys Thr Ser Phe Gly Ser Ser His Pro Ser Pro
50                  55                  60

Arg His Pro Ser Ala Ser Pro Leu Pro His Tyr Thr Ser Ser Pro Ala
65                  70                  75                  80

Pro Ser Thr Pro Arg Arg Asn Ile Phe Lys Arg Pro Phe Pro Pro Pro
                85                  90                  95

Ser Pro Ala Lys His Ile Gln Ser Ser Leu Val Lys Arg His Gly Ala
            100                 105                 110

Lys Pro Lys Glu Gly Gly Ala Ile Pro Glu Ala Val Asp Gly Glu Lys
            115                 120                 125

Pro Leu Asp Lys His Phe Gly Tyr His Lys Asn Phe Ala Thr Lys Tyr
            130                 135                 140

Glu Leu Gly His Glu Val Gly Arg Gly His Phe Gly His Thr Cys Tyr
145                 150                 155                 160
```

-continued

```
Ala Lys Val Arg Lys Gly Glu His Lys Gly Gln Ala Val Ala Val Lys
            165                 170                 175

Ile Ile Ser Lys Ala Lys Met Thr Thr Ala Ile Ala Ile Glu Asp Val
            180                 185                 190

Gly Arg Glu Val Lys Ile Leu Lys Ala Leu Thr Gly His Gln Asn Leu
            195                 200                 205

Val Arg Phe Tyr Asp Ser Cys Glu Asp His Leu Asn Val Tyr Ile Val
            210                 215                 220

Met Glu Leu Cys Glu Gly Gly Glu Leu Leu Asp Arg Ile Leu Ser Arg
225                 230                 235                 240

Gly Gly Lys Tyr Ser Glu Glu Asp Ala Lys Val Val Arg Gln Ile
            245                 250                 255

Leu Ser Val Val Ala Phe Cys His Leu Gln Gly Val Val His Arg Asp
            260                 265                 270

Leu Lys Pro Glu Asn Phe Leu Phe Thr Thr Lys Asp Glu Tyr Ala Gln
            275                 280                 285

Leu Lys Ala Ile Asp Phe Gly Leu Ser Asp Phe Ile Lys Pro Asp Glu
            290                 295                 300

Arg Leu Asn Asp Ile Val Gly Ser Ala Tyr Tyr Val Ala Pro Glu Val
305                 310                 315                 320

Leu His Arg Leu Tyr Ser Met Glu Ala Asp Val Trp Ser Ile Gly Val
            325                 330                 335

Ile Thr Tyr Ile Leu Leu Cys Gly Ser Arg Pro Phe Trp Ala Arg Thr
            340                 345                 350

Glu Ser Gly Ile Phe Arg Ala Val Leu Arg Ala Asp Pro Ser Phe Glu
            355                 360                 365

Glu Ala Pro Trp Pro Ser Ile Ser Pro Glu Ala Lys Asp Phe Val Lys
            370                 375                 380

Arg Leu Leu Asn Lys Asp Met Arg Lys Arg Met Thr Ala Ala Gln Ala
385                 390                 395                 400

Leu Thr His Pro Trp Ile Arg Ser Asn Asn Val Lys Ile Pro Leu Asp
            405                 410                 415

Ile Leu Val Tyr Arg Leu Val Arg Asn Tyr Leu Arg Ala Ser Ser Met
            420                 425                 430

Arg Lys Ala Ala Leu Lys Ala Leu Ser Lys Thr Leu Thr Glu Asp Glu
            435                 440                 445

Thr Phe Tyr Leu Arg Thr Gln Phe Met Leu Leu Glu Pro Ser Asn Asn
450                 455                 460

Gly Arg Val Thr Phe Glu Asn Phe Arg Gln Ala Leu Leu Lys Asn Ser
465                 470                 475                 480

Thr Glu Ala Met Lys Glu Ser Arg Val Phe Glu Ile Leu Glu Ser Met
            485                 490                 495

Asp Gly Leu His Phe Lys Lys Met Asp Phe Ser Glu Phe Cys Ala Ala
            500                 505                 510

Ala Ile Ser Val Leu Gln Leu Glu Ala Thr Glu Arg Trp Glu Gln His
            515                 520                 525

Ala Arg Ala Ala Tyr Asp Ile Phe Glu Lys Glu Gly Asn Arg Val Ile
            530                 535                 540

Tyr Pro Asp Glu Leu Ala Lys Glu Met Gly Leu Ala Pro Asn Val Pro
545                 550                 555                 560

Ala Gln Val Phe Leu Asp Trp Ile Arg Gln Ser Asp Gly Arg Leu Ser
            565                 570                 575

Phe Thr Gly Phe Thr Lys Leu Leu His Gly Ile Ser Ser Arg Ala Ile
```

Lys Asn Leu Gln Gln
              595

<210> SEQ ID NO 39
<211> LENGTH: 549
<212> TYPE: PRT
<213> ORGANISM: Physcomitrella patens

<400> SEQUENCE: 39

Met Gly Asn Thr Ser Ser Arg Gly Ser Arg Lys Ser Thr Arg Gln Val
1               5                   10                  15

Asn Gln Gly Val Gly Ser Gln Asp Thr Arg Glu Lys Asn Asp Ser Val
            20                  25                  30

Asn Pro Lys Thr Arg Gln Gly Gly Ser Val Gly Ala Asn Tyr Gly
        35                  40                  45

Gly Lys Pro Ser Ser Gly Ala Gln Ala Gly Glu Arg Ser Thr Ser Ala
    50                  55                  60

Pro Ala Ala Leu Pro Arg Pro Lys Pro Ala Ser Arg Ser Val Ser Gly
65                  70                  75                  80

Val Leu Gly Lys Pro Leu Ser Asp Ile Arg Gln Ser Tyr Ile Leu Gly
                85                  90                  95

Arg Glu Leu Gly Arg Gly Gln Phe Gly Val Thr Tyr Leu Cys Thr Asp
            100                 105                 110

Lys Met Thr Asn Glu Ala Tyr Ala Cys Lys Ser Ile Ala Lys Arg Lys
        115                 120                 125

Leu Thr Ser Lys Glu Asp Ile Glu Asp Val Lys Arg Glu Val Gln Ile
    130                 135                 140

Met His His Leu Ser Gly Thr Pro Asn Ile Val Val Leu Lys Asp Val
145                 150                 155                 160

Phe Glu Asp Lys His Ser Val His Leu Val Met Glu Leu Cys Ala Gly
                165                 170                 175

Gly Glu Leu Phe Asp Arg Ile Ile Ala Lys Gly His Tyr Ser Glu Arg
            180                 185                 190

Ala Ala Ala Asp Met Cys Arg Val Ile Val Asn Val Val His Arg Cys
        195                 200                 205

His Ser Leu Gly Val Phe His Arg Asp Leu Lys Pro Glu Asn Phe Leu
    210                 215                 220

Leu Ala Ser Lys Ala Glu Asp Ala Pro Leu Lys Ala Thr Asp Phe Gly
225                 230                 235                 240

Leu Ser Thr Phe Phe Lys Pro Gly Asp Val Phe Gln Asp Ile Val Gly
                245                 250                 255

Ser Ala Tyr Tyr Val Ala Pro Glu Val Leu Lys Arg Ser Tyr Gly Pro
            260                 265                 270

Glu Ala Asp Val Trp Ser Ala Gly Val Ile Val Tyr Ile Leu Leu Cys
        275                 280                 285

Gly Val Pro Pro Phe Trp Ala Glu Thr Glu Gln Gly Ile Phe Asp Ala
    290                 295                 300

Val Leu Lys Gly His Ile Asp Phe Glu Asn Asp Pro Trp Pro Lys Ile
305                 310                 315                 320

Ser Asn Gly Ala Lys Asp Leu Val Arg Lys Met Leu Asn Pro Asn Val
                325                 330                 335

Lys Ile Arg Leu Thr Ala Gln Gln Val Leu Asn His Pro Trp Met Lys
            340                 345                 350

-continued

```
Glu Asp Gly Asp Ala Pro Asp Val Pro Leu Asp Asn Ala Val Leu Thr
        355                 360                 365

Arg Leu Lys Asn Phe Ser Ala Ala Asn Lys Met Lys Lys Leu Ala Leu
    370                 375                 380

Lys Val Ile Ala Glu Ser Leu Ser Glu Glu Ile Val Gly Leu Arg
385                 390                 395                 400

Glu Met Phe Lys Ser Ile Asp Thr Asp Asn Ser Gly Thr Val Thr Phe
                405                 410                 415

Glu Glu Leu Lys Glu Gly Leu Leu Lys Gln Gly Ser Lys Leu Asn Glu
            420                 425                 430

Ser Asp Ile Arg Lys Leu Met Glu Ala Ala Asp Val Asp Gly Asn Gly
        435                 440                 445

Lys Ile Asp Phe Asn Glu Phe Ile Ser Ala Thr Met His Met Asn Lys
    450                 455                 460

Thr Glu Lys Glu Asp His Leu Trp Ala Ala Phe Met His Phe Asp Thr
465                 470                 475                 480

Asp Asn Ser Gly Tyr Ile Thr Ile Asp Glu Leu Gln Glu Ala Met Glu
                485                 490                 495

Lys Asn Gly Met Gly Asp Pro Glu Thr Ile Gln Glu Ile Ile Ser Glu
            500                 505                 510

Val Asp Thr Asp Asn Asp Gly Arg Ile Asp Tyr Asp Glu Phe Val Ala
        515                 520                 525

Met Met Arg Lys Gly Asn Pro Gly Ala Glu Asn Gly Gly Thr Val Asn
    530                 535                 540

Lys Pro Arg His Arg
545

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 40
caggaaacag ctatgacc                                                      18

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 41
ctaaagggaa caaaagctg                                                     19

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 42
tgtaaaacga cggccagt                                                      18

<210> SEQ ID NO 43
<211> LENGTH: 25
<212> TYPE: DNA
```

<213> ORGANISM: Artificial Sequence
<220> FEATURE:
<223> OTHER INFORMATION: Description of Artificial Sequence: Primer

<400> SEQUENCE: 43
ccacggtctt cggctgctgg tcgtg                                 25

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 44
gcagcacagc accaccagcg gctat                                 25

<210> SEQ ID NO 45
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 45
gcgcccagtg agtagctcca gcatt                                 25

<210> SEQ ID NO 46
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 46
atcccgggtg agtatcactt acggtggcga                            30

<210> SEQ ID NO 47
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 47
gcgttaactc gaccaaggtc actattccaa gca                        33

<210> SEQ ID NO 48
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 48
cggtgcccac ctcgttcctg tggtt                                 25

<210> SEQ ID NO 49
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 49
atcccgggag tgggtggttg gactgtaagg a                          31

<210> SEQ ID NO 50
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 50
gcgttaacct tcgtcttgga caggtagagg ttac     34

<210> SEQ ID NO 51
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 51
gactcagccc cgtaatcctt caaca     25

<210> SEQ ID NO 52
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 52
atcccgggca acgagaagca ttcgagatgg c     31

<210> SEQ ID NO 53
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 53
gcgttaacga gcatcacgat actcggtgat ttc     33

<210> SEQ ID NO 54
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 54
cgacggctaa taccacgttg gcgacca     27

<210> SEQ ID NO 55
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 55
atcccgggct gtgatgtcgg tgtggtgctc tgc     33

<210> SEQ ID NO 56
<211> LENGTH: 34
<212> TYPE: DNA
<213> ORGANISM: Artificial Sequence
<220> FEATURE:

<223> OTHER INFORMATION: Description of Artificial Sequence: Primer

<400> SEQUENCE: 56
gcgagctcgc accactgaat gatggagact cagg    34

<210> SEQ ID NO 57
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 57
cgaccgcagc ccatgaggaa gttat    25

<210> SEQ ID NO 58
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 58
atcccgggct cacgtagtgc actgaactct gtc    33

<210> SEQ ID NO 59
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 59
gcgttaacat gcccatcttc tcatactcag acc    33

<210> SEQ ID NO 60
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 60
ctcgcctacc aagccccatt agaaa    25

<210> SEQ ID NO 61
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 61
atcccgggtt gtcgaggacg gagagagaag ag    32

<210> SEQ ID NO 62
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 62
gcgttaacct taggaatcgt atggcagaga gct    33

```
<210> SEQ ID NO 63
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 63
gcttcacaat gttgggccct ccaca                                          25

<210> SEQ ID NO 64
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 64
gcgttaacgg gaggaaggtc gggggaagag acg                                 33

<210> SEQ ID NO 65
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 65
gcgagctcag cgcttcgcac aactgagaaa cct                                 33

<210> SEQ ID NO 66
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 66
acgagaaggt tggtgggctt caagt                                          25

<210> SEQ ID NO 67
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 67
atcccgggcg agccatggcg ccacttgctt                                     30

<210> SEQ ID NO 68
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 68
gcgttaacgc cgagcaacaa tgtctgctgg atg                                 33

<210> SEQ ID NO 69
<211> LENGTH: 25
<212> TYPE: DNA
<213> ORGANISM: Artificial Sequence
<220> FEATURE:
<223> OTHER INFORMATION: Description of Artificial Sequence: Primer
```

-continued

```
<400> SEQUENCE: 69
cccggtaagc catcggagtg tggaa                                            25

<210> SEQ ID NO 70
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 70
atcccgggct tgtattggct cggataattt                                       30

<210> SEQ ID NO 71
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 71
gcgttaacgg caatatctgc acagccgttc act                                   33

<210> SEQ ID NO 72
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 72
gtgtctcgct gggccaagga atgaa                                            25

<210> SEQ ID NO 73
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 73
atcccgggcg gtcgagtcgt attaggtgtt gtttc                                 35

<210> SEQ ID NO 74
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 74
gagctccggt aggtccgacc tcttcaattg                                       30

<210> SEQ ID NO 75
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 75
gacgacgcga agcccggtgt ggttga                                           26

<210> SEQ ID NO 76
<211> LENGTH: 31
```

```
<212> TYPE: DNA
<213> ORGANISM: Artificial Sequence
<220> FEATURE:
<223> OTHER INFORMATION: Description of Artificial Sequence: Primer

<400> SEQUENCE: 76
atcccgggag aggctgatct gatgctacag t                              31

<210> SEQ ID NO 77
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 77
atgagctctg gcggattggc gaggtagttc gac                            33

<210> SEQ ID NO 78
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 78
cggcgcaacg tagtatgcgc ttcca                                     25

<210> SEQ ID NO 79
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 79
cgcggtgaac aacaccttgc aggtgac                                   27

<210> SEQ ID NO 80
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 80
gctcgggtca gccctcaaca ccgca                                     25

<210> SEQ ID NO 81
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 81
gttaaagctt gtgcagcagt catgc                                     25

<210> SEQ ID NO 82
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 82
```

-continued atcccgggtg taggcgggcg aggttcgatg c                31

<210> SEQ ID NO 83
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 83
gcgttaacga caaccggagt agaacggcag tcca             34

<210> SEQ ID NO 84
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 84
agaagcgagg aatgggcagg gacga                       25

<210> SEQ ID NO 85
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 85
atcccgggcg aactgcgatc tgagattcca ac               32

<210> SEQ ID NO 86
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 86
gcgttaacga gatccaaccg aagccatcct acga             34

<210> SEQ ID NO 87
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 87
gcgctgcaga tttcatttgg agaggacacg                  30

<210> SEQ ID NO 88
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 88
cgcggccggc ctcagaagaa ctcgtcaaga aggcg            35

<210> SEQ ID NO 89
<211> LENGTH: 25
<212> TYPE: DNA
<213> ORGANISM: Artificial Sequence

```
<220> FEATURE:
<223> OTHER INFORMATION: Description of Artificial Sequence: Primer

<400> SEQUENCE: 89
gctgacacgc aagcctcgc tagtc                                              25

<210> SEQ ID NO 90
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 90
gcgttaactc gaccaaggtc actattccaa gca                                    33

<210> SEQ ID NO 91
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 91
gcgttaacct tcgtcttgga caggtagagg ttac                                   34

<210> SEQ ID NO 92
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 92
gcgttaacga gcatcacgat actcggtgat ttc                                    33

<210> SEQ ID NO 93
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 93
gcgagctcgc accactgaat gatggagact cagg                                   34

<210> SEQ ID NO 94
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 94
gcgttaacat gcccatcttc tcatactcag acc                                    33

<210> SEQ ID NO 95
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 95
gcgttaacct taggaatcgt atggcagaga gct                                    33
```

<210> SEQ ID NO 96
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 96
gcgagctcag cgcttcgcac aactgagaaa cct                       33

<210> SEQ ID NO 97
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 97
gcgttaacgg caatatctgc acagccgttc act                       33

<210> SEQ ID NO 98
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 98
gcgttaacgg caatatctgc acagccgttc act                       33

<210> SEQ ID NO 99
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 99
gagctccggt aggtccgacc tcttcaattg                           30

<210> SEQ ID NO 100
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 100
atgagctctg gcggattggc gaggtagttc gac                       33

<210> SEQ ID NO 101
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 101
gcgttaacga caaccggagt agaacggcag tcca                      34

<210> SEQ ID NO 102
<211> LENGTH: 34
<212> TYPE: DNA
<213> ORGANISM: Artificial Sequence
<220> FEATURE:
<223> OTHER INFORMATION: Description of Artificial Sequence: Primer

<400> SEQUENCE: 102
gcgttaacga gatccaaccg aagccatcct acga                              34

<210> SEQ ID NO 103
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 103
cccagtaata gcagggttgg aggaa                                        25

<210> SEQ ID NO 104
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 104
ggctgcctga agatccgcta cagag                                        25

<210> SEQ ID NO 105
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 105
cgtcaggcta ctttgcgtgg agcac                                        25

<210> SEQ ID NO 106
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 106
cggtgctggc taacaccagg ccaga                                        25

<210> SEQ ID NO 107
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 107
atcccgggca acgagaagca ttcgagatgg c                                 31

<210> SEQ ID NO 108
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 108
gcgttaacga gcatcacgat actcggtgat ttc                               33

<210> SEQ ID NO 109

```
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 109
cgtggcatct ctcccgatgt tctta                                    25

<210> SEQ ID NO 110
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 110
ggccaactga aggcgtgtca tgatc                                    25

<210> SEQ ID NO 111
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 111
ctcgagggct cgttcaccgt gacct                                    25

<210> SEQ ID NO 112
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 112
cggaggtaac agtagtcagg ctgctc                                   26

<210> SEQ ID NO 113
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 113
ccgcgaccct tccacgcatc agcat                                    25

<210> SEQ ID NO 114
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 114
cctccaggaa gcctgcgccg agaag                                    25

<210> SEQ ID NO 115
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 115
```

-continued ggacattgtc cgtgatcagc aatcga                                        26

<210> SEQ ID NO 116
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 116
cagcctctgg aacaaccaga cgctg                                         25

<210> SEQ ID NO 117
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 117
gtcaccgcga ggtacaagcc accac                                         25

<210> SEQ ID NO 118
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 118
gcagctctgg agctctgtac cacct                                         25

<210> SEQ ID NO 119
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 119
acggccacgt cgagaatctg agcaa                                         25

<210> SEQ ID NO 120
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 120
cgaagtgctc gcaagcaatg ccgaa                                         25

<210> SEQ ID NO 121
<211> LENGTH: 35
<212> TYPE: DNA
<213> ORGANISM: Artificial Sequence
<220> FEATURE:
<223> OTHER INFORMATION: Description of Artificial Sequence: Primer

<400> SEQUENCE: 121
atcccgggcg gtcgagtcgt attaggtgtt gtttc                              35

<210> SEQ ID NO 122
<211> LENGTH: 30
<212> TYPE: DNA

<213> ORGANISM: Artificial Sequence
<220> FEATURE:
<223> OTHER INFORMATION: Description of Artificial Sequence: Primer

<400> SEQUENCE: 122
gagctccggt aggtccgacc tcttcaattg                              30

<210> SEQ ID NO 123
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 123
gggcaactgt caatagcaga cctgga                                  26

<210> SEQ ID NO 124
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 124
gcaagtccca acgaacgtgt ctcgct                                  26

<210> SEQ ID NO 125
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 125
gcgaagatga cgactgctat tgcga                                   25

<210> SEQ ID NO 126
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 126
cgtgatgact ccaatgctcc atacg                                   25

<210> SEQ ID NO 127
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 127
gccagcatcg aggtcagtat ccggtgt                                 27

<210> SEQ ID NO 128
<211> LENGTH: 27
<212> TYPE: DNA
<213> ORGANISM: Artificial Sequence -continued

```
<220> FEATURE:
<223> OTHER INFORMATION: Description of Artificial Sequence: Primer

<400> SEQUENCE: 128
gtctgtggcc ttcagaggcg catcctc                                              27
```